United States Patent
Bowling et al.

(10) Patent No.: US 12,364,561 B2
(45) Date of Patent: *Jul. 22, 2025

(54) HAND-HELD PENDANT FOR CONTROLLING A SURGICAL ROBOTIC MANIPULATOR IN A SEMI-AUTONOMOUS MODE

(71) Applicant: Stryker Corporation, Kalamazoo, MI (US)

(72) Inventors: David Gene Bowling, Los Ranchos de Albuquerue, NM (US); John Michael Stuart, Rio Rancho, NM (US); Jerry A. Culp, Kalamazoo, MI (US); Donald W. Malackowski, Schoolcraft, MI (US); José Luis Moctezuma de la Barrera, Freiburg (DE); Patrick Roessler, Merzhausen (DE); Joel N. Beer, Albuquerque, NM (US)

(73) Assignee: Stryker Corporation, Portage, MI (US)

( * ) Notice: Subject to any disclaimer, the term of this patent is extended or adjusted under 35 U.S.C. 154(b) by 411 days.

This patent is subject to a terminal disclaimer.

(21) Appl. No.: 17/901,163

(22) Filed: Sep. 1, 2022

(65) Prior Publication Data
US 2023/0076453 A1 Mar. 9, 2023

Related U.S. Application Data

(63) Continuation of application No. 16/584,436, filed on Sep. 26, 2019, now Pat. No. 11,471,232, which is a
(Continued)

(51) Int. Cl.
*A61B 34/00* (2016.01)
*A61B 34/10* (2016.01)
(Continued)

(52) U.S. Cl.
CPC .............. *A61B 34/74* (2016.02); *A61B 34/10* (2016.02); *A61B 34/20* (2016.02); *A61B 34/30* (2016.02);
(Continued)

(58) Field of Classification Search
None
See application file for complete search history.

(56) References Cited

U.S. PATENT DOCUMENTS

| 4,425,818 A | 1/1984 | Asada et al. |
| 4,442,493 A | 4/1984 | Wakai et al. |

(Continued)

FOREIGN PATENT DOCUMENTS

| CN | 1168310 A | 12/1997 |
| CN | 1771114 A | 5/2006 |

(Continued)

OTHER PUBLICATIONS

R. Buckingham, Robotics in surgery a new generation of surgical tools incorporate computer technology and mechanical actuation to give surgeons much finer control than previously possible during some operations, IEE Review, Sep. 1994, pp. 193-196; 4pages.

(Continued)

*Primary Examiner* — Tamara L Weber
(74) *Attorney, Agent, or Firm* — Howard & Howard Attorneys PLLC

(57) ABSTRACT

A user control device for a surgical system. The surgical system includes a robotic manipulator to support and move a surgical instrument that has an energy applicator. One or more controllers operate the robotic manipulator in a semi-autonomous mode and calculate an instrument feed rate, which is the velocity at which the energy applicator advances along a tool path in the semi-autonomous mode. The user control device includes a housing configured as a
(Continued)

pendant configured to be held in one hand of a user. A first control member is mounted to the housing and can be depressed to initiate operation of the robotic manipulator in the semi-autonomous mode. A second control member is mounted to the housing and can be depressed to modify the instrument feed rate in the semi-autonomous mode.

20 Claims, 53 Drawing Sheets

Related U.S. Application Data continuation of application No. 16/262,375, filed on Jan. 30, 2019, now Pat. No. 10,463,440, which is a continuation of application No. 15/266,691, filed on Sep. 15, 2016, now Pat. No. 10,350,017, which is a continuation of application No. 13/958,834, filed on Aug. 5, 2013, now Pat. No. 9,480,534.

(60) Provisional application No. 61/792,251, filed on Mar. 15, 2013, provisional application No. 61/679,258, filed on Aug. 3, 2012.

(51) Int. Cl.
  *A61B 34/20* (2016.01)
  *A61B 34/30* (2016.01)
  *A61B 34/32* (2016.01)
  *A61B 34/37* (2016.01)
  *B25J 9/16* (2006.01)
  *B25J 13/00* (2006.01)
  *A61B 17/16* (2006.01)

(52) U.S. Cl.
  CPC .............. *A61B 34/32* (2016.02); *A61B 34/37* (2016.02); *A61B 34/70* (2016.02); *A61B 34/76* (2016.02); *B25J 9/161* (2013.01); *B25J 9/1633* (2013.01); *B25J 13/00* (2013.01); *A61B 17/16* (2013.01); *A61B 2034/104* (2016.02); *A61B 2034/107* (2016.02); *A61B 2034/2046* (2016.02); *A61B 2034/2055* (2016.02); *A61B 2034/2059* (2016.02); *Y10S 901/09* (2013.01)

(56) References Cited

U.S. PATENT DOCUMENTS

| | | | |
|---|---|---|---|
| 4,696,167 | A | 9/1987 | Matsui et al. |
| 4,833,617 | A | 5/1989 | Wang |
| 4,863,133 | A | 9/1989 | Bonnell |
| 4,916,635 | A | 4/1990 | Singer et al. |
| 4,979,949 | A | 12/1990 | Matsen, III et al. |
| 5,078,140 | A | 1/1992 | Kwoh |
| 5,086,401 | A | 2/1992 | Glassman et al. |
| 5,091,861 | A | 2/1992 | Geller et al. |
| 5,154,717 | A | 10/1992 | Matsen, III et al. |
| 5,231,693 | A | 7/1993 | Backes et al. |
| 5,279,309 | A | 1/1994 | Taylor et al. |
| 5,299,288 | A | 3/1994 | Glassman et al. |
| 5,339,799 | A | 8/1994 | Kami et al. |
| 5,343,391 | A | 8/1994 | Mushabac |
| 5,397,323 | A | 3/1995 | Taylor et al. |
| 5,399,951 | A | 3/1995 | Lavallee et al. |
| 5,408,409 | A | 4/1995 | Glassman et al. |
| 5,434,489 | A | 7/1995 | Cheng et al. |
| 5,445,144 | A | 8/1995 | Wodicka et al. |
| 5,452,238 | A | 9/1995 | Kramer et al. |
| 5,543,695 | A | 8/1996 | Culp et al. |
| 5,562,448 | A | 10/1996 | Mushabac |
| 5,569,578 | A | 10/1996 | Mushabac |
| 5,576,727 | A | 11/1996 | Rosenberg et al. |
| 5,629,594 | A | 5/1997 | Jacobus et al. |
| 5,630,431 | A | 5/1997 | Taylor |
| 5,638,267 | A | 6/1997 | Singhose et al. |
| 5,682,886 | A | 11/1997 | Delp et al. |
| 5,689,159 | A | 11/1997 | Culp et al. |
| 5,691,898 | A | 11/1997 | Rosenberg et al. |
| 5,695,500 | A | 12/1997 | Taylor et al. |
| 5,699,038 | A | 12/1997 | Ulrich et al. |
| 5,710,870 | A | 1/1998 | Ohm et al. |
| 5,711,299 | A | 1/1998 | Manwaring et al. |
| 5,721,566 | A | 2/1998 | Rosenberg et al. |
| 5,730,129 | A | 3/1998 | Darrow et al. |
| 5,731,804 | A | 3/1998 | Rosenberg |
| 5,734,373 | A | 3/1998 | Rosenberg et al. |
| 5,737,500 | A | 4/1998 | Seraji et al. |
| 5,739,811 | A | 4/1998 | Rosenberg et al. |
| 5,748,767 | A | 5/1998 | Raab |
| 5,762,458 | A | 6/1998 | Wang et al. |
| 5,767,548 | A | 6/1998 | Wondrak et al. |
| 5,767,648 | A | 6/1998 | Morel et al. |
| 5,767,839 | A | 6/1998 | Rosenberg |
| 5,769,092 | A | 6/1998 | Williamson, Jr. |
| 5,769,640 | A | 6/1998 | Jacobus et al. |
| 5,776,136 | A | 7/1998 | Sahay et al. |
| 5,784,542 | A | 7/1998 | Ohm et al. |
| 5,789,890 | A | 8/1998 | Genov et al. |
| 5,792,135 | A | 8/1998 | Madhani et al. |
| 5,792,147 | A | 8/1998 | Evans et al. |
| 5,806,518 | A | 9/1998 | Mittelstadt |
| 5,807,377 | A | 9/1998 | Madhani et al. |
| 5,815,640 | A | 9/1998 | Wang et al. |
| 5,820,623 | A | 10/1998 | Ng |
| 5,824,085 | A | 10/1998 | Sahay et al. |
| 5,831,408 | A | 11/1998 | Jacobus et al. |
| 5,835,693 | A | 11/1998 | Lynch et al. |
| 5,841,950 | A | 11/1998 | Wang et al. |
| 5,847,528 | A | 12/1998 | Hui et al. |
| 5,855,553 | A | 1/1999 | Tajima et al. |
| 5,855,583 | A | 1/1999 | Wang et al. |
| 5,871,018 | A | 2/1999 | Delp et al. |
| 5,880,976 | A | 3/1999 | DiGioia, III et al. |
| 5,882,206 | A | 3/1999 | Gillio |
| 5,891,157 | A | 4/1999 | Day et al. |
| 5,907,487 | A | 5/1999 | Rosenberg et al. |
| 5,907,664 | A | 5/1999 | Wang et al. |
| 5,929,607 | A | 7/1999 | Rosenberg et al. |
| 5,950,629 | A | 9/1999 | Taylor et al. |
| 5,952,796 | A | 9/1999 | Colgate et al. |
| 5,959,613 | A | 9/1999 | Rosenberg et al. |
| 5,966,305 | A | 10/1999 | Watari et al. |
| 5,971,976 | A | 10/1999 | Wang et al. |
| 5,976,156 | A | 11/1999 | Taylor et al. |
| 5,993,338 | A | 11/1999 | Kato et al. |
| 5,995,738 | A | 11/1999 | DiGioia, III et al. |
| 5,999,168 | A | 12/1999 | Rosenberg et al. |
| 6,002,859 | A | 12/1999 | DiGioia, III et al. |
| 6,020,876 | A | 2/2000 | Rosenberg et al. |
| 6,024,576 | A | 2/2000 | Bevirt et al. |
| 6,033,415 | A | 3/2000 | Mittelstadt et al. |
| 6,037,927 | A | 3/2000 | Rosenberg |
| 6,046,727 | A | 4/2000 | Rosenberg et al. |
| 6,050,718 | A | 4/2000 | Schena et al. |
| 6,063,095 | A | 5/2000 | Wang et al. |
| 6,067,077 | A | 5/2000 | Martin et al. |
| 6,084,587 | A | 7/2000 | Tarr et al. |
| 6,097,168 | A | 8/2000 | Katoh et al. |
| 6,102,850 | A | 8/2000 | Wang et al. |
| 6,104,158 | A | 8/2000 | Jacobus et al. |
| 6,111,577 | A | 8/2000 | Zilles et al. |
| 6,124,693 | A | 9/2000 | Okanda et al. |
| 6,157,873 | A | 12/2000 | DeCamp et al. |
| 6,163,124 | A | 12/2000 | Ito et al. |
| 6,181,096 | B1 | 1/2001 | Hashimoto et al. |
| 6,191,796 | B1 | 2/2001 | Tarr |
| 6,205,411 | B1 | 3/2001 | DiGioia, III et al. |
| 6,228,089 | B1 | 5/2001 | Wahrburg |
| 6,233,504 | B1 | 5/2001 | Das et al. |
| 6,236,875 | B1 | 5/2001 | Bucholz et al. |
| 6,236,906 | B1 | 5/2001 | Muller |

(56) References Cited

U.S. PATENT DOCUMENTS

| | | |
|---|---|---|
| 6,246,200 B1 | 6/2001 | Blumenkranz et al. |
| 6,278,902 B1 | 8/2001 | Hashimoto et al. |
| 6,281,651 B1 | 8/2001 | Haanpaa et al. |
| 6,300,937 B1 | 10/2001 | Rosenberg |
| 6,304,050 B1 | 10/2001 | Skaar et al. |
| 6,311,100 B1 | 10/2001 | Sarma et al. |
| 6,314,312 B1 | 11/2001 | Wessels et al. |
| 6,322,567 B1 | 11/2001 | Mittelstadt et al. |
| 6,325,808 B1 | 12/2001 | Bernard et al. |
| 6,329,777 B1 | 12/2001 | Itabashi et al. |
| 6,329,778 B1 | 12/2001 | Culp et al. |
| 6,330,837 B1 | 12/2001 | Charles et al. |
| 6,336,931 B1 | 1/2002 | Hsu et al. |
| 6,339,735 B1 | 1/2002 | Peless et al. |
| 6,341,231 B1 | 1/2002 | Ferre et al. |
| 6,342,880 B2 | 1/2002 | Rosenberg et al. |
| 6,347,240 B1 | 2/2002 | Foley et al. |
| 6,351,659 B1 | 2/2002 | Vilsmeier |
| 6,351,661 B1 | 2/2002 | Cosman |
| 6,352,532 B1 | 3/2002 | Kramer et al. |
| 6,366,272 B1 | 4/2002 | Rosenberg et al. |
| 6,368,330 B1 | 4/2002 | Hynes et al. |
| 6,369,834 B1 | 4/2002 | Zilles et al. |
| 6,377,839 B1 | 4/2002 | Kalfas et al. |
| 6,385,475 B1 | 5/2002 | Cinquin et al. |
| 6,385,508 B1 | 5/2002 | McGee et al. |
| 6,385,509 B2 | 5/2002 | Das et al. |
| 6,401,006 B1 | 6/2002 | Mizuno et al. |
| 6,405,072 B1 | 6/2002 | Cosman |
| 6,408,253 B2 | 6/2002 | Rosenberg et al. |
| 6,411,276 B1 | 6/2002 | Braun et al. |
| 6,413,264 B1 | 7/2002 | Jensen et al. |
| 6,414,711 B2 | 7/2002 | Arimatsu et al. |
| 6,417,638 B1 | 7/2002 | Guy et al. |
| 6,421,048 B1 | 7/2002 | Shih et al. |
| 6,423,077 B2 | 7/2002 | Carol et al. |
| 6,424,356 B2 | 7/2002 | Chang et al. |
| 6,428,487 B1 | 8/2002 | Burdorff et al. |
| 6,430,434 B1 | 8/2002 | Mittelstadt |
| 6,432,112 B2 | 8/2002 | Brock et al. |
| 6,434,415 B1 | 8/2002 | Foley et al. |
| 6,436,107 B1 | 8/2002 | Wang et al. |
| 6,441,577 B2 | 8/2002 | Blumenkranz et al. |
| 6,443,894 B1 | 9/2002 | Sumanaweera et al. |
| 6,450,978 B1 | 9/2002 | Brosseau et al. |
| 6,451,027 B1 | 9/2002 | Cooper et al. |
| 6,459,926 B1 | 10/2002 | Nowlin et al. |
| 6,461,372 B1 | 10/2002 | Jensen et al. |
| 6,463,360 B1 | 10/2002 | Terada et al. |
| 6,466,815 B1 | 10/2002 | Saito et al. |
| 6,468,265 B1 | 10/2002 | Evans et al. |
| 6,470,236 B2 | 10/2002 | Ohtsuki |
| 6,473,635 B1 | 10/2002 | Rasche |
| 6,486,872 B2 | 11/2002 | Rosenberg et al. |
| 6,490,467 B1 | 12/2002 | Bucholz et al. |
| 6,491,702 B2 | 12/2002 | Heilbrun et al. |
| 6,494,882 B1 | 12/2002 | Lebouitz et al. |
| 6,501,997 B1 | 12/2002 | Kakino |
| 6,507,165 B2 | 1/2003 | Kato et al. |
| 6,507,773 B2 | 1/2003 | Parker et al. |
| 6,514,082 B2 | 2/2003 | Kaufman et al. |
| 6,520,228 B1 | 2/2003 | Kennedy et al. |
| 6,522,906 B1 | 2/2003 | Salisbury, Jr. et al. |
| 6,533,737 B1 | 3/2003 | Brosseau et al. |
| 6,535,756 B1 | 3/2003 | Simon et al. |
| 6,542,770 B2 | 4/2003 | Zylka et al. |
| 6,562,055 B2 | 5/2003 | Walen |
| 6,620,174 B2 | 9/2003 | Jensen et al. |
| 6,636,161 B2 | 10/2003 | Rosenberg |
| 6,639,581 B1 | 10/2003 | Moore et al. |
| 6,665,554 B1 | 12/2003 | Charles et al. |
| 6,668,692 B1 | 12/2003 | Thiele et al. |
| 6,671,651 B2 | 12/2003 | Goodwin et al. |
| 6,676,669 B2 | 1/2004 | Charles et al. |
| 6,697,048 B2 | 2/2004 | Rosenberg et al. |
| 6,699,177 B1 | 3/2004 | Wang et al. |
| 6,702,805 B1 | 3/2004 | Stuart |
| 6,704,002 B1 | 3/2004 | Martin et al. |
| 6,704,683 B1 | 3/2004 | Hasser |
| 6,704,694 B1 | 3/2004 | Basdogan et al. |
| 6,711,432 B1 | 3/2004 | Krause et al. |
| 6,723,106 B1 | 4/2004 | Charles et al. |
| 6,728,599 B2 | 4/2004 | Wang et al. |
| 6,756,761 B2 | 6/2004 | Takahashi et al. |
| 6,757,582 B2 | 6/2004 | Brisson et al. |
| 6,778,850 B1 | 8/2004 | Adler et al. |
| 6,778,867 B1 | 8/2004 | Ziegler et al. |
| 6,781,569 B1 | 8/2004 | Gregorio et al. |
| 6,785,572 B2 | 8/2004 | Yanof et al. |
| 6,785,593 B2 | 8/2004 | Wang et al. |
| 6,788,999 B2 | 9/2004 | Green |
| 6,793,653 B2 | 9/2004 | Sanchez et al. |
| 6,799,106 B2 | 9/2004 | Fukushima et al. |
| 6,801,008 B1 | 10/2004 | Jacobus et al. |
| 6,804,547 B2 | 10/2004 | Pelzer et al. |
| 6,810,314 B2 | 10/2004 | Tashiro et al. |
| 6,827,723 B2 | 12/2004 | Carson |
| 6,832,119 B2 | 12/2004 | Miller |
| 6,833,846 B2 | 12/2004 | Hasser |
| 6,837,892 B2 | 1/2005 | Shoham |
| 6,856,888 B2 | 2/2005 | Kawai |
| 6,871,117 B2 | 3/2005 | Wang et al. |
| 6,892,110 B2 | 5/2005 | Inoue et al. |
| 6,892,112 B2 | 5/2005 | Wang et al. |
| 6,892,129 B2 | 5/2005 | Miyano |
| 6,895,306 B2 | 5/2005 | Ebisawa et al. |
| 6,903,721 B2 | 6/2005 | Braun et al. |
| 6,904,823 B2 | 6/2005 | Levin et al. |
| 6,919,701 B2 | 7/2005 | Nagata et al. |
| 6,941,224 B2 | 9/2005 | Fukuyasu |
| 6,958,752 B2 | 10/2005 | Jennings, Jr. et al. |
| 6,963,792 B1 | 11/2005 | Green |
| 6,978,166 B2 | 12/2005 | Foley et al. |
| 6,982,700 B2 | 1/2006 | Rosenberg et al. |
| 6,999,852 B2 | 2/2006 | Green |
| 7,003,368 B2 | 2/2006 | Koike et al. |
| 7,006,895 B2 | 2/2006 | Green |
| 7,030,585 B2 | 4/2006 | Iwashita et al. |
| 7,033,491 B2 | 4/2006 | Kozai et al. |
| 7,034,491 B2 | 4/2006 | Kozai et al. |
| 7,035,711 B2 | 4/2006 | Watanabe et al. |
| 7,035,716 B2 | 4/2006 | Harris et al. |
| 7,038,657 B2 | 5/2006 | Rosenberg et al. |
| 7,042,175 B2 | 5/2006 | Watanabe |
| 7,044,039 B2 | 5/2006 | Powell |
| 7,047,117 B2 | 5/2006 | Akiyama et al. |
| 7,055,789 B2 | 6/2006 | Libbey et al. |
| 7,056,123 B2 | 6/2006 | Gregorio et al. |
| 7,079,145 B2 | 7/2006 | Tonge et al. |
| 7,084,596 B2 | 8/2006 | Iwashita et al. |
| 7,084,867 B1 | 8/2006 | Ho et al. |
| 7,086,056 B2 | 8/2006 | Fukushima |
| 7,087,049 B2 | 8/2006 | Nowlin et al. |
| 7,092,791 B2 | 8/2006 | Terada et al. |
| 7,097,640 B2 | 8/2006 | Wang et al. |
| 7,102,314 B2 | 9/2006 | Hayashi |
| 7,102,635 B2 | 9/2006 | Shih et al. |
| 7,103,499 B2 | 9/2006 | Goodwin et al. |
| 7,139,601 B2 | 11/2006 | Bucholz et al. |
| 7,155,316 B2 | 12/2006 | Sutherland et al. |
| 7,181,315 B2 | 2/2007 | Watanabe et al. |
| 7,193,607 B2 | 3/2007 | Moore et al. |
| 7,204,844 B2 | 4/2007 | Jensen et al. |
| 7,206,626 B2 | 4/2007 | Quaid, III |
| 7,206,627 B2 | 4/2007 | Abovitz et al. |
| 7,209,117 B2 | 4/2007 | Rosenberg et al. |
| 7,212,886 B2 | 5/2007 | Nagata et al. |
| 7,215,326 B2 | 5/2007 | Rosenberg |
| 7,221,983 B2 | 5/2007 | Watanabe et al. |
| 7,225,404 B1 | 5/2007 | Zilles et al. |
| 7,239,940 B2 | 7/2007 | Wang et al. |
| 7,245,202 B2 | 7/2007 | Levin |
| 7,249,951 B2 | 7/2007 | Bevirt et al. |
| 7,260,437 B2 | 8/2007 | Senoo et al. |

(56) References Cited

U.S. PATENT DOCUMENTS

| | | |
|---|---|---|
| 7,260,733 B2 | 8/2007 | Ichikawa et al. |
| 7,280,095 B2 | 10/2007 | Grant |
| 7,283,120 B2 | 10/2007 | Grant |
| 7,319,466 B1 | 1/2008 | Tarr et al. |
| 7,346,417 B2 | 3/2008 | Luth et al. |
| 7,353,149 B2 | 4/2008 | Strunk et al. |
| 7,383,073 B1 | 6/2008 | Abovitz et al. |
| 7,390,325 B2 | 6/2008 | Wang et al. |
| 7,404,716 B2 | 7/2008 | Gregorio et al. |
| 7,421,303 B2 | 9/2008 | Zhang et al. |
| 7,422,582 B2 | 9/2008 | Malackowski et al. |
| 7,447,604 B2 | 11/2008 | Braun et al. |
| 7,454,268 B2 | 11/2008 | Jinno |
| 7,460,104 B2 | 12/2008 | Rosenberg |
| 7,460,105 B2 | 12/2008 | Rosenberg et al. |
| 7,466,303 B2 | 12/2008 | Yi et al. |
| 7,468,594 B2 | 12/2008 | Svensson et al. |
| 7,491,198 B2 | 2/2009 | Kockro |
| 7,493,244 B2 | 2/2009 | Leprevost |
| 7,505,883 B2 | 3/2009 | Leprevost |
| 7,526,456 B2 | 4/2009 | Zhang et al. |
| 7,542,826 B2 | 6/2009 | Hanzawa |
| 7,543,588 B2 | 6/2009 | Wang et al. |
| 7,573,461 B2 | 8/2009 | Rosenberg |
| 7,577,504 B2 | 8/2009 | Sawada et al. |
| 7,590,458 B2 | 9/2009 | Endo et al. |
| 7,610,182 B2 | 10/2009 | Smith et al. |
| 7,616,204 B2 | 11/2009 | Muller et al. |
| 7,623,944 B2 | 11/2009 | Dariush |
| 7,625,383 B2 | 12/2009 | Charles et al. |
| 7,646,161 B2 | 1/2010 | Albu-Schaffer et al. |
| 7,648,513 B2 | 1/2010 | Green et al. |
| 7,657,300 B2 | 2/2010 | Hunter et al. |
| 7,657,356 B2 | 2/2010 | Iwashita et al. |
| 7,660,623 B2 | 2/2010 | Hunter et al. |
| 7,667,687 B2 | 2/2010 | Cruz-Hernandez et al. |
| 7,683,565 B2 | 3/2010 | Quaid et al. |
| 7,688,016 B2 | 3/2010 | Aghili |
| 7,714,836 B2 | 5/2010 | Rodomista et al. |
| 7,725,162 B2 | 5/2010 | Malackowski et al. |
| 7,739,479 B2 | 6/2010 | Bordes et al. |
| 7,742,801 B2 | 6/2010 | Neubauer et al. |
| 7,744,608 B2 | 6/2010 | Lee et al. |
| 7,747,311 B2 | 6/2010 | Quaid, III |
| 7,764,767 B2 | 7/2010 | Beimler et al. |
| 7,765,890 B2 | 8/2010 | Inoue et al. |
| 7,769,571 B2 | 8/2010 | Bowers |
| 7,788,071 B2 | 8/2010 | Bond et al. |
| 7,800,609 B2 | 9/2010 | Tarr et al. |
| 7,806,891 B2 | 10/2010 | Nowlin et al. |
| 7,813,368 B2 | 10/2010 | Ootaka |
| 7,813,784 B2 | 10/2010 | Marquart et al. |
| 7,813,838 B2 | 10/2010 | Sommer |
| 7,815,644 B2 | 10/2010 | Masini |
| 7,818,044 B2 | 10/2010 | Dukesherer et al. |
| 7,824,424 B2 | 11/2010 | Jensen et al. |
| 7,831,292 B2 | 11/2010 | Quaid et al. |
| 7,835,784 B2 | 11/2010 | Mire et al. |
| 7,843,158 B2 | 11/2010 | Prisco |
| 7,853,356 B2 | 12/2010 | Tsai et al. |
| 7,853,358 B2 | 12/2010 | Joly |
| 7,881,917 B2 | 2/2011 | Nagatsuka et al. |
| 7,892,243 B2 | 2/2011 | Stuart |
| 7,895,411 B2 | 2/2011 | Maher et al. |
| 7,914,522 B2 | 3/2011 | Morley et al. |
| 7,916,121 B2 | 3/2011 | Braun et al. |
| 7,937,359 B1 | 5/2011 | Zhang et al. |
| 7,950,306 B2 | 5/2011 | Stuart |
| 7,969,288 B2 | 6/2011 | Braun et al. |
| 8,004,229 B2 | 8/2011 | Nowlin et al. |
| 8,005,571 B2 | 8/2011 | Sutherland et al. |
| 8,005,659 B2 | 8/2011 | Nelson et al. |
| 8,010,180 B2 | 8/2011 | Quaid et al. |
| 8,010,234 B2 * | 8/2011 | Henne ............ G05B 19/427 200/332.2 |
| 8,013,847 B2 | 9/2011 | Anastas |
| 8,049,457 B2 | 11/2011 | Okita et al. |
| 8,049,734 B2 | 11/2011 | Rosenberg et al. |
| 8,054,028 B2 | 11/2011 | Aoyama et al. |
| 8,090,475 B2 | 1/2012 | Blanc et al. |
| 8,095,200 B2 | 1/2012 | Quaid, III |
| 8,140,189 B2 | 3/2012 | Nagasaka |
| 8,155,790 B2 | 4/2012 | Oga et al. |
| 8,185,265 B2 | 5/2012 | Nagano |
| 8,271,134 B2 | 9/2012 | Kato et al. |
| 8,287,522 B2 | 10/2012 | Moses et al. |
| 8,391,954 B2 | 3/2013 | Quaid, III |
| 8,395,626 B2 | 3/2013 | Millman |
| 8,405,340 B2 | 3/2013 | Moon et al. |
| 8,428,776 B2 | 4/2013 | Letsky |
| 8,428,779 B2 | 4/2013 | Ohga et al. |
| 8,437,992 B2 | 5/2013 | Bond et al. |
| 8,442,806 B2 | 5/2013 | Ikits et al. |
| 8,489,238 B2 | 7/2013 | Ooga et al. |
| 8,498,744 B2 | 7/2013 | Odermatt et al. |
| 8,541,970 B2 | 9/2013 | Nowlin et al. |
| 8,560,047 B2 | 10/2013 | Haider et al. |
| 8,644,988 B2 | 2/2014 | Prisco et al. |
| 8,725,293 B2 | 5/2014 | Nagasaka |
| 8,740,882 B2 | 6/2014 | Jun et al. |
| 8,749,189 B2 | 6/2014 | Nowlin et al. |
| 8,749,190 B2 | 6/2014 | Nowlin et al. |
| 8,770,905 B2 | 7/2014 | Al-Mouhamed et al. |
| 8,786,241 B2 | 7/2014 | Nowlin et al. |
| 8,816,628 B2 | 8/2014 | Nowlin et al. |
| 8,823,308 B2 | 9/2014 | Nowlin et al. |
| 8,831,779 B2 | 9/2014 | Ortmaier et al. |
| 8,843,236 B2 | 9/2014 | Barajas et al. |
| 8,909,506 B2 | 12/2014 | Ito et al. |
| 8,975,853 B2 | 3/2015 | William Earl et al. |
| 9,060,796 B2 | 6/2015 | Seo |
| 9,084,613 B2 | 7/2015 | Qutub |
| 9,089,256 B2 | 7/2015 | Tognaccini et al. |
| 9,119,655 B2 | 9/2015 | Bowling et al. |
| 9,226,769 B2 | 1/2016 | Wen |
| 9,226,796 B2 | 1/2016 | Bowling et al. |
| 9,274,516 B2 | 3/2016 | Maier et al. |
| 9,364,291 B2 | 6/2016 | Bellettre et al. |
| 9,381,085 B2 | 7/2016 | Axelson, Jr. et al. |
| 9,480,534 B2 | 11/2016 | Bowling et al. |
| 9,566,122 B2 | 2/2017 | Bowling et al. |
| 9,566,125 B2 | 2/2017 | Bowling et al. |
| 9,654,183 B2 | 5/2017 | Ma |
| 9,681,920 B2 | 6/2017 | Bowling et al. |
| 9,687,310 B2 | 6/2017 | Nowlin et al. |
| 9,707,026 B2 | 7/2017 | Malackowski et al. |
| 9,707,043 B2 | 7/2017 | Bozung |
| 9,724,165 B2 | 8/2017 | Arata et al. |
| 9,770,306 B2 | 9/2017 | Hagag et al. |
| 9,795,445 B2 | 10/2017 | Bowling |
| 9,820,818 B2 | 11/2017 | Malackowski et al. |
| 9,937,014 B2 | 4/2018 | Bowling et al. |
| 10,314,661 B2 | 6/2019 | Bowling et al. |
| 10,350,017 B2 | 7/2019 | Bowling et al. |
| 10,420,619 B2 | 9/2019 | Bowling et al. |
| 10,426,560 B2 | 10/2019 | Bowling et al. |
| 10,463,440 B2 | 11/2019 | Bowling et al. |
| 10,905,518 B2 | 2/2021 | Wei et al. |
| 11,045,958 B2 | 6/2021 | Bowling et al. |
| 11,160,609 B2 | 11/2021 | Otto et al. |
| 11,179,210 B2 | 11/2021 | Bowling et al. |
| 11,666,784 B2 | 6/2023 | Wiener et al. |
| 2001/0018594 A1 | 8/2001 | Krag |
| 2002/0035321 A1 | 3/2002 | Bucholz et al. |
| 2003/0009313 A1 | 1/2003 | May et al. |
| 2003/0069591 A1 | 4/2003 | Carson et al. |
| 2003/0181934 A1 | 9/2003 | Johnston et al. |
| 2003/0187594 A1 | 10/2003 | Sherman et al. |
| 2003/0187626 A1 | 10/2003 | Catto |
| 2003/0208296 A1 | 11/2003 | Brisson et al. |
| 2003/0216816 A1 | 11/2003 | Ito et al. |
| 2003/0216836 A1 | 11/2003 | Treat et al. |
| 2004/0010190 A1 | 1/2004 | Shahidi |
| 2004/0024311 A1 | 2/2004 | Quaid |

(56) References Cited

U.S. PATENT DOCUMENTS

| | | |
|---|---|---|
| 2004/0034283 A1 | 2/2004 | Quaid |
| 2004/0034302 A1 | 2/2004 | Abovitz et al. |
| 2004/0077939 A1 | 4/2004 | Graumann |
| 2004/0106916 A1 | 6/2004 | Quaid et al. |
| 2004/0128030 A1 | 7/2004 | Nagata et al. |
| 2004/0148036 A1 | 7/2004 | Sunami |
| 2004/0157188 A1 | 8/2004 | Luth et al. |
| 2004/0243147 A1 | 12/2004 | Lipow |
| 2005/0145257 A1 | 7/2005 | Barrera |
| 2005/0166413 A1* | 8/2005 | Crampton ............... G01B 11/03 33/503 |
| 2005/0171553 A1 | 8/2005 | Schwarz et al. |
| 2005/0187742 A1 | 8/2005 | Collodi |
| 2006/0071625 A1 | 4/2006 | Nakata et al. |
| 2006/0091842 A1 | 5/2006 | Nishiyama |
| 2006/0109266 A1 | 5/2006 | Itkowitz et al. |
| 2006/0111813 A1 | 5/2006 | Nishiyama |
| 2006/0142657 A1 | 6/2006 | Quaid et al. |
| 2006/0155262 A1 | 7/2006 | Kishi et al. |
| 2006/0176242 A1 | 8/2006 | Jaramaz et al. |
| 2006/0257379 A1 | 11/2006 | Giordano et al. |
| 2006/0261770 A1 | 11/2006 | Kishi et al. |
| 2006/0262113 A1 | 11/2006 | Leprevost |
| 2006/0264742 A1 | 11/2006 | Neubauer et al. |
| 2006/0284587 A1 | 12/2006 | Teshima et al. |
| 2007/0013336 A1 | 1/2007 | Nowlin et al. |
| 2007/0073442 A1 | 3/2007 | Aghili |
| 2007/0085496 A1 | 4/2007 | Philipp et al. |
| 2007/0129846 A1 | 6/2007 | Birkenbach et al. |
| 2007/0142823 A1 | 6/2007 | Prisco et al. |
| 2007/0151389 A1 | 7/2007 | Prisco et al. |
| 2007/0151390 A1 | 7/2007 | Blumenkranz et al. |
| 2007/0156157 A1 | 7/2007 | Nahum et al. |
| 2007/0156285 A1 | 7/2007 | Sillman et al. |
| 2007/0249911 A1 | 10/2007 | Simon |
| 2007/0260394 A1 | 11/2007 | Dean |
| 2007/0265527 A1 | 11/2007 | Wohlgemuth |
| 2007/0270685 A1 | 11/2007 | Kang et al. |
| 2007/0287911 A1 | 12/2007 | Haid et al. |
| 2008/0001565 A1 | 1/2008 | Nakashima et al. |
| 2008/0009697 A1 | 1/2008 | Haider et al. |
| 2008/0010706 A1 | 1/2008 | Moses et al. |
| 2008/0046122 A1 | 2/2008 | Manzo et al. |
| 2008/0058776 A1 | 3/2008 | Jo et al. |
| 2008/0065111 A1 | 3/2008 | Blumenkranz et al. |
| 2008/0077158 A1 | 3/2008 | Haider et al. |
| 2008/0086029 A1 | 4/2008 | Uchiyama et al. |
| 2008/0114267 A1 | 5/2008 | Lloyd et al. |
| 2008/0161829 A1 | 7/2008 | Kang |
| 2008/0210477 A1 | 9/2008 | Takenaka et al. |
| 2008/0300478 A1 | 12/2008 | Zuhars et al. |
| 2009/0003975 A1 | 1/2009 | Kuduvalli et al. |
| 2009/0012532 A1 | 1/2009 | Quaid et al. |
| 2009/0024142 A1 | 1/2009 | Ruiz Morales |
| 2009/0036913 A1 | 2/2009 | Wiener et al. |
| 2009/0037033 A1 | 2/2009 | Phillips et al. |
| 2009/0043556 A1 | 2/2009 | Axelson et al. |
| 2009/0068620 A1 | 3/2009 | Knobel et al. |
| 2009/0069942 A1 | 3/2009 | Takahashi |
| 2009/0082784 A1 | 3/2009 | Meissner et al. |
| 2009/0088774 A1 | 4/2009 | Swarup et al. |
| 2009/0096148 A1 | 4/2009 | Usui |
| 2009/0099680 A1 | 4/2009 | Usui |
| 2009/0102767 A1 | 4/2009 | Shiomi |
| 2009/0105878 A1 | 4/2009 | Nagasaka |
| 2009/0112316 A1 | 4/2009 | Umemoto et al. |
| 2009/0149867 A1 | 6/2009 | Glozman et al. |
| 2009/0160855 A1 | 6/2009 | Wu |
| 2009/0192524 A1 | 7/2009 | Itkowitz et al. |
| 2009/0209884 A1 | 8/2009 | Van Vorhis et al. |
| 2009/0245992 A1 | 10/2009 | Kato |
| 2009/0248038 A1 | 10/2009 | Blumenkranz et al. |
| 2009/0259412 A1 | 10/2009 | Brogardh |
| 2009/0308683 A1 | 12/2009 | Suzuki |
| 2010/0030023 A1 | 2/2010 | Yoshie |
| 2010/0076474 A1 | 3/2010 | Yates et al. |
| 2010/0094312 A1 | 4/2010 | Ruiz Morales et al. |
| 2010/0094608 A1 | 4/2010 | Oh et al. |
| 2010/0137882 A1 | 6/2010 | Quaid, III |
| 2010/0154578 A1 | 6/2010 | Duval |
| 2010/0168723 A1 | 7/2010 | Suarez et al. |
| 2010/0168950 A1 | 7/2010 | Nagano |
| 2010/0174410 A1 | 7/2010 | Greer et al. |
| 2010/0286826 A1 | 11/2010 | Tsusaka et al. |
| 2010/0292707 A1 | 11/2010 | Ortmaier et al. |
| 2010/0312392 A1 | 12/2010 | Zimmermann |
| 2010/0317965 A1 | 12/2010 | Itkowitz et al. |
| 2010/0331855 A1 | 12/2010 | Zhao et al. |
| 2010/0331859 A1 | 12/2010 | Omori |
| 2011/0015649 A1 | 1/2011 | Anvari et al. |
| 2011/0040404 A1 | 2/2011 | Diolaiti et al. |
| 2011/0077590 A1 | 3/2011 | Plicchi et al. |
| 2011/0077923 A1 | 3/2011 | Bond et al. |
| 2011/0082468 A1 | 4/2011 | Hagag et al. |
| 2011/0082587 A1 | 4/2011 | Ziaei et al. |
| 2011/0106102 A1 | 5/2011 | Balicki et al. |
| 2011/0118751 A1 | 5/2011 | Balaji et al. |
| 2011/0130761 A1 | 6/2011 | Plaskos et al. |
| 2011/0142316 A1 | 6/2011 | Wang et al. |
| 2011/0152676 A1 | 6/2011 | Groszmann et al. |
| 2011/0160745 A1 | 6/2011 | Fielding et al. |
| 2011/0178639 A1 | 7/2011 | Kwon et al. |
| 2011/0190932 A1 | 8/2011 | Tsusaka et al. |
| 2011/0208256 A1 | 8/2011 | Zuhars |
| 2011/0217923 A1 | 9/2011 | Ma |
| 2011/0257653 A1 | 10/2011 | Hughes et al. |
| 2011/0263971 A1 | 10/2011 | Nikou et al. |
| 2011/0264107 A1 | 10/2011 | Nikou et al. |
| 2011/0264112 A1 | 10/2011 | Nowlin et al. |
| 2011/0277580 A1 | 11/2011 | Cooper et al. |
| 2011/0295247 A1 | 12/2011 | Schlesinger et al. |
| 2011/0295268 A1 | 12/2011 | Roelle et al. |
| 2011/0295658 A1 | 12/2011 | Bastos et al. |
| 2011/0301500 A1 | 12/2011 | Maguire et al. |
| 2011/0306873 A1 | 12/2011 | Shenal et al. |
| 2011/0306985 A1 | 12/2011 | Inoue et al. |
| 2012/0022546 A1 | 1/2012 | Hubschman et al. |
| 2012/0029529 A1 | 2/2012 | Jun et al. |
| 2012/0053597 A1 | 3/2012 | Anvari et al. |
| 2012/0059378 A1 | 3/2012 | Farrell |
| 2012/0071752 A1 | 3/2012 | Sewell et al. |
| 2012/0071893 A1 | 3/2012 | Smith et al. |
| 2012/0083801 A1 | 4/2012 | Nixon |
| 2012/0083922 A1 | 4/2012 | Kwak et al. |
| 2012/0120091 A1 | 5/2012 | Koudijs et al. |
| 2012/0123441 A1 | 5/2012 | Au et al. |
| 2012/0143084 A1 | 6/2012 | Shoham |
| 2012/0173021 A1 | 7/2012 | Tsusaka |
| 2012/0176306 A1 | 7/2012 | Lightcap et al. |
| 2012/0197182 A1 | 8/2012 | Millman et al. |
| 2012/0245595 A1 | 9/2012 | Kesavadas et al. |
| 2012/0283747 A1 | 11/2012 | Popovic |
| 2012/0323244 A1 | 12/2012 | Cheal et al. |
| 2012/0330429 A1 | 12/2012 | Axelson, Jr. et al. |
| 2013/0006267 A1 | 1/2013 | Odermatt et al. |
| 2013/0019883 A1 | 1/2013 | Worm et al. |
| 2013/0035690 A1 | 2/2013 | Mittelstadt et al. |
| 2013/0035696 A1 | 2/2013 | Qutub |
| 2013/0060278 A1 | 3/2013 | Bozung et al. |
| 2013/0096574 A1 | 4/2013 | Kang et al. |
| 2013/0116706 A1 | 5/2013 | Lee et al. |
| 2013/0127759 A1 | 5/2013 | Bae et al. |
| 2013/0169423 A1 | 7/2013 | Iorgulescu et al. |
| 2013/0172902 A1 | 7/2013 | Lightcap et al. |
| 2013/0172904 A1 | 7/2013 | Ikits |
| 2013/0172905 A1 | 7/2013 | Iorgulescu et al. |
| 2013/0176258 A1 | 7/2013 | Dahl et al. |
| 2013/0178868 A1 | 7/2013 | Roh |
| 2013/0204124 A1 | 8/2013 | Duindam et al. |
| 2013/0253702 A1 | 9/2013 | Lecours et al. |
| 2013/0304258 A1 | 11/2013 | Taylor et al. |
| 2013/0325029 A1 | 12/2013 | Hourtash et al. |
| 2013/0345718 A1 | 12/2013 | Crawford et al. |
| 2014/0039517 A1 | 2/2014 | Bowling et al. |

(56) References Cited

U.S. PATENT DOCUMENTS

| | | |
|---|---|---|
| 2014/0039681 A1 | 2/2014 | Bowling et al. |
| 2014/0052153 A1 | 2/2014 | Griffiths et al. |
| 2014/0052154 A1 | 2/2014 | Griffiths et al. |
| 2014/0052155 A1 | 2/2014 | Hourtash et al. |
| 2014/0081461 A1 | 3/2014 | Williamson et al. |
| 2014/0121837 A1 | 5/2014 | Hashiguchi et al. |
| 2014/0135795 A1 | 5/2014 | Yanagihara |
| 2014/0148818 A1 | 5/2014 | Komuro et al. |
| 2014/0195205 A1 | 7/2014 | Benker et al. |
| 2014/0222023 A1 | 8/2014 | Kim et al. |
| 2014/0222207 A1 | 8/2014 | Bowling et al. |
| 2014/0244221 A1 | 8/2014 | Tonge et al. |
| 2014/0244222 A1 | 8/2014 | Tonge et al. |
| 2014/0275955 A1 | 9/2014 | Crawford et al. |
| 2014/0276952 A1 | 9/2014 | Hourtash et al. |
| 2014/0276953 A1 | 9/2014 | Swarup et al. |
| 2014/0277742 A1 | 9/2014 | Wells et al. |
| 2014/0316431 A1 | 10/2014 | Hourtash et al. |
| 2014/0358505 A1 | 12/2014 | Hashash et al. |
| 2014/0378999 A1 | 12/2014 | Crawford et al. |
| 2015/0010202 A1 | 1/2015 | Tuzel et al. |
| 2015/0012715 A1 | 1/2015 | Aronovich et al. |
| 2015/0032126 A1 | 1/2015 | Nowlin et al. |
| 2015/0032164 A1 | 1/2015 | Crawford et al. |
| 2015/0051733 A1 | 2/2015 | Nowlin et al. |
| 2015/0081098 A1 | 3/2015 | Kogan |
| 2015/0223941 A1 | 8/2015 | Lang |
| 2015/0289941 A1 | 10/2015 | Bowling et al. |
| 2015/0374446 A1 | 12/2015 | Malackowski et al. |
| 2016/0089211 A1 | 3/2016 | Bowling |
| 2017/0000577 A1 | 1/2017 | Bowling et al. |
| 2017/0128147 A1 | 5/2017 | Bowling et al. |
| 2017/0172680 A1 | 6/2017 | Bowling et al. |
| 2017/0245955 A1 | 8/2017 | Bowling et al. |
| 2018/0071026 A1 | 3/2018 | Malackowski et al. |
| 2019/0192249 A1 | 6/2019 | Bowling et al. |
| 2019/0269476 A1 | 9/2019 | Bowling et al. |
| 2020/0022768 A1 | 1/2020 | Bowling et al. |
| 2020/0030046 A1 | 1/2020 | Bowling et al. |
| 2021/0308872 A1 | 10/2021 | Bowling et al. |
| 2022/0047346 A1 | 2/2022 | Bowling et al. |

FOREIGN PATENT DOCUMENTS

| | | | |
|---|---|---|---|
| CN | 101243979 A | | 8/2008 |
| CN | 101484086 A | | 7/2009 |
| CN | 101772328 A | | 7/2010 |
| CN | 102208835 A | | 10/2011 |
| CN | 102445920 A | | 5/2012 |
| CN | 102470016 A | | 5/2012 |
| CN | 101227870 B | | 8/2012 |
| CN | 101770235 B | | 9/2012 |
| CN | 102743180 A | | 10/2012 |
| CN | 102612350 B | | 11/2015 |
| CN | 105939687 B | | 8/2019 |
| DE | 102006007858 A1 | | 8/2007 |
| EP | 1234641 A1 | | 8/2002 |
| EP | 1680007 A2 | | 7/2006 |
| EP | 1871267 A1 | | 1/2008 |
| EP | 1754448 B1 | | 3/2008 |
| EP | 1973487 A2 | | 10/2008 |
| EP | 2666428 A1 | | 11/2013 |
| JP | 2002187078 A | | 7/2002 |
| JP | 2002283276 A | | 10/2002 |
| JP | 2012130543 A | | 7/2012 |
| KR | 100629469 B1 | | 9/2006 |
| KR | 20100048052 A | | 5/2010 |
| SU | 1115870 A1 | | 9/1984 |
| WO | 9611624 A2 | | 4/1996 |
| WO | 9937220 A1 | | 7/1999 |
| WO | 0021450 A1 | | 4/2000 |
| WO | 0035366 A1 | | 6/2000 |
| WO | 0059397 A1 | | 10/2000 |
| WO | 0060571 A1 | | 10/2000 |
| WO | 200200131 A1 | | 1/2002 |
| WO | 0224051 A2 | | 3/2002 |
| WO | 02060653 A2 | | 8/2002 |
| WO | 02065931 A1 | | 8/2002 |
| WO | 02074500 A2 | | 9/2002 |
| WO | 02076302 A2 | | 10/2002 |
| WO | 2003086714 A2 | | 10/2003 |
| WO | 03094108 A2 | | 11/2003 |
| WO | 2004014244 A2 | | 2/2004 |
| WO | 2004019785 A2 | | 3/2004 |
| WO | 2004001569 A3 | | 6/2004 |
| WO | 2004069036 A2 | | 8/2004 |
| WO | 2005009215 A2 | | 2/2005 |
| WO | 2005122916 A1 | | 12/2005 |
| WO | 2006058633 A1 | | 6/2006 |
| WO | 2006063156 A1 | | 6/2006 |
| WO | 2006091494 A1 | | 8/2006 |
| WO | 2007017642 A1 | | 2/2007 |
| WO | 2007111749 A2 | | 10/2007 |
| WO | 2007117297 A2 | | 10/2007 |
| WO | 2007133251 A2 | | 11/2007 |
| WO | 2007136739 A2 | | 11/2007 |
| WO | 2007136768 A2 | | 11/2007 |
| WO | 2007136769 A2 | | 11/2007 |
| WO | 2007136771 A2 | | 11/2007 |
| WO | 2009059330 A2 | | 5/2009 |
| WO | 2010088959 A1 | | 8/2010 |
| WO | 2010102384 A1 | | 9/2010 |
| WO | 2011021192 A1 | | 2/2011 |
| WO | 2011088541 A1 | | 7/2011 |
| WO | 2011106861 A1 | | 9/2011 |
| WO | 2011109041 A1 | | 9/2011 |
| WO | 2011113483 A1 | | 9/2011 |
| WO | 2011133873 A1 | | 10/2011 |
| WO | 2011133927 A2 | | 10/2011 |
| WO | 2011134083 A1 | | 11/2011 |
| WO | 2011128766 A3 | | 12/2011 |
| WO | 2012018816 A2 | | 2/2012 |
| WO | 2012018823 A2 | | 2/2012 |
| WO | 2013020026 A1 | | 2/2013 |
| WO | 2013117909 A1 | | 8/2013 |
| WO | 2013181507 A1 | | 12/2013 |
| WO | 2013192598 A1 | | 12/2013 |
| WO | 2014022786 A2 | | 2/2014 |
| WO | 2014121262 A2 | | 8/2014 |
| WO | 2014151550 A2 | | 9/2014 |
| WO | 2015061638 A1 | | 4/2015 |
| WO | 2016115306 A1 | | 7/2016 |

OTHER PUBLICATIONS

R. Khadem; C.C. Yeh; M.Sadeghi-Tehrani; M.R. Bax; J.A. Johnson; J.L. Welch; E.P. Wilkinson; R. Shahidi, Comparative Tracking Error Analysis of Five Different Optical Tracking Systems, Computer Aided Surgery, 2000, pp. 38-107, vol. 5, Stanford,CA,USA; 10 pages.

R. Khadem; C.C. Yeh; M.Sadeghi-Tehrani; M.R. Bax; J.A. Johnson; J.L. Welch; E.P. Wilkinson; R. Shahidi, Comparative Tracking Error Analysis of Five Different Optical Tracking Systems, Computer Aided Surgery, 2000, pp. 98-107, vol. 5, Stanford, CA, USA; 10 pages.

R. Rohling; P. Munger; J.M. Hollerbach; T. Peter, Comparison of Relative Accuracy Between a Mechanical and an Optical Position Tracker for Image-Guided Neurosurgery, Journal of Image Guided Surgery, 1995, pp. 30-34, vol. 1, No. 1; 4 pages.

R. Taylor et al., "A Steady-Hand Robotic System for Microsurgical Auegementation", MICCAI99: the Second International Conference on Medical ImageComputing and Computer-Assisted Intervention, Cambridge, England, Sep. 19-22, 1999. MICCAI99 Submission#1361999, pp. 1031-1041, Springer-Verlag Berlin Heidelberg; 11 pages.

R. Taylor, P. Jensen, L. Whitcomb, A. Barnes, R. Kumar, D. Stoianovici, P, Gupta, Z. Wang, E.Dejuan and L. Kavoussi, A Steady-Hand Robotic System for Microsurgical Augementation, MICCAI99: the Second International Conference on Medical ImageComputing and Computer-Assisted Intervention, Cambridge,

(56) References Cited

OTHER PUBLICATIONS

England, Sep. 19-22, 1999. MICCAI99 Submission #1361999, pp. 1031-1041, Springer-Verlag Berlin Heidelberg; 11 pages.
R.A. Abovitz, Human-Interactive Medical Robotics, Abstract for CAOS 2000, 2000, pp. 71-72; 2 pages.
R.E. Ellis et al., "A surgical planning and guidance system for high tibial osteotomy", Computer Aided Surgery, Apr. 16, 1999, 264-274, vol. 4, Wiley-Liss, Inc.; 11 pages.
R.H. Taylor et al., "An Image-directed Robotic System for Hip Replacement Surgery", Oct. 1990, pp. 111-116, vol. 8, No. 5; 7 pages.
R.H. Taylor; B.D. Mittelstadt; H.A. Paul; W. Hanson; P. Kazanzides; J.F. Zuhars; B. Williamson; B.L. Musits; E. Glassman; W.L. Bargar, An Image-Directed Robotic System for Precise Orthopaedic Surgery, Robotics and Automation, IEEE Transactions on,Jun. 1994, pp. 261-275, vol. 10, Issue 3, IEEE; 15 pages.
R.H. Taylor; C.B. Cutting; Y.-Y. Kim; A.D. Kalvin; D. Larose; B.Haddad; D. Khoramabadi; M. Noz; R. Olyha; N. Bruun; D. Grimm, A Model-Based Optimal Planning and Execution System with Active Sensing and Passive Manipulation for Augmentation of HumanPrecision in Computer-Integrated Surgery, Section 4 Robotic Systems and Task-Level Programming, Experimental Robotics II, The 2nd International Symposium, Lecture Notes in Control and Information Sciences, pp. 177-195, vol. 190, Springer BerlinHeidelberg, Toulouse, FR, Jun. 25-27, 1991; 19 pages.
R.H. Taylor; H. A. Paul; B.D. Mittelstadt; W. Hanson; P. Kazanzides; J. Zuhars; E. Glassman; B.L. Musits; B. Williamson; W.L. Bargar, An Image-directed Robotic System for Hip Replacement Surgery, Oct. 1990, pp. 111-116, vol. 8, No. 5; 7 pages.
R.M. Satava, History of Robotic Surgery the early chronicles a personal historical perspective, Surgical Laparoscopic Endoscopic Percutaneous Technology, Feb., 2002, vol. 12 pp. 6-16, WebSurg; 6 pages.
R.M. Satava, Surgical robotics the early chronicles a personal historical perspective, Surgical Laparoscopic Endoscopic Percutaneous Technology, Feb. 2002, vol. 12 pp. 6-16, WebSurg; 6 pages.
R.O. Buckingham, Safe Active Robotic Devices for Surgery, Systems, Man and Cybernetics, 1993. 'Systems Engineering in the Service of Humans', Conference Proceedings., International Conference on, Oct. 17-20, 1993, pp. 355-358, vol. 5, IEEE, LeTougeut; 4 pages.
R.V. O'Toole, III; B. Jaramaz; A.M. Digioia, III; C.D. Visnic; R.N. Reid, Biomechanics for Preoperative Planning and Surgical Simulations in Orthopaedics, Computers in Biology and Medicine, Mar. 1995, pp. 183-191, vol. 25, Issue 2; 8 pages.
RE Ellis; CY Tsp; JF Rudan; MM Harrison, A surgical planning and guidance system for high tibial osteotomy, Computer Aided Surgery, Apr. 16, 1999, 264-274, vol. 4, Wiley-Liss, Inc.; 11 pages.
S. Hapeld; C. Burghart; I. Bertovic; J. Raczkowsky; H. Worn; U. Rembold; J. Muhling, Intraoperative Navigation Techniques Accuracy Tests and Clinical Report, In: Computer Assisted Radiology and Surgery (CARS'98), Tokyo, Jun. 1998, pp. 670-675,Elseview Science B.V.; 6 pages.
S. J. Harris; W. J. Lin; K. L. Fan; R. D. Hibberd; J. Cobb; R. Middleton; B. L. Davies, Experiences with Robotic Systems for Knee Surgery, CVRMed-MRCAS'97, Lecture Notes in Computer Science, 1997, pp. 757-766, vol. 1205, Springer Berlin Heidelberg, London, UK; 10 pages.
S. Lavallee, P. Sautot, J. Troccaz P. Cinquin and P. Merloz, Computer Assisted Spine Surgery a technique for accurate transpedicular screw fixation using CT data and a 3-D optical localizer, Journal of Image Guided Surgery, 1995, pp. 65-73; 9 pages.
S. Lembcke, Realtime Rigid Body Simulation Using Impulses, 2006, Morris, MN, US; 5 pages.
S.C. Ho; R.D. Hibberd; B.L. Davies, Robot Assisted Knee Surgery Establishing a force control strategy incorporating active motion constraint, IEEE Engineering in Medicine and Biology, May/Jun. 1995, pp. 292-300, vol. 14, No. 3; 9 pages.

S.C. Ho; R.D. Hibberd; J. Cobb; B.L. Davies, Force Control for Robotic Surgery, ICAR '95, 1995, pp. 21-32, London, UK; 12 pages.
S.J. Davies et al., "Active compliance in robotic surgery—the use of force control as a dynamic constraint", Proceedings of the Institution of Mechanical Engineers, Part H: Journal of Engineeringin Medicine, Apr. 1, 1997, pp. 285-292, vol. 211,Sage.
S.J. Harris; M. Jakopec; J. Cobb; B.L. Davies, Intra-operative Application of a Robotic Knee Surgery System, Medical Image Computing and Computer-Assisted Intervention—MICCAI'99, 1999, pp. 1116-1124, vol. 1679, Springer-Verlag Berlin Heidelberg; 9pages.
S.L. Delp; S. D. Stulberg; B. Davies; F. Picard; F. Leitner, Computer Assisted Knee Replacement, Clinical Orthopaedics, Sep. 1998, pp. 49-56, vol. 354, Lippincott-Raven Publishers; 8 pages.
Sugita, Haohiko et al., "Bone Cutting Robot with Soft Tissue Collision Avoidance Capability by a Redundant Axis for Minimally Invasive Orthopedic Surgery", IEEE/ICME International Conference on Complex Medical Engineering, 2007, 4 pages.
T. J. Levison, J. E. Moody, B. Jaramaz, C. Nikou, A. M. Digioia, Surgical Navigation for THR A Report on Clinical Trial Utilizing HipNav, MICCAI 2000, LNCS 1935, pp. 1185-1187, 2000, Springer-Verlag Berlin Heidelberg; 3 pages.
T. Schmidt; W. Hentschel, EasyGuide Neuro, A New System for Image-Guided Planning, Simulation and Navigation in Neurosurgery, Biomedical Engineering, vol. 40, Supplement 1, 1995, pp. 233-234, Hamburg, DE; 2 pages.
T. Wang et al., "A robotized surgeon assistant", Intelligent Robots and Systems '94, Advanced Robotic Systems and the Real World, IROS '94. Proceedings of the IEEE/RSJ/GI International Conference on, Sep. 12-16, 1994, pp. 362-869, vol. 2, IEEE,Munich, Germany; 8 pages.
T. Wang; M. Fadda; M. Marcacci; S. Martelli; P. Dario; A. Visani, A robotized surgeon assistant, Intelligent Robots and Systems '94. 'Advanced Robotic Systems and the Real World', IROS '94. Proceedings of the IEEE/RSJ/GI International Conference on, Sep. 12-16, 1994, pp. 862-869, vol. 2, IEEE, Munich, Germany; 8 pages.
T.C. Kienzle, III et al., "An Integrated CAD-Robotics System for Total Knee Replacement Surgery", Systems, Man and Cybernetics, 1992., IEEE International Conference on, Oct. 18-21, 1992, pp. 1609-1614, vol. 2,IEEE, Chicago, IL, USA; 6 pages.
T.C. Kienzle, III, S.D. Stulberg, M. Peshkin, A. Quaid, J. Lea, A. Goswami, C.H. Wu, Total Knee Replacement Computer-assisted surgical system uses a calibrated robot, Engineering in Medicine and Biology, May 1995, pp. 301-306, vol. 14, Issue 3, IEEE; 35 pages.
T.C. Kienzle, III; S.D. Stulberg; M. Peshkin; A. Quaid; C.-H. Wu, An Integrated CAD-Robotics System for Total Knee Replacement Surgery, Systems, Man and Cybernetics, 1992., IEEE International Conference on, Oct. 18-21, 1992, pp. 1609-1614, vol. 2,IEEE, Chicago, IL, USA; 6 pages.
U. Rembold and C. R. Burghart, Surgical Robotics: An Introduction, Journal of Intelligent and Robotic Systems vol. 30, No. 1, pp. 1-28, 2001, Kluwer Academic Publishers; 28 pages.
U. Seibold, B. Kubler, and G. Hirzinger, Prototype of Instrument for Minimally Invasive Surgery with 6-Axis Force Sensing Capability, Robotics and Automation, 2005. ICRA 2005. Proceedings of the 2005 IEEE International Conference on, Apr. 18-22, 2005, pp. 498-503, IEEE, Barcelona, Spain; 6 pages.
U. Spetzger; G. Laborde; J.M. Gilsbach, Frameless Neuronavigation in Modern Neurosurgery, Minimally Invasive Neurosurgery, Dec. 1995, pp. 163-166, vol. 38; 4 pages.
U.S. Appl. No. 16/262,375, filed Jan. 30, 2019.
U.S. Appl. No. 16/409,024, filed May 10, 2019.
U.S. Appl. No. 16/555,838, filed Aug. 29, 2019.
US 5,428,487, 8/2002, Burdorff et al. (withdrawn)
W. Korb; D. Engel; R. Boesecke; G. Eggers; B. Kotrikova; R. Marmulla; J. Raczkowsky; H. Worn; J. Muhling; S. Hassfeld, Development and First Patient Trial of a Surgical Robot for Complex Trajectory Milling, Computer Aided Surgery, 2003, vol. 8, pp. 247-256, CAS Journal LLC; 10 pages.
W. Siebert; S. Mai; R. Kober; P.F. Heeckt, Technique and first clinical results of robot-assisted total knee replacement, The Knee, Sep. 2002, pp. 173-180, vol. 9, Issue 3, Elsevier B.V.; 8 pages.

(56) References Cited

OTHER PUBLICATIONS

W.L. Bargar; A. Bauer; M. Borner, Primary and Revision Total Hip Replacement Using the Robodoc System, Clinical Orthopaedics and Related Research, Sep. 1998, pp. 82-91, No. 354; 10 pages.
Wang, Qiong et al., "Impulse-Based Rendering Methods for Haptic Simuation of Bone-Burring", IEEE Transactions on Haptics, vol. 5, No. 4, October-Dec. 2012, pp. 344-355.
Written Opinion for Application No. PCT/US2013/053451 dated Mar. 19, 2014; 12 pages.
Y. Koseki; K. Chinzei; N. Koyachi; T. Arai, Robotic assist for MR-guided surgery using leverage and parallelepiped mechanism, Medical Image Computing and Computer-Assisted Intervention—MICCAI 2000, Lecture Notes in Computer Science, 2000, pp. 940-948, vol. 1935, Springer Berlin Heidelberg; 9 pages.
Y. Louhisalmi; T. Leinonen, Development of a Robotic Surgical Assistant, 1994, pp. 1043-1044, IEEE, Linnanmaa, Oulu, FI; 2 pages.
English language abstract for CN 1168310 A extracted from espacenet.com database on Apr. 17, 2024, 1 page.
English language abstract and machine-assisted English translation for SU 1115870 A1 extracted from espacenet.com database on Apr. 17, 2024, 7 pages.
English language abstract and machine-assisted English translation for CN 1771114 extracted from espacenet.com database on Aug. 19, 2020, 21 pages.
English language abstract and machine-assisted English translation for CN101227870 B extracted from www.espacenet.com on Aug. 29, 2017; 53 pages.
English language abstract and machine-assisted English translation for CN101484086 A extracted from www.espacenet.com on Aug. 29, 2017; 34 pages.
English language abstract and machine-assisted English translation for CN101770235 B extracted from www.espacenet.com on Aug. 29, 2017; 18 pages.
English language abstract and machine-assisted English translation for DE 10 2006 007 858 extracted from espacenet.com database on Aug. 19, 2020, 5 pages.
English language abstract and machine-assisted English translation for EP 1 754 448 extracted from espacenet.com database on Jan. 30, 2019, 15 pages.
English language abstract and machine-assisted English translation for JP 2002-283276 extracted from Japanese Patent Office database on Nov. 19, 2020, 67 pages.
English language abstract and machine-assisted English translation for JP 2012-130543 extracted from espacenet.com database on Aug. 19, 2020, 13 pages.
English language abstract and machine-assisted English translation for KR 20100048052 extracted from espacenet.com database on Aug. 19, 2020, 7 pages.
English language abstract and machine-assisted English translation for WO 00/21450 A1 extracted from www.Espacenet.org on Aug. 11, 2014; 37 pages.
English language abstract and machine-assisted English translation for WO 00/21450 AI extracted from www.Espacenet.org on Aug. 11, 2014; 37 pages.
English language abstract and machine-assisted English translation for WO 2000/21450 A1 extracted from www.Espacenet.org on Aug. 11, 2014; 37 pages.
English language abstract and machine-assisted English translation for WO 2000/21450 AI extracted from www.Espacenet.org on Aug. 11, 2014; 37 pages.
English language abstract and machine-assisted English translation for WO 2000/59397 A1 extracted from www.Espacenet.org on Aug. 11, 2014; 33 pages.
English language abstract and machine-assisted English translation for WO 2002/065931 A1 extracted from www.Espacenet.org on Aug. 11, 2014; 30 pages.
English language abstract and machine-assisted English translation for WO 2002/074500 A2 extracted from www.Espacenet.org on Aug. 11, 2014; 25 pages.
English language abstract and machine-assisted English translation for WO 2005/009215 A2 extracted from www.Espacenet.org on May 8, 2014; 68 pages.
English language abstract and machine-assisted English translation for WO 2006/091494 A1 extracted from www.Espacenet.org on May 8, 2014; 178 pages.
English language abstract and machine-assisted English translation for WO 2007/117297 A2 extracted from www.Espacenet.org on May 8, 2014; 66 pages.
English language abstract for CN 101227870 extracted from espacenet.com database on Jun. 17, 2019, 2 pages.
English language abstract for CN 101243979 extracted from espacenet.com database on Aug. 19, 2020, 1 page.
English language abstract for CN 101484086 extracted from espacenet.com database on Jun. 17, 2019, 2 pages.
English language abstract for CN 101770235 extracted from espacenet.com database on Jun. 17, 2019, 2 pages.
English language abstract for CN 102208835 extracted from espacenet.com database on Sep. 21, 2017, 2 pages.
English language abstract for CN 102445920 extracted from espacenet.com database on Aug. 19, 2020, 1 page.
English language abstract for CN 102470016 extracted from espacenet.com database on Sep. 21, 2017, 2 pages.
English language abstract for CN 102612350 extracted from espacenet.com database on Jun. 17, 2019, 2 pages.
English language abstract for CN 105939687 B extracted from espacenet.com database on Jun. 13, 2022, 2 pages.
English language abstract for EP 1 680 007 A2 not found; however, see English language equivalent U.S. Pat. No. 7,831,292 B2 and original document extracted www.Espacenet.org on May 8, 2014; 3 pages.
English language abstract for EP 1 871 267 A1 not found; however, see English language equivalent International Publication No. WO 2006/091494 A1 and original document extracted www.Espacenet.org on May 8, 2014; 3 pages.
English language abstract for EP 1 973 487 A2 not found; however see English language equivalent WO 2007/117297 A2 and original document extracted www.Espacenet.org on May 8, 2014; 3 pages.
English language abstract for JP 2002-187078 extracted from espacenet.com database on Jan. 14, 2021, 2 pages.
English language abstract for KR 100629469 B1 extracted from espacenet.com database on Jun. 23, 2021, 2 pages.
F. A. Matsen; J.L. Garbini; J.A. Sidles; B. Pratt; D. Baumgarten; R. Kaiura, Robotic Assistance in Orthopaedic Surgery a Proof of Principle Using Distal Femoral Arthroplasty, Clinical Orthopaedic Related Research, Nov. 1993, pp. 178-186, vol. 296; 9pages.
F. Leitner, F. Picard, R. Minfelde, H.-J. Schulz, P. Cinquin and D. Saragaglia, Computer-Assisted Knee Surgical Total Replacement, CVRMed-MRCAS'97, Lecture Notes in Computer Science vol. 1205, 1997, pp. 629-638, Springer Berlin Heidelberg, Jan. 1, 1997; 10 pages.
G. Brandt, A. Zimolong, L. Carrat, P. Merloz, H.-W. Staudte, S. Lavallee, K. Radermacher, G. Rau, "CRIGOS: A Compact Robot for Image-Guided Orthopedic Surgery," Information Technology in Biomedicine, IEEE Transactions on, vol. 3, No. 4, pp. 252-260, Dec. 1999; 9 pages.
G. Brisson, T. Kanade, A. Digioia and B. Jaramaz, Precision Freehand Sculpting of Bone, Medical Image Computing and Computer-Assisted Intervention—MICCAI 2004, Lecture Notes in Computer Science, vol. 3217, Jan. 1, 2004, pp. 105-112, Springer-VerlagBerlin Heidelberg 2004; 8 pages.
G. Van Ham et al., "Accuracy study on the registration of the tibia by means of an intramedullary rod in robot-assisted total knee arthroplasty", PosterSession—Knee Arthroplasty-Valencia Foyer, 46th Annual Meeting, Orthopaedic Research Society, Mar. 12-15, 2000, Orlando, Florida, p. 450.
G. Van Ham; J. Bellemans; L. Labey; J. Vander Sloten; R. Van Audekercke; G. Van Der Perre; J. De Schutter, Accuracy study on the registration of the tibia by means of an intramedullary rod in robot-assisted total knee arthroplasty, PosterSession—Knee Arthroplasty—Valencia Foyer, 46th Annual Meeting, Orthopaedic Research Society, Mar. 12-15, 2000, Orlando, Florida, p. 450; 1 pages.

(56) References Cited

OTHER PUBLICATIONS

G. Van Ham; K. Denis; J. Vander Sloten; R. Van Audekercke; G. Van Der Perre; J. De Schutter; E. Aertbelien; S. Demey; J. Bellemans, Machining and Accuracy Studies for a Tibial Knee Implant Using a Force-Controlled Robot, Computer Aided Surgery, Feb. 1998, pp. 123-133, vol. 3, Wiley-Liss, Inc., Heverlee BE; 11 pages.

H. A. Paul, W. L. Bargar, B. Mittlestadt, P. Kazanzides, B. Musits, J. Zuhars, P. W. Cain, B. Williamson and F. G. Smith, Robotic Execution of a Surgical Plan, Systems, Man and Cybernetics, 1992., IEEE International Conference on, Oct. 18-21, 1992,pp. 1621-1623, IEEE, Sacramento, California, US; 3 pages.

H. Haider, O. A. Barrera and K. L. Garvin, Minimally Invasive Total Knee Arthroplasty Surgery Through Navigated Freehand Bone Cutting, Journal of Arthroplasty, Jun. 2007, vol. 22, No. 4, pp. 535-542, Elsevier B.V.; 8 pages.

H.A. Paul et al., "A Surgical Robot for Total Hip Replacement Surgery", International Conference on Robotics and Automation, 1992, pp. 606-611, IEEE, Nice, FR; 6 pages.

H.A. Paul; B. Mittlestadt; W.L. Bargar; B. Musits; R.H. Taylor; P. Kazanzides; J. Zuhars; B. Williamson; W. Hanson, A Surgical Robot for Total Hip Replacement Surgery, International Conference on Robotics and Automation, 1992, pp. 606-611, IEEE, Nice, FR; 6 pages.

Delannoy et al., "Modeling Moment of Inertia for Virtual Interactive Environments", IEEE Symposium on Virtual Environments, Human-Computer Interfaces and Measurement Systems, 2004, pp. 142-146.

Peterlik et al., "Constraint-Based Haptic Rendering of Multirate Compliant Mechanisms", IEEE Transactions on Haptics, vol. 4, No. 3, 2011, pp. 175-187.

Peters et al., "A Unifying Framework for Robot Control With Redundant DOFs", Autonomous Robots, vol. 24, Issue 1, 2008, pp. 1-12.

A. Ansara; D. Rodrigues; J.P. Desai; K. Daniilidis; V. Kumar; M. F.M. Campos, Visual and haptic collaborative tele-presence, Computers & Graphics, 2001, pp. 789-798, vol. 25, Elsevier, Inc.; 10 pages.

A. Kato et al., "A frameless, armless navigational system for computer-assisted neurosurgery", Technical note, Journal of Neurosurgery, vol. 74, May 1991, pp. 845-849; 5 pages.

A.E. Quaid, III; R.A. Abovitz, Haptic Information Displays for Computer-Assisted Surgery, Robotics and Automation, 2002 Proceedings. ICRA '02. IEEE International Conference on, May 2002, pp. 2092-2097, vol. 2, IEEE, Washington DC, USA; 6 pages.

A.M. Digioia, III; B. Jaramaz; B. D. Colgan, Computer Assisted Orthopaedic Surgery Image Guided and Robotic Assistive Technologies, Clinical Orthopaedics & Related Research :. Sep. 1998, pp. 8-16, vol. 354, Lippincott Williams & Wilkins, Pittsburgh, PA, USA; 9 pages.

B. Davies, "Active Constraints for Robotic Knee Surgery", May 4, 2006, The Institution of Engineering and Technology, Ref. No. 2006/11372, pp. 31-48.

B. Davies, A review of robotics in surgery, Proceedings of the Institution of Mechanical Engineers, Part H: Journal of Engineering in Medicine Jan. 1, 2000, vol. 214, No. 1, pp. 129-140, Sage Publications; 13 pages.

B. Davies, Computer-assisted and robotics surgery, International Congress and Symposium Series 223, 1997, pp. 11-82, Royal Society of Medicine Press Limited; 12 pages.

B. Jaramaz; C. Nikou; D.A. Simon; A.M. Digioia III, Range of Motion After Total Hip Arthroplasty Experimental Verification of the Analytical Simulator, CVRMed-MRCAS'97, Lecture Notes in Computer Science, Feb. 20, 1997, pp. 573-582, vol. 1205, Springer Berlin Heidelberg, Pittsburgh, PA, USA; 14 pages.

B. L. Davies, Robotics in minimally invasive surgery, Through the Keyhole: Microengineering in Minimally Invasive Surgey, IEE Colloquium on, Jun. 6, 1995, pp. 5/1-5/2, London, UK; 2 pages.

B. Preising et al., "A Literature Review Robots in Medicine", Engineering in Medicine and Biology Magazine, IEEE (vol. 10, Issue: 2), Jun. 1991, pp. 13-22, IEEE; 10 pages.

B. Preising; CA Davis; T.C. Hsia and B. Mittelstadt, A Literature Review Robots in Medicine, Engineering in Medicine and Biology Magazine, IEEE (vol. 10, Issue: 2), Jun. 1991, pp. 13-22, IEEE; 10 pages.

B.K. Redlich; C. Burghart; R. Krempien; T. Redlich; A. Pernozzoli; H. Grabowski; J. Muenchenberg; J. Albers; S. Hafeld; C. Vahl; U. Rembold; H. Woern, Robot assisted craniofacial surgery first clinical evaluation, Computer Assisted Radiology andSurgery, 1999, pp. 828-833; 7 pages.

B.L. Davies et al., "Acrobot-using robots and surgeons synergistically in knee surgery", Advanced Robotics, 1997. ICAR '97. Proceedings., 8th International Conference on, Jul. 7-9, 1997, pp. 173-178, IEEE, Monterey, CA, USA.

B.L. Davies, Robotics in minimally invasive surgery, Through the Keyhole: Microengineering in Minimally Invasive Surgery, IEE Colloquium on, Jun. 6, 1995, pp. 5/1-5/2, London, UK; 2 pages.

B.L. Davies; K.L. Fan; R.D. Hibberd; M. Jakopec; S.J. Harris, Acrobot-using robots and surgeons synergistically in knee surgery, Advanced Robotics, 1997. ICAR '97. Proceedings., 8th International Conference on, Jul. 7-9, 1997, pp. 173-178, IEEE, Monterey, CA, USA; 6 pages.

B.L. Davies; S. Starkie; S.J. Harris; E. Agterhuis; V. Paul; L.M. Auer, Neurobot a special-purpose robot for neurosurgery, Robotics and Automation, 2000. Proceedings. ICRA '00. IEEE International Conference on, Apr. 2000, pp. 4103-4108, vol. 4, IEEE, San Francisco, CA, USA; 6 pages.

B.L. Davies; S.J. Harris; W.J. Lin; R.D. Hibberd; R. Middleton; J.C. Cobb, Active compliance in robotic surgery—the use of force control as a dynamic constraint, Proceedings of the Institution of Mechanical Engineers, Part H: Journal of Engineeringin Medicine, Apr. 1, 1997, pp. 285-292, vol. 211, Sage; 9 pages.

Bender, J. et al., "Constraint-based collision and contact handling using impulses," Proceedings of the 19th International Conference on Computer Animation and Social Agents. Geneva, Switzerland, 2006, pp. 1-9.

Bowyer, Stuart A. et al., "Active Constrainsts/Virtual Fixtures: A Survey", IEEE Transactions on Robotics, vol. 30, No. 1, Feb. 2014, pp. 138-157.

C. Burghart; J. Keitel; S. Hassfeld; U. Rembold; H. Woern, Robot Controlled Osteotomy in Craniofacial Surgery, First International Workshop on Haptic Devices in Medical Applications Proceedings, Jun. 23, 1999, pp. 12-22, Paris, FR; 13 pages.

C. Doignon; F. Nageotte; M. De Mathelin, Segmentation and guidance of multiple rigid objects for intra-operative endoscopic vision, Proceeding WDV'05/WDV'06/ICCV'05/ECCV'06 Proceedings of the 2005/2006 International Conference on Dynamical Vision, 2006, pp. 314-327, Springer-Verlag Berlin, Heidelberg, Illkirch, FR; 14 pages.

C. Hyosig et al., "Autonomous Suturing using Minimally Invasive Surgical Robots", Control Applications, Sep. 25-27, 2000. Proceedings of the 2000 IEEE International Conference on, 2000, pp. 742-747, IEEE, Anchorage, AK, USA; 6 pages.

C. Meng; T. Wang; W. Chou; S. Luan; Y. Zhang; Z. Tian, Remote surgery case robot-assisted teleneurosurgery, Robotics and Automation, 2004. Proceedings. ICRA '04. 2004 IEEE International Conference on, Apr. 26-May 1, 2004, pp. 819-823, vol. 1, IEEE, New Orleans, LA, USA; 5pages.

C. Sim; S.N. Wan; Y.T. Ming; L. Yong-Chong; T.Y. Tseng, Image-Guided Manipulator Compliant Surgical Planning Methodology for Robotic Skull-Base Surgery, Medical Imaging and Augmented Reality, 2001. Proceedings. International Workshop on, Jun. 10-12, 2001, pp. 26-29, IEEE, Shatin, HK; 4 pages.

C.B. Zilles et al., "A Constraint-Based God-object Method for Haptic Display", Intelligent Robots and Systems 95. 'Human Robot Interaction and Cooperative Robots', Proceedings. 1995 IEEE/RSJ International Conference on , Aug. 5-9, 1995, pp. 146-151, vol. 3, IEEE, MIT, Cambridge, MA, USA; 6 pages.

C.B. Zilles; J.K. Salisbury, A Constraint-Based God-object Method for Haptic Display, Intelligent Robots and Systems 95. 'Human Robot Interaction and Cooperative Robots', Proceedings. 1995 IEEE/RSJ International Conference on Aug. 5-9, 1995, pp. 146-151, vol. 3, IEEE, MIT, Cambridge, MA, US; 6 pages.

(56) References Cited

OTHER PUBLICATIONS

C.N. Riviere and N.V. Thakor, Modeling and Canceling Tremor in Human-Machine Interfaces, Engineering in Medicine and Biology Magazine, IEEE, vol. 15, Issue 3, May/Jun. 1996, pp. 29-36, IEEE; 8 pages.
C.O.R. Grueneis; R.J. Richter; F.F. Hennig, Clinical Introduction of the Caspar System Problems and Initial Results, 4th International Symposium of Computer Assited Orthopaedic Surgery, CAOS'99, Abstracts from CAOS '99, 1999, p. 160, Davos,Switzerland; 1 pages.
C.R. Burghart, Robotergestutzte Osteotomie in der craniofacialen Chirurgie (Robot Clipped osteotomy in craniofacial surgery), Jul. 1, 1999, GCA-Verlag, 2000; 250 pages.
Constantniescu, Daniela et al., "Haptic Rendering of Rigid Contacts Using Impulsive and Penalty Forces", Transactions on Robotics, 2004, 14 pages.
D Kozlowski, R. Stoughton, W.S. Newman, R. Hebbar, Automated Force Controlled Assembly Utilizing a Novel Hexapod Robot Manipulator, Automation Congress, 2002 Proceedings of the 5th Biannual World, 2002, pp. 547-552, vol. 14, IEEE; 6 pages.
D. A. Simon; R. V. O'Toole; M. Blackwell; F. Morgan; A. M. Digioia; T. Kanade, Accuracy validation in mage-guided orthopaedic surgery, In Medical Robotics and Computer Assisted Surgery, 1995, pp. 185-192, Wiley; 8 pages.
D. Engel et al., A Safe Robot System for Craniofacial Surgery, Robotics and Automation, 2001. Proceedings 2001 ICRA. IEEE International Conference on (vol. 2), pp. 2020-2024, IEEE; 5 pages.
D. Engel, J. Raczkowsky and H. Worn, A Safe Robot System for Craniofacial Surgery, Robotics and Automation, 200t Proceedings 2001 ICRA. IEEE International Conference on (vol. 2), pp. 2020-2024, IEEE; 5 pages.
D. Tonet et al., "An Augmented Reality Navigation System for Computer Assisted Arthroscopic Surgery of the Knee", Medical Image Computing and Computer-Assisted Intervention—MICCAI 2000, Lecture Notes in Computer Science, 2000, pp. 1158-1162, vol. 1935, Springer Berlin Heidelberg; 5 pages.
D. Y. Choi and C. N. Riviere, Flexure-based Manipulator for Active Handheld Microsurgical Instrument, Engineering in Medicine and Biology Society, 2005. Proceedings of the 2005 IEEE Engineering in Medicine and Biology 27th Annual Conference of theDigital Object Identifier, 2005, pp. 5085-5088, IEEE, Shanghai, China, Sep. 1-4, 2005; 4 pages.
D.A. Simon et al., "Accuracy validation in image-guided orthopaedic surgery", In Medical Robotics and Computer Assisted Surgery, 1995, pp. 185-192, Wiley; 8 pages.
D.P. Gravel, W.S. Newman, Flexible robotic assembly efforts at Ford Motor Company, Intelligent Control, 2001. (ISIC '01). Proceedings of the 2001 IEEE International Symposium on, 2001, pp. 173-182, IEEE, Detroit, Michigan, US; 10 pages.
D.P. Gravel, W.S. Newman, Flexible Robotic Assembly, Measuring the Performance and Intelligence of Systems: Proceedings of the 2000 PerMIS Workshop, NIST Interagency/Internal Report (Nistir)—970, Aug. 14-16, 2000, pp. 412-418, Sep. 1, 2001 NIST; 11pages.
Davies, B.L et al., "ACROBOT—Using Robots and Surgeons Synergistically in Knee Surgery", Advanced Robotics, 1997; ICAR '97; Prooceedings, 8th International Conference on Jul. 7-9, 1997, IEEE, Monterey,. CA, USA, pp. 173-178.
Davies, B.L et al., "Active Constraints for Robotic Knee Surgery", May 4, 2006, The Institution of Engineering and Technology, Ref. No. 2006/11372, pp. 31-48.
E. Bainville, I. Bricault, P. Cinquin and S. Lavallee, Concepts and Methods of Registration for Computer-Integrated Surgery, Computer Assisted Orthopedic Surgery (CAOS), 1999, pp. 15-34, Hogrefe & Huber Publishers, Bern; 22 pages.
E. Catto, Iterative Dynamics with Temporal Coherence, Feb. 22, 2005, Menlo Park, CA, US; 24 pages.
E. Catto, Soft Constraints Reinventing the Spring, Game Developer Conference, 2011; 51 pages.
E. Catto, Soft Constraints Reinventing the Spring, published at least by Jan. 17, 2012; 51 pages.
E. Watanabe; T. Watanabe; S. Manaka; Y. Mayanagi; K. Takakura, Three-Dimensional Digitizer (Neuronavigator); New Equipment for Computed Tomography-Guided Stereotaxic Surgery, Surgical Neurology, Jun. 1987, pp. 543-547, vol. 27, Issued 6, ElsevierInc., 5 pages.
E.H. Spencer, The ROBODOC Clinical Trial a Robotic Assistant for Total Hip Arthroplasty, Orthopaedic Nursing, Jan.-Feb. 1996, pp. 9-14, vol. 15, Issue 1; 6 pages.
English language abstract and machine-assisted English translation for CN 102612350 B extracted from www. espacenet.com on Aug. 29, 2017; 23 pages.
English language abstract and machine-assisted English translation for CN 102743180 extracted from espacenet.com database on Aug. 19, 2020, 15 pages.
H.A. Paul; B. Mittlestadt; W.L. Bargar; B. Musits; R.N. Taylor; P. Kazanzides; J. Zuhars; B. Williamson; W Hanson, A Surgical Robot for Total Hip Replacement Surgery, International Conference on Robotics and Automation, 1992, pp. 606-611, IEEE,Nice,FR; 6 pages.
H.A. Paul; W.L. Bargar; B. Mittlestadt; B. Musits; R. H. Taylor; P. Kazanzides; J. Zuhars; B. Williamson; W. Hanson, Development of a Surgical Robot for Cementless Total Hip Arthroplasty, Clinical Orthopaedics and Related Research, Dec. 1992, pp. 57-66, No. 285, Sacramento, CA, USA; 10 pages.
Hennekens, D. et al., "Continuous Impulsive Force Controller for Forbidden-Region Virtual Fixtures", IEEE International Conference on Robotics and Automation, 2008, 6 pages.
International Search Report for Application No. PCT/US2013/053451 dated Mar. 19, 2014; 8 pages.
International Search Report for Application No. PCT/US2014/025975 dated Sep. 15, 2015, 10 pages.
International Search Report for Application No. PCT/US2016/049955 dated Nov. 11, 2016, 5 pages.
International Search Report for Application No. PCT/US2017/066071 dated Mar. 27, 2018, 2 pages.
J Levison, J. E. Moody, B. Jaramaz, C. Nikou, A. M. Digioia, Surgical Navigation for THR a Report on Clinical Trial Utilizing HipNav, MICCAI 2000, LNCS 1935, pp. 1185-1187, 2000, Springer-Verlag Berlin Heidelberg; 3 pages.
J. Andreas B/Erentzen, Octree-based Volume Sculpting, Proc. Late Breaking Hot Topics, IEEE Visualization '98, pp. 9-12, 1998; 4 pages.
J. Andreas Bentzen, Octree-based Volume Sculpting, Proc. Late Breaking Hot Topics, IEEE Visualization '98, pp. 9-12, 1998; 4 pages.
J. K. Salisbury, Active Stiffness Control of a Manipulator in Cartesian Coordinates, Decision and Control including the Symposium on Adaptive Processes, 1980 19th IEEE Conference on, Dec. 1980, pp. 95-100, vol. 19, IEEE, Stanford, CA, USA; 7 pages.
J. L. Moctezuma, F. Gosse and H.-J. Schulz, A Computer and Robotic Aided Surgery System for Accomplishing Osteotomies, First International Symposium on Medical Robotics and Computer Assisted Surgery, Sep. 22-24, 1994, Pittsburgh, Pennsylvania, US; 6pages.
J. Raczkowsky; J. Munchenberg; L Bertovic; C. Burghart, Ein Robotersystem fur craniomaxillofaciale chirurgische Eingriffe (A robotic system for surgical procedures craniomaxillofaciale), Computer Forsch. Entw., 1999, pp. 24-35, vol. 14,Springer-Verlag; 12 pages.
J. Rembold and C. R. Burghart, Surgical Robotics: An Introduction, Journal of Intelligent and Robotic Systems vol. 30, No. 1, pp. 1-28, 2001, Kluwer Academic Publishers; 28 pages.
J. Seibold, B. Kubler, and G. Hirzinger, Prototype of Instrument for Minimally Invasive Surgery with 6-Axis Force Sensing Capability, Robotics and Automation, 2005. ICRA 2005. Proceedings of the 2005 IEEE International Conference on, Apr. 18-22, 2005, pp. 498-503, IEEE, Barcelona, Spain; 6 pages.
J. Spetzger; G. Laborde; J.M. Gilsbach, Frameless Neuronavigation in Modern Neurosurgery, Minimally Invasive Neurosurgery, Dec. 1995, pp. 163-166, vol. 38; 4 pages.
J. T. Lea, D. Watkins, A. Mills, M. A. Peshkin, T. C. Kienzle, III and S. D. Stulberg, Registration and immobilization in robot-assisted

(56) References Cited

OTHER PUBLICATIONS surgery, Journal of Image Guided Surgery, Computer Aided Surgery, 1995, vol. 1, Vo. 2, pp. 80-87; 11 pages.
J. T. Lea, Registration Graphs a Language for Modeling and Analyzing Registration in Image-Guided Surgery, Dec. 1998, Evanston, Illinois, US; 49 pages.
J. Troccaz et al., "A passive arm with dynamic constraints a solution to safety problems in medical robotics", Systems, Man and Cybernetics, 1993. 'Systems Engineering in the Service of Humans', Conference Proceedings., InternationalConference on,Oct. 17-20, 1993, pp. 166-171, vol. 3, IEEE, Le Touquet, FR; 6 pages.
J. Troccaz, M. Peshkin and B. Davies, Guiding systems for computer-assisted surgery introducing synergistic devices and discussing the different approaches, Medical Image Analysis, Jun. 1998, vol. 2, No. 2, pp. 101-119, Elsevier B.V.; 19 pages.
J. Troccaz; S. Lavallee; E. Hellion, A passive arm with dynamic constraints a solution to safety problems in medical robotics, Systems, Man and Cybernetics, 1993. 'Systems Engineering in the Service of Humans', Conference Proceedings., InternationalConference on, Oct. 17-20, 1993, pp. 166-171, vol. 3, IEEE, Le Touquet, FR; 6 pages.
J. Troccaz; Y. Delnondedieu, Semi-Active Guiding Systems in Surgery. A Two-DOF Prototype of the Passive Arm with Dynamic Constraints (PADyC), Mechatronics, Jun. 1996, pp. 399-421, vol. 6, Issue 4, 1996, Elsevier Ltd., UK; 23 pages.
J.E. Colgate; M.C. Stanley; J.M. Brown, Issues in the Haptic Display of Tool Use, Intelligent Robots and Systems 95. 'Human Robot Interaction and Cooperative Robots', Proceedings. 1995 IEEE/RSJ International Conference on, Aug. 5-9, 1995, pp. 140-145, vol. 3, IEEE, Pittsburgh, PA, USA; 6 pages.
J.L. Moctezuma et al., "A Computer and Robotic Aided Surgery System for Accomplishing Osteotomies," First International Symposium on Medical Robotics and Computer Assisted Surgery, Sep. 22-24, 1994, Pittsburgh, Pennsylvania, US; 6 pages.
J.L. Moctezuma, F. Gosse and H.-J. Schulz, A Computer and Robotic Aided Surgery System for Accomplishing Osteotomies, First International Symposium on Medical Robotics and Computer Assisted Surgery, Sep. 22-24, 1994, Pittsburgh, PA, US; 6 pages.
Julio J. Santos, "A Stereotactic/Robotic System for Pedicle Screw Placement", Interactive Technology and the New Paradigm for Healthcare, (Proceedings of theMedicine Meets Virtual Reality III Conference, San Diego, 1995), pp. 326-333, IOS Press andOhmsha; 8 pages.
Julio J. Santos-Munne, Michael A. Peshkin, Srdjan Mirkovic, S. David Stulberg, Thomas C. Kienzle III, A Stereotactic/Robotic System for Pedicle Screw Placement, Interactive Technology and the New Paradigm for Healthcare, (Proceedings of theMedicine Meets Virtual Reality III Conference, San Diego, 1995), pp. 326-333, IOS Press and Ohmsha; 8 pages.
K. Bouazza-Marouf; I. Browbank; J.R. Hewit, Robot-assisted invasive orthopaedic surgery, Mechatronics in Surgery, Jun. 1996, pp. 381-397, vol. 6, Issue 4, UK; 17 pages.
K. Hyosig; J.T. Wen, Autonomous Suturing using Minimally Invasive Surgical Robots, Control Applications, Sep. 25-27, 2000. Proceedings of the 2000 IEEE International Conference on, 2000, pp. 742-747, IEEE, Anchorage, AK, USA, 6 pages.
K. Hyosig; J.T. Wen, EndoBot a Robotic Assistant in Minimally Invasive Surgeries, Robotics and Automation, 2001. Proceedings 2001 ICRA. IEEE International Conference on, Seoul, KR, 2001, pp. 2031-2036, vol. 2, IEEE, Troy, NY, USA; 6 pages.
Kato A., Yoshimine T., Hayakawa T., Tomita Y., Ikeda T., Mitomo M., Harada K., Mogami H., A frameless, armless navigational system for computer-assisted neurosurgery. Technical note, Journal of Neurosurgery, vol. 74, May 1991, pp. 845-849; 5 pages.
Kato A., Yoshimine T., Kayakawa T., Tomita Y., Ikeda T., Mitomo M., Harada K., Mogami H., A frameless, armless navigational system for computer-assisted neurosurgery. Technical note, Journal of Neurosurgery, vol. 74, May 1991, pp. 845-849; 5 pages.

Kiguchi, Kazuo et al., "Intelligent Position/Force Controller for Industrial Robot Manipulators-Application of Fuzzy Neural Networks", IEEE Transactions on Industrial Electronics, vol. 44, No. 6, Dec. 1997, pp. 753-761.
Kim et al., "A Teleoperated Minimally Invasive Surgical System With an Additional Degree of Freedom Manipulator", Fourth International Conference on Sensor Technologies and Applications, 2010, pp. 90-94.
Kuo et al., "Development of Active IR-Based Surgical Marker Tracking and Positioning Systems", IEEE International Conference on Man and Cybernetics System, vol. 3, 2005, pp. 2443-2448.
L.P. Nolte et al., "A Novel Approach to Computer Assisted Spine Surgery", Proc. First International Symposium on Medical Robotics and Computer Assisted Surgery, Pittsburgh, 1994, pp. 323-328; 7 pages.
Lango et al., "Navigation in Laparoscopy—Prototype Research Platform for Improved Image-Guided Surgery", Minimally Invasive Therapy, vol. 17, No. 1, 2008, pp. 17-33.
M. Fadda, D. Bertelli, S. Martelli, M. Marcacci, P. Dario, C. Paggetti, D. Caramella and D. Trippi, Computer Assisted Planning for Total Knee Arthroplasty, 1997, pp. 619-628; 10 pages.
M. Fadda, T. Wang, M. Marcacci, S. Martelli, P. Dario, G. Marcenaro, M. Nanetti, C. Paggetti, A. Visani and S. Zaffagnini, Computer-Assisted Knee Arthroplasty at Rizzoli Institutes, First International Symposium on Medical Robotics and ComputerAssisted Surgery, Sep. 22-24, 1994, pp. 26-30, Pittsburgh, Pennsylvania, US; 6 pages.
M. Fadda; S. Martelli; P. Dario; M. Marcacci; S. Zaffagnini; A. Visani, Premiers Pas Vers La Dissectomie et la Realisation de Protheses du Genou a L'Aide de Robots, Innov. Tech. Bio. Med., 1992, pp. 394-409, vol. 13, No. 4; 16 pages.
M. Fleute; S. Lavallee; R. Julliard, Incorporating a statistically based shape model into a system for computer-assisted anterior cruciate ligament surgery, Medical Image Analysis, Oct. 1999, pp. 209-222, vol. 3, No. 3, FR; 14 pages.
M. Jakopec; S.J. Harris; Y B.F. Rodriguez; P. Gomes; J. Cobb; B.L. Davies, The first clinical application of a "hands-on" robotic knee surgery system, Computer Aided Surgery, 2001, pp. 329-339, vol. 6, Issue 6, Wiley-Liss, Inc.; 11 pages.
Mako Surgical Corp., "MAKOplasty Partial Knee Application User Guide", 206388, Rev 03, Aug. 2013, pp. 1-112.
O. Tonet; G. Megali; S. D'Attanasio; P. Dario; M. C. Carrozza; M. Marcacci; S. Marta; P. F. La Palombara, An Augmented Reality Navigation System for Computer Assisted Arthroscopic Surgery of the Knee, Medical Image Computing and Computer-AssistedIntervention—MICCAI 2000, Lecture Notes in Computer Science, 2000, pp. 1158-1162, vol. 1935, Springer Berlin Heidelberg; 5 pages.
Office Action for U.S. Appl. No. 14/845,820, dated Mar. 29, 2017; 19 pages.
Orto Maquet and Caspar: An Automated Cell for Prosthesis Surgery, Robotics World, Sep./Oct. 1999, pp. 30-31, Circular No. 87 on Reader Reply Card; 2 pages.
P. Kazanides et al., "Architecture of a Surgical Robot", Systems, Man and Cybernetics, 1992., IEEE International Conference on, Oct. 18-21, 1992, pp. 1624-1629, vol. 2, IEEE, Chicago, IL, USA; 6 pages.
P. Kazanzides; J. Zuhars; B. Mittelstadt; B. Williamson; P. Cain; F. Smith; L. Rose; B. Musits, Architecture of a Surgical Robot, Systems, Man and Cybernetics, 1992., IEEE International Conference on, Oct. 18-21, 1992, pp. 1624-1629, vol. 2, IEEE, Chicago, IL, USA; 6 pages.
P. Shinsuk, Safety Strategies for Human-Robot Interaction in Surgical Environment, SICE-ICASE, 2006. International Joint Conference, Oct. 18-21, 2006, pp. 1769-1773, IEEE, Bexco, Busan, SK; 5 pages.
R. Abovitz, Digital surgery the future of medicine and human-robot symbiotic interaction, Industrial Robot: An International Journal, 2001, pp. 401-406, vol. 28, Issue 5, Hollywood, FL, USA; 5 pages.
Mustafa, Kurt et al., "Feedrate Optimisation/Scheduling on Sculptured Surface Machining: A Comprehensive Review, Applications and Future Directions", Int J Adv Manuf Technol, vol. 55, 2011, pp. 1037-1067.

(56) References Cited

OTHER PUBLICATIONS

Petersik, Andreas et al., "Realistic Haptic Interaction in vol. Sculpting for Surgery Simulation", IS4TM, Springer-Verlag, Berlin, 2003, pp. 194-202.
Heger, Stefan et al., "User-Interactive Registration of Bone with A-Mode Ultrasound", IEEE Engineering in Medicine and Biology, vol. 24, No. 2, 2005, pp. 85-95.
English language abstract for CN 101772328 A extracted from espacenet.com database on Jul. 2, 2024, 2 pages.

* cited by examiner

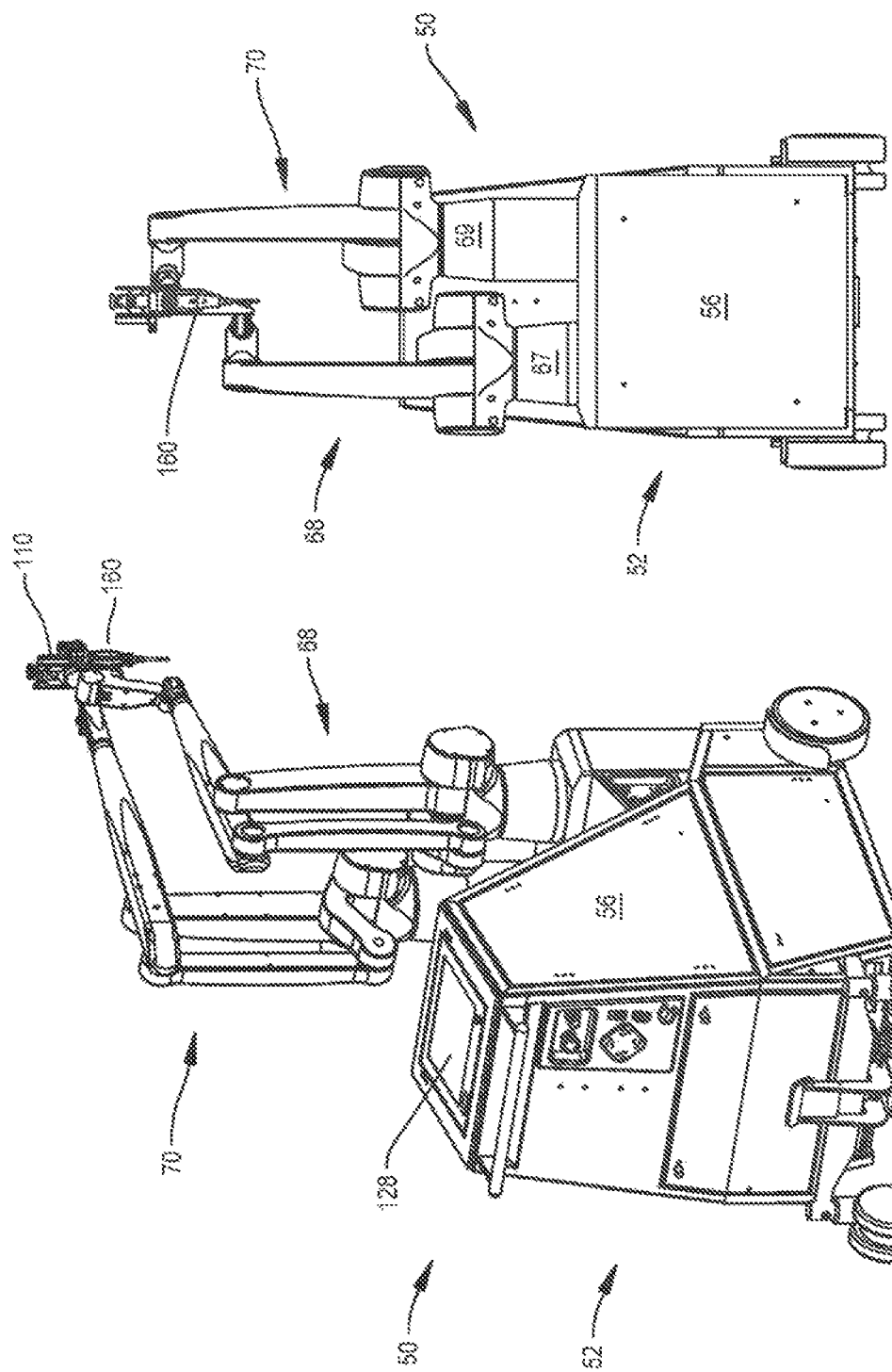

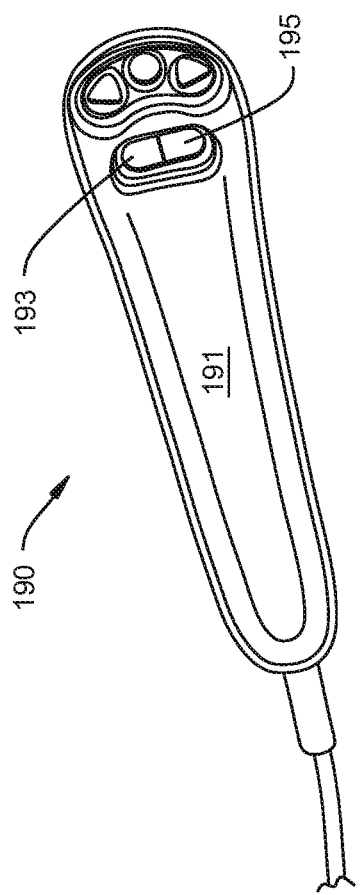
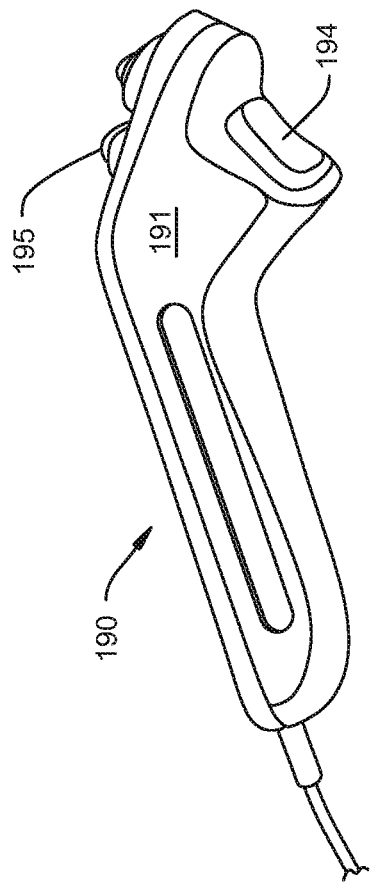
FIG. 2A
FIG. 2B

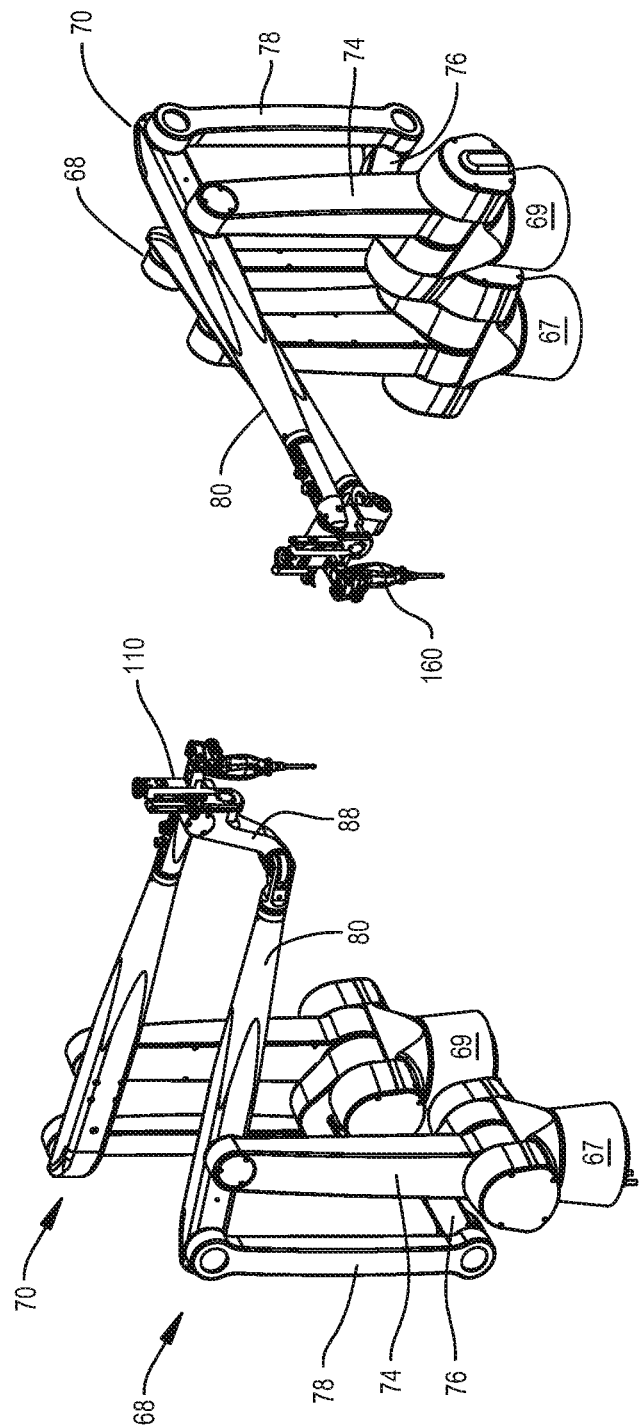

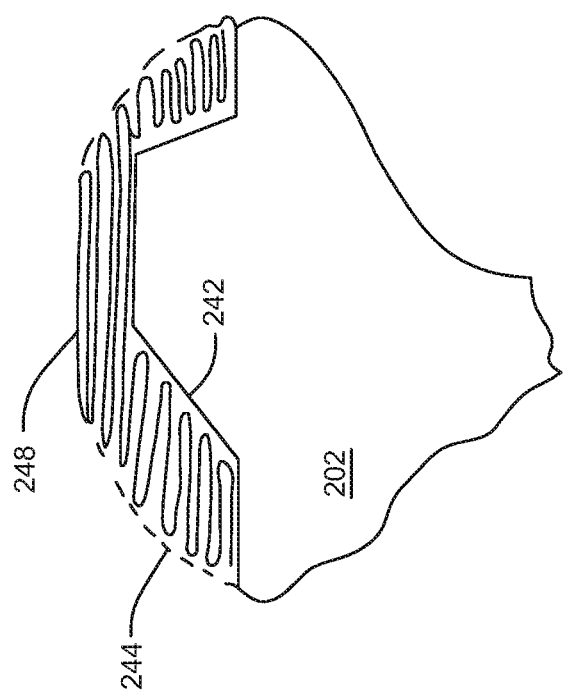
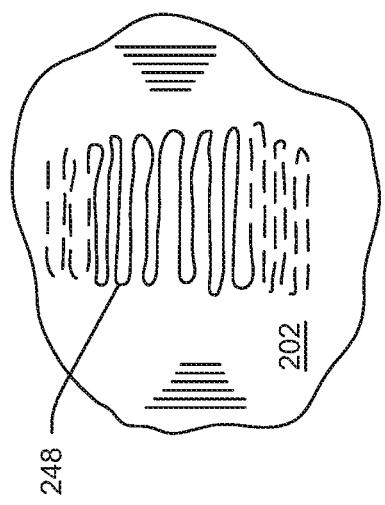

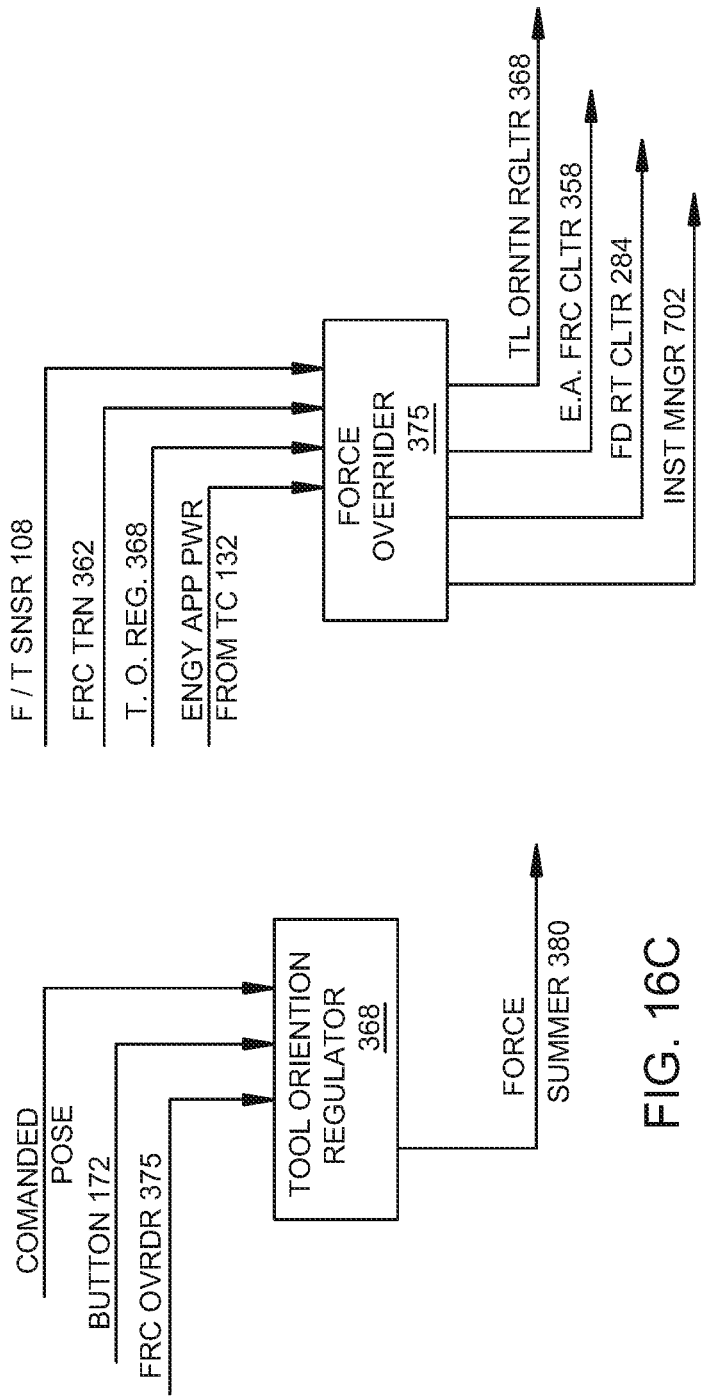

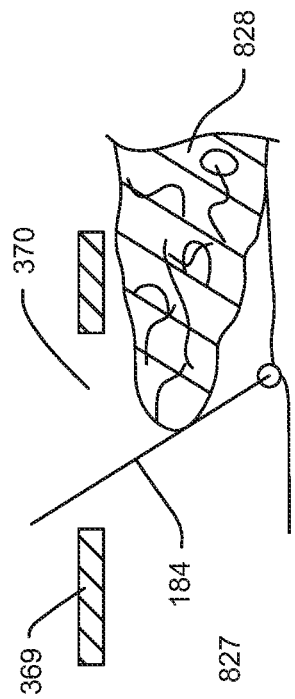
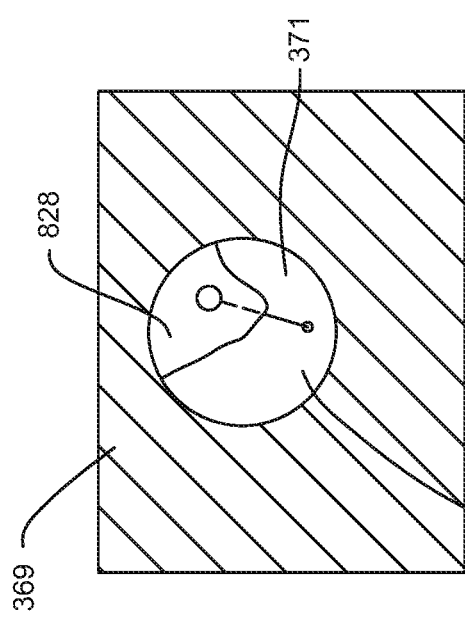
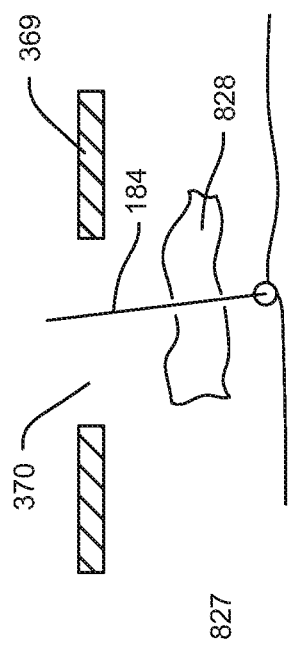
FIG. 32C
FIG. 32A
FIG. 32B

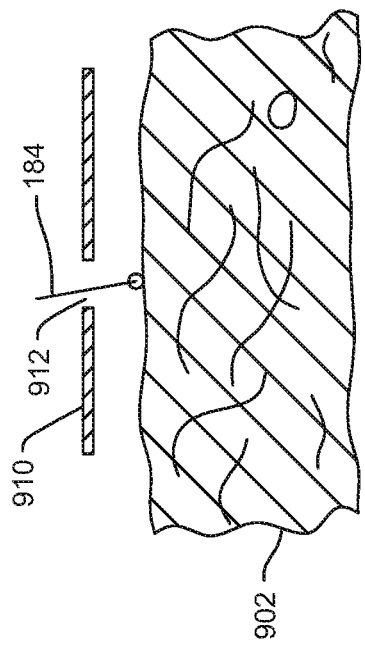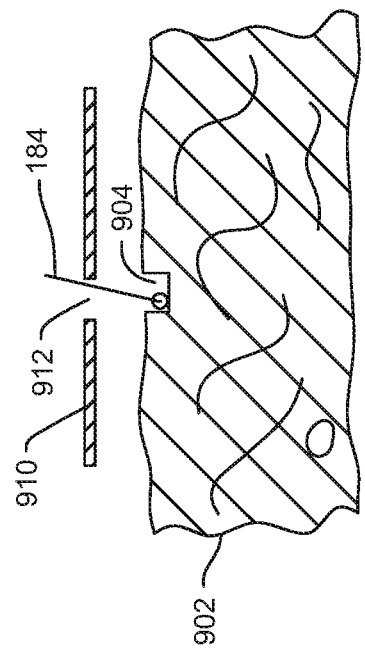

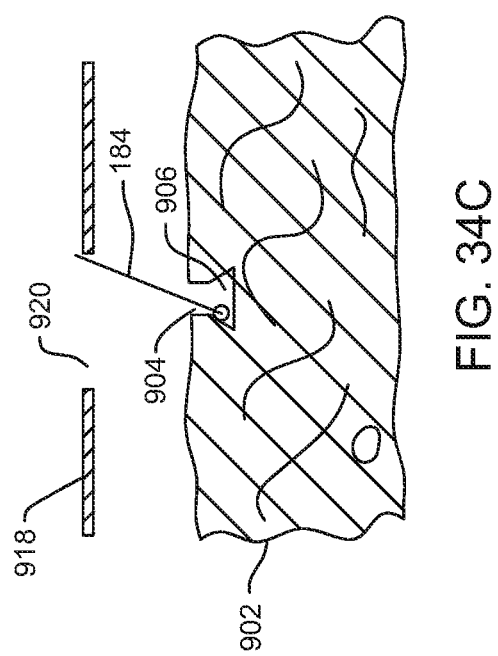

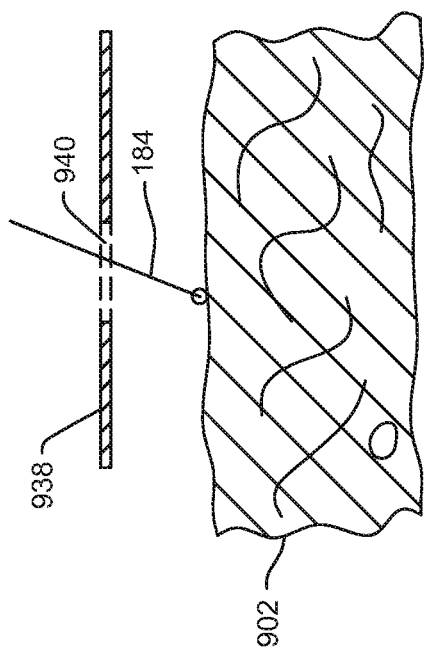
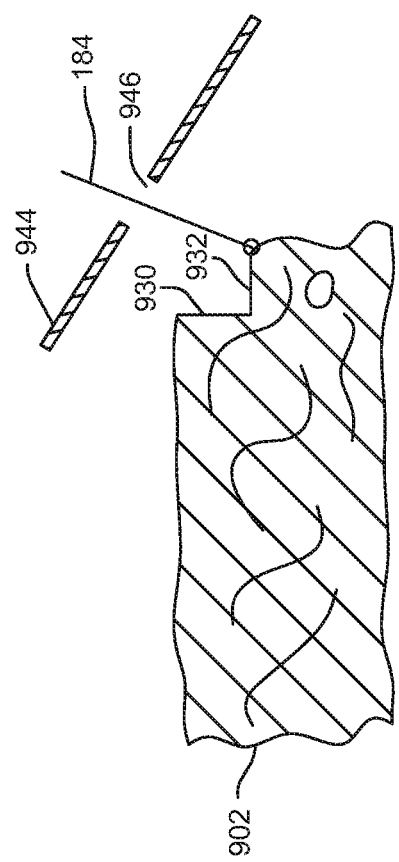

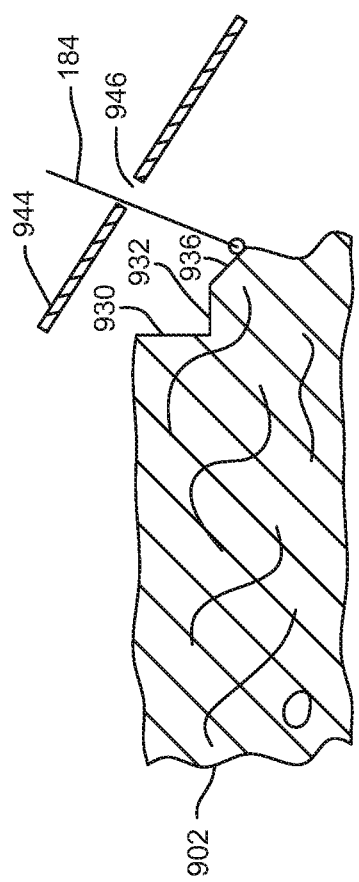

HAND-HELD PENDANT FOR CONTROLLING A SURGICAL ROBOTIC MANIPULATOR IN A SEMI-AUTONOMOUS MODE

CROSS-REFERENCE TO RELATED APPLICATIONS

This application is a continuation of U.S. Nonprovisional patent application Ser. No. 16/584,436, filed Sep. 26, 2019, which is a continuation of U.S. Nonprovisional patent application Ser. No. 16/262,375, filed Jan. 30, 2019, now U.S. Pat. No. 10,463,440, which is a continuation of U.S. Nonprovisional patent application Ser. No. 15/266,691, filed Sep. 15, 2016, now U.S. Pat. No. 10,350,017, which is a continuation of U.S. Nonprovisional patent application Ser. No. 13/958,834, filed Aug. 5, 2013, now U.S. Pat. No. 9,480,534, which claims the benefit of both U.S. Provisional Patent App. No. 61/679,258, filed on Aug. 3, 2012, and U.S. Provisional Patent App. No. 61/792,251, filed on Mar. 15, 2013, the advantages and disclosures of each of these applications are hereby incorporated by reference in their entirety.

FIELD

This invention relates generally to a hand-held control pendant for controlling operation of a robotic manipulator in a semi-automated mode.

BACKGROUND

Recently, medical practitioners have found it useful to use robotic devices to assist in the performance of surgical procedures. A robotic device typically includes a moveable arm that comprises one or more linkages. The arm has a free, distal end that can be placed with a very high degree of accuracy. A surgical instrument designed to be applied to the surgical site is attached to the free end of the arm. The practitioner is able to precisely position the arm so as to by extrapolation, precisely position the surgical instrument at the site on the patient at which the instrument is to perform a medical or surgical procedure. One advantage of using a robotic system to hold the instrument is that the system arm, unlike the arms and hands of a surgeon, are not subjected to muscle strain or neurological actions like twitching. Thus, in comparison to when an instrument is hand held and therefore hand positioned, using a medical robotic system it is possible to hold an instrument steady, or move the instrument along a defined path with a higher degree of accuracy.

Further some robotic surgical systems are designed to be used with surgical navigation systems. A surgical navigation system is a system that is able to generate data that provides a relatively precise indication of the surgical instrument relative to the location of the patient against which the instrument is applied. When a surgical robotic system is provided with the data indicating the position of the instrument relative to the patient, the robotic system may be able to position the instrument to ensure that it is applied to the tissue of the patient against which the instrument is supposed to be applied. This substantially eliminates the likelihood that the instrument will be applied to tissue against which the instrument should not be applied.

Some medical robotic systems are designed to work in what is referred to as a "semi-autonomous" mode. In this mode of operation, the robotic system actuates the arm so as to cause the instrument to move against the patient's tissue in a preprogrammed path. This is useful if, for example, the instrument is some sort of cutting device and the goal of the particular procedure is to remove a pre-defined section of the patient's tissue. By way of reference, if a robotic system operates in an "autonomous" mode of operation, the robot, once actuated, performs the procedure with essentially no input from the surgeon. In a "semi-autonomous" mode of operation, the practitioner is able to assert commands to control the operation of the robot. For example, some semi-autonomous robots are constructed so that, in order for the robot to displace the instrument, the practitioner must actuate a command by continually depressing a control button or switch associated with the robot. Upon the negation of the actuate command by the practitioner, the advancement of the instrument by the robot at least temporarily stops.

Some robotic systems are not traditional robots in that once activated, they do not automatically move the attached instrument along a pre-programmed path of travel. These systems include control systems through which the practitioner enters commands indicating where the attached instrument is to be positioned. Based on these practitioner-entered commands, this type of system actuates the system's arm/arms to cause the essentially simultaneous, real time, movement of the instrument. These robotics systems are considered to operate in a manual mode.

To date though, it has been difficult to provide a robotic system able to, during the performance of a single procedure, switch between semi-autonomous and manual modes of operation. For example, it is believed that many times a surgeon may want to initially manually operate the instrument in order to remove a large mass of tissue. This part of the procedure is sometimes referred to as debulking. Then, to remove tissue to define the surfaces of the remaining tissue, the surgeon may want the robotic system to semi-autonomously perform fine positioning of the instrument. This part of the procedure is sometimes known as the finishing cut.

Moreover, there are times when it may be desirable to switch from semi-autonomous positioning of the instrument back to manual positioning. For example, in an orthopedic joint replacement procedure, the practitioner may want the instrument, a cutting tool, to move in a programmed path in order to precisely shape the bone to which the instrument is applied. This precise bone shaping facilitates the precise fitting of the implant to the face of the bone exposed by the cutting tool. However, there may be a situation in which, after the procedure begins, it becomes apparent that the instrument may collide with an object at the surgical site against which such contact is undesirable. This object may be tissue that has moved into the surgical site or a second instrument positioned at the site. In this situation, it should be possible for the practitioner to momentarily interrupt the programmed movement of the tool, manually control the tool to reposition the instrument, and then return the tool to the programmed movement.

SUMMARY

According to a first aspect, a surgical system is provided, comprising: a robotic manipulator configured to support and move a surgical instrument that includes an energy applicator; at least one controller configured to operate the robotic manipulator in a semi-autonomous mode and being configured to calculate an instrument feed rate, wherein the instrument feed rate is a velocity at which the energy applicator advances along a tool path in the semi-autonomous mode; and a hand-held pendant coupled to the at least one controller, wherein the hand-held pendant comprises a first control member to initiate operation of the robotic manipulator in the semi-autonomous mode and a second control member to modify the instrument feed rate in the semi-autonomous mode.

According to a second aspect, a user control device is provided for a surgical system that includes a robotic manipulator being configured to support and move a surgical instrument that includes an energy applicator, and at least one controller configured to operate the robotic manipulator in a semi-autonomous mode and being configured to calculate an instrument feed rate, wherein the instrument feed rate is a velocity at which the energy applicator advances along a tool path in the semi-autonomous mode, the user control device comprising: a housing configured as a pendant configured to be held in one hand of a user; a first control member mounted to the housing and being configured to be depressed to initiate operation of the robotic manipulator in the semi-autonomous mode; and a second control member mounted to the housing and being configured to be depressed to modify the instrument feed rate in the semi-autonomous mode.

According to a third aspect, a method is provided of operating a surgical system, the surgical system comprising a robotic manipulator configured to support and move a surgical instrument that includes an energy applicator, a hand-held pendant comprising a first control member and a second control member, and at least one controller coupled to the robotic manipulator and the hand-held pendant, the method comprising the at least one controller performing the following steps: initiating operation of the robotic manipulator in a semi-autonomous mode in response to receiving user input from the first control member of the hand-held pendant; advancing the energy applicator along a tool path in the semi-autonomous mode according to an instrument feed rate; and modifying the instrument feed rate during operation of the robotic manipulator in the semi-autonomous mode in response to receiving user input from the second control member of the hand-held pendant.

BRIEF DESCRIPTION OF THE DRAWINGS

The invention is pointed out with particularity in the claims. The above and further features and advantages of this invention are understood from following Detailed Description taken in conjunction with the following drawings in which:

FIG. 2 is a perspective view of a manipulator of this invention to which both a surgical instrument and a navigation tracker are attached;

FIGS. 2A and 2B are, respectively, top and side views of a pendant used to regulate the operation of the manipulator;

FIG. 3 is front view of the manipulator;

FIG. 4 is a perspective view of the arms of the manipulator;

FIG. 5 is an alternative perspective view of the manipulator arms;

FIG. 15A is a side view of a bone depicting how tool paths are formed to define the sections of the bone to which the surgical instrument is applied;

FIG. 15B is a top view of a bone depicting the arrangement of the tool maps;

FIGS. 16A-16D depict the sub-modules internal to the tool path force calculator;

FIGS. 32A, 32B and 32C, are, respectively, top, side and cross section views of how, even with the presence of a obstruction 828 above the tool path, the manipulator is able to adjust the orientation of the instrument to hold the energy applicator on the tool path while maintaining the common axis within the reference surface aperture;

FIGS. 34A, 34B and 34C are a second set of cross sectional views that depict how the position of the orientation reference surface and the aperture defined in the surface are reset during the operation of the manipulator.

FIGS. 35A, 35B, and 35C are a second set of cross section views that depict how the position and orientation of the reference surface and aperture defined by in the reference surface are reset during operation of the manipulator.

DETAILED DESCRIPTION

I. Overview

Figure 1:
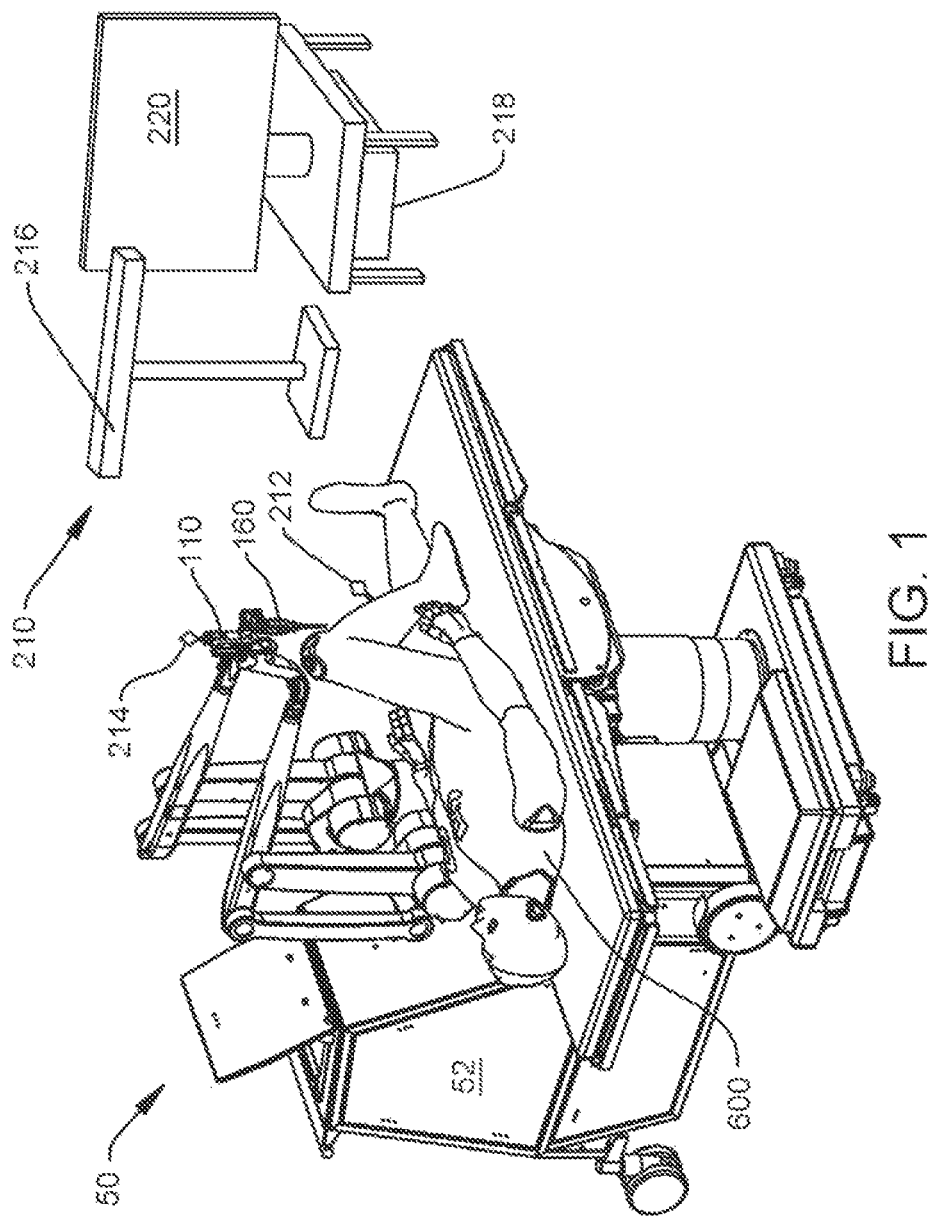
FIG. 1 is an overview of how a manipulator of this invention is used to position and advance a surgical instrument on a patient.

This invention relates generally to a new and useful surgical manipulator that positions a surgical instrument or tool on or in the patient. The surgical manipulator positions the surgical instrument so that the end of instrument that is to be applied to the tissue is only applied to the tissue to which the instrument should be applied.

The manipulator can be operated in either a manual mode or a semi-autonomous mode. When the manipulator is operated in the manual mode, the manipulator monitors the forces and torques the practitioner places on the instrument in order to position the instrument. These forces and torques are measured by a sensor that is part of the manipulator. In response to the practitioner applied forces and torques, the manipulator essentially moves the instrument in real time. The movement of the instrument by the manipulator can therefore be considered to be movement of the instrument that emulates the desired positioning of the instrument by the practitioner.

When the manipulator is in the manual mode, the manipulator determines the relative location of the instrument to a boundary. This boundary defines the limits of the tissue beyond which the instrument should not be placed. In the event it appears that the practitioner wants to position the instrument beyond the boundary, the manipulator does not allow this movement of the instrument. For example, should the manipulator determine that the practitioner's repositioning of the instrument is resulting in the instrument approaching a boundary which the instrument should not cross, the manipulator prevents the instrument from movement beyond the boundary.

The practitioner may continue to attempt to reposition the instrument to a location beyond which the tip should not be applied. The manipulator does not move the tip such that the tip is repositioned beyond the boundary. The manipulator does, however, reorient the instrument according to the force detected from the practitioner. This reorienting of the instrument without allowing tip repositioning indicates to the practitioner that the instrument tip has reached a boundary that should not be crossed. The manipulator still does not respond to move the tip along the boundary.

When the manipulator is operated in a semi-autonomous mode, the manipulator calculates the forces and torques necessary to move the instrument along a predefined path of travel. Based on these forces and torques, the manipulator moves the instrument along the predefined path of travel.

It is a further feature that the practitioner is able to engage in some manual adjustment of the position of the instrument while the manipulator moves the instrument during the semi-autonomous operation. One such adjustment is that the practitioner can adjust the orientation of the instrument while the instrument moves along the programmed path of travel.

In some versions, when the manipulator advances the instrument, it does so based on a determination of forces and torques that need to be applied to a virtual rigid body. This virtual rigid body is a model of the instrument and the energy applicator. Based on these forces and torques, the manipulator advances the instrument. When the manipulator operates in the manual mode, a component of these forces and torques are forces and torques that, as a consequence of their being applied to the virtual rigid body, result in the manipulator positioning the instrument in such a manner that the instrument does not cross the boundary. When the manipulator operates in the semi-autonomous mode, forces and torques applied to the virtual rigid body include additional components. In response to the presence of these additional force and torque components, the manipulator advances the instrument so the energy applicator moves along the predefined tool path.

In some versions, the manipulator includes a number of interconnected links. These links may be connected together in series and/or parallel. In one embodiment of this invention, these links form two parallel four bar linkages. The instrument is connected to the distal end of the links. Generally, each pair of adjacent links is connected by a joint. The position of the links is set by actuators associated with the joints.

FIGS. 1 and 2 illustrate an exemplary manipulator 50 used to apply a surgical instrument 160 to a patient 600. Manipulator 50 includes an end effector 110 that is the component of the manipulator to which the surgical instrument 160 is attached. Manipulator 50 positions the end effector 110 to position and orient the surgical instrument 160 so that the instrument performs the intended medical/surgical procedure on the patient. The manipulator 50 is used in conjunction with a surgical navigation system 210. The surgical navigation system 210 monitors the position of the end effector 110 and the patient 600. Based on this monitoring, the surgical navigation system 210 determines the position of the surgical instrument 160 relative to the site on the patient to which the instrument is applied.

A hand held pendant 190 (FIG. 2A) is also attached to manipulator 50. Pendant 190 is used in some operating modes to regulate operation of the manipulator and instrument 160.

Manipulator 50 of this invention can operate in a manual mode. When the manipulator operates in the manual mode, the manipulator responds to the forces and torques the practitioner places on the instrument 160 to position the instrument. In response to these forces and torques, the manipulator mechanically moves the instrument in a manner that emulates the movement that would have occurred based on the forces and torques applied by the practitioner. As the instrument 160 moves, the surgical manipulator 50 and surgical navigation system 210 cooperate to determine if the instrument is within a defined boundary. Often, but not always, this boundary is within the patient and beyond which the instrument should not be applied. Based on these data, the manipulator 50 selectively limits the extent to which the instrument 160 moves. Specifically, the manipulator constrains the manipulator from movement that would otherwise result in the application of the instrument outside of the defined boundary. Thus, should the practitioner apply forces and torques that would result in the advancement of the instrument beyond the boundary, the manipulator does not emulate this intended positioning of the instrument.

The manipulator 50 can also operate in a semi-autonomous mode. To operate the manipulator 50 in this mode, a path of travel along which the instrument 160 should be applied to the tissue is generated. At least the basic version of this path is generated prior to the start of the procedure. Based on these forces and torques, as well as other data, the manipulator generates data describing a commanded pose to which the instrument should be advanced. ("Pose" is understood to be the position and orientation of the system component being discussed.) Once the commanded pose is generated, the manipulator advances the instrument to that pose. As when in the manual mode, when the instrument is operated in the semi-autonomous mode, the manipulator does not advance the instrument 160 beyond the boundary.

II. Hardware

As seen in FIGS. 2 and 3, the manipulator 50 includes a cart 52. Cart 52 includes a wheel mounted frame (frame not illustrated). A shell 56 is disposed over the frame.

Manipulator 50 includes lower and upper arms 68 and 70, respectively. Arms 68 and 70 extend upwardly from shoulders 67 and 69, respectively. The shoulders 67 and 69 are located above cart shell 56. Each shoulder 67 and 69 and associate arm 68 and 70, respectively, collectively have three degrees-of-freedom relative to a horizontal base plane of the cart 52. Shoulder 69, the shoulder to which upper arm 70 is mounted, is located above shoulder 67, the shoulder to which lower arm 68 is mounted. Both shoulders 67 and 69 are rotatably attached to the cart frame. Each shoulder 67 and 69 rotates around an axis that extends perpendicular to the horizontal base plane of the cart 52. The rotation of each shoulder 67 and 69 results in the like displacement of the associated arm 68 or 70, respectively. As is apparent below, the shoulders need not always move in unison or have the same end position. The angular position of each shoulder 67 and 69 relative to a reference location on the cart 52 is referred to as the joint angle of the shoulder.

As seen in FIGS. 4 and 5, each arm 68 and 70 includes a four bar linkage. In these Figures, the arms are in their nominal home positions. Each arm 68 and 70 includes an upper link 74 that is pivotally mounted to the shoulder 67 or 69. While upper links 74 are able to pivot, in FIGS. 4 and 5 they are shown extending above the shoulders and approximately perpendicular to the ground plane. A driver link 76 is also pivotally mounted to shoulder 67 or 69. Driver link 76 is mounted to the shoulder 67 or 69 so as to pivot around the same axis around which upper link 74 pivots. Each driver link extends rearwardly away from the associated shoulder 67 or 69. (Here, "rearward" is the direction away from the patient. "Forward" is in the direction of towards the patient.) In the depicted version, the driver links 76, unlike the other links, are not generally in the form of straight beams. Instead, each driver link 76 is formed with a bend (bend not identified). The bent shape of the driver links 76 facilitates the clearance of links about the shoulders 67 and 69.

A four bar link 78 is pivotally mounted to the rear free end of each driver link 76. Four bar link 78 extends upwardly from the associated driver link 76 and is generally parallel with the upper link 74. A driven link 80 is the remaining rigid link of each arm 68 and 70. Each driven link 80 has an upper section, not identified, that is pivotally attached to the free end of the associated proximal four bar link 78. Each driven link 80 is also pivotally attached to the free end of the associated upper link 74. Each driven link 80 has a forward section, not identified, that extends outwardly beyond the upper link 74. Owing to shoulders 67 and 69 being of different heights above ground level, the drive link 80 integral with upper arm 70 is located above the drive link integral with lower arm 68.

Each link 74, 76, 78 and 80, like each shoulder 67 and 69, rotates. The connection between two links is referred to as a joint. The angle between two links is the joint angle of the joint connecting the links.

Figure 7:
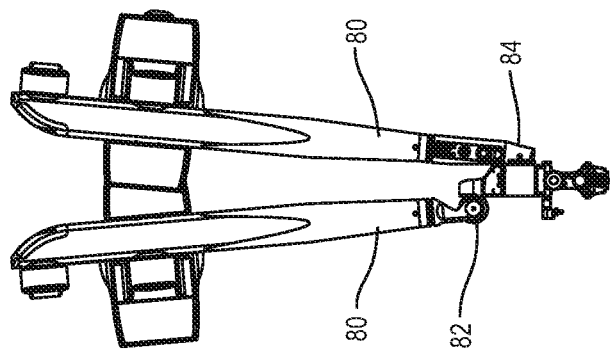
FIG. 7 is a top view of the manipulator arms.
Figure 6:
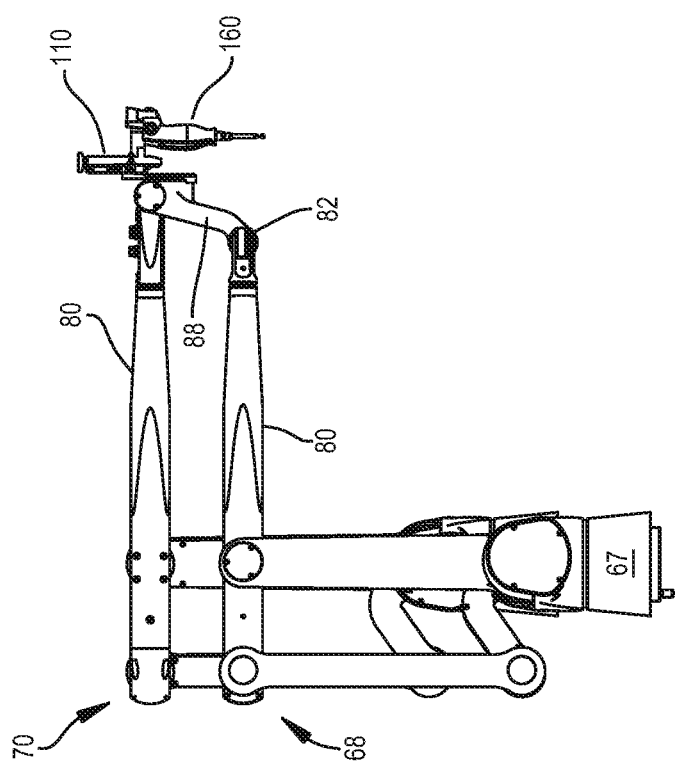
FIG. 6 is a side view of the manipulator arms wherein the lower arm is seen in the foreground.

A rigid coupler 88, also part of the manipulator 50, extends between the distal ends of the driven links 80. As seen in FIGS. 6 and 7, a wrist 82 connects coupler 88 to lower arm driven link 80. Wrist 82 is connected to the lower arm driven link 80. Wrist 82 is a three degree of freedom wrist. A wrist 84 connects coupler 88 to the distal end of the upper arm driven link 80. Wrist 84 is a two degree of freedom wrist. A description of some of the features of this type of manipulator as well as a description of an alternative set of links that can be used to position the end effector 110 is contained in U.S. Pat. No. 7,950,306, entitled "MANIPULATOR", issued May 31, 2011 the contents of which are explicitly incorporated herein by reference.

Figure 13A:
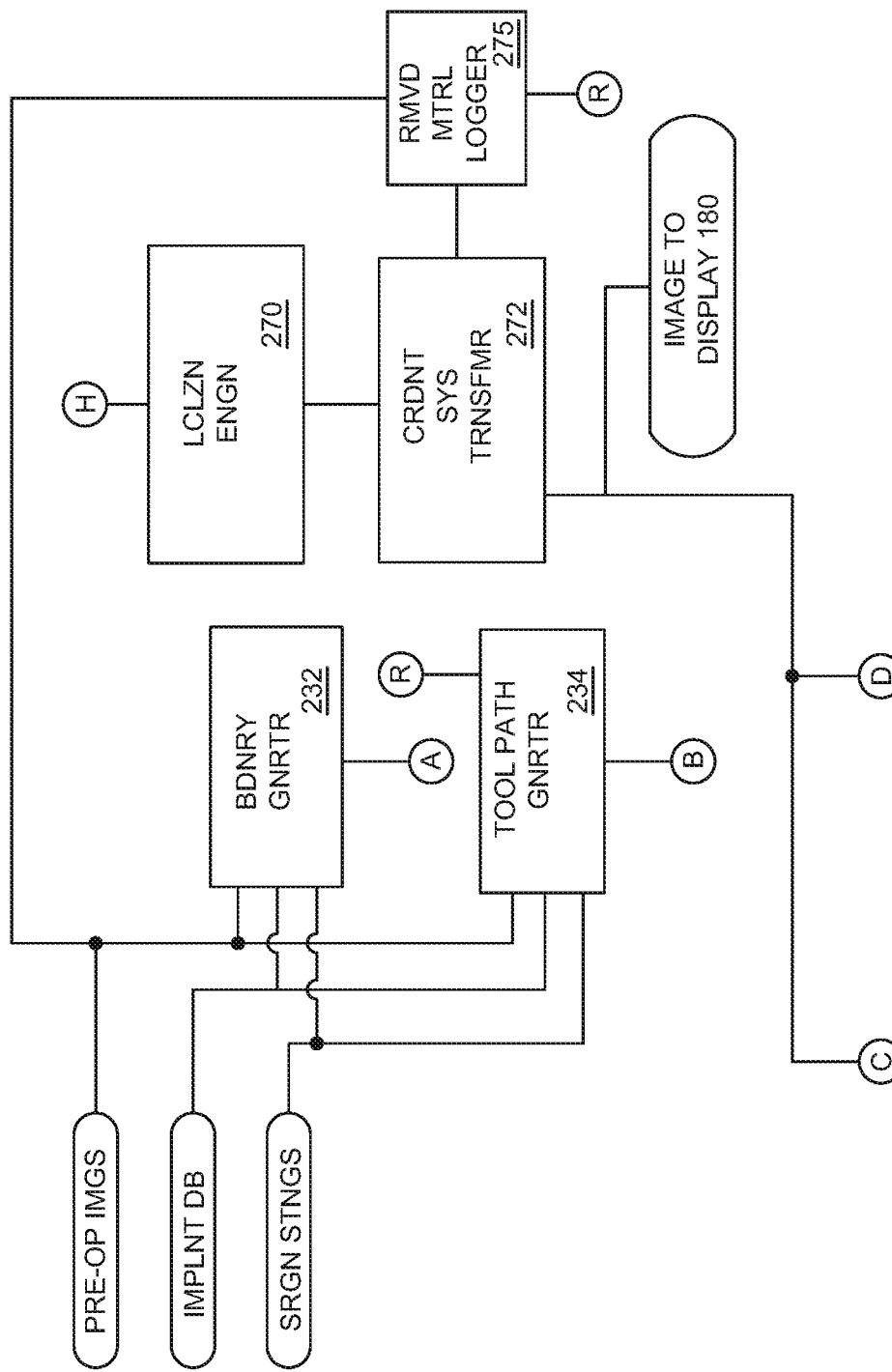
FIG. 13A through 13E form a block diagram of software modules that are run to regulate the actuation of the manipulator.
Figure 13B:
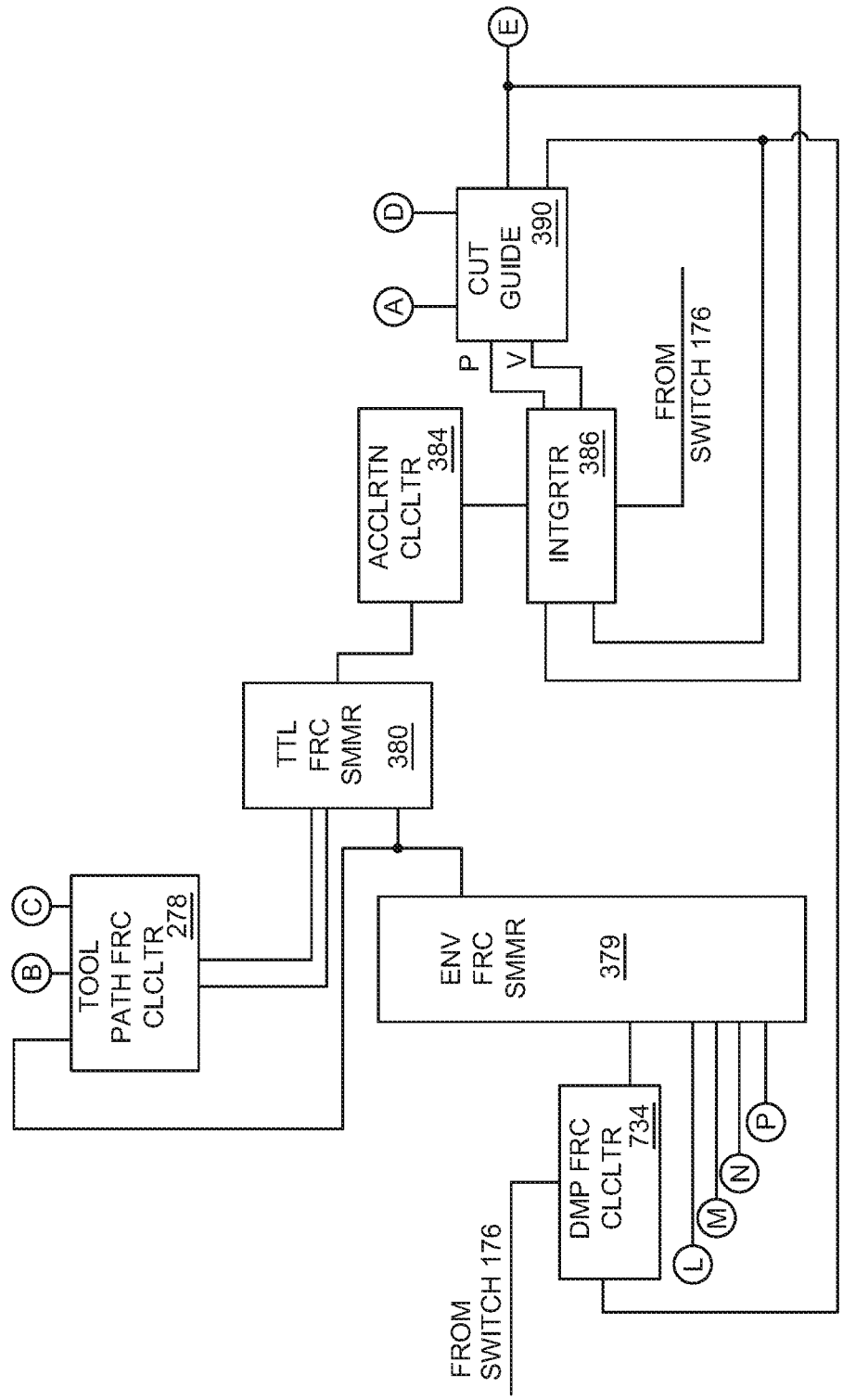
Figure 13C:
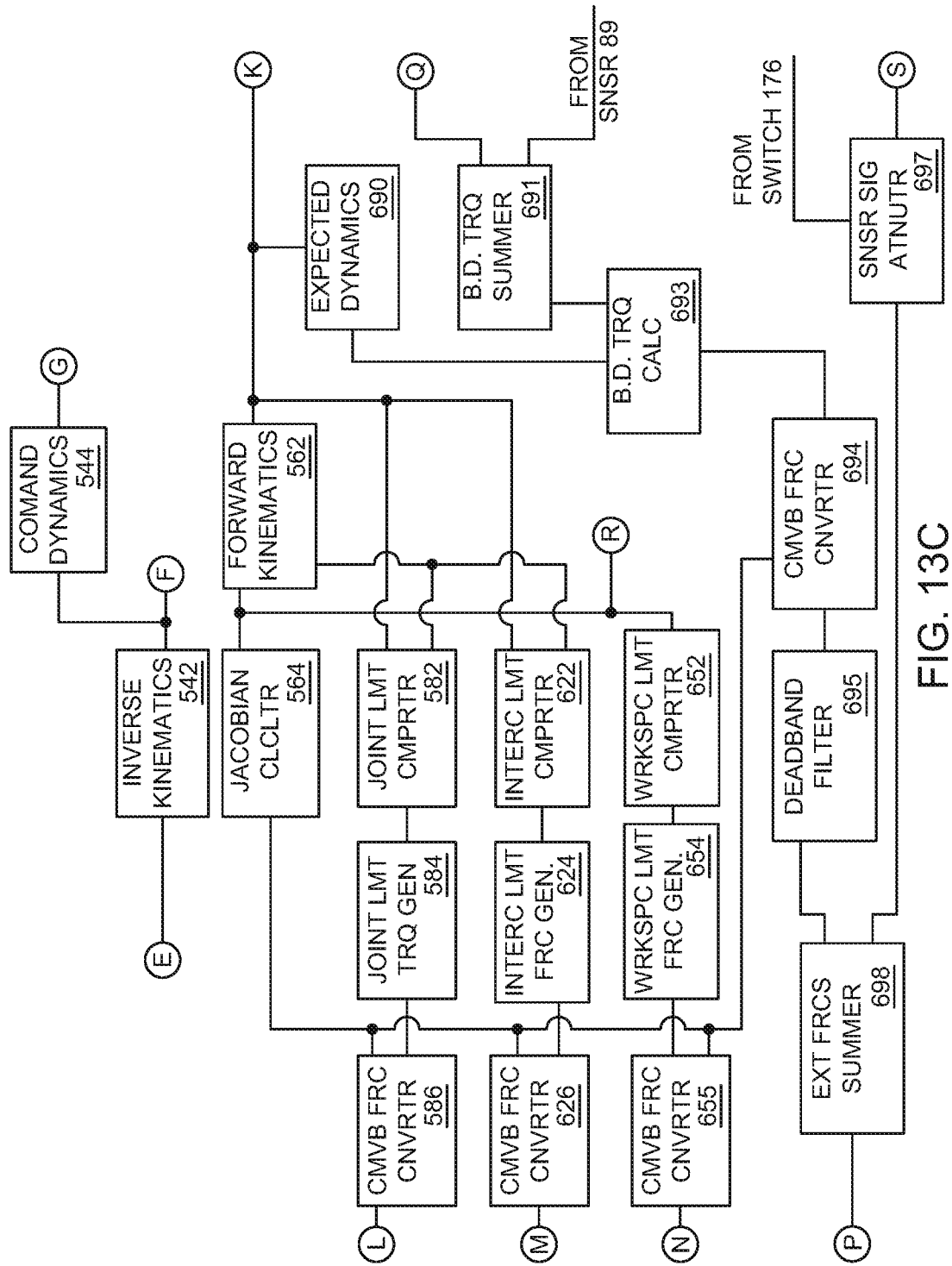
Figure 13D:
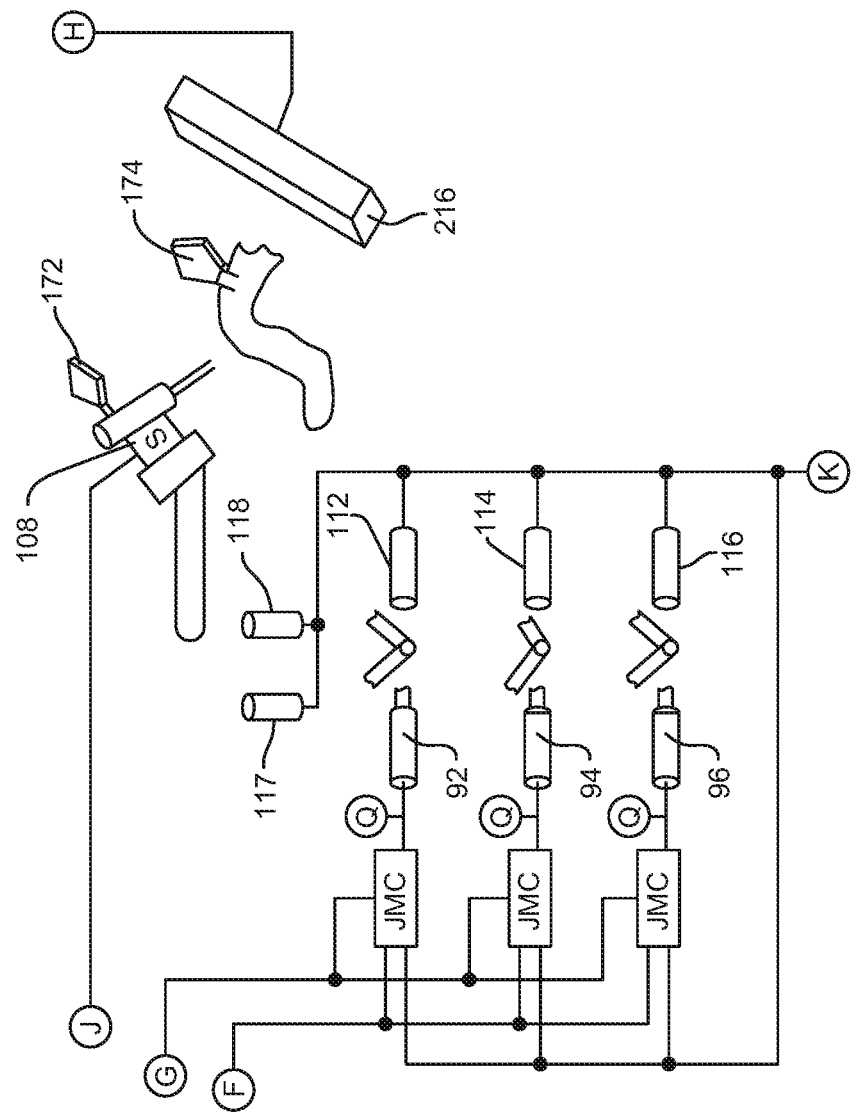
Figure 13E:
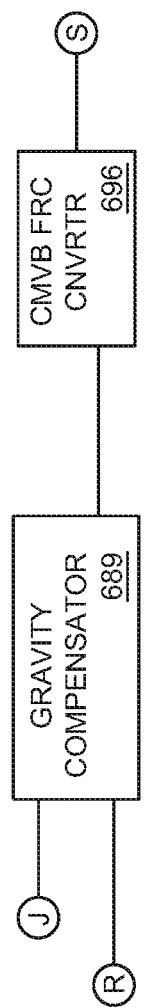

Three actuators 92, 94 and 96, one of each shown diagrammatically in FIG. 13D, are associated with each arm 68 and 70. Each actuator 92 is mounted to the cart frame adjacent the shoulder 72 integral with the associated arm 68 or 70.

Actuators 94 and 96 are mounted in the shoulder 67 or 69 integral with the associated arm 68 or 70. Actuator 94 is connected to the upper link 74 to selectively pivot the upper link. Actuator 96 is connected to the driver link 76 to pivot the driver link 76. The pivoting of the driver link 76 results in the displacement of the attached four bar link 78. The movement of the four bar link 78 results in the pivoting of the attached driven link 80. Specifically, the driven link 80 pivots about the axis around which the driven link 80 is attached to the associated upper link 74. These particular gear assemblies are essentially "zero backlash" gear assemblies. There is essentially no looseness between interlocking gears. This feature of the gears contributes to the precision positioning of the shoulders 72 and links 74, 76, 78 and 80.

Arms 68 and 70 and coupler 88 collectively form an over actuated mechanism. This means the actuation of one link must be accompanied by the corresponding movement of one or more of the other actuated links.

Figure 14:
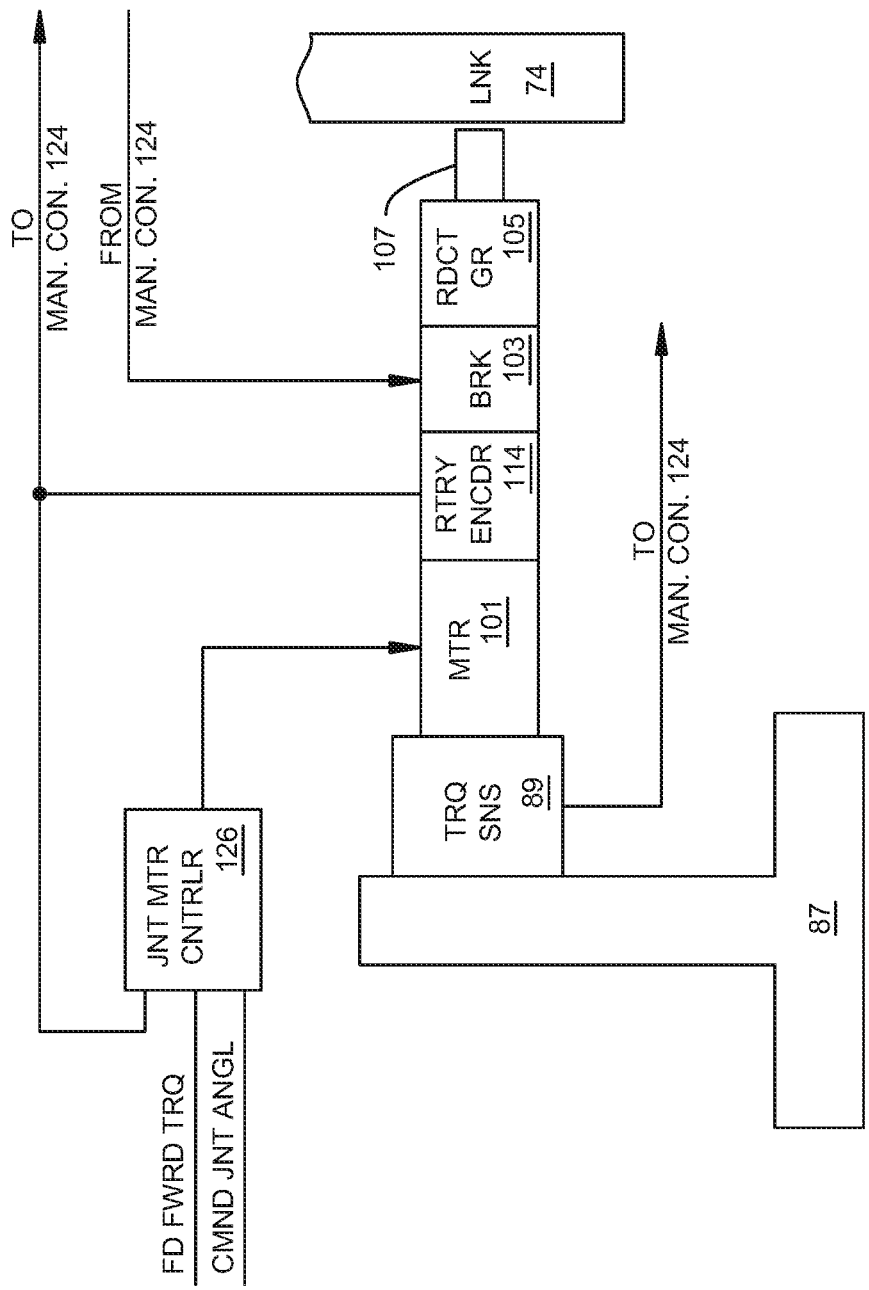
FIG. 14 is a block diagram of the components forming one of the joint actuators.

A number of components are associated with each actuator 92, 94 and 96. FIG. 14 arbitrarily shows the components associated with actuator 94. Specifically, the actuator includes a permanent magnet synchronous motor 101 attached to a structural frame 87 internal to the shoulder 67 or 69. The motor 101 is not attached directly to the frame 87. Instead a torque sensor 89 is located between the frame 87 and motor 101.

Associated with the motor 101 is the below described rotary encoder 114. A brake 103 locks rotation of the motor shaft when the motor is not powered. The locked/unlocked states of the brakes 103 are controlled by the manipulator controller 124. When the manipulator 50 is powered down, manipulator controller 124 sets the brakes 103 from the unlocked to the locked state. Thus, when manipulator 50 is powered down, brakes 103 are the components integral with shoulders 67 and 69 and arms 68 and 70 that prevent movement of the arms.

A reduction gear 105 converts the rotational movement of the output shaft of the motor rotor (not illustrated) into rotational moment that drives the shoulder 67 or 69 or link 74 or 76 to which the motor is attached. In some versions, the reduction gear is a harmonic gear drive. Output shaft 107 of the reduction gear assembly 105 is shown connected to upper link 74. In some versions, the motor, the rotary encoder, the brake and reduction gear assembly are a single unit.

While not shown, integral with each actuator is a transfer gear assembly. The transfer gear assemblies integral with actuators 92 comprises the gears that rotate the associated shoulder 67 or 69. The transfer gear assemblies integral with actuators 94 comprise the gears that pivot the upper links 74. The transfer gear assemblies integral with actuators 96 comprise the gears that pivot the driver link 76. The transfer gear assemblies are essentially "zero backlash" gear assemblies. This means there is essentially no looseness between interlocking gears. This feature of the gear assemblies contributes to the precise positioning of shoulder 67 and 69 and arms 68 and 70.

Associated with each arm 68 and 70 are three of the above mentioned rotary encoders 112, 114 and 116. One of each shown in FIG. 13D. Each rotary encoder 112, 114 and 116 is a sensor that monitors the angular position of one of the three motor driven components of the arm 68 or 70 with which the encoder is associated. Rotary encoder 112 monitors the rotation of the arm shoulder 67 or 69. Rotary encoder 114 monitors the rotation of the arm upper link 74. Rotary encoder 116 monitors the rotation of the arm driver link 76.

In the described version, each rotary encoder 112, 114 and 116 monitors the rotation of the shaft integral with the motor 101 internal to the associated actuators 92, 94 and 96, respectively. (Motor shafts not illustrated). The rotation of each actuator motor shaft is directly proportional to the rotation of the shoulder or arm link driven by the motor. Each rotary encoder 112, 114 and 116 monitors both the extent to which the rotor of the associated motor shaft is rotated as well as the direction of rotation (clockwise or counterclockwise).

In other versions, each encoder 112, 114 and 116 monitors the extent of rotation and rotational direction of one of the gears of the transfer gear assembly that connects the motor shaft to the shoulder or arm link the motor displaces. There is a first order linear relationship between the degrees of rotation of this gear and the joint angle of the joint set by the associated motor. Alternatively, each encoder 112, 114 and 116 is a sensor that directly measures the joint angle of the joint with which the sensor is associated.

In some versions, encoders 112, 114 and 116 are absolute encoders. An absolute encoder, upon start up of the manipulator 50, generates signals that immediately indicate the position of the component (motor rotor shaft or gear shaft) the encoder monitors. In other versions, the encoders are incremental encoders. Upon start up of the manipulator 50, an incremental encoder is set to a zero state. Once set at the zero state, the incremental encoder provides data indicating the extent to which the component the encoder monitors is displaced. With this type of encoder, prior to the use of the manipulator, the arms 68 and 70 may be moved to a home or zero state position. Once the arms are so moved, the incremental counts maintained by the encoders are zeroed out. After the zeroing processing, the incremental counts output by the motor are used to provide an inferential indication of the position of the arms 68 and 70.

In some versions rotary encoders 112, 114 and 116 are multi-turn absolute encoders. This type of absolute encoder, after measuring a full rotation of 360°, outputs a signal indicating that the further present rotational angle is in addition to the first, or additional 3600 of rotation. For example, when the encoder during the third rotation of the shaft being monitored measures a rotation of 10°, the encoder outputs a signal indicating that the shaft has undergone 7300 of rotation.

Manipulator 50 includes two additional encoders, encoder 117 and 118. Encoders 117 and 118 are associated with the driven link 80 integral with upper arm 70. In FIG. 13D, encoders 117 and 118 are depicted internal to the upper arm driven link 80. Encoders 117 and 118 generate signals representative of the angular position of wrist 84 relative to the upper arm driven link 80. As discussed above, wrist 84 rotates in two degrees of freedom relative to the adjacent driven link. Each encoder 117 and 118 generates signals representative of the angular position of the wrist around one of the axes around which the wrist rotates.

The end effector 110 is rigidly attached to coupler 88. In some versions, the end effector is removably attached to coupler 88. While not shown or described in detail, it should be understood that the end effector 110 includes a coupling assembly 111, identified in FIG. 10, which firmly and releasably holds the surgical instrument 160 to the coupler 88. The coupling assembly 111 is designed to ensure that when the instrument is subjected to significant forces, these forces do not cause the slippage of the surgical instrument 160 relative to the end effector 110. The end effector may be capable of movement in one or more degrees of freedom. Such end effectors may include the surgical instruments disclosed in U.S. patent application Ser. No. 13/600,888, entitled, "Surgical Instrument Including Housing, a Cutting Accessory that Extends from the Housing and Actuators that Establish the Position of the Cutting Accessory Relative to the Housing", hereby incorporated by reference.

Also mounted to coupler 88 is a sensor 108, seen symbolically in FIG. 13D. Sensor 108 is configured to output variable signals that are a function of the force and torque to which the end effector 110 is disposed. While the exact structure of sensor 108 is not described herein, it should be understood that the sensor is a six degrees of freedom sensor. Sensor 108 thus outputs signals representative of three mutually orthogonal forces and three torques about the axes of the forces that are applied to the instrument or energy applicator.

Figure 11:
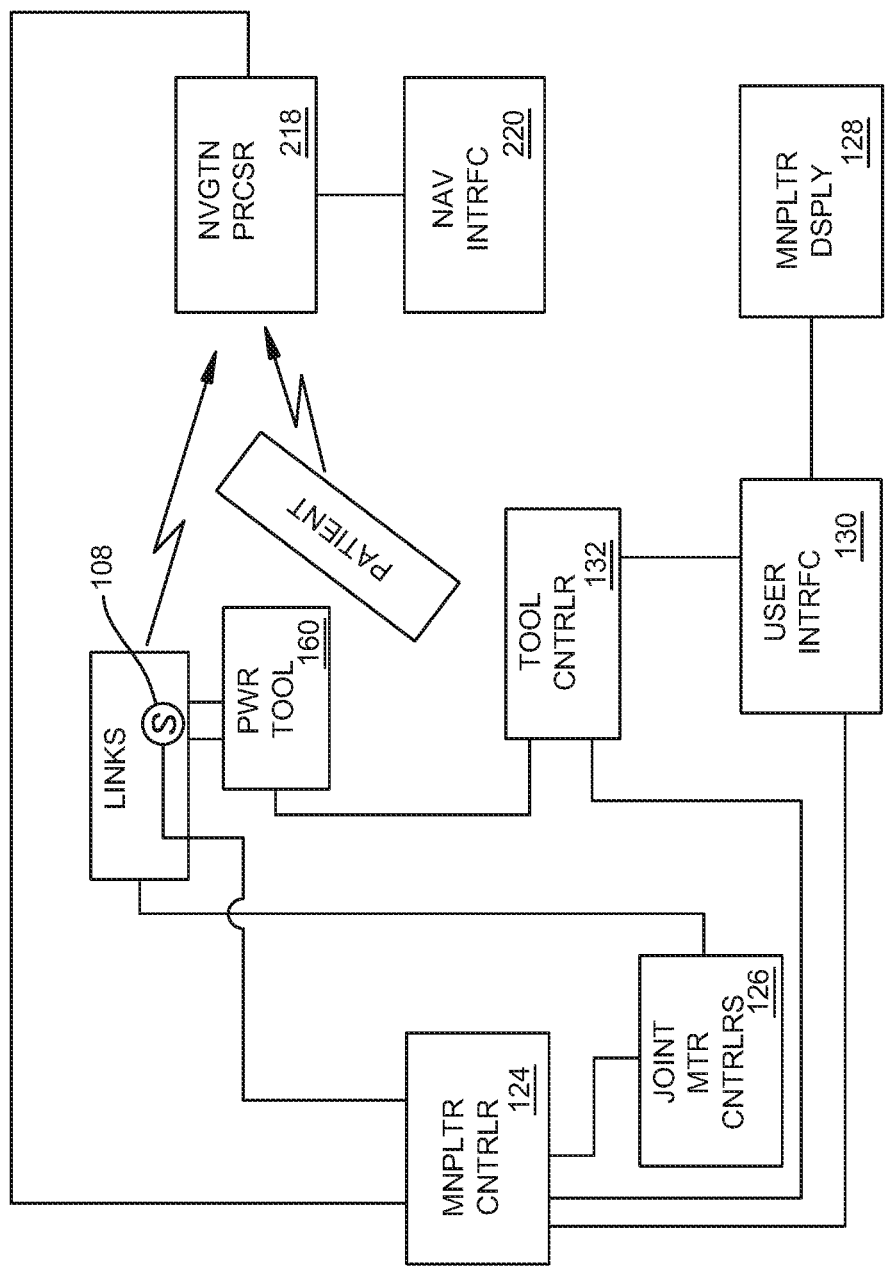
FIG. 11 is a block diagram of a number of the processors that collectively cooperate to control the actuation of the manipulator and attached surgical instrument.

Also mounted to cart 52, is a manipulator controller 124 and joint motor controllers 126, which are depicted in block form in FIG. 11. Manipulator controller 124 can be a high speed general purpose digital computer. One such computer is the iHawk computer available from Concurrent Computer having a x8 SuperMicro motherboard. This computer has dual quad core processors. In some versions, the manipulator controller has less or more processing cores. In still other versions, the manipulator controller 124 has 16 or more processing cores. Manipulator controller 124, typically also has multiple graphical processing units. In one embodiment, manipulator controller 124 determines the location to which the surgical instrument 160 should be moved based on data from force/torque sensor 108, encoders 112, 114, 116, 117 and 118, surgical navigation system 210, as well as other information. Based on this determination, manipulator controller 124 determines the extent to which each arm-forming link needs to be moved in order to reposition the surgical instrument 160. The data regarding where the links are to be positioned are forwarded to the joint motor controllers 126.

Each joint motor controller 126 regulates the application of energization signals to a single one of the joint motors 101. The primary function of the joint motor controller 126 is to apply energization signals to the associated motor 101 so that the motor drives the associated joint to an angle that approaches the below discussed commanded joint angle. The signal from the rotary encoder 114 is employed as a feedback signal representative of the actual joint angle to perform this type of motor regulation. Some controllers 126 calculate the energization signals using cascaded position, speed, and current control loops. Each control loop is often implemented using proportional-integral-derivative control. A signal representative of the feed forward torque is often added to the input of the current control loop to improve the responsiveness of the controller 126.

Internal to the joint motor controller 126 is a drive circuit (not illustrated). A power signal from a power supply integral with the manipulator (power supply not illustrated) is applied to the drive circuit. This drive circuit, in response to the last control loop output signal, converts the power signal into an appropriate energization signal that is applied to the motor 101. In many versions of manipulator 50 the energization signal is in the form of a three phase pulse width modulated (PWM) voltage signal. This signal often has a voltage amplitude of between 10 and 200 Volts and a PWM frequency between 20 and 200 kHz. The drive circuit supplies back to the current control loop the signal representative of the current drawn by the motor 101. This signal is output to other software modules run on the manipulator controller 124 as the measured motor current signal.

When motor 101 is a permanent magnet synchronous motor, controller 124 also regulates the application of the energization signals so the driven currents are in correct phase with rotor position. This is known as motor commutation. Some controllers perform commutation control based on field oriented control techniques. To perform this regulation of the current signals, the joint motor controller 126 relies on the signals that indicate the position of the motor rotor. Signals from the rotary encoders 112, 114 and 116, are used as a feedback signal. In one version, REL-230-36 Motor Controllers from Harmonic Drive LLC of Peabody, Massachusetts are employed as joint motor controllers 126.

A touch screen display 128 or other user input/output unit is also mounted to cart 52. Display 128 is attached to a user interface 130 also attached to the cart. One such user interface 130 is the C6320 Touch Screen from Beckhoff Automation of Verl, Germany. User interface 130 controls the presentation of information on the display 128 and initially processes user-generated commands entered over the display. The majority of these commands are applied to the manipulator controller 124.

User interface 130 is the manipulator processor to which the signals output by pendant 190 are transmitted.

Cart 52 includes a tool controller 132. Tool controller 132 supplies energization signals to the surgical instrument 160. Tool controller 132 typically includes: a power supply; power control circuit; a user interface; an application specific data processing unit (components not illustrated). The power supply converts the line voltage into power signals that can be applied to the surgical instrument 160. The power controller circuit selectively applies the power signals to the power generating unit integral with the instrument 160. The user interface 130 allows the practitioner to enter instructions regarding how he/she wants the instrument to function. The tool controller 132 receives the instructions entered over the user interface and other data necessary to operate the instrument. Based on these data, the tool controller 132 outputs energization signals that cause the instrument to operate in the manner instructed by the practitioner. A more detailed discussion of a tool controller is contained in U.S. Pat. No. 7,422,582, control console to which powered surgical handpieces are connected, the console configured to simultaneously energize more than one and less than all of the handpieces, the contents of which are incorporated herein by reference.

In some versions, the manipulator display 128 functions as the user interface and output display for the tool controller 132. Commands to set and adjust the operational settings of the tool controller 132 and instrument 160 are forwarded from the user interface 130 to the tool controller 132.

Figure 10:
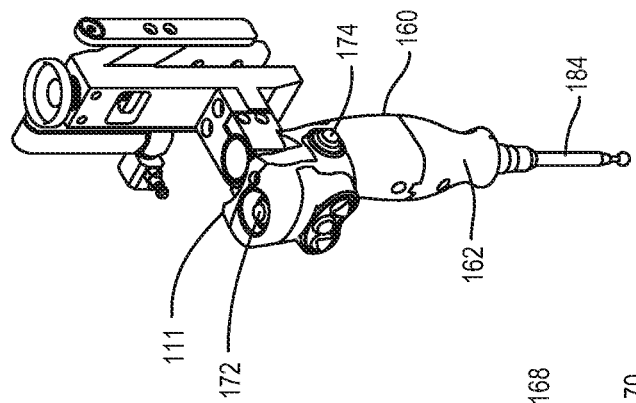
FIG. 10 is perspective view of the end effector and attached surgical instrument.
Figure 9:
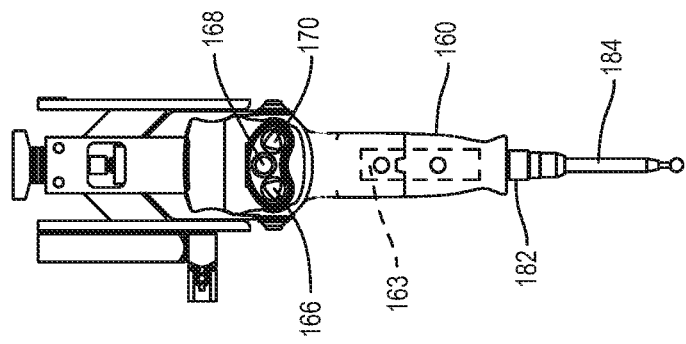
FIG. 9 is a front view of the end effector and attached surgical instrument.
Figure 8:
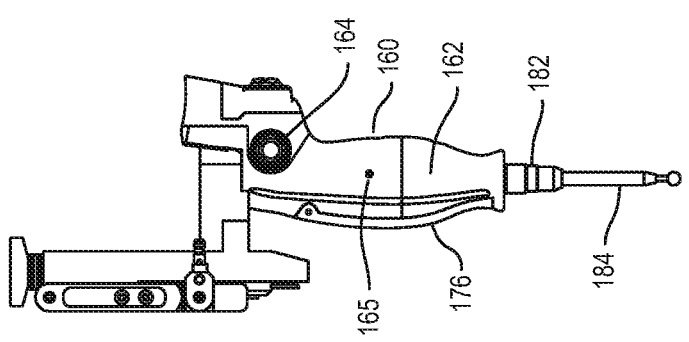
FIG. 8 is a side view of the end effector and a surgical instrument, here a powered drill, attached to the end effector.

Surgical instrument 160, seen in FIGS. 8-10, includes a shell 162 that is the outer body of the instrument. Internal to the shell 162 is a power generating unit 163, represented by a dashed rectangle in FIG. 9. The power generating unit 163 converts the electrical power received from the tool controller 132 into an appropriate form of power. If for example, instrument 160 is a motorized surgical instrument, power generating unit 163 is the instrument motor. If the instrument vibrates, power generating unit 163 is the component that converts the electrical energy that causes the desired mechanical vibrations. If the instrument 160 outputs light (photonic) energy, the power generating unit is the unit that converts the electrical energy into light energy.

Six control buttons are mounted to instrument shell 160. Two buttons, buttons 164 and 174 are mounted to the opposed sides of the shell 160. Buttons 164 and 174 are normally open momentary contact switches that are connected in parallel. When the practitioner wants to actuate the instrument 160, the practitioner depresses either one of the buttons 164 or 174. The open/closed state of the circuit regulated by buttons 164 and 174 are monitored by the user interface 130, connections not shown. Interface 130 forwards these state data to the manipulator controller 124. Manipulator controller 124, based in part on the state of these control members, sends commands to the tool controller 132. Based on these commands, the tool controller 132 selectively applies energization signals to the power generating unit 163 internal to instrument 160. The two buttons 164 and 174 are provided so the practitioner can actuate the instrument 160 by depressing a button located on either side of the instrument.

Buttons 166, 168 and 170 are located on the front face of the instrument shell 162. Buttons 166, 168 and 170 are provided to facilitate operation of the surgical navigation system 210. This particular operation of the surgical navigation system is not part of the present invention.

The sixth button, button 172 is mounted to the top of the instrument. Button 172 is a momentary contact push button switch. As discussed below, button 172 is depressed when the practitioner wants to change the orientation of the instrument when in the semi-autonomous mode. As will be apparent below, the changing of the orientation of the instrument means the repositioning of the instrument and energy applicator 184 so that the both devices pivot around the distal end tip of the energy applicator while the distal end tip of the energy applicator 184 continues to advance along the planned path while in the semi-autonomous mode.

A switch 176, seen in FIG. 8, is pivotally mounted to instrument shell 162. Switch 176 is mounted to the proximally directed side of the shell 162. Switch 176 is a normally open momentary contact switch. Switch 176 is the control member the practitioner depresses when he/she wants to manually set the pose of the instrument. It should be understood that the "pose" of a component is the position and orientation of the component. The open/closed states of button 172 and switch 176 are monitored by manipulator controller 124 and user interface 130, connections not shown.

Extending forward from instrument shell 162 is the energy applicator 184. The energy applicator 184 is the component that applies the energy output by the instrument power generating unit 163 to the site at which the procedure is being performed on the patient. If the power generating unit 163 is a motor, the energy applicator 184 may be a drill, a saw blade or a bur. If the power generating unit is an ultrasonic vibrator, the energy applicator 184 is a tip. If the power generating unit outputs photonic energy, the energy applicator 184 is some sort of member that is transparent to the wavelength of light emitted by the power generator. Generally, the distal end of the energy applicator 184, often referred to as the distal end tip, is the portion of the instrument energy applicator 184 that is applied to the tissue on which the procedure is to be performed.

Many instruments 160 include a coupling assembly, represented by ring 182 in FIG. 9. The coupling assembly releasably holds the energy applicator 184 to the shell 162 and releasably connects the energy applicator 184 to the power generating unit 163.

One motorized surgical instrument that may function as instrument 10 as well as a complementary energy applicator 184 are disclosed in U.S. Pat. No. 6,562,055, Cutting Attachment For Surgical Handpiece Designed To Be Selectively Coupled To The Handpiece, the contents of which are explicitly incorporated herein by reference.

For the manipulator 50 to emulate the positioning of the instrument by the practitioner, it should be appreciated that the instrument and energy applicator 184 are modeled as a virtual rigid body. This virtual rigid body is considered to have a virtual mass. The virtual mass of the virtual rigid body is typically within the same order of magnitude as the actual mass of the instrument 160 and energy applicator 184. Owing to mechanical and electrical limitations, often the virtual mass is greater than the actual mass. By extension, it is understood that the virtual rigid body has its own center of mass. In FIG. 8 this is represented by point 165 which is a point internal to the handpiece shell 162. This is a point that would be perceived as the center of mass of the actual instrument. Often, but not always, this point is on or within the instrument. Here "center of mass" is understood to be the point around which the instrument and energy applicator 184 would rotate if a force is applied to another point of the instrument. The center of mass of the virtual rigid body is close to, but is often not the same as, the actual center of mass of the instrument 160 with the energy applicator 184 attached.

The center of mass of the virtual rigid body can be determined empirically. Once the instrument and energy applicator 184 are attached to the manipulator, the position of the center of mass can be reset to accommodate the preferences of the individual practitioners.

Pendant 190, now described by reference to FIGS. 2A and 2B, is also used to regulate operation of the manipulator 50. Pendant 190 as seen in FIG. 2A, includes a shell 191 shaped to be held in one hand. Three normally open control members are mounted to shell. These control members are used to regulate semi-autonomous operation of the manipulator 50. One control member, trigger 194 is located on the underside of the shell. Trigger 194 is depressed to place the manipulator in the mode in which the manipulator performs semi-autonomous advancement of the instrument 160. The two additional control members, buttons 193 and 195, are located on the top surface of the shell 191. Buttons 193 and 195 regulate the rate at which the manipulator 50, when in the semi-autonomous mode, advances the instrument. One of the buttons, button 193, is depressed to slow the rate of semi-autonomous instrument advancement. Button 195 is depressed to advance the rate of semi-autonomous advancement. The speed at which the instrument engages in semi-autonomous advancement is referred to as the feed rate of the instrument. Ergonomically, pendant 190 is designed so that the practitioner can, with the thumb and fingers of one hand depress trigger 194 and, at the same time, depress either button 193 or button 195.

Pendant 190 includes additional control members (not identified). These members allow the practitioner to enter commands and data into the surgical navigation system 210. A cable 197 connects pendant 190 to cart 52.

The surgical navigation system 210 used with manipulator 50 of this invention is now described by reference to FIGS. 1, 11 and 13D. Surgical navigation system 210 includes one tracker, tracker 212, that is firmly affixed to the patient 600. Often tracker 212 is firmly affixed to a section of bone adjacent where the tissue to which the instrument energy applicator 184 is to be applied.

A second tracker, tracker 214, seen in FIG. 1, is firmly attached to the end effector 110. Since the instrument positioned by the manipulator 50 is firmly attached to the end effector, tracker 214 is sometimes referred to as the tool tracker.

A localizer 216 receives signals from or transmits signals to the trackers 212 and 214. If the localizer 216 receives light signals from the trackers 212 and 214, the localizer may be called a camera. The surgical navigation system also includes a navigation processor 218. If the localizer 216 receives signals from the trackers 212 and 214, the localizer outputs to the processor 218 signals based on the position and orientation of the trackers to the localizer (localizer to processor 218 connection not shown). If the trackers 212 and 214 receive signals from the localizer 216, the trackers output to the processor 218 signals based on the position and orientation of the trackers to the localizer. Based on the received signals, navigation processor 218 generates data indicating the relative positions and orientations of the trackers 212 and 214 to the localizer 216. In some versions, the surgical navigation system 210 could include the trackers, sensor system, localizer, and/or computer system disclosed in U.S. Pat. No. 7,725,162 to Malackowski et al., issued on May 25, 2010, entitled, "Surgery System", hereby incorporated by reference.

As discussed below, prior to the start of the procedure, additional data are loaded into the navigation processor 218. Based on the position and orientation of the trackers 212 and 214 and the previously loaded data, navigation processor 218 determines the position of the distal end of instrument energy applicator 184 and the orientation of the instrument relative to the tissue against which the energy applicator 184 is to be applied. Navigation processor 218 forwards these data to the manipulator controller 124.

The navigation processor 218 also generates image signals that indicate the relative position of the instrument energy applicator 184 to the surgical site. These image signals are applied to an interface 220, also part of the surgical navigation system 210. Interface 220, based on these signals, generates images that allow the practitioner to view the relative position of the instrument energy applicator 184 to the surgical site. Interface 220 includes a touch screen or other input/output device that allows entry of commands.

Figure 12:
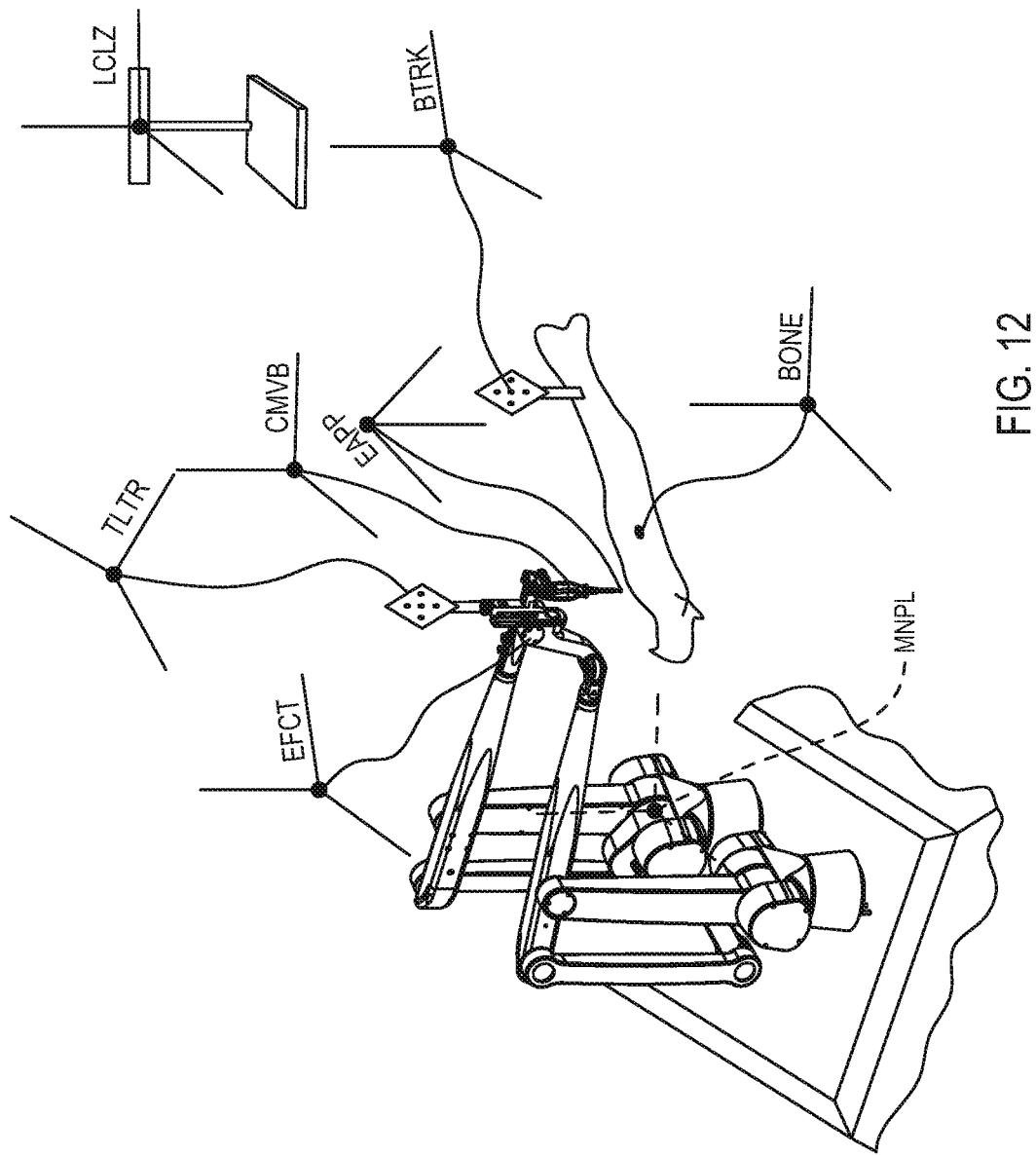
FIG. 12 is a diagrammatic illustration of the different coordinate systems associated with the patient and the elements that regulate the actuation of the manipulator.

Manipulator controller 124 and navigation processor 218 cooperate to position the end effector 110 so that the energy applicator 184 is appropriately positioned at the site at which the procedure is to be performed on the patient 600. As part of this positioning, manipulator controller 124 does not position the energy applicator 184 outside of defined boundaries. To perform this process, controller 124 and processor 218 collectively keep track of the poses of a number of different system components and the patient 600. Each component pose can be considered tracked relative to a world coordinate system. The world coordinate system has an origin and an orientation (i.e., a set of X- Y- and Z-axes) that, for the procedure being performed, are both static. The coordinate system of the manipulator 50 is the world coordinate system, MNPL, as seen in FIG. 12. In one version, the origin of manipulator coordinate system MNPL is a point along the axis through the shoulder 69 associated with upper arm 70. This point is the intersection of the axis around which the shoulder 69 rotates and the axes around which the arm links 74 and 76 rotate. In FIG. 12, to distinguish between the structure of the manipulator upper arm 70 and the manipulator coordinate system MNPL, the coordinate system is shown in dashed lines.

A second static coordinate system that is associated with this invention is the coordinate system of the localizer 216, LCLZ.

Each tracked component has its own coordinate system separate from coordinate system MNPL and coordinate system LCLZ. Each of these coordinate systems has an origin that can be identified as a point relative to the origin of the manipulator coordinate system MNPL. A vector defines the position of the origin of each of these coordinate systems relative to another one of the other coordinate systems. The location of a coordinate system is thus understood to be the location of the origin of the coordinate system. Each of these coordinate systems also has an orientation that, more often than not, is different from the orientation of manipulator coordinate system MNPL. The orientation of a coordinate system can be considered the angular positions of the X-, Y- and Z-axes of the coordinate system relative to the corresponding axes of the manipulator coordinate system MNPL. A rotation matrix describes the orientation of a coordinate system relative to another coordinate system. The rotation matrix consists of the unit vectors of the axis of one coordinate system expressed in the other coordinate system. The position vector and the rotation matrix that define the relation of one coordinate system to another collectively form the homogenous transformation matrix. The symbol $^{i-1}_{i}T$ is the notation for the homogenous transformation matrix that identifies the position and orientation of coordinate system i with respect to coordinate system i−1.

Two components of the system that have their own coordinate systems are the bone tracker 212 and the tool tracker 214. In FIG. 12 these coordinate systems are represented as, respectively, bone tracker coordinate system BTRK and tool tracker coordinate system TLTR.

Navigation system 210 monitors the position of the patient 600 by monitoring the position of bone tracker 212, the tracker firmly attached to bone of the patient 600. The patient's coordinate system is considered to be the bone coordinate system BONE, the coordinate system of the bone to which the bone tracker 212 is firmly attached. Prior to the start of the procedure, pre-operative images of the location of the site on the patient at which the procedures are performed are generated. These images may be based on MRI scans, radiological scans or computed tomography (CT) scans of the surgical site. These images are mapped to the bone coordinate system BONE using methods not material to the present invention. These images are fixed in the bone coordinate system BONE.

During the initial phase of the procedure, the bone tracker 212 is firmly affixed to the bone of the patient. Using process steps not part of the present invention, the pose of coordinate system BONE is mapped to coordinate system BTRK. Given the fixed relationship between the bone and the bone tracker 212, the pose of coordinate system BONE remains fixed relative to coordinate system BTRK throughout the procedure. The pose-describing data are stored in memory integral with both manipulator controller 124 and navigation processor 218.

In addition to coordinate system MNPL, there are additional coordinate systems associated with the manipulator 50. The end effector 110 has its own coordinate system, coordinate system EFCT. There is also a coordinate system associated with the virtual model of the instrument 160. This coordinate system has its origin at the center of mass of the virtual rigid body. Given the origin of this coordinate system, this coordinate system is referred to as coordinate system CMVB. The Z-axis of instrument coordinate system CMVB is centered on the longitudinal axis that extends through the instrument 160 and the energy applicator 184. The energy applicator 184 has its own coordinate system, system EAPP. The origin of the coordinate system EAPP is the distal end tip of the energy applicator 184. The Z-axis of the energy applicator 184 coordinate system EAPP is aligned with the longitudinal axis of the energy applicator 184. This Z-axis extends outwardly away from the distal end tip of the energy applicator 184. This is why in FIG. 12 the Z-axis of coordinate system EAPP is shown with an orientation that is generally in the negative direction of the Z-axes of the other coordinate systems. An additional coordinate system associated with manipulator 50 is the previously described coordinate system of the tool tracker 214, system TLTR.

Not depicted in FIG. 12 are representations of some of the minor coordinate systems. As discussed below, these coordinate systems are only referenced occasionally during the operation of the manipulator. These coordinate systems are not illustrated in FIG. 12 to reduce the complexity of this Figure.

It should be appreciated that, upon assembly of the components of this invention for use, the poses of coordinate system EFCT, the virtual rigid body coordinate system CMVB, the energy applicator coordinate system EAPP and the tool tracker coordinate system TLTR are fixed relative to each other. Accordingly, upon assembly of the components, the poses of these coordinate systems relative to each other are determined. These coordinate system and pose data are stored in a memory integral with the end effector 110, coupling assembly 111, instrument 160 or energy applicator 184. There may be some versions where these data are stored in the memory integral to the manipulator controller 124.

III. Software

FIG. 13A through 13E depict basic software modules executed by the manipulator controller 124 and navigation processor 218. FIGS. 13A through 13E also represent how the software modules interact with hardware to actuate the manipulator so surgical instrument 160 is displaced.

FIG. 13A depicts some software modules run on the navigation processor 218. One of these modules is the boundary generator (BDNRY GNRTR) 232. Boundary generator 232 is a software module that generates a map that defines one or more boundaries between the tissue to which the instrument energy applicator 184 should be applied and the tissue to which the energy applicator 184 should not be applied. This boundary is typically generated when energy applicator 184 is used to remove a volume of tissue. These types of energy applicators include, but are not limited to: burs; drill bits; saw blades; ultrasonic vibrating tips; electrode tips; RF electrodes; cauterizing and ablation tips; and light emitting tips.

An input into the boundary generator 232 includes the preoperative images (PRE-OP IMGS) of the site on which the procedure is to be performed. If the manipulator is used to selectively remove tissue so the patient can be fitted with an implant, a second input into the boundary generator 232 is a map of the shape of the implant. The initial version of this map may come from an implant database (IMPNT DB). This is because the shape of the implant defines the boundaries of the tissue that should be removed to receive the implant. This relationship is especially true if the implant is an orthopedic implant intended to be fitted to the bone of the patient.

A third input into boundary generator 232 is the surgeon's settings (SRGN STNGS). These settings include the practitioner's settings indicating to which tissue the energy applicator 184 should be applied. If the energy applicator 184 is used to remove tissue, the settings identify the boundaries between the tissue to be removed and the tissue that remains after application of the energy applicator 184. If the manipulator 50 is used to assist in the fitting of a orthopedic implant, these settings define where over the tissue the implant should be positioned. These settings may be entered preoperatively using a data processing unit. Alternatively, these settings may be entered through an input/output unit associated with one of the components of the system such as with navigation interface 220.

Based on the above input data and instructions, boundary generator 232 generates a map that defines the instrument energy applicator 184 boundaries.

In practice, prior to the start of the procedure an initial version of the map may be set by the practitioner at the surgical site. At the start of the procedure, data that more precisely defines the implant that is to be actually fitted to the patient is loaded into the boundary generator 232. These data may come from a storage device associated with the implant such as a memory stick or an RFID tag. For ease of understanding the invention, these data can be considered a component of the implant database data supplied to the boundary generator 232. These data are based on post manufacture measurements of the specific implant. These data provide a definition of the shape of the specific implant that, due to manufacturing variations, may be slightly different than the previously available stock definition of implant shape. Based on this implant-specific data, the boundary generator 232 generates a final definition of the cutting guide, the boundaries between the tissue to be removed and the tissue that should remain in place. Implants that could be implanted into the patient include those shown in U.S. patent application Ser. No. 13/530,927, filed on Jun. 22, 2012 and entitled, "Prosthetic Implant and Method of Implantation", hereby incorporated by reference. The implants disclosed in this patent application could thus be used to define the cutting guide and thereafter be implanted in the patient after the appropriate amount of material, such as bone, is removed. Other implants are also contemplated.

In one version, the boundary generator 232 generates the boundary between the tissue that is to be excised and the tissue that is to remain in place as a set of contiguous defined surface areas. In one more specific version, these surface areas are polygons. More particularly, these surface areas are triangles. The corners of each polygon are defined by points in the bone coordinate system BONE. In FIG. 15A, surface 242 is the boundary between where tissue is to be removed and the tissue that is to remain in place. Sometimes the boundary is referred to as a mesh. An individual area section that defines a portion of the boundary or mesh is referred to as a tile.

A tool path generator (TOOL PATH GNRTR) 234 is a second software module run on the navigation processor 218. Tool path generator 234 receives the same general inputs as those applied to the boundary generator 232. Based on these inputs, the tool path generator 234 generates a tool path 248 as seen in FIGS. 15A and 15B. FIG. 15A represents a bone 202, a section of which is to be removed to receive an implant. Surface 242 is a boundary beyond which the energy applicator 184 should not be applied. Surface 242 is therefore also the outline of the bone 202 remaining after the removal procedure, the bone to which the implant is to be mounted. Dashed line 244 represents the perimeter of the bone that is to be removed using manipulator 50. In FIG. 15A the tool path is represented by the back and forth line 248. The smoothness and quality of the finished surface depends in part of the relative positioning of the back and forth line 248. More specifically, the closer together each back and forth pass of the line, the more precise and smooth is the finished surface.

In addition, the configuration of the tool path 248 also contributes to the quality of the finished surface. For example, in one path configuration, the circumference of the surface boundary is cut first with the tool path migrating inward toward the center. In this configuration, there is no allowance for the outflow of the removed material. In another configuration, the tool path starts at the center of the section of bone to be removed and proceeds in an outward direction. In this way, the removed material has outflow path and does not interfere with the removal process.

In FIG. 15A the tool path 248 is shown as only being within the perimeter of the tissue being removed. The location of the tool path 248 is a function of the geometry of the distal end of the energy applicator 184. For example, the center of the distal end of the energy applicator 184 may be the origin of coordinate system EAPP. In this implementation, when the tool path is generated, the tool path generator 232 accounts for the fact that the energy applicator 184 actually extends beyond the origin of coordinate system EAPP. If the energy applicator 184 is a spherical bur, this means that the tool path segments closest to boundary 242 are typically spaced away from boundary a distance at least equal to the radius of the bur head.

Tool path 248 is not plotted in a single plane. In FIG. 15B tool path 248 is shown as comprising a number of layers wherein top most segments are shown as set of solid connected lines and dashed lines represent segments located below the top segments.

Figure 15C:
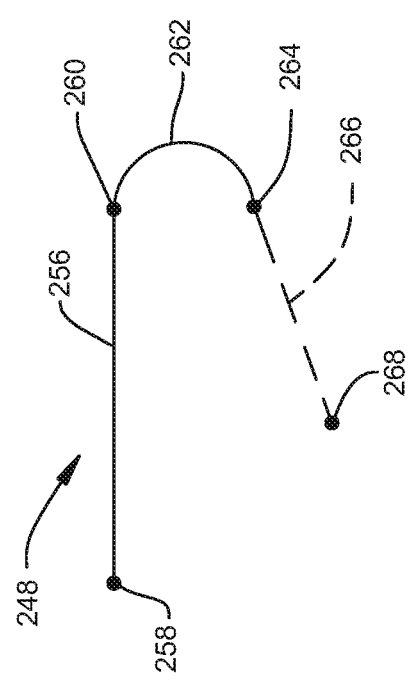
FIG. 15C illustrates how a single tool path may comprises a set of path segments of different length and orientation.

As seen in FIG. 15C, the tool path 248 includes a number of path segments. Each segment includes the set of points along which the origin of coordinate system EAPP should travel. As seen in the Figure, individual segments 256, 262 and 266 may be straight or curved. Each segment 256, 262 and 266 has an origin and a terminus. Point 258, is both the origin of tool path 248 and the origin of segment 256. The terminus of one segment will be the origin of the abutting segment. Thus, point 260 is both the terminus of segment 256 and the origin of segment 262. Point 264, is the terminus of segment 262 and the origin of segment 266. Point 268 is the terminus of segment 266. Point 268 may also be the terminus of tool path 248 and the origin of another tool path that is not illustrated. In FIG. 15C, segment 266 is depicted as a sequence of dashed lines, from origin to terminus, of decreasing size. This is to diagrammatically depict that the path in addition to having X and Y components, has a Z component that is into or out of the page on which FIG. 15C is depicted.

Tool path generator 234 receives as inputs the image of the tissue, data defining the shape of the boundary, and the surgeon's setting regarding the location of the boundary. For an orthopedic surgical procedure, the boundary is typically the shape of the implant; the surgeon setting is often the position of the implant. Based on these data, the tool path generator 234 defines the tool path 248. Each tool path segment 256, 262 and 266 is defined as a vector or a curve that extends between points present in bone coordinate system BONE. It should be understood that the path segments are defined in three dimensions. This is because the instrument energy applicator 184 is not just applied in a single plane to the tissue. The energy applicator 184 also moves up or down in order to contact tissue in the plane above or below the plane in which it is presently located.

Once a procedure begins, the tool path generator 234 receives additional data. These data are the data from the below described removed material logger 275 that identifies the sections of the tissue to which the energy applicator 184 has been applied. Based on these data, the tool path generator 234 revises the path segments of the tool path. These revisions are performed to avoid the generation of path segments that would have the energy applicator 184 transit through spaces left void as a consequence of the previous removal of tissue. Adaptation or revision of the cutting path may include a high velocity jump wherein the energy applicator 184 jumps across a known gap in the volume of removed tissue (also referred to as a sub-volume) at a high velocity. Revision of the cutting path may also include a circuitous path that routes around areas where bone has been previously removed. Further, adaptation of the cutting path may also include sub-volume areas that are labeled as complete and would not be part of any autonomous cutting path if that mode was used to complete any part of the remaining bone removal.

A localization engine 270 is a third software module that can be considered part of the surgical navigation system 210. In some versions, the localization engine 270 is run on the manipulator controller 124. Components of the localization engine 270 may also run on navigation processor 218. Localization engine 270 receives as inputs the signals localizer 216 outputs as a function of the signals received from trackers 212 and 214. Based on these signals received from the bone tracker 212, localization engine 270 determines the pose of the bone coordinate system BONE relative to the localizer coordinate system LCLZ. Based on the signals received from the tool tracker 214, the localization engine 270 determines the pose of the tool tracker coordinate system TLTR relative to the localizer coordinate system LCLZ.

The localization engine 270 forwards the signals representative of the poses of trackers 212 and 214 to a coordinate transformer 272. Coordinate transformer 272 is a navigation system software module that runs on navigation processor 218. Coordinate transformer 272 is a software module that references the data that defines the relationship between the preoperative images of the patient and the patient tracker 212. Coordinate transformer 272 also stores the data indicating the pose of the instrument energy applicator 184 relative to the tool tracker 214.

Navigation processor 218 includes the removed material logger 275. The removed material logger 275 contains a map of the volume of the tissue to which the energy applicator 184 is to be applied. Often this is a map of a volume of tissue that is to be removed. In FIG. 13A, this map is shown being based on the preoperative images of the patient. Other data that goes into maintaining this map may come from the data describing the shape of the implant and the personal setting of the surgeon, connections not shown. Other sources of data for defining this volume including mapping data obtained at the start of the procedure. These data may be obtained by applying a pointer to landmarks on the tissue to which the energy applicator 184 is to be applied.

Logger 275 also collects data identifying the on-patient locations to which the energy applicator 184 is applied. In one implementation of this invention, these data are the data that describes the locations to which the end effector and, by extension, the energy applicator 184, have advanced. These data may be based on the below described data from the manipulator that tracks the movement of the arms 68 and 70. These data may be based on the commanded or measured pose data. Alternatively, these data may be generated based on the data describing the movement of the tool tracker. Logger 275 transforms these data regarding movement of the end effector and the tool tracker into data that defines where, relative to the bone 202, the energy applicator 184 has moved. Logger 275 stores these data.

Based on these data, the logger 275 generates image data suitable for presentation on one of the displays that indicates the extent to which the energy applicator 184 has been applied to the tissue. These image data may be presented on navigation interface 220. The images present by the logger may indicate surface sections of tissue to which the energy applicator 184 has not been applied and sections of tissue to which the energy applicator 184 has been applied. The images presented by the logger also identify the sections of tissue to which it is not necessary to apply the energy applicator 184; the tissue outside of the boundary area. This tissue includes tissue beyond the boundaries exposed by the removal of tissue.

Logger 275 provides data indicating the sections of the tissue to which the energy applicator 184 has and has not been applied to the tool path generator 234.

As mentioned above, the pose of coordinate system EAPP is typically fixed relative to coordinate system TLTR. The location of patient's tissue and the representation of the tissue are typically fixed relative to the bone tracker coordinate system BTRK.

During the procedure, the coordinate transformer 272 receives the data indicating the relative poses of the trackers 212 and 214 to the localizer 216. Based on these data and the previous loaded data, the coordinate transformer 272 generates data indicating the relative position and orientation of both the origin of coordinate system EAPP, and the bone tracker coordinate system, BTRK to the manipulator coordinate system MNPL. Based on these data, coordinate transformer 272 generates data indicating the position and orientation of the distal end of the energy applicator 184 relative to the tissue against which the instrument is applied. Image signals representative of these data are forwarded to interface 220 enabling the surgeon to view this information.

Two additional sets of software modules are run on the manipulator controller 124. One set of software modules perform behavior control. Behavior control is the process of generating instructions that indicate the next commanded pose for the energy applicator 184.

The second set of software modules perform what is known as motion control. One aspect of motion control is the control of the manipulator 50. In the below discussed motion control process, the motion control process receives data defining the next commanded pose of the energy applicator 184 from the behavior control process. Based on these data, the motion control process determines the next position of the joint angles of manipulator 50. A second aspect of motion control is the providing feedback to the behavior control modules based on the constraints of the manipulator. These constraints include the joint angle limits of the manipulator and the goal of insuring that plural links do not move closer than a minimum distance towards each other. A further component of this feedback control is the ensuring that the energy applicator 184 is kept within a defined workspace boundary. Movement of energy applicator 184 is limited to the area within this workspace boundary to ensure that the dexterity of the instrument 160 is not diminished. The motion control modules also monitor the state of the manipulator 50 to detect if external forces/torques are being applied to or objects are in contact with the manipulator 50 or instrument 160.

Feedback data generated by the motion control processes are applied to the behavior control processes. Based on these data, the behavior control processes adjusts the manipulator's movement of the instrument and energy applicator 184. The behavior control processors perform this adjustment by using these data as variables for establishing the next commanded pose for the energy applicator 184. Once this next commanded pose is established, the motion control processes cause the manipulator 50 to advance the energy applicator 184 towards this position.

FIG. 13B depicts the software modules that form the behavior control processes. One of these modules is the tool path force calculator (TOOL PATH FRC CLCLTR) 278. Tool path force calculator 278 calculates two variables. A first one of these variables are the forces and torques that when applied to the virtual rigid body, results in the advancement of the distal end of the energy applicator 184. The second one of these variables are forces and torques applied to the virtual rigid body to maintain the orientation of the instrument 160 within an acceptable range of orientations. Tool path force calculator 278 includes a number of sub modules.

Figure 16A:
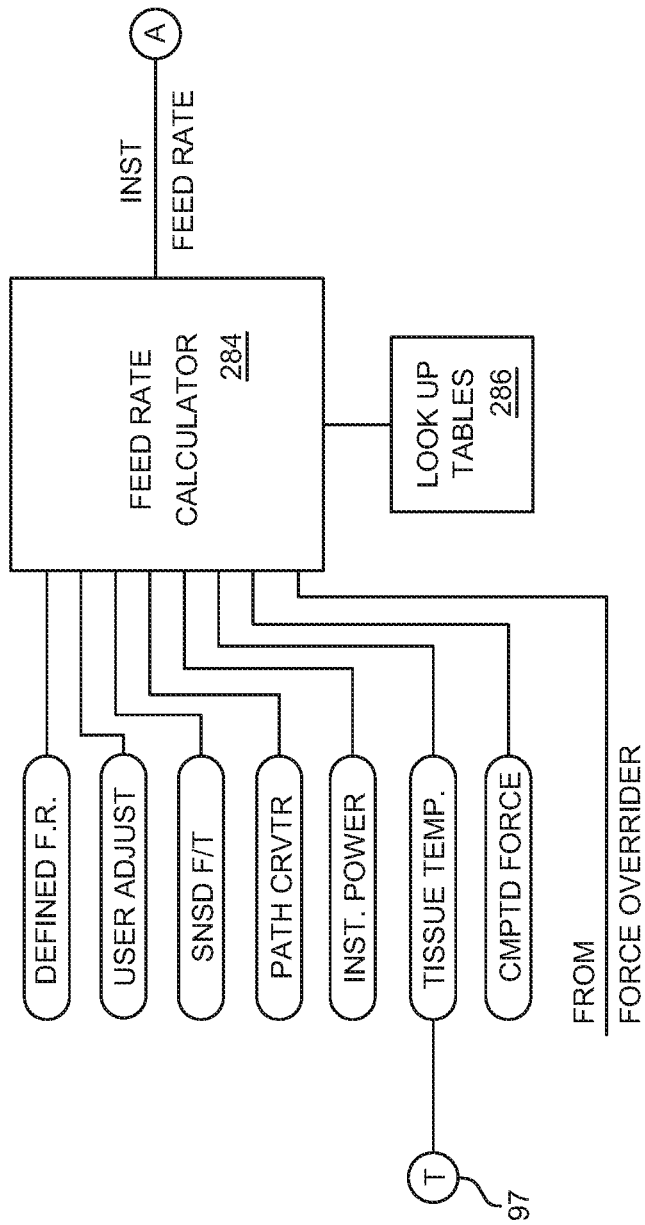

One of the modules that form the tool path force calculator 278 is the feed rate calculator 284, as seen in FIG. 16A. Feed rate calculator 284 determines the velocity, referred to as the instrument feed rate, at which the distal end of the energy applicator 184 should move as it travels along an individual path segment. The primary input into the feed rate calculator 284 is the defined feed rate (DEFINED F.R.) In its most fundamental form, the defined feed rate is a scalar value. In practice, the manipulator controller 124 is often provided with plural defined feed rates. A specific defined feed rate is assigned to each path segment. This feed rate assignment may be performed preoperatively. The feed rates can then be adjusted at the start of or during the procedure. Two or more contiguous path segments may be assigned the same defined feed rate. These feed rates are generated based on variables such as: the shape of the void space; the type of energy applicator 184; the health of the patient; the nature of the tissue to which the energy applicator 184 is applied; and the geometry of the path segment. In practice, the defined feed rate is typically between 5 and 400 mm/sec.

In practice, the defined feed rate is generated by the tool path generator 234, connection not shown.

Feed rate calculator 284 adjusts the defined feed rate to produce the instrument feed rate. In one version, this adjustment is performed by multiplying the defined feed rate by a number of coefficients. Each coefficient is generally between 0 and 1.0. Coefficients may have values that exceed 1.0. Each of these coefficients changes as a function of a variable that is also applied to the feed rate calculator 284. The first of these variables is the user adjustment (USER ADJUST) of the feed rate. This is the adjustment of the feed rate that the practitioner performs, in real time, as the procedure progresses. The practitioner makes this adjustment of the feed rate by depressing pendant buttons 193 and 195. The feed rate calculator 284 outputs a coefficient as a function of the practitioner entered command to increase or decrease the instrument feed rate.

A second variable used to selectively scale the defined feed rate is force and torque to which the energy applicator 184 is exposed (SNSD F/T). The energy applicator 184 is rigidly attached to the instrument 160 and the instrument is rigidly attached to the end effector 110. Accordingly, the signals output by the end effector force/torque sensor 108 are the signals representative of the forces and torques to which energy applicator 184 is exposed. Feed rate calculator 284 sets the instrument rate based on the principle that there is relationship between the amount of force/torque that the manipulator applies to the instrument and energy applicator 184 and the rate of instrument advancement. Generally, it is a goal of modern medical practice to minimize the heating of tissue that is not being removed. One reason for this goal is to minimize the attendant damage this needless heating can cause to the tissue. Accordingly, manipulator 50 of this invention is configured to, when it is determined that an appreciable amount of force and/or torque is applied to the instrument or energy applicator 184, slow the advancement of the instrument along the path segment.

One example of where this adjustment of instrument feed rate is useful is when the energy applicator 184 travels across a path segment through both cortical bone and cancellous bone. Cortical bone, the outer bone, is relatively hard. Cancellous bone, the inner bone, is more porous and less resistant to removal than cortical bone. Accordingly, if the energy applicator 184 moves across both types of bone at a constant speed, more force/torque is needed to be applied to move the applicator across the cortical bone than the cancellous bone. This means that, without adjustment of instrument speed, the cortical bone would be subject to more potentially damage inducing heating than the adjacent section of cancellous bone. This feature of the manipulator of this invention minimizes this potential for the unwanted heating by slowing the rate of advancement for the instrument energy applicator 184 when the force/torque sensor 108 provides signals indicating that the amount of force/torque required to advance the instrument increases.

Once the energy applicator 184 moves from cutting the cortical bone to cancellous bone, the force/torque required to advance the instrument decreases. In this situation, the rate at which the instrument is advanced can be speeded up without appreciably increasing the extent to which the bone to which the energy applicator 184 is applied is heated. The feed rate calculator 284 therefore increases the calculated rate of the advancement of the instrument. This reduces the amount of time it takes to perform the procedure on the patient. This is desirable because it is a further goal of modem surgical practice to minimize the time it takes to perform the procedure on the patient. One reason this time minimization is desired is because it lessens the amount of time the patient's internal tissue is exposed and open to infection. Also, performing the procedure as quickly as possible lessens both the likelihood of surgeon fatigue and the amount of time the patient must be held under anesthesia.

Feed rate calculator 284 determines a force/torque adjustment coefficient as based on one, two or three of: (1) the magnitude of a six component vector comprised of the individual force and torque components; (2) the magnitude of a three component vector comprised of the individual force components; and (3) the magnitude of a vector comprised of any combination of individual force and/or torque components. Alternatively, the coefficient is based on one or more of the largest force or torque components. Based on one or more of these variables, feed rate calculator 284, by reference to data in an associated look-up table 286, determines a force/torque adjustment coefficient.

In addition to adjusting the instrument feed rate, the speed of the energy applicator 184 may also be varied. More specifically, where the energy applicator 184 is a bur, the speed of the cutting teeth of the bur may be adjusted and optimized to improve the accuracy of the tissue removal and to minimize heat generation at the tissue. The optimal speed of the bur cutting teeth is a factor of cutter rotational speed and cutter diameter, which are optimized based on the tooth geometry and the type of material being removed.

A third variable upon which the instrument feed rate is adjusted is the curvature of the path segment (PATH CRVTR). This adjustment is performed to ensure that when the instrument is displaced along a curved path of travel, the instrument is not displaced at such a high rate of speed that the momentum causes the energy applicator 184 to move away from the path of travel. Generally, when the path of travel is linear or has a relatively small curvature, the defined feed rate is not adjusted based on the curvature. When the feed rate calculator 284 receives an indication that the instrument energy applicator 184 is traveling along a path segment with a relatively large curvature, or a small radius, the calculator downwardly adjusts the defined feed rate, based on this variable in order to produce the instrument feed rate.

Figure 16B:
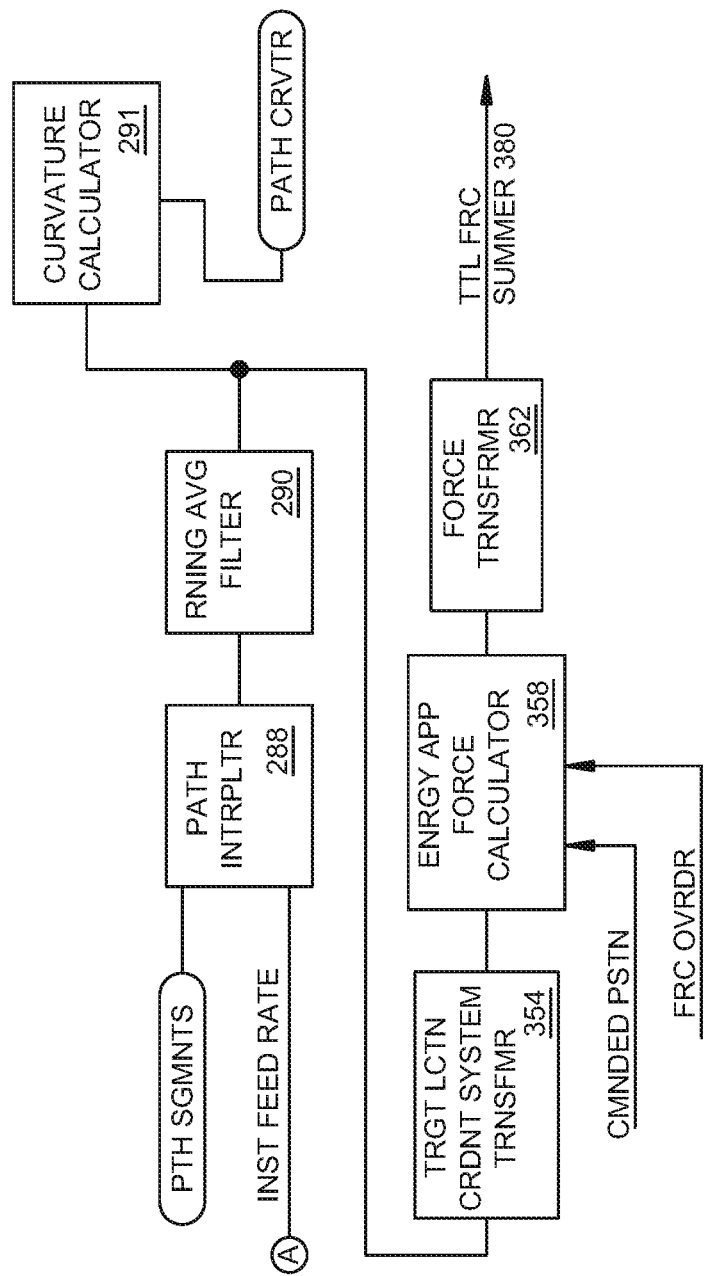

The feed rate calculator 284 receives an indication of the curvature, the PATH CRVTR variable, of the path along which the energy applicator 184 is traveling from a curvature calculator 291 (FIG. 16B). As discussed below, the curvature calculator 291 is another sub-module component of the tool path force calculator 278. Based on this input variable, the feed rate calculator 284 refers to one of the look up tables 286 to determine a coefficient that reflects the extent to which the defined feed rate should be adjusted. Generally, when the path of travel is linear or has a curvature approaching zero, the defined feed rate is not adjusted based on the curvature. The coefficient is at or near 1.0. When the feed rate calculator 284 receives an indication that the instrument energy applicator 184 is traveling along a path segment with a relatively large curvature, the calculator downwardly adjusts the defined feed rate, based on this variable in order to produce the instrument feed rate. The retrieved coefficient decreases from unity. In some versions, if the curvature is 0.05 mm$^{-1}$ or lower, feed rate calculator 284 does not attenuate the instrument feed rate based on the curvature of the segment along which the energy applicator 184 is advancing.

A fourth variable upon which the defined feed rate is adjusted to produce the instrument feed rate is instrument power (INST POWER). This variable is the amount of power the instrument applies through the energy applicator 184 to the patient. Instrument power is employed as an input variable for adjusting instrument feed rate because generally as the power the instrument applies to the tissue increases, the extent to which the tissue is heated by this power is increased. As discussed above, it is desirable to minimize the extent to which the tissue is subjected to the potentially damaging heating. There may also be situations in which, the large outputting of power by the instrument indicates that manipulator is entering a state in which, if instrument feed rate is not reduced, the performance of the energy applicator 184 will drop. For example, if a large amount of power needs to be applied to the bur, this increase in power may indicate that the bur may be entering a state in which it is having difficulty removing the material it should remove. To ensure that the bur performs as expected, it is then desirable to reduce the rate of advancement of the bur. This can help improve the accuracy with which material is removed. Improving the accuracy of tissue removal enhances the surface finish and definition of the tissue that remains after application of the bur.

Accordingly, when there is an indication that the power applied by the instrument 160 increases, feed rate calculator 284 outputs a reduced instrument feed rate.

In constructions in which the instrument 160 is a motorized tool, the power variable can be the amount of torque output by the tool motor.

Generally, there is a directly proportional relationship between the current applied to the tool and the torque output by the tool. Accordingly, a measure of the current drawn by the tool is employed as the instrument power variable. The instrument power signal representative of this variable is generated by the tool controller 132 and applied to the manipulator controller 124. More particularly, a circuit internal to the instrument controller 132 that monitors the current drawn by the instrument outputs a signal representative of the current drawn by the instrument. This signal is the root signal upon which either an analog or digital INST POWER signal applied to feed rate calculator 284 is generated.

The feed rate calculator 284, based on the INST POWER signal and by reference to one of the look up tables 286, determines a coefficient that indicates the extent to which the defined feed rate should be scaled based on the instrument power to determine the instrument feed rate.

A fifth variable that is used as a factor for adjusting the defined feed rate to produce the instrument feed rate is tissue temperature (TISSUE TEMP.) This is due to the above-mentioned goal of modern surgical practice to minimize the extent that the patient's uncut tissue is heated. Temperature sensor 97 provides an indication of the tissue temperature (TISSUE TEMP). In the Figures temperature sensor 97 is shown only symbolically in FIG. 16A. Typically, the sensor 97 is mounted to the instrument 160. Again, the signal output by sensor 97 may be representative of the temperature of the tissue or the temperature of the energy applicator 184. Often the signal output by the temperature sensor 97 is routed through tool controller 132 to manipulator controller 124. In addition to the temperature of the uncut tissue, another factor for adjusting the defined feed rate may include the temperature of the chips removed by the energy applicator 184. The chips from and material removed are often referred to as "slurry." The temperature of the slurry may be measured in any suitable manner including temperature sensor 97.

Feed rate calculator 284, based on the temperature represented by the TISSUE TEMP signal and by reference to one of the look-up tables 286, determines the appropriate tissue temperature feed rate adjustment coefficient. If the TISSUE TEMP signal indicates that the tissue temperature is within an acceptable range, this coefficient may be at or near 1.0. Alternatively, if the TISSUE TEMP signal indicates that the tissue or energy applicator 184 temperature is approaching or above a level at which there may be appreciable damage to the tissue, the retrieved coefficient may decrease from unity.

A sixth variable employed by the feed rate calculator 284 to generate the instrument feed rate is the computed force (CMPTD FORCE). As discussed below, this computed force is the force that is applied to the virtual rigid body. In response to this force, the motion control processes advance energy applicator 184 along the tool path. The computed force is computed by another one of the behavior control process software modules. This computed force, (which can include torque components), serves as an input variable from which a commanded position for the end effector is determined.

Feed rate calculator 284 generates the instrument feed rate so there is an inverse relationship between the computed force and the instrument feed rate. In the event the computed force is increased to effect the desired advancement of the energy applicator 184, feed rate calculator 284 reduces the instrument feed rate. This reduction of instrument feed rate reduces the likelihood that the manipulator will advance the energy applicator 184 at a speed above which the accuracy of the application of the energy applicator 184 to the tissue will be adversely effected.

In some versions of this invention, the feed rate calculator, based on the magnitude of the computed force and reference to one of the look up tables 286, determines a coefficient. This coefficient represents the extent to which the defined feed rate should be scaled as a function of the magnitude of the computed force.

Feed rate calculator 284 multiplies the defined feed rate by the above six coefficients. The product of this process is the instrument feed rate. This is the rate at which the energy applicator 184 should be advanced along the current path segment.

An additional input into feed rate calculator 284 is a signal asserted from a below discussed force overrider 375, also a component of the tool path force calculator 278. In response to the assertion of a signal from the force overrider 375, feed rate calculator 284 outputs a zero speed instrument feed rate. Often feed rate calculator 284 ramps the instrument to the zero speed feed rate. Once the force overrider 375 stops asserting the signal to the feed rate calculator 284, based on the input of other commands from the practitioner, the feed rate calculator 284 returns to outputting a non zero speed instrument feed rate.

A path interpolator (PATH INTRPLTR) 288, seen in FIG. 16B, is another sub-module component of the tool path force calculator 278. Path interpolator 288 determines target positions for coordinate system EAPP. The pose of distal end of the instrument energy applicator 184 is understood to be fixed relative to coordinate system EAPP. These target positions are points along which the distal end of energy applicator 184 should travel to perform the desired task. Inputs into the path interpolator include: the data defining the origin and terminus of a path segment; the data indicating if the segment is straight or curved and, if curved, the characteristics of the curve. Another input into the path interpolator 288 is the instrument feed rate from feed rate calculator 284. This is the rate at which the instrument should travel along the path segment as determined by the feed rate calculator 284.

Based on the above input variables, the path interpolator 288 determines the target position of the distal end of the energy applicator 184 according to the following steps:

1) The origin of coordinate system EAPP is assumed to be at an initial position. The initial position is a position along the path segment over which the energy applicator 184 should travel. If the energy applicator 184 is at the beginning point of the segment, this point is the initial position of coordinate system EAPP. Both the initial position and the target position are points in the bone coordinate system BONE.
2) Based on the instrument feed rate, the distance along which the energy applicator 184 would travel along the segment in a single time frame is calculated. In some versions, the period of a time frame is 0.1 to 2 milliseconds.
3) Based on the initial position, the length of the calculated distance and the location of the segment terminus, path interpolator 288 generates data defining the target position. A further variable used to determine target positions are data from the tool path generator describing the characteristics of the path segment: straight or curved; and, if curved, the radius of curvature.
4) Steps 1 through 3 are repeated until it is determined that the coordinate system EAPP has reached the terminus of the path segment. After the calculation of the first target position spaced from the segment origin, the target position calculated in each frame is employed as the initial position upon which the calculation of the next frame's target position is based.
5) Once the target position equals the terminus position for a path segment, interpolator 288 repeats steps 1 through 4 to generate a set of target positions that are located along the new segment.

During the time period of a single frame, the distance the energy applicator 184 is able to travel may be greater than the distance to the terminus position for the current segment. If the path interpolator 288 determines that the energy applicator 184 would be in this state, the interpolator, for a time point starting when it is determined that the energy applicator 184 would be at the terminus of the current path segment, generates data indicating where the energy applicator 184 should be located at along the next path segment at the end of that frame.

The target positions are output from the path interpolator 288 to a series of cascaded running average filters 290, (RNING AVG FILTER), also a component of the tool path force calculator 278. The running average filters 290 average the individual target positions to produce filtered target positions. The particular running average filters employed in this invention are finite impulse response filters. The running average filters generate filtered target positions as a function of time, the length of the filter. This time period is typically between 5 and 50 milliseconds. Consequently, the resulting distance filtered is a function of filter time period and instrument feed rate.

Cascaded running average filters are employed in this process to ensure that higher order derivatives of the target positions are continuous. In some versions, three cascaded filters are employed. This makes the resulting filtered path have continuous derivatives up through jerk. This filtering essentially ensures that the actuators are not driven beyond their capabilities to advance the energy applicator 184 along the tool path 248.

Figure 17:
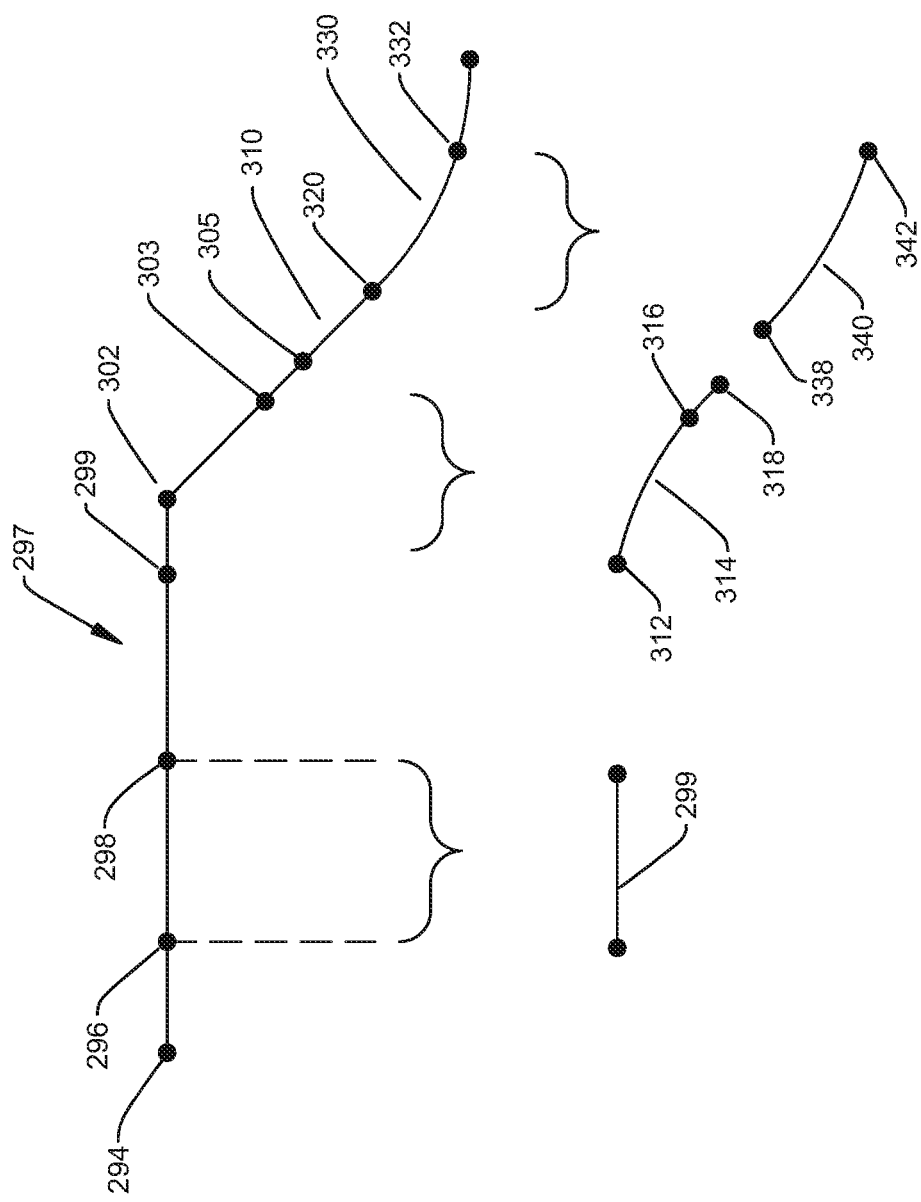
FIG. 17 diagrammatically depicts how a tool path segments are averaged by the rolling average filter.

The filtering performed by these filters is illustrated by reference to FIG. 17. Here, points 294 and 302 represent, respectively, the initial and final target positions of the energy applicator 184 as it moves along path segment 297. Point 302 is also the initial position along from which the energy applicator 184 moves as it travels along path segment 310. Path segment 297 is completely linear. In the running average process, filters average the locations of a number of points along the portion of the path being averaged to determine a mean location. Points 296 and 298 are two spaced apart target positions along path segment 297. If target positions between points 296 and 298 form a straight line and the distance between the points is greater than the distance the energy applicator 184 travels during the length of the filter, the results of this running average form a straight line. As in any filter, there is a lag in time between the input of these positions to the output of the equivalent filtered output positions.

During this running average process, it should be understood that, to produce the filtered target position equivalent to point 296 data, regarding the unfiltered target positions behind point 296 are input variables into the filters.

Target position 302 is the origin of path segment 310. Path segment 310 is linear and angles away from path segment 297. The running average filter 290 eventually produces filtered target positions from target position 299, a point on path segment 297 and target position 303, a point on path segment 310. The resultant averaged target positions are represented by segment 314. These filtered target positions are based on the assumption that the distance between target positions 299 and 303 is greater than the distance the energy applicator 184 travels during the length of the filter. Here, point 312 is identical in position to point 299. Point 316 is identical in position to point 303. Point 318 is identical to point 305. The set of filtered target positions between filtered target positions points 312 and 316 defines a curve. This curve represents the averaged transition from the target positions defining segment 297 to the target positions defining segment 310. From filtered target position 316 to filtered target position 318 the set of target positions is linear. This is because during this portion of the averaging process no points other than those along path segment 310 are input into the averaging equation.

Target position 320 is the terminus of straight segment 310 and the origin of curved segment 330. Based on the locations of the points bounded by and including target position 320 and target position 332, a point in the middle of curved segment 330, filters 290 produce another set of averaged target positions. These averaged target positions are represented by segment 340. Segment 340 extends between filtered target position 338 and filtered target position 342. Given that target position 320 is the terminus of linear path segment 310, the corresponding filtered target position, point 338 is slightly displaced from the actual position. In locations where the target positions to be filtered define a curve, the filtered versions of these target positions typically define a curve which has a larger radius than the radius of points being filtered.

For some procedures it is desirable to substantially minimize the difference between the filtered and unfiltered target positions. One such procedure is the forming of bores in bones. Another procedure is the precise shaping of bone to facilitate precise seating of an implant. For these procedures, the manipulator is set to reduce the defined rate that is applied to the feed calculator 284, (process not shown). This results in the generation of filtered target positions that define path segments that are essentially identical to the path segments defined by the unfiltered set of target positions.

The filtered target positions are applied to the curvature calculator 291. The curvature calculator 291, based on data defining multiple spaced apart filtered target positions, determines the curvature of the current filtered path. Data representative of this curvature are forwarded to the feed rate calculator 284 as the PATH CRVTR variable.

The filtered target positions are also forwarded to a target location coordinate transformer 354, also a sub-module component of the tool path force calculator 278. Coordinate transformer 354 maps each filtered target position, which is in coordinate system BONE into coordinate system MNPL. This filtered target position of the origin of coordinate system EAPP is applied to an energy applicator force calculator 358, also part of tool path force calculator 278.

A second input into calculator 358 is a representation of the actual position of coordinate system EAPP. In many implementations of this invention, the commanded position is employed as the representation of the actual position. The commanded position is the position component of the commanded pose. One advantage of employing the commanded position as the representation of actual position is that it is a leading indicator of the actual position. This feed forward effect facilitates responsive control of the movement of the instrument. This fosters movement of the energy applicator 184 that only minimally deviates from the tool path.

When manipulator 50 is first activated, the initial commanded pose is determined by solving the forward kinematics of the end effector 110. This process is understood to mean determining the pose of coordinate system CMVB as a function of the joint angles of the shoulders 67 and 69 and arms 68 and 70. This pose is relative to coordinate system MNPL. Since the origin of coordinate system EAPP is fixed relative to coordinate system CMVB, the forward kinematic solution of the virtual rigid body results in a like determination of the first initial pose of coordinate system EAPP in coordinate system MNPL.

Energy applicator force calculator 358 determines a set of forces and torques that would be applied to the virtual rigid body. In response to the application of these forces and torques to the virtual rigid body, motion control processes cause manipulator 50 to advance coordinate system EAPP along the tool path 248. The forces and torques applied to the virtual rigid body that results in the setting of the orientation of the instrument are not material to the calculations performed by the calculator 358.

After this first determination of the initial pose of the origin of energy applicator coordinate system EAPP, manipulator controller 124 assumes that at the end of each frame, the origin of coordinate system EAPP moved to the commanded pose calculated at the start of the frame. This commanded pose is generated by a below described cut guide 390. The commanded position component of the commanded pose is supplied by the cut guide 390 to the energy applicator force calculator 358.

Accordingly, two inputs into the energy applicator force calculator 358 are the commanded position of coordinate system EAPP and the next targeted position of this coordinate system. This latter position is the input from the target location coordinate system transformer 354. Both these positions are points in coordinate system MNPL. A third input into the tool tip force generator is the velocity of coordinate system CMVB at the start of the frame, velocity $V_0$. The means by which velocity $V_0$ is calculated is discussed below. The fourth input into the energy applicator force calculator 358 is the velocity at which the energy applicator 184 should move as it advances along the path, velocity $V_1$. Velocity $V_1$ is a vector based on the target position from the previous frame and the current target position. Velocity $V_1$ is the velocity relative to the manipulator coordinate system MNPL. Velocity $V_1$ therefore includes the effects of the movement of bone coordinate system BONE relative to the manipulator coordinate system MNPL. Velocities $V_0$ and $V_1$ are understood to include both linear and rotational components.

Energy applicator force calculator 358 calculates a force that would move the origin of coordinate system EAPP from its current position to the filtered target position. In one version of this invention, calculator 358 determines this force by determining the impulse that needs to be applied to the virtual rigid body at the origin of coordinate system EAPP. The impulse, I, is the change of momentum that is applied to an object. Accordingly, impulse/change of momentum in its most general form, I, is calculated according to the formula $$I = \int F dt = m(v_{FNL} - v_{INTL}) \quad (1)$$

Here, F is force; m is the mass of the object to which the impulse is applied; vINTL is the initial velocity; and vFNL is the final velocity. The object is to calculate the force that would need to be applied to the distal end tip of the energy applicator 184, which is the origin of coordinate system EAPP, to cause the applicator to advance to velocity V1. Equation (1) assumes that the velocities are those present at the center of mass of the object to which the force is applied and the velocities are the velocities present at this point. While the initial velocity V0 is that of coordinate system CMVB and is known, the final velocity V1 is the velocity of the energy applicator 184.

Force F is applied to the virtual rigid body. As mentioned above, force F is not applied to the origin of coordinate system CMVB; this force is applied to the origin of coordinate system EAPP. To account for these factors, the impulse equation is rewritten as follows:

$$(J_{SA} M^{-1} J_{SA}^T) F_{EAPP} = \frac{D_{xyz} V_1 - J_{SA} V_0}{\Delta t} \quad (2)$$

Here, $D_{xyz}$ is the direction in which the impulse is to be applied. Direction $D_{xyz}$ includes two unit vectors. One of these unit vectors defines the direction along which the force is to act. The second unit vector defines the direction around which the torque is to act. Often, it is only necessary to calculate the force component. To accomplish this, the torque component of vector $D_{xyz}$ is set to the null vector. Force $F_{EAPP}$ is a scalar force along direction $D_{xyz}$. Jacobian $J_{SA}$ is the Jacobian matrix from the origin of coordinate system CMVB expressed in coordinate system CMVB to the origin of the energy applicator coordinate system EAPP along the direction $D_{xyz}$. Because Jacobian $J_{SA}$ only maps to the component along direction $D_{xyz}$, $J_{SA}$ is a non-square Jacobian. Matrix M is the mass/inertia of the virtual instrument. Direction $D_{xyz}$ is computed by the energy applicator force calculator 358. The variables upon which direction $D_{xyz}$ is based are the commanded position and filtered target position of the energy applicator 184. By employing the direction $D_{xyz}$ vector, Equation (2) is reduced from six equations and six unknowns to one equation with one unknown.

It is further necessary to account for two additional factors. One is that instrument and energy applicator 184 are modeled as a rigid body and the velocities are specified in a non-inertial coordinate system. This body is therefore subjected to inertial forces. The effect of these inertial forces, which include torques, must be modeled. These inertial forces are calculated according to the following formula:

$$F_{inertial} = \begin{bmatrix} -\omega \times V \\ -\omega \times I\omega \end{bmatrix} \quad (3)$$

Here, $F_{inertial}$ is a vector consisting of the inertial forces and torques. Velocity V is the velocity of coordinate system CMVB. Rotational velocity $\omega$ is the rotational velocity of coordinate system CMVB. Inertia I is the virtual inertia tensor in coordinate system CMVB. Both velocities $\omega$ and V are expressed in coordinate system CMVB The second additional factor is that environmental forces discussed below, collective force $F_{ENV}$, act on the virtual rigid body. Components of the environmental force include a joint limit force, an interference limit force, a workspace boundary force and a damping force. An additional component of the environmental force is external forces applied to the manipulator 50, the instrument 160 and the energy applicator 184. The external forces include the effect of the resistance of the tissue to which the energy applicator 184 is applied. Another component of the external force is the force the practitioner places on the instrument. The components of environmental force $F_{ENV}$ are discussed in detail below.

Accordingly, force $F_{EAPP}$ is calculated according to the formula:

$$(J_{SA} M^{-1} J_{SA}^T) F_{EAPP} = \frac{D_{xyz} V_1 - J_{SA} V_0}{\Delta t} - J_{SA} M^{-1} (F_{inertial} + F_{ENV}) \quad (4)$$

Here, $F_{inertial}$ are the inertial forces acting on the instrument and energy applicator 184. Force $F_{ENV}$ is received from a below discussed environmental force summer 379 and is expressed in coordinate system CMVB. Time period $\Delta t$ is equal to the integration time period employed by the below discussed integrator 386.

In practice, if the energy applicator 184 is simply repositioned based on the calculation of velocity vectors the position of the energy applicator 184 has a tendency to drift from the path segment along which the applicator should advance. This drift occurs due to such factors as rounding errors, machine precision and the inherent limits associated with discrete time modeling. Drift can also occur as a consequence of the micro-environmental disturbances in the vicinity of the instrument. To compensate for this drift, a correction force is added to the calculation of the force applied to the virtual rigid body. The general description of these forces is:

$$\frac{\epsilon \Delta d}{\Delta t^2} + \frac{CF_{EAPP}}{\Delta t}$$

Distance $\Delta d$ is defined to be the negative of the magnitude of the distance the energy applicator 184 has drifted from the path segment. In one implementation, distance $\Delta d$ is computed by determining the negative of the magnitude of the distance between the actual position and the target position. In one implementation, the commanded position is employed as the representation of the actual position of the energy applicator 184. Coefficients E and C are scale factors. When the above terms are added to Equation (4), the final form of the equation to solve for the force applied to the virtual rigid body at the origin of coordinate system EAPP is:

$$\left(J_{SA}M^{-1}J_{SA}{}^T + I\frac{C}{\Delta t}\right)F_{EAPP} = \qquad (5)$$

$$\frac{D_{xyz}V_1 - J_{SA}V_0}{\Delta t} - J_{SA}M^{-1}(F_{inertial} + F_{ENV}) - \frac{\epsilon \Delta d}{\Delta t^2}$$

Matrix I is the identity matrix.

The energy applicator force calculator 358 therefore solves for force $F_{EAPP}$, the force along direction $D_{xyz}$ applied to the virtual rigid body at the origin of coordinate system EAPP. In response to the presence of force $F_{EAPP}$, the motion control processes cause the manipulator 50 to advance energy applicator 184 along the path segment at the appropriate velocity. As mentioned above $F_{EAPP}$ is scalar. Force transformer module 362 transforms this scalar to force $F_{INST}$. Force $F_{INST}$ is the vector of forces and torques applied to the virtual rigid body at the origin of coordinate system CMVB to advance the energy applicator 184 at the desired velocity. These forces and torques are calculated according to the following equation:

$$F_{INST} = J_{SA}{}^T F_{EAPP} \qquad (6)$$

Force $F_{INST}$ is a vector consisting of three separate forces and three separate torques applied to the virtual rigid body at the origin of coordinate system CMVB. Force $F_{INST}$ is expressed in coordinate system CMVB.

The forces and torques comprising $F_{INST}$ are applied from force transformer module 362 to a force summer 380. As described below, the force summer 380 is another one of the behavior control modules that runs on the manipulator controller 124.

Tool path force calculator 278 also includes an instrument orientation regulator 368 seen in FIG. 16C. Orientation regulator 368 determines the forces and torques that need to be applied to the virtual rigid body to ensure that, as the manipulator 50 moves the instrument 160, the instrument maintains an acceptable orientation relative to the tissue against which the energy applicator 184 is applied. Instrument orientation regulation is desirable because as discussed above, the energy applicator force calculator 358 generates data defining forces and torques applied to the virtual rigid body that result in the advancement of the energy applicator 184 when in the semi-autonomous mode. External forces and torques are also applied to the manipulator 50, instrument 160 and energy applicator 184. In response to these external forces, manipulator 50 computes additional forces and torques that are applied to the virtual rigid body. The application of either one of these sets of forces and torques to the virtual rigid body can result in the manipulator 50 positioning the instrument so that the instrument appreciably drifts from an acceptable range of orientations. Should the instrument drift from this range of orientations, the efficiency of the energy applicator 184 may be reduced. Also, as a result of this orientation drift, the instrument may move to a position in which it could potentially abut other tissue or other instruments adjacent the tissue against which the energy applicator 184 is applied. This contact could inhibit the further advancement of the energy applicator 184.

Orientation regulator 368 determines the restoring forces and torques that need to be applied to the virtual rigid body to prevent this drift.

Figure 18A:
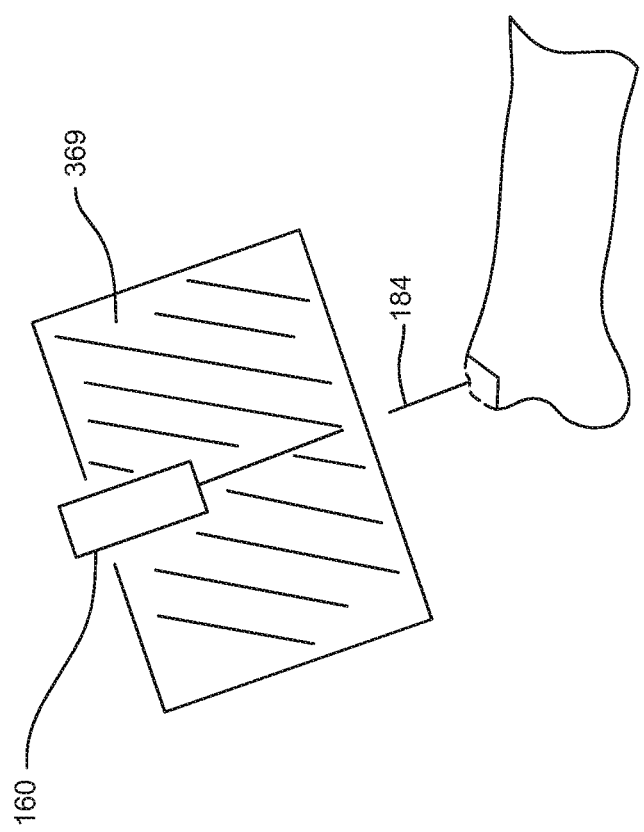
FIGS. 18A through 18D are a set of diagrammatic depictions of how the points and boundaries used by the orientation regulator are generated.
Figure 18B:
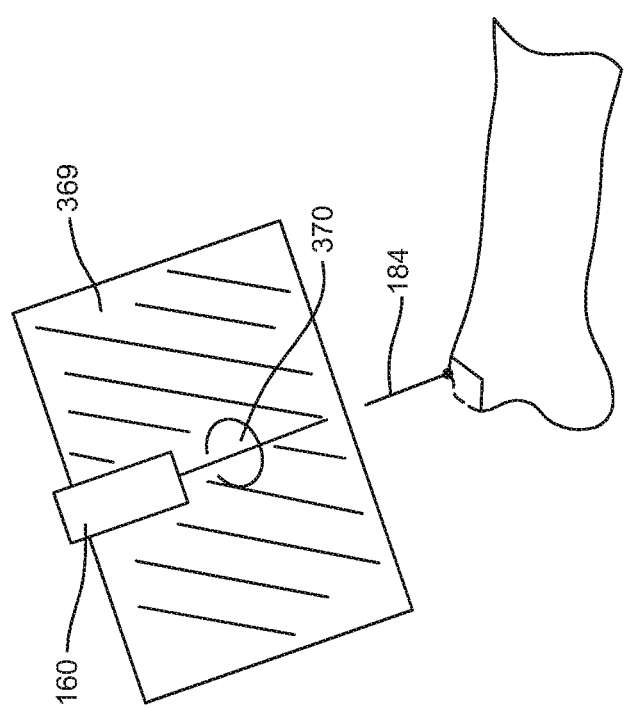
Figure 18C:
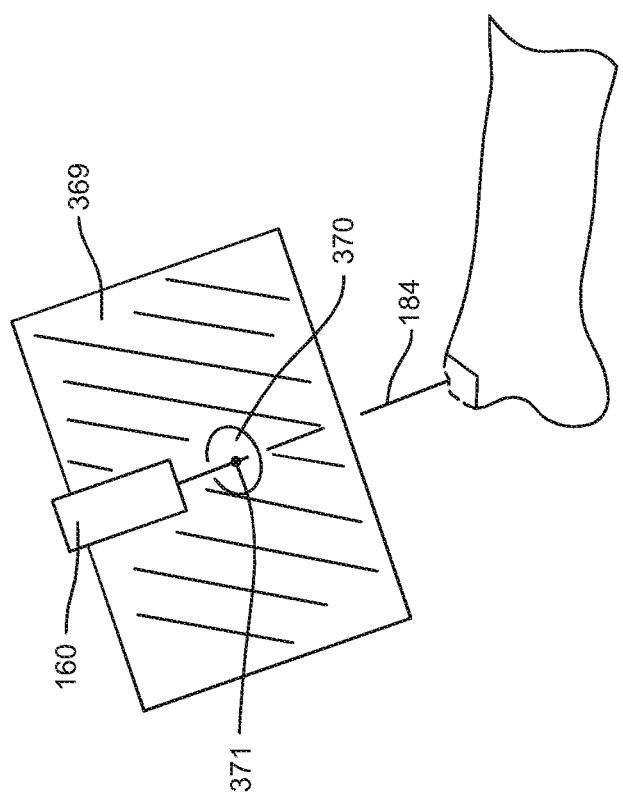

In most versions, orientation regulator 368 is set to operate when the manipulator advances the instrument in the semi-autonomous mode. When commands are first entered to begin semi-autonomous advancement of the instrument, orientation regulator 368 defines a reference surface 369 that is located above the distal end of the energy applicator 184, as shown in FIG. 18A. To perform this process, orientation regulator 368 is required to know the actual pose of the instrument. In some versions, the commanded pose is employed as the representation of the actual pose. In the Figures, surface 369 is depicted as a plane but in practice is not so limited. Reference surface 369 is typically located approximately 5 to 20 cm above the distal end of the energy applicator 184. In some versions, the reference surface is positioned to intersect the origin of coordinate system CMVB. If the reference surface is a plane, upon manipulator initialization, regulator 368 often defines the plane as being perpendicular to the longitudinal axis of the instrument 160. The orientation regulator 368 then defines an aperture 370 in the reference surface 369, as shown in FIG. 18B. Aperture 370 is typically, but not limited to, a circle. The aperture 370 is centered around the point where the longitudinal axis of the instrument or energy applicator 184 intersect the reference surface 369. In the described version, these axes are assumed to be linear and are collectively referred to as the "common axis". In the figures, this point of intersection is called out as centering point 371. If aperture 370 is in the form of a circle, the aperture may have a radius of between 2 to 5 cm. Surface 369 and aperture 370 are typically fixed relative to the coordinate system BONE. This ensures that the representation of these geometric landmarks move with the patient. The surface 369 and aperture 370 are typically defined in either manipulator coordinate system MNPL or bone coordinate system BONE.

Figure 18D:
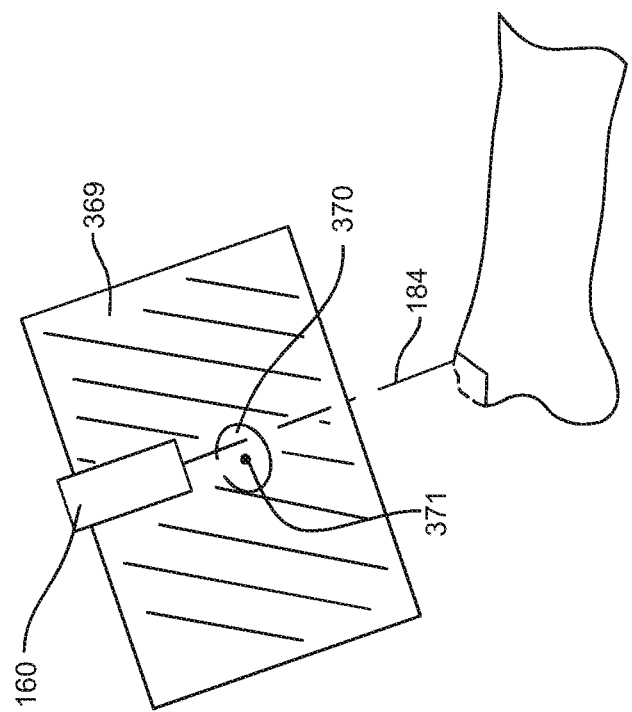

At the start of the frame, the orientation regulator 368 has the data describing the commanded pose of the instrument 160. Owing to the repositioning of the instrument 160 by the manipulator 50, the common axis may be displaced from the centering point 371 as seen in FIG. 18D. This displacement occurs because neither aperture 370 nor centering point 371 moves with the displacement of the instrument and energy applicator 184. If the instrument 160 is so displaced, orientation regulator 368 determines an orientation restoring force that, applied to the virtual rigid body, results in manipulator 50 moving the instrument so that the common axis moves towards the centering point 371.

The process by which orientation regulator 368 determines the orientation restoring forces and torques start with the orientation regulator determining the point along the common axis that intersects the reference surface 369. Orientation regulator 368 determines the current location of the common axis based on representation of the actual pose, the commanded pose. Orientation regulator 368 then determines the distance from this point to the centering point 371. Based on these data, the orientation regulator 368 determines the restoring forces and torques that would pivot instrument 160 towards centering point 371. In one version, these forces and torques are determined according to the following formula:

$$F_{R\_MAG} = f(DIST_{INST-CP}) + f(V_{INST-CP}) \quad (7)$$

In some cases:

$$f(DIST_{INST-CP}) = K_{ORNT} DIST_{INST-CP} \quad (7A)$$

$$f(V_{INST-CP}) = D_{ORNT} V_{INST-CP} \quad (7B)$$

Here, $F_{R\_MAG}$ is the magnitude of the restoring force applied to the virtual rigid body along the reference surface 369 to pivot the instrument towards the centering point. Force $F_{R\_MAG}$ would act along the vector from the point where the instrument axis intersects reference surface 369 to the centering point 371. In Equation (7), force $F_{R\_MAG}$ has a distance component and a velocity component. Distance $DIST_{INST-CP}$ is the distance between the point where the common axis intersects reference surface 369 and centering point 371. Distance $DIST_{INST-CP}$ is a positive scalar. Velocity $V_{INST-CP}$ is the time derivative of distance $DIST_{INST-CP}$.

Coefficient $K_{ORNT}$ is a spring coefficient. This coefficient may be variable. One reason for this is that when the common axis is very close to the centering point 371, it may not be necessary to apply an appreciable restoring force to the instrument. This is because, while it is desirable that the common axis be located on the centering point 371, it is not a requirement for the operation of the manipulator. Accordingly, when the common axis is relatively close to the centering point 371, spring constant $K_{ORNT}$ may be relatively low or even zero. If the common axis is spaced further from centering point 371, it may be desirable to increase the application of these restoring forces and torques.

Coefficient $D_{ORNT}$ is a damping coefficient. The damping coefficient may be variable. In some versions, this coefficient is a function of distance $DIST_{INST-CP}$ and/or velocity $V_{INST-CP}$. Varying coefficient $D_{ORNT}$ may be desirable to enhance the stability of the movement of the instrument.

Figure 19:
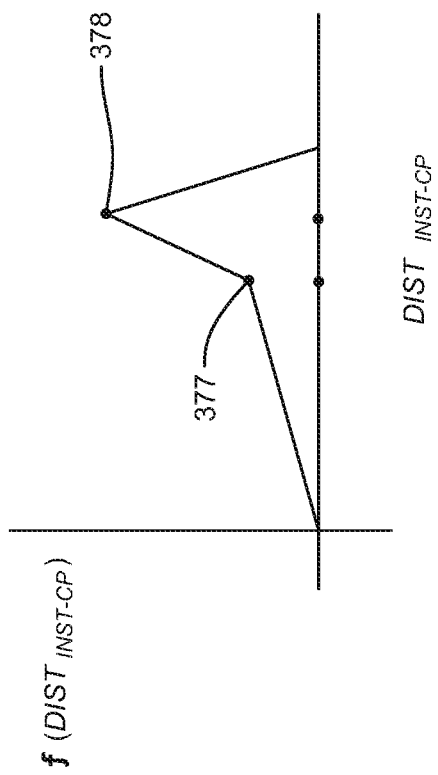
FIG. 19 is a graphical depiction the relationship between the offset of the instrument from the target orientation and the force that the orientation regulator determines should be applied to the virtual rigid body to compensate for the offset.

In FIG. 19 the magnitude of the distance component of the force in Equation (7) is shown. In this Figure, there is a steep increase in the application of the force from inflection point 377 to peak 378. Inflection point 377 is located at the perimeter of aperture 370. Accordingly, should the common axis continue beyond this location, the orientation regulator 368 generates data indicating that a significant restoring force needs to be applied to the virtual rigid body to maintain the instrument within the aperture. The magnitude of this restoring force significantly increases as the instrument moves incrementally beyond aperture 371.

Orientation regulator 368 may determine that the instrument has moved an appreciable distance beyond aperture 370. This is the distance at which peak 378 is located. If orientation regulator 368 determines this condition exists, the regulator 368 no longer generates data indicating that a large restoring force should be applied. This is because there may be instances, when the instrument is being displaced in a semi-autonomous mode, it is desirable to move instrument outside the normal range of orientations. For example, there may be an obstacle that blocks advancement of the energy applicator 184 along the programmed path segment. This obstacle might be a protruding tissue or a surgical instrument. So that this obstacle does not block the advancement of the energy applicator 184, the instrument may need to assume an orientation outside of the normal range of orientations. Alternatively, the practitioner may attempt to force the reorientation of the instrument 160 without first depressing button 172. Should this event occur, the fact that the orientation regulator 368 allows the instrument to move outside of the normal range of orientations allows the practitioner to engage in such reorienting of the instrument.

Accordingly, as the instrument moves more than 0.5 to 2.0 cm beyond the aperture, the magnitude of the distance component ramps down to nominal levels. This level may equal zero. Prior to allowing this force to fall to zero, the manipulator may present a message on the user interface requesting that the practitioner confirm that the orientation regulator 368 at least temporarily suspend regulation of instrument orientation. While awaiting this confirmation, the manipulator may suspend advancement of the energy applicator 184 along the path segment.

Once orientation regulator 368 starts to generate data indicating that only a nominal/zero orientation restoring force $F_{R\_MAG}$ should be applied to the virtual rigid body, the practitioner may manually reorient the instrument so that the axis is at or in close proximity to the aperture 370. Should this event occur, the orientation regulator 368 may return to outputting data indicating that a more than nominal restoring force should be applied. In some constructions of the manipulator 50, for the orientation regulator 368 to return to outputting a more than nominal orientation restoring force, the practitioner is required to press and release button 172. Orientation regulator 368 redefines the reference surface 369, the aperture 370 and centering point 371 based on instrument orientation when button 172 is released. Once these landmarks are redefined, the orientation regulator 368 returns to outputting more than nominal orientation restoring forces.

In practice, orientation regulator 368 does not actually execute Equation (7) to determine the orientation restoring force $F_{R\_MAG}$. Instead, the orientation regulator 368 maintains look up tables of restoring forces (tables not illustrated). The inputs to determine the appropriate restoring force are representations of distance $DIST_{INST-CP}$ and velocity $V_{INST-CP}$.

Once restoring force $F_{R\_MAG}$ is determined, orientation regulator 368 converts this force into a vector. Orientation regulator 368 performs this conversion by multiplying force $F_{R\_MAG}$ by the unit direction vector from the point where the instrument axis intersects the reference plane 368 to the centering point 371. The unit direction vector is expressed in coordinate system MNPL. This multiplication produces a force vector $F_{RSTR}$ also in coordinate system MNPL. This vector defines the restoring force that is applied to the virtual rigid body where the longitudinal axis of the body instrument intersects the reference surface 369. This point is not the origin of coordinate system CMVB.

Orientation regulator 368 therefore converts force $F_{RSTR}$ into the equivalent forces and torques that should be applied to the virtual rigid body at the origin of coordinate system CMVB. This conversion is performed according to the following formula:

$$F_{ORNT} = J_{ORNT}^{-T} F_{RSTR} \quad (8)$$

Force $F_{ORNT}$ is the force and torque vector that is applied to the origin of coordinate system CMVB to reposition the instrument axis towards the centering point. This force is expressed in coordinate system CMVB. Jacobian $J_{ORNT}$ is the Jacobian from where the instrument axis intersects the reference surface 369 expressed in coordinate system MNPL to the origin of coordinate system CMVB expressed in coordinate system CMVB. These forces and torques, which are in the coordinate system CMVB are also applied by the tool path force calculator 278 to total force summer 380.

Orientation regulator 368 receives as inputs other signals. These signals include signals from instrument button 172 and the below discussed force overrider 375. The responses of the orientation regulator 368 to the assertion and negation of these signals is discussed below.

FIG. 16D illustrates another module integral to the tool path force calculator 278, the force overrider 375. One input into force overrider 375 are signals representative of the forces and torques applied to force torque sensor 108. A second input into force overrider 375 are signals representative of the force $F_{INST}$ that application of which to the virtual rigid body results in the advancement of the energy applicator 184 on the tool path. These signals are from the energy applicator force calculator 358. These signals are shown coming from the force transformer 362. A third input into the force overrider 375 is force $F_{ORNT}$, collectively the forces and torques the tool orientation force regulator 368 determines would maintain the instrument axis within aperture 370. A fourth input into force overrider is signals representative of the power applied by the energy applicator 184. For an instrument having a motor as a power generating unit, the torque produced may function as indicia of instrument power. The current drawn by the instrument may be employed as a representation of the power applied by the energy applicator 184. In FIG. 16D this is why the signal ENGRY APP PWR is shown coming from the tool controller 132.

Figure 27:
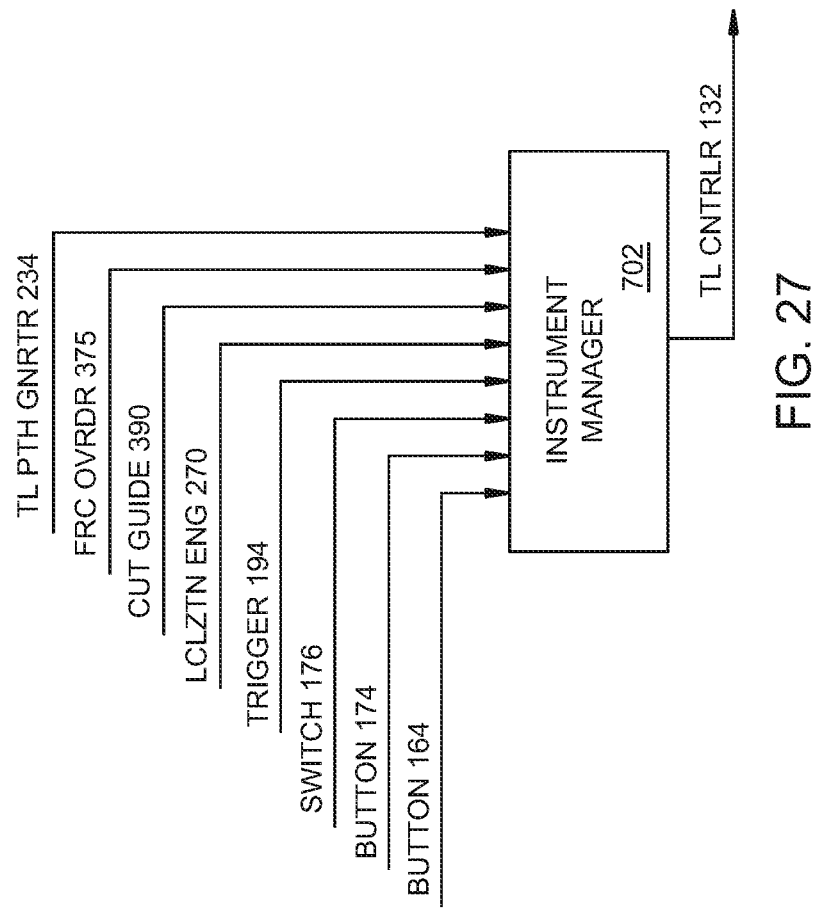
FIG. 27 is a block diagram of the inputs into and output from the instrument manager.

Each of these signals is thus representative of a force or torque that is applied to or output by the instrument 160 and/or energy applicator 184. Force overrider 375 compares each of these forces/torques to one or more limit values. If one set of these forces/torques exceeds a lower limit value, the force overrider deactivates the instrument and stops the advancement of the instrument. Depending on which set of force/torques exceeded the limit value, the force overrider may not deactivate the instrument and stop advancement until the limit value is continuously exceeded for a set time period. This delay may be programmed into the force overrider 375 to minimize the instances of momentary spikes in applied or output force/torque interrupting operation of the manipulator. This delay period is typically between 10 and 500 milliseconds. The deactivation of the instrument is represented by the assertion of a signal to an instrument manager 702 (FIG. 27). In response to the receipt of this signal, instrument manager 702 sends a command to the tool controller 132. This command causes the controller 132 to negate the application of energization signals to the instrument power generating unit 163. The cessation of movement along the tool path is represented by the assertion of a signal to the feed rate calculator 284. In response to this signal, the feed rate calculator 284 ramps the instrument feed rate to zero.

If one set of these forces/torques exceeds a higher limit level, force overrider 375 causes the manipulator to transition from semi-autonomous operation to manual mode operation. As with the lower limit level, the force overrider 375 may not cause this transition of the manipulator 50 until after the particular force/torque limit is exceeded for a continuous time period. This time period is typically less than the time period associated with the corresponding force/torque lower limit. This time limit is lower because the sensing of higher magnitude applied or output force/torque means that there is a greater likelihood that the manipulator may be in an undesirable state. Reducing the time period before which the force overrider 375 responds to this force/torque information essentially ensures that when the higher limit level is exceeded, the overrider takes the corrective action associated with this condition instead of responding to the lesser corrective action associated with the lower limit force/torque level being exceeded.

To reset the operation of the manipulator to the manual mode, the force overrider 375 asserts signals to the energy applicator force calculator 358 and the tool orientation regulator 368. When energy applicator force calculator 358 receives this command signal from overrider 375, the calculator ramps force $F_{INST}$ to zero. When tool orientation regulator receives this command signal from overrider 375, the regulator ramps force $F_{ORNT}$ to zero.

From the above, it is now understood that tool path force calculator 278 produces information regarding the forces and torques that are applied to the center of mass of the virtual rigid body to: (1) move the energy applicator 184 along the path segment; and (2) maintain the instrument within an acceptable range of orientations. Data describing both these forces and torques are applied to a total force summer 380. The forces and torques used to advance the energy applicator 184 and maintain tool orientation are calculated separately. Accordingly, in FIG. 13B, these two sets of forces and torques are depicted as two separate addends into force summer 380.

Force summer 380 is a separate behavior control software module run on the manipulator controller 124. An additional addend into force summer 380 is the environmental force $F_{ENV}$ output from environmental force summer 379. Force summer 380, based on these three inputs, produces two sums: forces $F_{TTL}$; and torques $T_{TTL}$. These sums are, respectively, the totals of the forces and torques that the manipulator would apply to the center of mass of the virtual rigid body. Both forces $F_{TTL}$ and torques $T_{TTL}$ are expressed in coordinate system CMVB. In both the manual or semi-autonomous modes of operation, manipulator 50 advances instrument 160 as a function of these total forces and torques.

An acceleration calculator 384, another behavior control software module run on the manipulator controller 124, receives the total force and torque vectors, respectively, $F_{TTL}$ and $T_{TTL}$ from force summer 380. In FIG. 13B a single connection from summer 380 to calculator 384 is shown. Acceleration calculator 384 determines the extent to which the origin of coordinate system CMVB should be accelerated based on the application of forces $F_{TTL}$ and torques $T_{TTL}$. This acceleration is both translational and rotational. As mentioned above the instrument and the energy applicator 184 are modeled as a virtual rigid body. The equations of motion for this body are:

$$F_{TTL} = m\dot{V} + \omega \times V \quad (9)$$

$$T_{TTL} = I\dot{\omega} + \omega \times I\omega \quad (10)$$

Here: m is the virtual mass of the virtual rigid body; V is the linear velocity of coordinate system CMVB; $\dot{V}$ is the linear acceleration of coordinate system CMVB; ω is the rotational velocity of coordinate system CMVB; $\dot{\omega}$ is the rotational acceleration of coordinate system CMVB. These velocities and accelerations are expressed in coordinate system CMVB. Tensor I is the virtual inertia tensor of the virtual rigid body expressed in coordinate system CMVB.

Therefore, acceleration calculator 384 is also loaded with the virtual mass and virtual inertia of the virtual rigid body. This value is typically constant. Acceleration calculator 384 assumes that linear velocity V and angular rotation ω are the immediately past calculated values for these variables. Acceleration calculator 384, given the above known variables is therefore able to solve for both the linear and rotational accelerations, respectively, $\dot{V}$ and $\dot{\omega}$. It should be appreciated that $\dot{V}$ and $\dot{\omega}$ are vectors.

Vectors $\dot{V}$ and $\dot{\omega}$ are both applied to an integrator 386, another behavior control software module run on the manipulator controller 124. Integrator 386 also receives from the below described cut guide 390 a commanded pose and a commanded velocity for coordinate system CMVB expressed in coordinate system MNPL. These commanded pose and commanded velocity data are used by the integrator 386 as the initial conditions for the integrations for the current frame. The integrator 386 converts the velocity from coordinate system MNPL to coordinate system CMVB. This conversion is necessary to employ the velocity as an initial condition in the integrations.

For the first frame integrations upon manipulator initialization, as previously described, the commanded pose is based on the data from the below discussed forward kinematics module 562. The commanded velocity is set to zero.

Integrator 386 performs a first integration to determine both the linear and rotational velocities, V and ω, of coordinate system CMVB. Integrator 386 then rotates linear velocity V into its equivalent in manipulator coordinate system MNPL. The integrator 386 may then limit the magnitude of these velocities to ensure that the motion of the manipulator is within the operational limits of the manipulator. This velocity limiting may also be performed to ensure that the rate at which the manipulator advances the instrument does not exceed the desired rates for the procedure. Integrator is able to independently limit the magnitudes of the linear and rotational velocities.

These velocities are then integrated to determine the new position of the origin of the coordinate system CMVB in coordinate system MNPL.

Integrator 386 also converts the rotational velocities to quaternion rates. These quaternion rates are expressed in coordinate system MNPL. The quaternion rates are integrated to obtain the quaternions. The quaternions are then used to form the rotation matrix of the new orientation of the coordinate system CMVB in the manipulator coordinate system MNPL. Collectively, this rotation matrix and the vector defining the position of the coordinate system CMVB in the manipulator coordinate system MNPL form the homogenous transformation matrix of the coordinate system CMVB with respect to manipulator coordinate system MNPL. This transformation matrix specifies a pose of the virtual rigid body. This pose is applied to the below described cut guide.

Integrator 386 also monitors the state of switch 176. When the integrator 386 determines that switch 176 has been transitioned from the asserted to the not asserted state, the integrator momentarily ramps down the signals indicating the velocities V and ω to zero. This ramping down is performed prior to the second integration to both the linear and rotational velocity. Integrator 386 does not hold the velocity to zero. This allows other forces such as the below described back drive forces and joint limit forces to continue to influence the movement of the manipulator after switch 176 is no longer asserted.

In some versions, integrator 386 does not directly ramp the velocity to zero. Instead, when switch 176 is no longer asserted, the velocity is indirectly driven to zero by momentarily increasing the below described damping force applied to force summer 379.

The results of the velocity and position integrations are applied to a cut guide 390. Cut guide 390 is a behavior controller software module that runs on the manipulator controller 124. The cut guide 390 is the software module that, when the manipulator is operated in the manual mode, prevents the manipulator from positioning the energy applicator 184 beyond the boundaries of the volume in which the applicator is to be applied. Cut guide 390 is thus the software module that ensures that the manual mode positioning of the energy applicator 184 is boundary constrained.

When the manipulator 50 is operated in the semi-autonomous mode the path segments along which the energy applicator 184 advances are inherently within the boundaries of the volume in which the energy applicator 184 should be applied. Cut guide 390 remains the initial recipient of the pose generated by the integrator 386. Thus, when the manipulator 50 operates in the semi-autonomous mode, cut guide 390 functions as a safety that prevents unintended movement of the energy applicator 184 beyond the defined boundary.

Figure 20A:
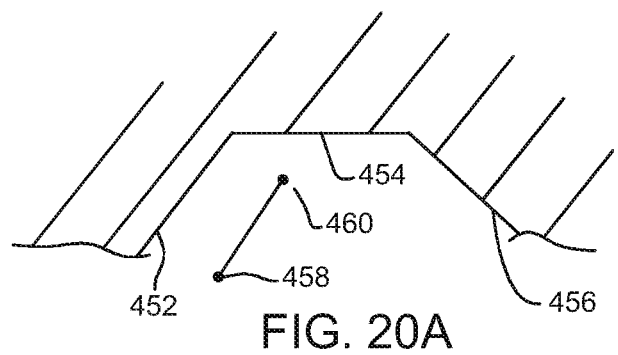
FIGS. 20A, 20B and 20C are diagrammatic depictions of the energy applicator repositioning that is performed by the cut guide.
Figure 20B:
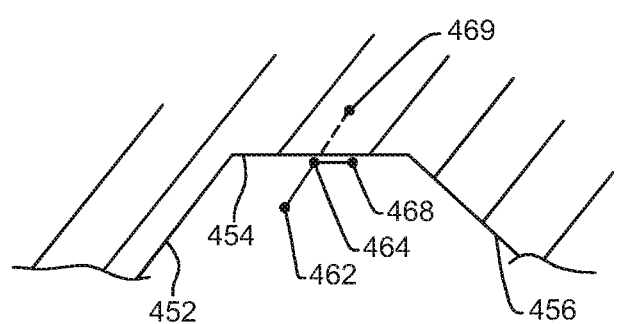
Figure 20C:
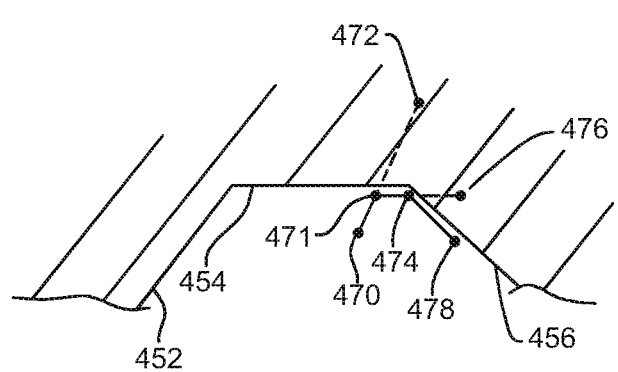

One input into cut guide 390 is the pose generated by integrator 386. This integrator-generated pose is of the origin of coordinate system CMVB relative to coordinate system MNPL. A second input is the velocity, linear and rotational, generated by integrator 386. A third input into the cut guide 390 is the data from the boundary generator 232 that define the boundaries between the volume where the energy applicator 184 is and is not to be applied. In FIGS. 20A, 20B and 20C, these boundaries are called out by line segments 452, 454 and 456. FIGS. 20A-20C are understood to be two-dimensional section views through a three-dimensional surface.

Cut guide 390 also receives a fourth input from coordinate system transformer 272. These are data defining transformations of coordinate systems relative to each other. These include transformations relating coordinate systems CMVB, EAPP, BONE and MNPL.

The above pose and velocity inputs are initially expressed in coordinate system MNPL. Cut guide 390 transforms each of these inputs into coordinate system BONE, step 482. This transformation is performed because the boundaries beyond which the energy applicator 184 should not be applied are typically fixed in coordinate system BONE. For ease of processing, it is therefore more convenient to perform the following analyses in bone coordinate system BONE.

Figure 21A:
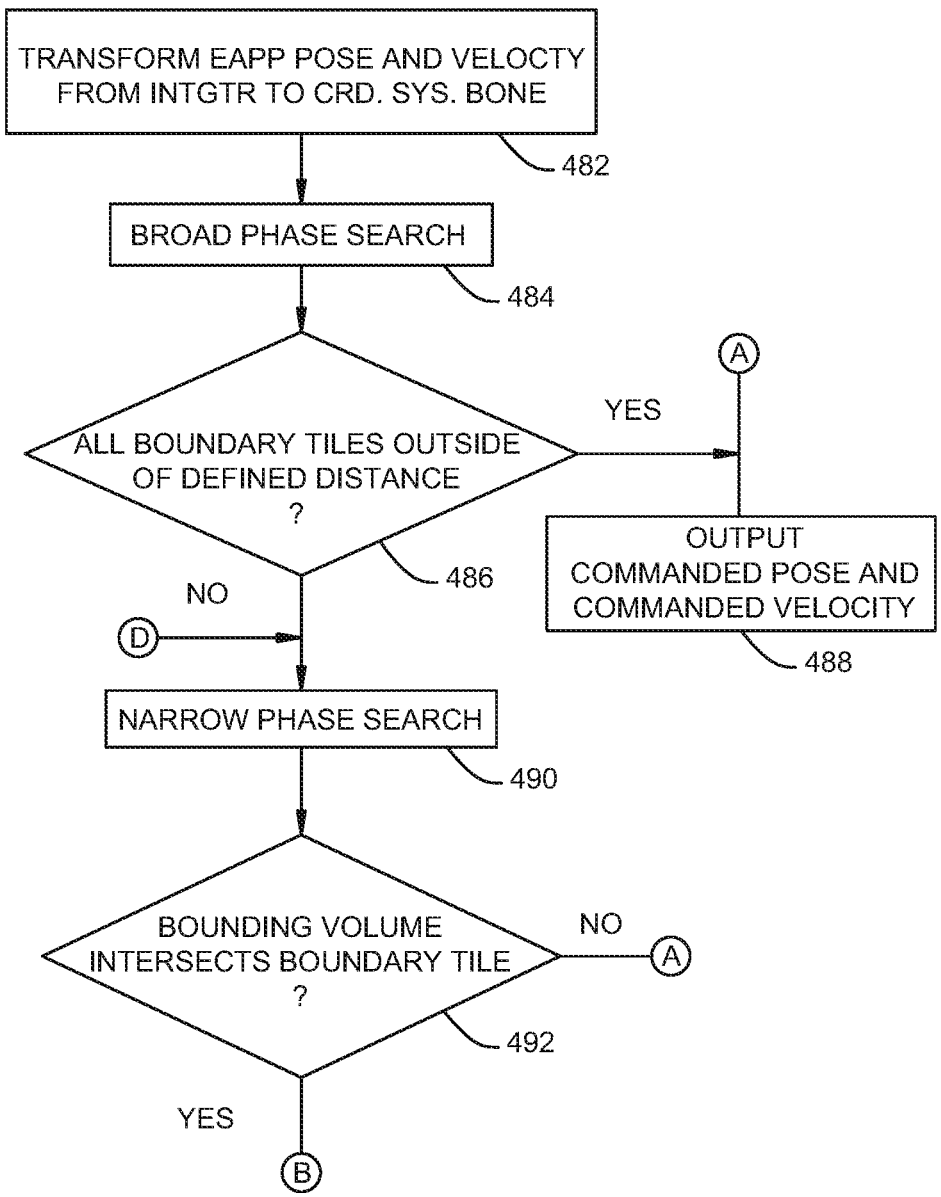
FIGS. 21A, 21B and 21C form a flow chart of the process steps executed by the cut guide.
Figure 21B:
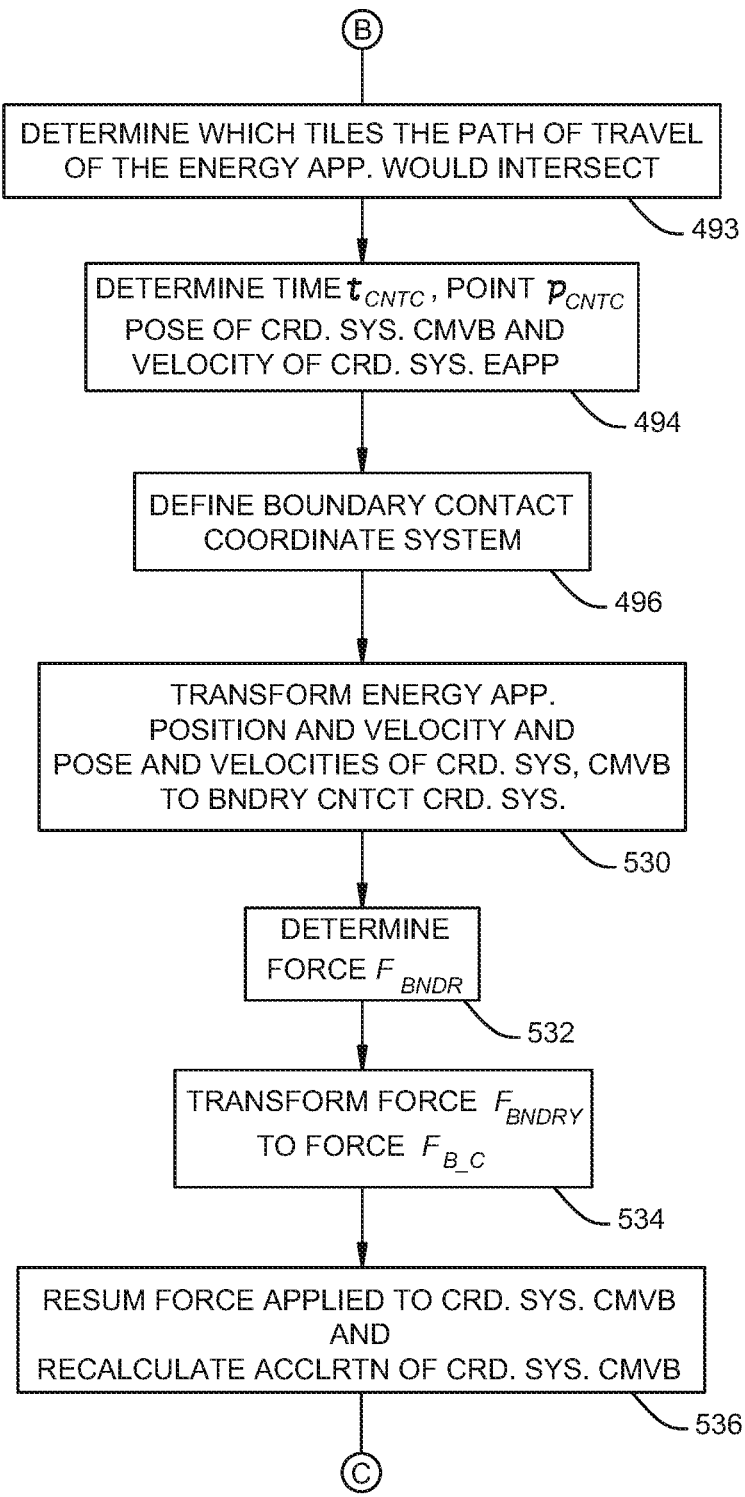
Figure 21C:
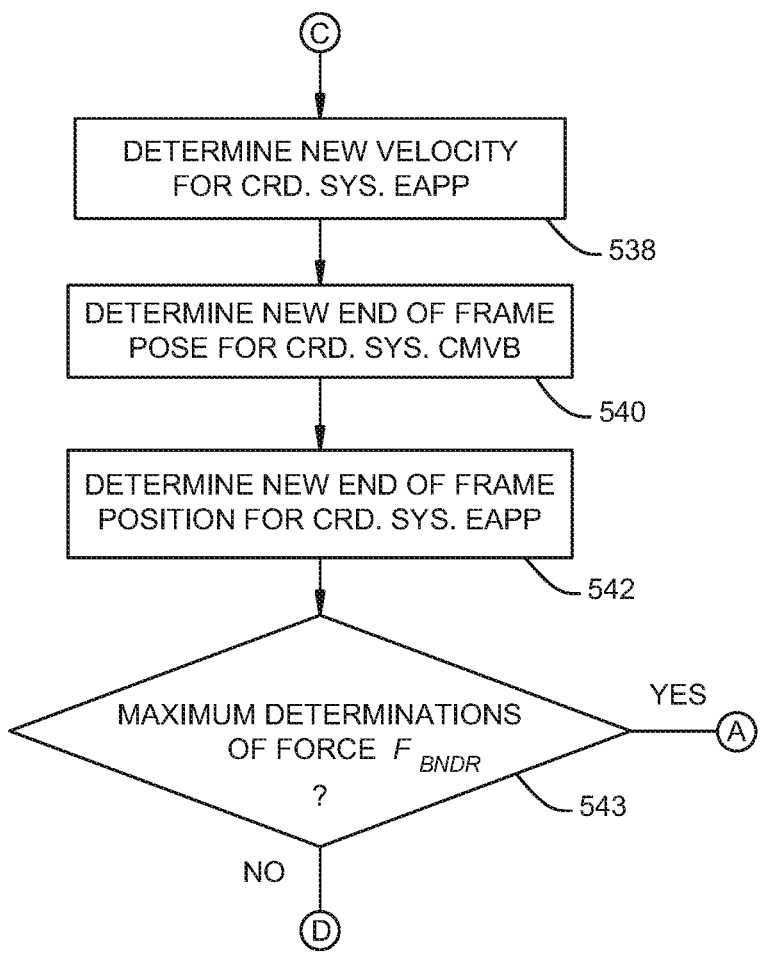

The operation of the cut guide 390 is initially explained by reference to the flow charts of FIGS. 21A-21C. While not shown as a step, cut guide 390, based on the previous commanded pose, calculates the previous commanded position of the origin of coordinate system EAPP. Based on the integrator-generated pose, the cut guide 390 calculates an integrator-generated position of the origin of coordinate system EAPP.

In a step 484, cut guide 390 identifies any boundary-defining tiles the energy applicator 184 could cross during the frame. This step is often described as a broad phase search. Step 484 is performed by identifying the set of tiles that are within a defined distance of the previous commanded position of the energy applicator 184. In FIG. 20A, this is point 458. This distance is a function of: the dimensions of the energy applicator 184; the velocity of the energy applicator 184 relative to the tiles (the velocity of advancement during the past frame is acceptable); the time period of the frame; a scalar defining a characteristic size of the boundary defining sections; and a rounding factor.

As a result of the execution of broad phase search, step 484, cut guide 390 may determine that, in the frame for which this analysis is being performed, all of the tiles are outside of the defined distance, step 486. This means that, by the end of frame for which this analysis is being performed, the energy applicator 184 will not have advanced to a location beyond the boundary. This is illustrated by FIG. 20A where the integrator-defined position of the energy applicator 184, point 460, is spaced well away from the closest boundary.

Since the continued advancement of the energy applicator 184 is within the boundary of the volume in which the energy applicator 184 is to be applied, the cut guide 390 does not modify either the pose or the velocity of coordinate system CMVB as generated by the integrator 386. In a step 488, the cut guide 390 outputs a commanded pose and a commanded velocity. If this version of step 488 is executed as a result of it being determined that all the boundary tiles are outside of the defined distance, the pose and velocity generated by integrator 386 are output by the cut guide 390 as a commanded pose and a commanded velocity.

As part of the execution of the above version and the other below described versions of step 488, cut guide 390 transforms the commanded pose and velocity from coordinate system CMVB so this pose and velocity are expressed in coordinate system MNPL. The commanded velocity, it is understood is a vector that comprises both linear and rotational components.

As a result of the execution of step 484, cut guide 390 may alternatively identify a broad set of boundary-defining tiles that are within the defined distance of the energy applicator 184. In a step 490, the cut guide 390 then identifies a narrow set of boundary-defining tiles that are within the broad set of tiles that the energy applicator 184 could cross. This step is often referred to as the narrow phase search. This narrow phase search can be performed by initially defining a bounding volume. This bounding volume extends between what are considered to be initial and final positions of the energy applicator 184. If this is the first execution of step 490, the initial position is set to the previous commanded position; the final position is set to the integrator-generated position.

In its most elemental form, this bounding volume is a line segment between the initial and final positions of the energy applicator 184. The bounding volume may have a cross sectional area geometry that is constant along the length of the volume. The bounding volume may have a cross sectional section that comprises one or more borders that is curved and/or straight in shape. The bounding volume may have a shape that is function of the shape of the energy applicator 184 and the initial and final orientations of the energy applicator 184.

Once the bounding volume is defined, as part of the narrow phase search of step 490, the cut guide 390 determines which, if any, of the broad set of tiles are intersected by this volume. The tiles intersected by the bounding volume are the narrow set tiles.

As a result of evaluation of step 490 it may be determined that none of the broad set of tiles are intersected by the bounding volume; the narrow set is an empty set. This is the evaluation of step 492. If this evaluation tests true, cut guide 390 interprets this condition as indicating that the final position of the energy applicator 184 is within the volume defined by the boundaries. If the energy applicator 184 is so located, cut guide 390 proceeds to the above-described step 488. If this is the first execution of step 490, in this version of step 488, the pose and velocity generated by integrator 386 are output by the cut guide 390 as a commanded pose and a commanded velocity.

Alternatively, as a result of the evaluation of step 492 it may be determined that the bounding volume crosses one or more tiles; the narrow set contains one or more tiles. If this is the determination of the evaluation of step 492, the cut guide 390 interprets this condition as indicating that the final position of the energy applicator 184 is beyond a boundary. This condition is illustrated by FIG. 20B. Here point 462 is the initial position of the energy applicator 184. Point 469 is the final position.

If the condition of FIG. 20B exists, a step 493 is performed to determine which of the narrow set of tiles the energy applicator 184 would cross first. If the bounding volume is a line, the cut guide 390, for each tile, determines the percentage of distance the energy applicator 184 will advance during the frame prior to the crossing of the applicator with the tile. The tile crossed at the lowest percentage of distance is the tile understood to be crossed first. If the bounding volume has a non-zero cross sectional area, processes not part of this invention are used to determine crossing distances.

Figure 22:
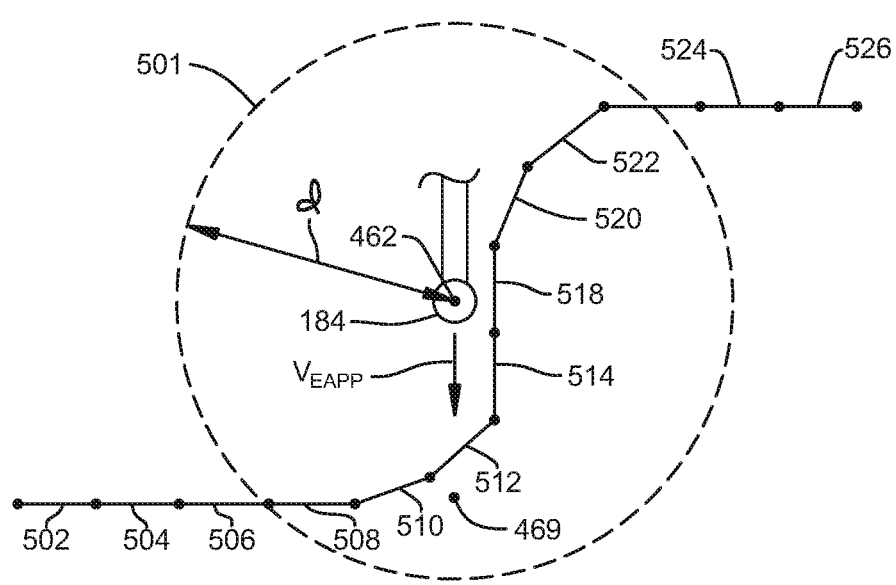
FIG. 22 is a illustration of how a boundary defining tile closest to the energy applicator may not be the tile that the applicator will most likely intersect.

By reference to FIG. 22 it can be seen that the boundary defining tiles closest to the energy applicator 184 may not be the tiles that the energy applicator 184 could cross. Here as a result of the process of step 484, it was initially determined that tiles 506-522 are within distance d, a volume represented by dashed circle 501, the distance the energy applicator 184 could potentially move within the time frame.

The closest tile to the energy applicator 184 is tile 518. However, the energy applicator 184 is moving along a trajectory that is, for purposes of illustration, straight and downward in FIG. 22, towards point 469. Therefore, in the evaluation of step 493, cut guide determines that tile 512 is the tile the bounding volume would intersect.

Once cut guide 390 generally determines which boundary-defining tile the energy applicator 184 will cross, in a step 494 cut guide 390 determines a time $t_{CNTC}$ and a point $P_{CNTC}$. Time $t_{CNTC}$ is the time period relative to the start of the frame, when the energy applicator 184 will cross the boundary. This time is determined based on the percentage of distance the energy applicator 184 will advance during the frame prior to contacting the boundary. This determination is made based on the assumption that, during any given frame, the velocity of the energy applicator 184 is constant. Point $P_{CNTC}$ is the point in coordinate system BONE where the energy applicator 184 will cross the tile. This point is determined by calculating where the path of advancement of the energy applicator 184 crosses the tile. Both calculations use as input variables the initial and final positions of the energy applicator 184 and data defining the perimeter of the boundary tile. These location-specifying data are in coordinate system BONE.

Also as part of step 494, cut guide 390 determines the pose of coordinate system CMVB and the velocity of this coordinate system at time $t_{CNTC}$. This pose is calculated based on the initial pose of coordinate system CMVB, the initial velocity of this coordinate system and time $t_{CNTC}$. If this is the first execution of step 494, cut guide 390 assigns the previous commanded pose of coordinate system CMVB to be the initial pose. If this is the first execution of step 494, cut guide 390 assigns the previous commanded velocity of coordinate system CMVB to be the initial velocity. Both the linear and rotational velocities of coordinate system CMVB are assumed to be constant throughout the frame. Therefore, both the initial linear and rotational velocities are assumed to be the linear and rotational velocities at time $t_{CNTC}$. The above determinations are made with reference to coordinate system BONE.

Also as part of step 494, the linear and rotational velocities of coordinate system EAPP are determined at time $t_{CNTC}$. These velocities are based on the velocities of coordinate system CMVB and the fixed pose of coordinate system EAPP relative to coordinate system CMVB. The linear and rotational velocities of coordinate system EAPP are calculated with reference to coordinate system BONE.

Cut guide 390 also defines a boundary contact coordinate system, step 496. This coordinate system is defined so as to have a z-axis that is orthogonal to the surface section of the boundary that would be crossed by the energy applicator 184. As part of the process of defining the boundary contact coordinate system, the position and orientation of this coordinate system relative to the coordinate system BONE is determined. The origin of this coordinate system is point $P_{CNTC}$.

Figure 23A:
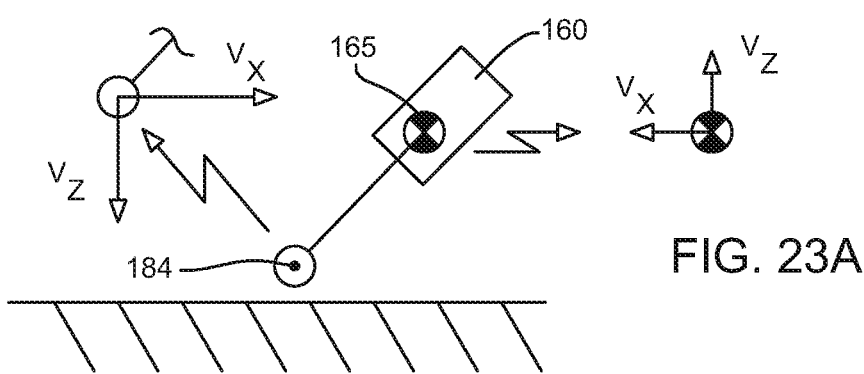
FIGS. 23A and 23B are diagrammatic depictions of the velocity changes the instrument and energy applicator undergo as a consequence of the cut guide's prevention of the movement of the energy applicator beyond the defined boundary.

Cut guide 390 then determines a force $F_{BNDR}$ applied to the virtual rigid body at the origin of coordinate system EAPP to stop the unwanted progression of the energy applicator 184 beyond the boundary. The method by which force $F_{BNDR}$ is determined is explained by initial reference to FIG. 23A. This Figure represents the velocities of coordinate system CMVB and the energy applicator 184 as the applicator moves towards boundary. For ease of illustration, velocities along only the X- and Z-axes of the boundary contact coordinate system are illustrated. As seen in FIG. 23A, the energy applicator 184 moves at high velocities to the right in the x-axis and downwardly in the z-axis. Simultaneously, the virtual rigid body, more particularly the origin of coordinate system CMVB, moves at slower velocities to the left in the X-axis and upwardly along the Z-axis. Owing to the orientation and relative magnitude of these velocities, what is occurring in this motion is that the energy applicator 184 is rotating counterclockwise relative to the coordinate system CMVB while there is some minor displacement of the virtual rigid body.

Cut guide 390 determines a boundary constraining force applied to the origin of coordinate system EAPP that prevents the energy applicator 184 from advancing in the z-axis of the boundary contact coordinate system.

Figure 23B:
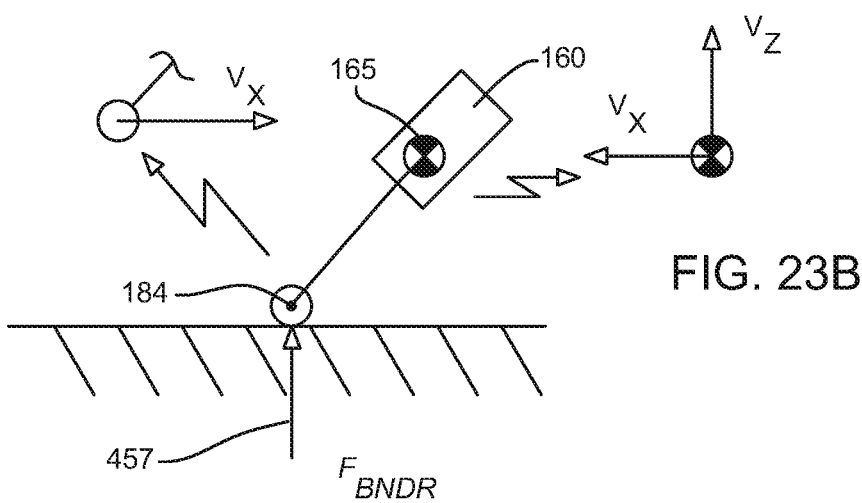

Accordingly, in step 530, the cut guide 390 transforms the positions and velocities of coordinate system EAPP and the pose and velocities of coordinate system CMVB into the boundary contact coordinate system. In a step 532, the cut guide determines a scalar force $F_{BNDR}$ that, if applied to the origin of coordinate system EAPP at time $t_{CNTC}$, would stop the advancement of the applicator in the direction normal and towards the boundary. As represented by arrow 457 in FIG. 23B, force $F_{BNDR}$ acts along the z axis in the boundary contact coordinate system. Cut guide 390 may use one of a number of different methods to determine the magnitude of force $F_{BNDR}$.

For example, it is possible to use an impulse method to compute force $F_{BNDR}$. In one such method, a version of Equation (5) with components expressed in the boundary contact coordinate system is employed to determine $F_{BNDR}$. In this application of Equation (5), $F_{BNDR}$ is substituted for $F_{EAPP}$. In this case velocity $V_1$ is the desired velocity of the energy applicator 184 at time $t_{CNTC}$. Therefore, the Z-component of velocity $V_1$ is zero. This is because the goal of this application of the Equation is to determine the force that, if applied to the origin of coordinate system EAPP, would cause the Z-axis velocity to drop to zero relative to the boundary. The other components of velocity $V_1$ are not relevant. This is due to the choice of the direction vector $D_{xyz}$ discussed below. Velocity $V_0$ is the velocity of coordinate system CMVB at the start of the frame. Time $t_{CNTC}$ is employed as $\Delta t$. The linear component of direction vector $D_{xyz}$ is the unit vector defining the normal direction of the surface of the boundary at point $P_{CNTC}$. This vector is therefore [0, 0, 1]. The rotational component of vector $D_{xyz}$ is set to the null vector. In this application of Equation (5) $J_{BNDRY}$ replaces $J_{SA}$. Jacobian $J_{BNDRY}$ is the Jacobian from the origin of coordinate system CMVB to the origin of the boundary coordinate system along direction vector $D_{xyz}$.

In this application of Equation (5) mass matrix M is expressed in boundary contact coordinate system. Force $F_{cg_{ext}}$ is the output of force summer 380. For forces $F_{inertial}$ and $F_{cg_{ext}}$ to be used they must first be expressed in the boundary contact coordinate system. Components C and E are often set to zero. This eliminates the need to determine $\Delta d$.

There may be situations in which the energy applicator 184 simultaneously contacts plural boundary-defining tiles. When the energy applicator 184 is so positioned, the plural tiles simultaneously apply plural forces to the energy applicator 184. Collectively, these forces must displace the energy applicator 184 along a path that does not cross any of the tiles. Performing the calculations to determine the force that would need to be applied to the origin of coordinate system EAPP to ensure this movement is a linear complementarity problem. This problem is of the form in which, for each force and velocity pair, the force must be equal to or greater than zero and the velocity also equal to or greater than zero. To solve this problem it is therefore necessary for the Jacobian matrix of this version of Equation (5) to include extra rows.

It should be understood also that this impulse is applied to a point on the virtual rigid body, the origin of energy applicator 184 coordinate system EAPP that is spaced from the origin of coordinate system CMVB. Once $F_{BNDRY}$ is determined, this scalar force is converted to an equivalent set of boundary constraining forces and torques, $F_{B\_C}$, that would need to be applied to the virtual rigid body at the origin of coordinate system CMVB, step 534. This conversion may be according to the following formula:

$$F_{B\_C} = J_{BNDRY}^T F_{BNDRY} \qquad (11)$$

Force $F_{B\_C}$ is expressed in the boundary contact coordinate system.

Force $F_{B\_C}$ is then summed with $F_{cg_{ext}}$. Using the methods described with reference to Equations (9) and (10), cut guide 390 determines the new accelerations of the coordinate system CMVB, step 536. The above sum of forces and torques are substituted for $F_{TTL}$ and $T_{TTL}$ in these applications of the Equations.

Based on these acceleration values, using the methods employed by the integrator 386, the cut guide 390 determines the velocities of coordinate system CMVB at time $t_{CNTC}$, using an integration interval ending at time $t_{CNTC}$, step 538. If this is the first execution of this step, the beginning of the frame is the beginning of integration interval. If this is a subsequent execution of this step, this integration interval starts at a time after the beginning of the frame.

Next, a second execution of the methods employed by the integrator 386 is performed to determine the velocities and pose of coordinate system CMVB at the end of the frame. This second execution is performed using an integration interval extending from time $t_{CNTC}$ to the end of the frame.

The above integrator processes performed by the cut guide 390 are performed in the boundary contact coordinate system. During a single iteration of the boundary constraining force generating process, the pose of boundary contact coordinate system is fixed relative to coordinate system BONE. Therefore, by performing these processes in the boundary contact coordinate system, the movement of the patient's anatomy is taken into account when calculating the boundary constraining forces. Often it is assumed that the boundary contact coordinate system is an inertial coordinate system with constant velocity and no acceleration relative coordinate system MNPL during the integration interval. The outputs of these integrator processes are then converted from boundary contact coordinate system to coordinate system BONE.

At this time in the boundary constraining process, the pose of coordinate system CMVB at time $t_{CNTC}$ becomes the new initial pose of this coordinate system. From this pose, a new initial position of coordinate system EAPP is determined. This position is the position of the energy applicator 184 adjacent but not over the boundary. In FIG. 20B, this is point 464. The pose of coordinate system CMVB at the end of the frame becomes the new final pose of this coordinate system, step 540. From this pose a new final position of coordinate system EAPP is determined, step 542. In FIG. 20B this position is represented by point 468. It should be understood that, as a result of the application of $F_{B\_C}$, to the virtual rigid body, the position of coordinate system EAPP moves along, but does not cross, the boundary. In FIG. 20B, this is represented as the advancement of the energy applicator 184 from point 464 to point 468

Figure 23C:
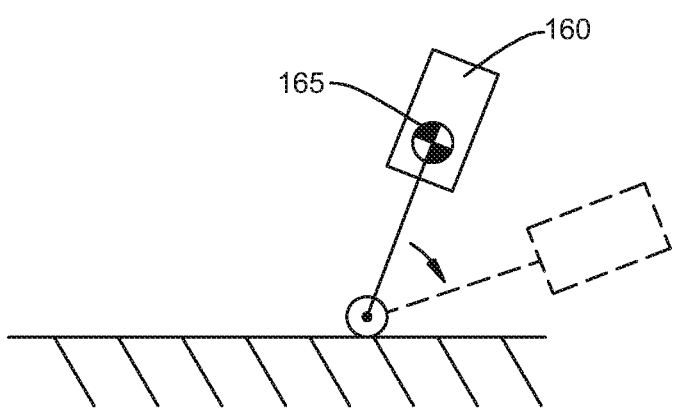
FIG. 23C is a diagrammatic depiction of the change in position of the instrument and energy application as a consequence of the cut guide's prevention of the movement of the energy applicator beyond the defined boundary.

It should further be appreciated that as a result of the application of $F_{B\_C}$, there will be appreciable change in the position of coordinate system CMVB. This difference is represented by the differences in position of point 165 from FIG. 23B to 23C. In comparison to the depiction in FIG. 23B, in FIG. 23C, coordinate system CMVB is displaced both downwardly and to the right more than it would if not subject to the boundary constraining forces. This is represented by the dashed line representation of the instrument 160 and energy applicator 184.

In FIG. 20B, the energy applicator 184 is shown advancing on a path approximately parallel and adjacent to boundary 454. Energy applicator 184 of the virtual rigid body advances along this path until the end of frame.

After the advancement of the energy applicator 184 is constrained to prevent the applicator from crossing one boundary, there is a possibility that, within the same time frame, the energy applicator 184 could cross a second boundary. This scenario is depicted in FIG. 20C. Here point 470 is the previously commanded position, the first initial position, of the energy applicator 184. Point 472 represents the integrator-generated position, the first final position, if advancement of the energy applicator 184 is not boundary constrained. It can be seen that point 472 is beyond a boundary. Cut guide 390 therefore determines a boundary constraining force that would need to be applied to the virtual rigid body to prevent the energy applicator 184 from crossing boundary 454.

Point 471, is the point adjacent boundary 454 where, by applying a first boundary constraining force, cut guide 390 prevents the energy applicator 184 from crossing boundary 454. Point 471 is therefore the second initial position of the energy applicator 184 in the frame.

Point 476 represents the second final position of the energy applicator 184 if the virtual rigid body is only subjected to a single boundary constraining force. In FIG. 20C it is observed that the path of travel between points 471 and 476 crosses boundary 456. Cut guide 390 is therefore further configured to prevent one boundary constraining diversion of the energy applicator 184 from causing the applicator to cross another boundary.

Cut guide 390 prevents this trespass by, after step 542 is executed, performing a subsequent narrow phase search of the tiles, step 490 is reexecuted. Prior to performing this subsequent narrow phase search, step 490, the cut guide executes a step 543. In step 543 the cut guide 390 evaluates whether or not the cut guide 390 has performed a maximum number of allowed recalculations of the boundary constraining force $F_{BNDRY}$ that can be applied to the origin of coordinate system EAPP. The purposes of performing step 543 are discussed below. If the cut guide has not performed the maximum number of recalculations of the boundary constraining force, cut guide proceeds to the subsequent step 490 reexecution of the narrow phase search.

In this subsequent narrow phase search process, the newly defined initial and final positions of the energy applicator 184 are, in step 490, employed to define a new bounding volume. Again also in step 490 a determination is made regarding whether or not this volume intersects any boundaries. During a subsequent execution of step 492, the evaluation may indicate that the set of tiles the bounding volume crosses is the empty set. As with the first execution of step 492, if this evaluation tests true, the cut guide 390 interprets the results as indicating that, should the energy applicator 184 advance to the final position, the applicator will not cross the boundaries. This is the evaluation result the cut guide would make with regard to the advancement of the energy applicator 184 from point 464 to 468 in FIG. 20B.

As a result of this subsequent evaluation of step 492 testing true, cut guide 390 executes a version of step 488. It should be understood that this execution of step 488 is occurring after a second or later execution of step 492. Accordingly, in this version of step 488, the cut guide 390 outputs the last determined end of frame pose and last determined end of frame velocity of coordinate system CMVB to be, respectively, the commanded pose and commanded velocity of this coordinate system.

In the second narrow phase search of energy applicator 184 advancement of FIG. 20C, the bounding volume is between points 471 and 476. This volume crosses boundary 456. The subsequent evaluation of step 492 will test false. Consequently, steps 493, 494, 496, 530, 532, 534, 536, 538, 540, 542 and 543 are reexecuted. As a result of the reexecution of these steps, the cut guide 390 determines the characteristics of a subsequent boundary constraining force that needs to be applied to the virtual rigid body. Cut guide 390 then determines a subsequent final position to which the energy applicator 184 would advance upon the application of this subsequent boundary constraining force.

In FIG. 20C it is seen that it is necessary to apply a subsequent boundary constraining force to the virtual rigid body to prevent the energy applicator 184 from, at point 474, crossing the boundary. As a consequence of the application of this subsequent boundary constraining force, the energy applicator 184, advances to point 478. The final pose of coordinate system CMVB when the energy applicator 184 is at this point 478 is the end-of-frame commanded pose output by the cut guide 390.

Thus, for a single time frame in which the energy applicator 184 is advanced, the cut guide 390 may perform multiple analyses to determine the positions of the energy applicator 184 relative to the boundaries. If necessary, the cut guide 390 applies multiple boundary constraining forces to the virtual rigid body to prevent the energy applicator 184 from crossing boundaries.

In some versions, the cut guide is limited in the number of times, in a single frame it can generate data regarding a boundary constraining force that should be applied to the virtual rigid body. This is due to limitations in the processing capability of manipulator controller 124. In some versions, the cut guide is limited to between 4 and 16 iterations and more often 6 to 12 iterations per frame. This is why the cut guide executes the evaluation of step 543. If the cut guide determines that it has performed the maximum number of boundary constraining force generations, the cut guide executes a version of step 488. In this version of the execution of step 488, the last initial pose and velocity are output as, respectively, the commanded pose and the commanded velocity for coordinate system CMVB. This is because this pose and velocity are the last pose and velocity stored by the cut guide 390 for the state in which the energy applicator 184 is within the boundaries.

The commanded pose and commanded velocity of coordinate system CMVB relative to coordinate system MNPL are the final output of the behavior control processes.

The commanded pose of coordinate system CMVB is applied to the inverse kinematics module 542 shown in FIG. 13C. The inverse kinematics module 542 is one of the motion control modules executed by the manipulator controller 124. Based on the commanded pose and preloaded data, the inverse kinematic module 542 determines the desired joint angle of the joints of the manipulator 50. The preloaded data are data that define the geometry of the links and joints. In some versions, these data are in the form Denavit-Hartenberg parameters.

There are constructions of this invention in which a closed form solution to the inverse kinematics is not known. This is often the case with overactuated parallel mechanisms such as the mechanism described in this application. In such situations, the inverse kinematics are solved using numerical methods such as the iterative Newton Raphson method. The inverse kinematics model calculates the joint angles for both the active and passive joints of the manipulator. The active joints are the joints the angles of which are driven by joint actuators. The passive joints are the joints the angles of which are set as a result of the positioning of the active joints. The passive joints are: the joints between the upper links 74 and the driven links 80; the joints between the four bar links 78 and the driven links 80; and the joints between the driven links 80 and coupler 88.

Each desired joint angle for an active joint is applied to the associated joint motor controller 126. The joint motor controller 126 regulates the positioning of the joint. These joint angles applied to controllers 126 are referred to as commanded joint angles.

While not illustrated, it should be understood that some manipulators include modules that perform load balancing and/or arm compensation. This is true of manipulators that include parallel arms. These modules are almost always provided if the manipulator includes overactuated parallel arms. The load balancing is performed to ensure that the arms share the load associated with advancing the instrument to the commanded poses. This load balancing is performed to minimize the extent to which each arm resists the movement of the other arm. Load balancing is also performed to redistribute torque among the actuators. The torque is redistributed to minimize the instances in which any individual actuator is required to apply a significant percentage of the total torque output by the manipulator.

Arm compensation is performed because one arm is typically positioned to regulate the positioning of the other arm. For example, often at least some of the commanded joint angles of the lower arm 68 are often finely adjusted to ensure precise positioning of the passive joint angles associated with the upper arm 70. The design of the load balancing and arm compensation modules is specific to the nature of the links integral with the manipulator. This may be practiced with link assemblies different than the described link assemblies.

The desired joint angles generated by the inverse kinematic module are applied to a command dynamics module 544, also a motion control module. Command dynamics module differentiates the sequence of joint angles for each joint. These differentiations are performed to, for each joint, generate data indicating its angular velocity and acceleration. Command dynamics module also has a data describing the mass and inertia properties of each of the links.

Based on the above data, command dynamics module 544 performs an inverse dynamics calculation for the motion of the links and joints. This inverse dynamics calculation produces, for each active joint, the torque that should be applied to the joint to cause motion of the joint to the commanded joint angle. This torque is referred to as the feed forward torque. In some versions, this torque is calculated based on the iterative Newton-Euler method. Alternatively, these torques can be calculated using the Lagrangian method.

While not shown in FIG. 13D, the signals representative of the forces and torques detected by sensor 108 are sometimes applied to command dynamics module 544. By employing these signals as additional input variables in the dynamics calculation, module 544 produces more accurate calculations of the feed forward torque.

There are periods in which the manipulator 50 holds the instrument 160 in a static pose. During these periods, the velocities and accelerations of the joints fall to zero. Even during these time periods, command dynamic module 544 outputs data indicating that the joint motors should still produce non-zero torques. This is because the joint motors need to output at least some torque to prevent the arm links from slipping from their static positions. This is because, even when the arm links are not exposed to direct mechanical forces, the arms are still subjected to the force of gravity.

Each joint motor controller 126 receives three inputs. One input is the commanded joint angle for the associated joint from the inverse kinematics module. The second input is the feed forward torque for the joint from the commanded dynamics module 544. The third input is the input signal from the rotary encoder 112, 114 or 116 associated with the joint. Each motor controller 126 also stores as a constant, the gear ratio of the reduction gears 105 of the actuator 92, 94 or 96 with which the controller is associated. Based on these rotor angle data and the gear ratio data, the controller 126 generates data that represents the actual joint angle of the joint. This is known as the measured joint angle.

Based on the above inputs, the joint motor controller 126 determines the energization signals that should be applied to the associated motor 101 that cause the motor to drive the joint towards the commanded joint angle. It should be understood that the measured joint angle is used as the representation of the actual joint angle. The feed forward torque from the command dynamics module is the feed forward torque signal added to the input of the current control loop of the controller 126. Prior to adding this indication of feed forward torque to the current control loop, controller 124 adjusts the torque from joint torque to motor torque based on the gear ratio. The torque is then adjusted from motor torque to motor current based on a stored torque constant of the motor.

As a consequence of the application of the energization signals applied to the motors 101, the active joints are driven towards their commanded joint angles. The resultant displacement of the shoulders and links results in the passive joints being driven towards their desired joint angles.

The measured joint angles of the six active joints generated by the joint motor controllers 126 are forwarded to a forward kinematics module 562. Also applied to the forward kinematics module 562 are the signals from encoders 117 and 118. These signals are the measured joint angles for the passive joints integral with these encoders. Based on the measured joint angles and preloaded data, the forward kinematics module 562 determines a representation of the actual pose of the end effector 110, coordinate system EFCT, relative to coordinate system MNPL. The preloaded data are data that define the geometry of the links and joints. In some versions, these data are in the form Denavit-Hartenberg parameters.

Forward kinematics module 562 also calculates joint angles for the passive joints to which encoders are not attached. These calculated joint angles function as representations of the actual joint angles for the passive joints to which encoders are not attached. The forward kinematics module 562 calculates these joint angles as part of the process of determining the actual pose of the end effector 110.

Based on the measured pose of the end effector, forward kinematics module 562 produces data describing the measured pose of coordinate system CMVB and coordinate system EAPP both relative to coordinate system MNPL. This is because coordinate systems EFCT, CMVB and EAPP have fixed poses relative to each other.

The measured pose of coordinate system CMVB is applied to a Jacobian calculator 564. Jacobian calculator 564, based on this measured pose, calculates Jacobian matrices relating motion within individual coordinate spaces to motion of the origin of coordinate system CMVB expressed in coordinate system CMVB. One such coordinate space is joint space. Joint space is a vector consisting of all the joint angles of the manipulator. One of the calculated matrices is the Jacobian matrix between joint space and coordinate system CMVB, Jacobian $J_{JNT}$. A second coordinate space is interference space. Interference space is a vector that includes minimum distances between the below-discussed potentially colliding pairs of links. In some cases, these minimum distances are distances along the common normals between the potentially colliding pairs of links. A second calculated matrix is the Jacobian matrix between interference space and coordinate system CMVB, Jacobian $J_{INF}$. Coordinate system EAPP is a third coordinate space. Calculator 564 calculates the Jacobian matrix between the origin of coordinate system EAPP, expressed in coordinate system MNPL, to the origin of coordinate system CMVB, Jacobian $J_{WSB}$.

Often calculator 564 initially calculates the inverse Jacobian of the desired Jacobian using numerical methods. Once the inverse Jacobian is calculated, calculator 564 determines the desired Jacobian by computing an inverse of the inverse Jacobian. In the case of a non-square Jacobian matrix, the pseudoinverse must be used to compute this inverse.

The measured joint angles from encoders 112-118 and the calculated joint angles from forward kinematics module 562 are applied to a joint limit comparator 582. Joint limit comparator 582 and the associated modules generate signals that prevent each joint, active and passive, from moving beyond a specific range of motion. A minimum and maximum joint limit angle is defined for each joint. For proper operation of the manipulator, each joint angle should be between the associated joint limit angles. Joint limit comparator 582 employs the measured or calculated joint angle for each joint as the representation of the actual joint angle for the joint.

Associated with each joint limit angle is a joint boundary angle. The joint boundary angle is an angle within the range of motion of the joint that is relatively close to the joint limit angle. For example, if the minimum joint limit angle associated with a joint is 10° the minimum boundary angle may be between 12 and 20°. If the maximum joint angle of a joint is 115°, the maximum boundary angle may be between 105° and 113°. Joint limit comparator 582 determines the differences between the representation of actual joint angle to the minimum and maximum boundary joint angles, step 591 of FIG. 24. This difference is known as a boundary exceeded angle, angle $ANGLE_{B\_E}$.

If the representation of actual joint angle is greater than the minimum boundary joint angle and less than the maximum joint boundary angle, the joint is considered acceptably spaced away from the joint limit angles for the joint. There is no need to apply forces and torques to the virtual rigid body that would prevent movement of the joint towards the closest joint limit. Accordingly, in a step 591 if the above conditions tests true, joint limit comparator outputs a boundary exceeded angle of 0° (step not shown). If the above condition tests false, joint limit comparator 582 outputs a boundary exceeded angle that is the signed difference of the representation of actual joint angle and the crossed boundary angle (step not shown). Typically, the sign is negative if the minimum joint boundary angle is crossed and positive if the maximum joint boundary angle is crossed.

Figure 24:
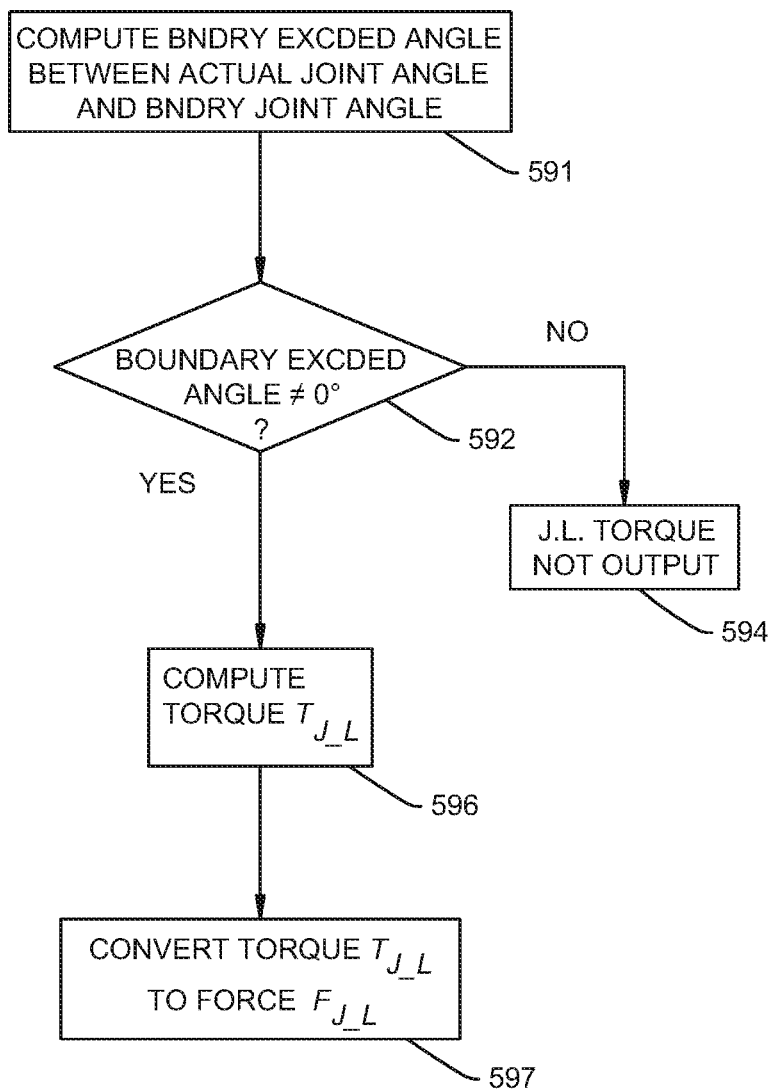
FIG. 24 is a flow chart of the process by which joint limit constraining force may be generated.

Step 592 represents the evaluation of the boundary exceeded angle. If this angle is equal to zero for a particular joint angle, manipulator controller 124 interprets this information as indicating that manipulator 50 can continue to freely move the joint towards the closest boundary joint angle. In FIG. 24 this is represented by, step 594, the motion control software's not outputting a joint limit torque.

If the boundary exceeded angle is non-zero, the angle is applied to a joint limit torque generator 584, step not shown. Generator 584, based on the input series of boundary exceeded angles, computes a time derivative of these angles. This time derivative is angular velocity $V_{B\_E}$. Joint limit torque generator 584 outputs a torque that would be applied to the joint to prevent the manipulator from being moved in such a way that joint will move further beyond the boundary angle towards the adjacent joint limit angle, step 596. This torque, torque $T_{J\_L}$, is determined according to the following formula:

$$T_{J\_L}=f(ANGLE_{B\_E})+f(V_{B\_E}) \quad (13)$$

In some cases:

$$f(ANGLE_{B\_E})=K_{B\_E}ANGLE_{B\_E} \quad (13A)$$

$$f(V_{B\_E})=D_{B\_E}V_{B\_E} \quad (13B)$$

Coefficient $K_{B\_E}$ is a spring coefficient. This coefficient may be variable. This is because as the joint angle approaches the adjacent joint limit angle there would be a need to appreciably increase the torque that limits joint movement towards this angle. Consequently, there is often greater than first order relationship between the magnitude of this torque and the absolute difference between the crossed boundary angle and the representation of actual joint angle.

Coefficient $D_{B\_E}$ is a damping coefficient. The damping coefficient may be variable. In some versions, this coefficient is a function of the boundary exceed angle $ANGLE_B$-E and/or velocity $V_{B\_E}$. Varying coefficient $D_{B\_E}$ may be desirable to enhance the stability of the movement of the instrument.

In practice, joint limit torque generator 584 does not actually execute Equation (13) to determine the joint limit torque. Instead, the generator 584 maintains look up tables of limiting torques (tables not illustrated). The inputs to determine the appropriate limiting torques are representations of boundary exceeded angle $ANGLE_B$-E and angular velocity $V_{B\_E}$. If the boundary exceeded angle is 0°, torque $T_{J\_L}$ is inherently a zero torque.

Joint limit torque generator 584 applies the plurality of torques $T_{J\_L}$, one for each joint, to CMVB force converter 586, step not shown. A second input into force converter 586 is the previously generated Jacobian $J_{JNT}$ from Jacobian calculator 564. The force converter 584 places the individual torques $T_{J\_L}$ into a column vector, $\vec{T}_{J\_L}$. Force converter converts these torques $\vec{T}_{J\_L}$ into the equivalent forces and torques, force $F_{J\_L}$, that should be applied to the virtual rigid body at the origin of coordinate system CMVB, step 597. This conversion is performed according to the following formula:

$$F_{J\_L} = J_{JNT}^{-T} \vec{T}_{J\_L} \tag{14}$$

Force $F_{J\_L}$ is expressed in coordinate system CMVB. Force $F_{J\_L}$ is one of the inputs applied to force summer 379, (step not shown).

Another software module to which the measured and calculated joint angles are applied is the interference limit comparator 622. Comparator 622 employs these angles as representations of the actual joint angles. In brief, the interference limit comparator 622 and associated modules outputs data describing forces that should be applied to the virtual rigid body if the movement of the arms could potentially result in link collisions. Here a "link" is more than just the links 72, 74, 76 and 80, that form each arm 68 and 70. A "link," for the purpose of the processing performed by comparator 622, is any structural member, moving or rigid, that, as a result of the movement of one of the joints could collide with another component of the manipulator. For example, if the manipulator 50 is constructed so that one of the arm links could potentially collide with an outer surface of the cart 52, comparator 622 would consider the cart surface to be a link. The shells in which the actuators are disposed if they could potentially collide with a link, are also considered to be links.

One reason to prevent these collisions is to prevent the movement of the links relative to each other that could result in pinch points forming between the links. Preventing these collisions also avoids the damage caused by such collisions.

It should be understood that each link of the manipulator may not potentially be capable of a collision with every other link of the manipulator. For example, the four bar link 78 and driven link 80 of each arm 68 and 70 cannot, due to the inherent construction of the manipulator 50, collide with each other. Nevertheless, the driven link 80 of arm 68 can collide with the driven link 80 of arm 70. Most pairs of potentially colliding links consists of a link integral with arm 68 and a link integral with the other arm, arm 70.

Figure 25:
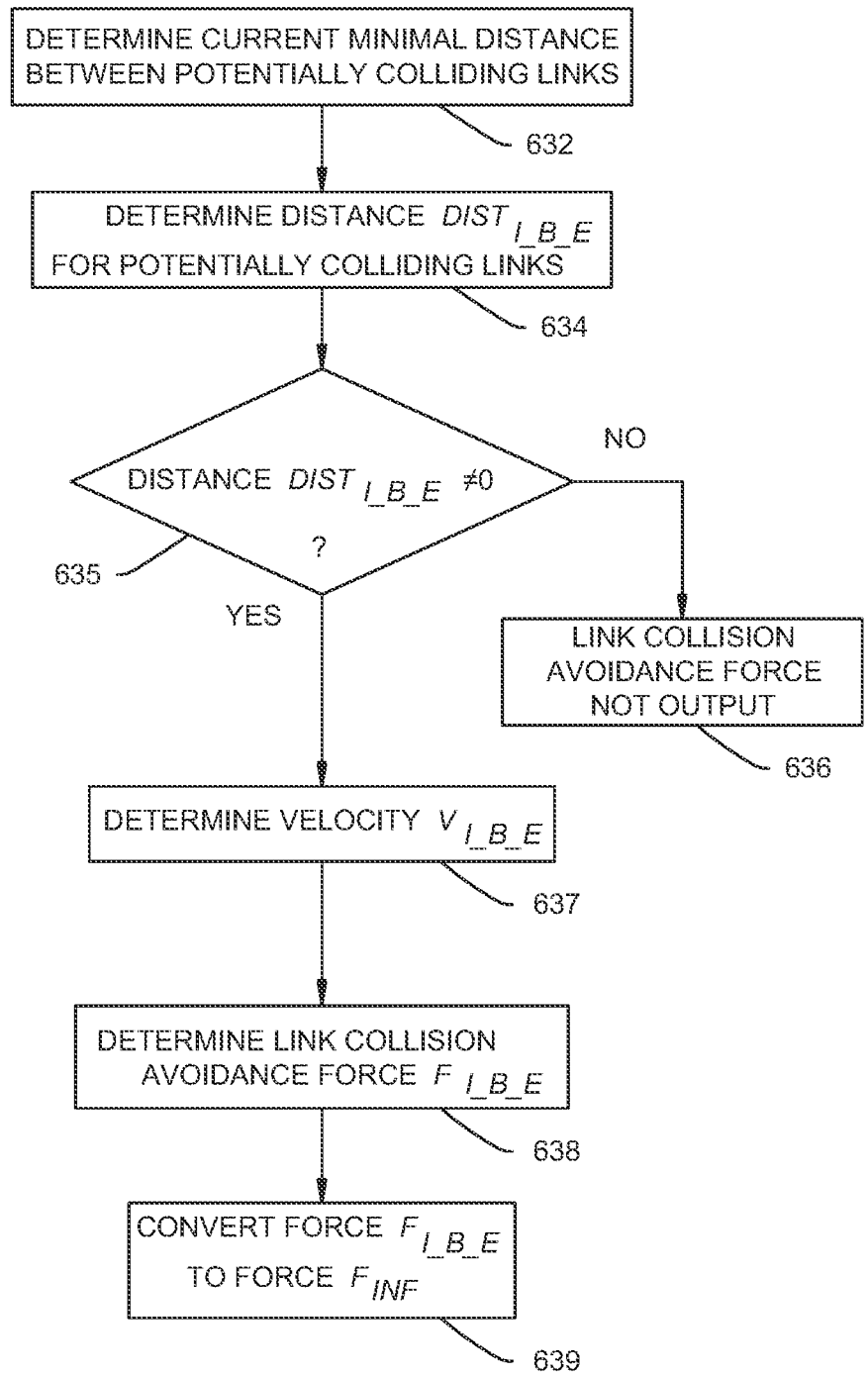
FIG. 25 is a flow chart of the process by which an interference angle constraining force may be generated.
Figure 26:
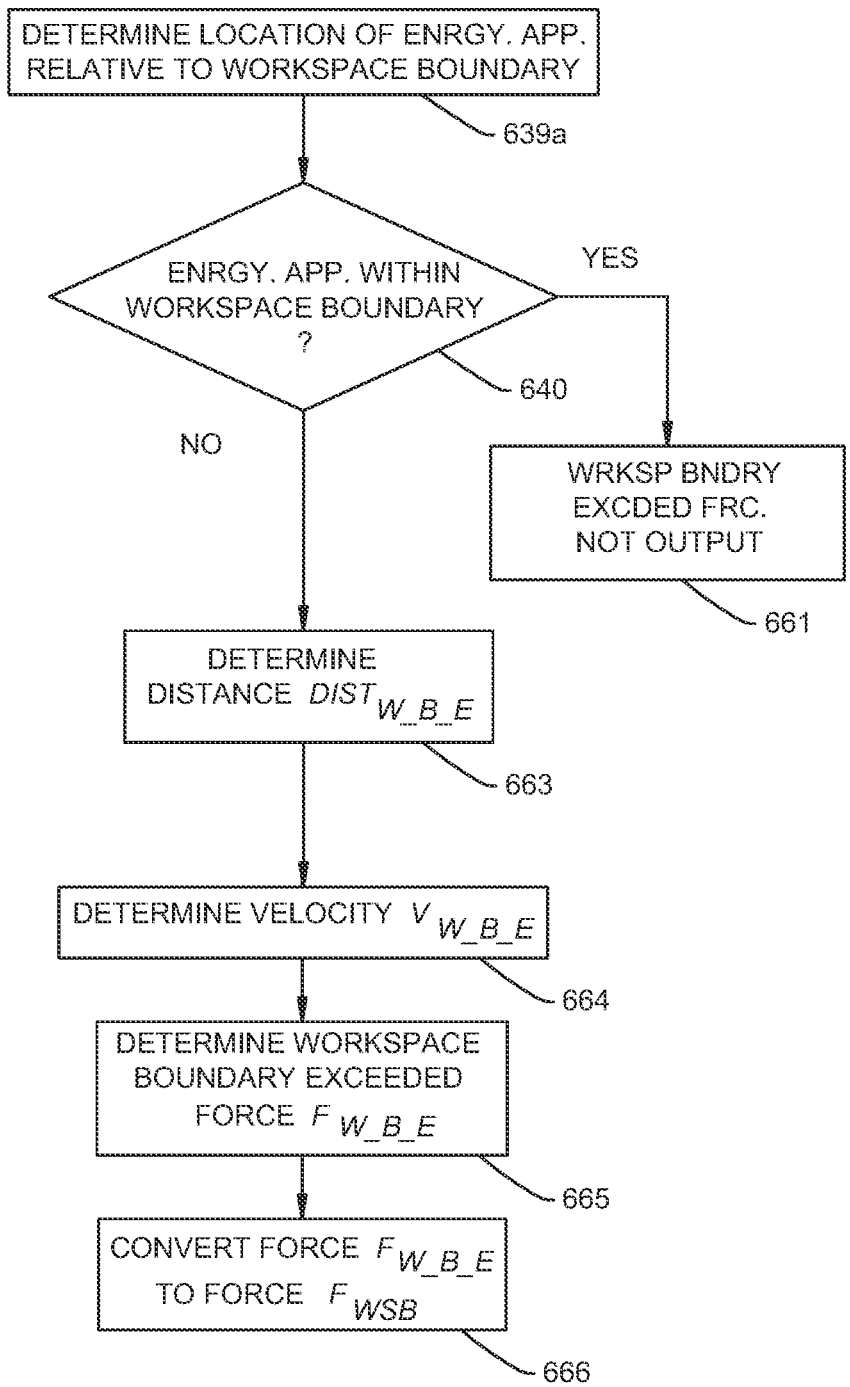
FIG. 26 is a flow chart of the process by which a workspace constraining force may be generated.

Based on the representations of the actual joint angles, interference limit comparator 622 determines a minimum distance between each pair of potentially colliding links, step 632 in FIG. 25. In some embodiments, this minimum distance is the distance along the common normal between the links. To make this determination, comparator 622, using data and processes similar to that employed by forward kinematics module 562, determines the pose of each joint. Based on the pose data, module 622 models each link as one or more line segments between each joint. Based on the line segment models, module 622 determines the common normal distance, the minimum distance, between each pair of potentially colliding links.

In step 634, the interference limit comparator 622 calculates a difference between the minimum distance for each pair of potentially colliding links and a boundary distance for the pair of links. This boundary distance is the distance below which movement of the links towards each other is undesirable. It should be appreciated that this movement includes movement in which only one link moves towards the other link. This boundary distance is greater than what could be considered a collision avoided distance. Here, the collision avoided distance is a distance which is a minimal clearance distance between the links. The collision avoided distance is a distance for the pair of potentially colliding pair of links that is greater than the smallest distance between the links that would be considered to form a pinch point between the links.

The boundary distance is determined for each pair of potentially colliding links is typically determined prior to the start of the procedure. The boundary distance can be determined by modeling each link including a longitudinal axis that is surrounded by a three dimensions volume. This volume may have a cylindrical or capsule like shape. Alternatively, the shape may be in the form of parallel pipette. This volume may have a more complex shape. The outer surface of this volume is typically located at least 3 cm beyond the actual outer surface of the modeled link. In some versions this volume has an outer diameter of at least 5 cm or at least 10 cm beyond the actual surface of the link. If the volume is capsule-like or cylindrical, the boundary distance for each pair of potentially colliding links comprises the sum of the radii for each of link encasing capsules or cylinders.

The difference between the minimum distance and a boundary distance for a pair of potentially colliding links is the interference boundary exceeded distance, distance $DIST_{I\_B\_E}$.

If the minimum distance for a pair of links is greater than the associated boundary distance, the manipulator 50 is considered in a condition in which the links are spaced sufficiently far apart from each other that movement of the links towards each other would not result in formation of a pinch point or collision. For each pair of potentially colliding links in this condition, comparator returns an interference boundary exceeded distance of zero (step not shown).

If the minimum distance for a pair of links is less than the associated boundary distance, interference limit comparator 622 outputs the absolute value of the difference as distance $DIST_{I\_B\_E}$, step not shown.

In a step 635, for the pairs of potentially colliding links, the interference boundary exceeded distance, distance $DIST_{I\_B\_E}$ is evaluated. If this distance is zero, the motion control processes do not output a force that would prevent the links from continuing to move together, step 636.

If the interference boundary exceeded distance, distance $DIST_{I\_B\_E}$ is non-zero, the distance is applied to an interference limit force generator 624, step not shown. Generator 624, based on the input series of interference boundary exceeded distances, computes a time derivative of these distances, step 637. This time derivative is a linear velocity $V_{I\_B\_E}$. Interference limit force generator 624 outputs a force that would be applied along the line of minimum distance between the links to prevent the manipulator from being moved in such a way that will result in the further closing of the distance between the potentially colliding links, step 638. For some constructions, this line is along the common normal between the links. This force, force $F_{I\_B\_E}$, is determined according to the following formula:

$$F_{I\_B\_E} = f(DIST_{I\_B\_E}) + f(V_{I\_B\_E}) \qquad (15)$$

In some cases:

$$f(DIST_{I\_B\_E}) = K_{C\_A} DIST_{I\_B\_E} \qquad (15A)$$

$$f(V_{I\_B\_E}) = D_{C\_A} V_{I\_B\_E} \qquad (15B)$$

Coefficient $K_{C\_A}$ is a spring coefficient. This coefficient may be variable. This is because as the minimum distance approaches the collision stopped distance, there is a need to appreciably increase the force that limits the movement of the links towards each other. Consequently, there is often greater than first order relationship between the magnitude of this force and the interference boundary exceeded distance.

Coefficient $D_{C\_A}$ is a damping coefficient. The damping coefficient may be variable. In some versions, this coefficient is a function of distance $DIST_{I\_B\_E}$ and/or velocity $V_{I\_B\_E}$. Varying coefficient $D_{C\_A}$ may be desirable to enhance the stability of the movement of the instrument.

In practice, interference limit force generator 624 does not actually execute Equation (15) to determine the collision preventing force. Instead, the generator 624 maintains look up tables of collision preventing forces (tables not illustrated). The inputs to determine collision preventing forces are representations of the interference boundary exceeded distance $DIST_{I\_B\_E}$ and velocity $V_{I\_B\_E}$. If the interference boundary exceeded distance is zero, force $F_{I\_B\_E}$ is inherently a zero force. Interference limit force generator 624 generates a plurality of forces $F_{I\_B\_E}$ one for each potentially colliding pair of links.

The plural forces $F_{I\_B\_E}$ generated by generator 624 are applied to a CMVB force converter 626, step not shown. A second input into force converter 626 is the previously generated Jacobian $J_{INF}$ from Jacobian calculator 564. Force converter 626 places the individual forces $F_{I\_B\_E}$ into a column vector, $\vec{F}_{I\_B\_E}$. Force converter converts forces $F_{I\_B\_E}$ into the equivalent forces and torques, force $F_{INF}$, which should be applied to the origin of coordinate system CMVB of the virtual rigid body, step 639. This conversion is performed according to the following formula:

$$F_{INF} = J_{INF}^{-T} \vec{F}_{I\_B\_E} \qquad (16)$$

Force $F_{INF}$ is expressed in coordinate system CMVB. Force $F_{INF}$ is one of the inputs applied to force summer 379, step not shown.

Another module that is part of the motion control processes performed by the manipulator controller 124 is a workspace limit comparator 652. Workspace limit comparator 652 determines if the energy applicator 184 is reaching the boundary of a defined workspace. The limit of this workspace is spaced from the origin of the coordinate system MNPL and is defined by reference to this coordinate system. The workspace is within the volume in which energy applicator 184 can move if shoulders 67 and 69 and links 72 and 74 are allowed to move to the full extensions of their ranges of motion. This workspace, sometimes referred to as the "dexterous workspace," is less than the volume of the space within the full range of motion of the manipulator 50. This is because, as the energy applicator 184 moves towards the limit of its inherent boundary, the ability to adjust the orientation of the instrument and energy applicator 184 is reduced. By way of example, at an extreme, in order to position the energy applicator 184 at the location where it is spaced a maximum distance from the origin of manipulator reference frame, the arms can only be in one position, a fully extended position. Since the arms can only be in a single position, by extension the instrument and energy applicator 184 can only be aligned in one orientation. To ensure that the practitioner has at least some ability to so reorient the energy applicator 184, the manipulator 50 does not allow the energy applicator 184 to advance outside of this workspace.

It should be appreciated that, owing to the physical construction of the manipulator 50, this workspace is typically not in the form of a simple geometric structure such as a sphere or a cube. The workspace is often defined by a set of contiguous volumes each of which has a different shape and or size. Thus, while the distance to the ceiling of the workspace above and distal to the origin of the manipulator may be a distance of 1.5 m from the origin of the manipulator coordinate system, the distance to the base of the workspace below the origin of the manipulator coordinate system may be 0.2 m. In these and other versions, the proximal end of the workspace may be located distal to origin of the coordinate system MNPL. Thus in some versions the arms may be able to move the instrument within a workspace that may extend from a location 0.5 m distal from the origin of the coordinate system MNPL to a location 2.0 m distal from the same point.

The virtual surfaces around the manipulator defining the workspace are collectively referred to as the workspace limit. Within the workspace limit there is a workspace boundary. The workspace boundary is located typically 1 to 5 cm inwardly from the workspace limit. Like the workspace limit, the workspace boundary is defined in coordinate system MNPL.

The workspace limit comparator 652 receives as an input a representation of the actual position of the energy applicator 184, the origin of coordinate system EAPP. In one version, this representation of the actual position of the origin of coordinate system EAPP on the position is calculated by the forward kinematics module 562. Based on the representation of energy applicator 184 position, comparator 652 determines the location of the energy applicator 184, the origin of coordinate system EAPP, relative to the workspace boundary, step 639*a*. Step 640 represents the evaluation that occurs after this initial determination is made. If the energy applicator 184 is within the workspace boundary, the motion control processes do not apply forces to ensure the energy applicator 184 remains within the workspace limit. This is represented by the branching to step 661.

If the evaluation of step 661 tests false, comparator 652 calculates a positive workspace boundary exceeded distance, distance $DIST_{W\_B\_E}$, step 663. This distance is the distance along a line from the origin of coordinate system EAPP back to a point on the workspace boundary such that the line is normal to the surface of the boundary. This distance is typically the shortest distance from the origin of coordinate system EAPP back to the workspace boundary. As part of step 663, a unit direction vector, vector $D_{W\_B\_E}$, along this line from the origin of coordinate system EAPP towards the workspace boundary is determined. Vector $D_{W\_B\_E}$ is expressed in coordinate system MNPL.

The workspace boundary exceeded distance is applied to a workspace limit force generator 654, step not shown. Generator 654, based on the input series of workspace boundary exceeded distances, computes a time derivative of these distances, step 664. This time derivative is a linear velocity $V_{W\_B\_E}$.

In a step 665 workspace boundary exceeded force generator 654 outputs a force that would be applied along the normal line from the origin of coordinate system EAPP back to the workspace that would prevent the energy applicator 184 from being moved further away from the workspace boundary towards the workspace limit. The magnitude of this force, force $F_{W\_B\_E}$, is determined according to the following formula:

$$F_{W\_B\_E} = f(DIST_{W\_B\_E}) + f(V_{W\_B\_E}) \quad (17)$$

In some cases:

$$f(DIST_{W\_B\_E}) = K_{WS\_E} DIST_{W\_B\_E} \quad (17A)$$

$$f(V_{W\_B\_E}) = D_{WS\_E} V_{W\_B\_E} \quad (17B)$$

Coefficient $K_{WS\_E}$ is a spring coefficient. This coefficient may be variable. This is because as the energy applicator 184 moves outwardly from the workspace boundary towards the workspace limit, there is a need to appreciably increase the force that prevents the continued movement of the energy applicator 184 towards the workspace limit. Consequently, there is often greater than first order relationship between the magnitude of this force and the workspace boundary exceeded distance.

Coefficient $D_{WS\_E}$ is a damping coefficient. The damping coefficient may be variable. In some versions, this coefficient is a function of distance $DIST_{W\_B\_E}$ and/or velocity $V_{W\_B\_E}$. Varying coefficient $D_{WS\_E}$ may be desirable to enhance the stability of the movement of the instrument.

In practice, workspace boundary force generator 654 does not actually execute Equation (17) to determine the workspace boundary exceeded force. Instead, the generator 654 maintains look up tables of these forces (tables not illustrated). The inputs to determine collision preventing forces are representations of the workspace boundary exceeded distance $DIST_{I\_B\_E}$ and velocity $V_{I\_B\_E}$. If the workspace boundary exceeded distance is zero, force $F_{W\_B\_E}$ is inherently a zero force.

Scalar force $F_{W\_B\_E}$ is converted into a vector force, $\vec{F}_{W\_B\_E}$ according to the following equation:

$$\vec{F}_{W\_B\_E} = F_{W\_B\_E} D_{W\_B\_E} \quad (17C)$$

Force $\vec{F}_{W\_B\_E}$ is expressed in coordinate system MNPL.

Force $F_{W\_B\_E}$ is applied to a CMVB force converter 655, step not shown. A second input into force converter 655 is Jacobian $J_{WSB}$ from Jacobian calculator 564. The force converter converts force $F_{W\_B\_E}$ into the equivalent forces and torques, force $F_{WSB}$, that should be applied to the origin of coordinate system CMVB of the virtual rigid body, step 666. This conversion is performed according to the following formula:

$$F_{WSB} = J_{WSB}^{-T} \vec{F}_{W\_B\_E} \quad (18)$$

Force $F_{WSB}$ is expressed in coordinate system CMVB. Force $F_{WSB}$ is one of the forces applied to force summer 379, step not shown.

The behavior controller also includes modules that provide data about external forces and torques that are applied to the manipulator 50, the instrument 160 and energy applicator 184. These external forces and torques include the resistance of the tissue to instrument advancement and practitioner applied forces and torques.

One method of determining external forces and torques is to determine the magnitude of backdrive torques output by the joint motors 101. Backdrive torques are output by joint motors 101 in response to external forces and torques placed on the manipulator, instrument and energy applicator 184. The backdrive torques are the torques output by the joint motors 101 beyond the torques needed to overcome inertia and the force of gravity.

Backdrive torques function as representations of external forces and torques because each joint motor 101 and associated joint motor controller 126 form a position control loop. The joint motor controller 126 regulates the joint angle of the joint with which the controller is associated. Each controller 126 continually adjusts the torque the associated motor 101 outputs to, as closely as possible, ensure that the motor drives the associated joint to the commanded joint angle. When the instrument is subjected to external forces and torques, these forces and torques momentarily disrupt the advancement of the instrument to the commanded pose. This, in turn, momentarily disrupts the advancement of one or more of the joints to their commanded joint angles. The control loops typically operate at a much higher bandwidth than the behavior and motion control processes. The control loops therefore, essentially simultaneously with the application of the external forces and torques, adjust the torques output by the joint motors 101 to compensate for these forces and torques. Thus, the torques output by the joint motors represent a sum of torques. These torques are the torques needed to overcome inertia and gravity and the torques needed to overcome the external forces and torques, the back drive torques.

To calculate the backdrive torques, the manipulator controller 124 determines the torques that joint motors 101 should output if external forces and torques are not present. These torques are determined by an expected dynamics module, module 690. The inputs into expected dynamics module 690 are the measured joint angles from encoders 112, 114, 116, 117 and 118 and the calculated joint angles from forward kinematics module 562. Using the methods employed by command dynamics module 544, expected dynamics module 690 calculates, for the active joints, estimates of torques consistent with the observed movement of the joints. These torques are estimates of the torques that would be applied in the absence of external forces and torques applied to the manipulator, the instrument or the energy applicator 184. These torques are referred to as the expected torques.

The second set of variables upon which the backdrive torques are determined is the actual torques that the joint motors apply to the arms 68 and 70 to advance the instrument 160 towards the commanded pose. Manipulator 50 employs two methods for obtaining representations of the actual torques. One method is the measuring of the torques output by the joint motors 101, more accurately, the reduction gears 105. In practice, signals representative of the currents applied to the joint motors 101 from the joint motor controllers 126 are often employed as signals representative of the joint motor/reduction gear torques. This is because there is a linear relationship between the current applied to a motor 101 and the torque output by the motor.

The second method of determining representations of actual torques is to monitor the torques the joint motors 101 output as measured by torque sensors 89.

A backdrive torque summer 691 receives as inputs the currents applied to the joint motors 101 and the signals output by torque sensors 89. Torque summer 691 blends these inputs to produce a single stream of output data representative of the actual joint torque. In some versions, backdrive torque summer 691 produces a weighted average of these two representations of actual torques. These average torque values reflect the strengths in accuracies in torque measurements that are inherent but different in the two separate methods of determining actual joint torque. Torque sensors 89 may produce signals that are incrementally more sensitive to changes in torque output. The torque measurements based on the applied current in some cases are more representative of the output torque over a broader range of torques.

The representation of actual joint torques produced by torque summer 691 is applied to a backdrive torque calculator 693. The second input into calculator 693 is the set of expected joint torques. Calculator 693 computes the difference between these two sets of torques. This difference is an estimate of the backdrive torques, torque $T_{BDR}$, Outputted to compensate for the external forces and torques. Torque $T_{BDR}$ is a column vector that includes estimates of the backdrive torques applied to the active joints. The components of torque $T_{BDR}$ for the passive joints are set to zero.

If external forces and torques are not present, the representations of actual joint torques should be equal to the expected joint torques. If this condition exists, the output from the backdrive torque calculator 693, torque $T_{BDR}$, is essentially the zero vector.

Torque $T_{BDR}$ is applied to a CMVB force converter 694. A second input into force converter 694 is Jacobian $J_{JNT}$ from the Jacobian calculator 564. Force converter 694 converts torque $T_{BDR}$ into the equivalent forces and torques, force $F_{BDR}$, which should be applied to the origin of coordinate system CMVB of the virtual rigid body. This conversion is performed according to the following formula:

$$F_{BDR} = J_{JNT}^{-T} T_{BDR} \quad (19)$$

Force $F_{BDR}$ is expressed in coordinate system CMVB. Force $F_{BDR}$ is in the same direction as the direction of the external forces and torques applied to the manipulator 50, the instrument 160 and energy applicator 184.

Backdrive force $F_{BDR}$ are applied to a deadband filter 695. Deadband filter 695 only passes through for subsequent processing backdrive forces with absolute values above certain defined threshold values stored in the filter 695. In some versions there is a threshold for each component of force $F_{BDR}$. Alternatively, the thresholds are based on the magnitude of the force component and the magnitude of the torque component of force $F_{BDR}$.

The outputs of filter 695 are based on the differences between the components of backdrive forces $F_{BDR}$ and the threshold values. Components of force $F_{BDR}$ with absolute values below the threshold values are set to zero. This filtering offsets the inherent limitations in modeling the structure of the manipulator 50. These limitations are due in part to the difficulty in accounting for extra loads, such as the existence of cables that may be attached to the manipulator arms 68 and 70. These limitations also compensate for the difficulty in modeling friction and the dynamics of the manipulator.

Force/torque sensor 108 provides manipulator controller 124 a second indicia of the external forces and torques applied to the manipulator 50, the instrument 160 and energy applicator 184. The output signals from sensor 108 are applied to a gravity compensator 689, depicted in FIG. 13E. Gravity compensator 689 outputs signals representative of the applied forces and torques from which the effect of gravity on the sensor 108, the instrument 160 and energy applicator 184 have been substantially eliminated.

These compensations are typically subtracted from the signals representative of the sensed forces and torques. The compensation is often performed by reference to values stored in look up tables integral with the compensator 689. These values may be positive or negative. The specific compensation value subtracted from any individual signal representative of measured force and torque is generally a function of the orientation of the instrument. A second input into compensator 689 is therefore data representative of the actual orientation of the instrument. The orientation component of the measured pose from the forward kinematics module 562 can function as this representation of actual instrument orientation.

The data for compensation value tables maintained by compensator 689 can be defined each time the manipulator 50 is initially activated. To obtain these data, the arms 68 and 70, position the instrument 160 and attached energy applicator 184 in a number of predefined orientations. Compensator 689, based on the output from sensor 108 when the instrument is in each of these orientations, generates the data for the look up tables. Alternatively, the data for the tables are calculated using predefined data regarding the sensor 108 and data defining the mass properties of the components attached to the distally directed portion of the sensor. These data may include data stored in a memory integral to the instrument.

As a result of this compensation the practitioner, when holding the instrument, is neither exposed to the actual force of gravity working against the instrument nor an emulated version of this force. This reduces the physical fatigue to which the practitioner may otherwise be exposed when holding the instrument for extended periods.

Compensator 689 also compensates for inherent errors in the signals output by the sensor. These errors include offsets due to temperature drift. Compensator 689 compensates for these errors by adding or subtracting offset values that are specific for the sensor. These offset values may also be a function of sensor orientation. These offset values are often stored in look up tables integral with the compensator 689. These look up tables are separate from the tables in which the gravity-compensating offset values are stored.

The gravity compensated signals from sensor 108 are applied to a CMVB force converter 696. Converter 696 converts these forces and torques from a coordinate system specific to sensor 108 into the equivalent forces and torques applied to coordinate system CMVB. The Jacobian employed by CMVB force converter 696 is a Jacobian with constant coefficients that is defined at the start of the procedure in which the manipulator is employed. This Jacobian is based on the relative pose between the coordinate system of sensor 108 and coordinate system CMVB. Converter 696 thus outputs representations of the forces and torques measured by sensor 108 that are expressed in coordinate system CMVB.

The output of converter 696 is applied to an attenuator 697 internal to manipulator controller 124. Attenuator 697 selectively attenuates the signals from zero values to their unattenuated levels. In some versions of this invention, the ramping is performed using finite impulse response digital filters. The extent to which attenuator 697 attenuates these signals is a function of the depressed/released state of switch 176. When switch 176 is depressed, attenuator 697 ramps the signals down to their fully attenuated, zero values. Upon the release of switch 176, the signals are ramped to their unattenuated levels. The ramping down/ramping up is typically performed over a period of between 10 to 500 milliseconds. The actual time periods of these two ramping processes need not be equal. In some versions of this invention, the ramping is performed using finite impulse response digital filters. The output from attenuator 697 are force $F_{FTS}$. Force $F_{FTS}$ is expressed in coordinate system CMVB.

This signal ramping reduces the extent to which large impulse forces are applied to the instrument when switch 176 is initially depressed or released.

Force $F_{BDR}$ from CMVB force converter 694 and force $F_{FTS}$ are applied to an external forces summer 698. Summer 698 produces a weighted sum of these two representations of the external forces and torques, force $F_{EXT}$. Force $F_{EXT}$ includes a force vector component, $\vec{F}_{EXT}$ and a torque vector component, $\vec{T}_{EXT}$. External forces force summer 698 outputs the force vector component according to the following equation:

$$\vec{F}_{EXT} = A_{BDR}\vec{F}_{BDR} + A_{FTS}\vec{F}_{FTS} \tag{20A}$$

Here, $\vec{F}_{BDR}$ is the force vector component of $F_{BDR}$. Vector $\vec{F}_{FTS}$ is the force vector component of $F_{FTS}$. The torque vector component of external forces $F_{EXT}$ is calculated using a similar equation:

$$\vec{T}_{EXT} = B_{BDR}\vec{T}_{BDR} + B_{FTS}\vec{T}_{FTS} \tag{20B}$$

Here, $\vec{T}_{BDR}$ is the torque vector component of $F_{BDR}$. Vector $\vec{T}_{FTS}$ is the torque vector component of $F_{FTS}$.

In Equations (20A) and (20B) $A_{BDR}$, $A_{FTS}$, $B_{BDR}$ and $B_{FTS}$ are the weighting factor coefficients for the individual force and torque variables. These weighting factors may not be constant for the full range of external forces and torques applied to the manipulator, the instrument or energy applicator 184. These weighting factors may be varied to compensate for characteristics associated with the sources of the representations of the external forces and torques. For example, when relatively low external forces and torques are applied to the instrument, the sensor 108 may provide the more accurate representation of these forces and torques. Accordingly, when the manipulator is in this state, weighting factors $A_{FTS}$ and $B_{FTS}$ are relatively high and weighting factors $A_{BDR}$ and $B_{BDR}$ and are relatively low.

When the external forces and torques are relatively large, the output signals from the same sensor 108 may be saturated. For this construction of manipulator 50, the backdrive torques are representative of the external forces and torques over a wider dynamic range. Accordingly, when the external forces and torques are relatively large, weighting factors $A_{BDR}$ and $B_{BDR}$ are relatively high and weighting factors $A_{FTS}$ and $B_{FTS}$ and are relatively low.

The weighting factors typically range from 0.0 to 1.0. As a result of empirical testing, in some versions, the maximum values of weighting factors $A_{BDR}$ and $B_{BDR}$ are set to values above unity. The factors $A_{xxx}$ and $B_{xxx}$ for each pair typically add to unity. In some versions, this sum may be less than or greater than unity.

Force $F_{EXT}$ is expressed in coordinate system CMVB. External forces summer applies force $F_{EXT}$ to force summer 379.

Damping forces and torques are also components of the forces $F_{TTL}$ and torques $T_{TTL}$ output by force summer 380. Collectively, the damping forces and torques are identified as force $F_{DMP}$. Damping force $F_{DMP}$ is generated to provide a resistance to movement of the instrument that emulates the natural motion of the instrument.

Damping force $F_{DMP}$ is generated by damping force calculator 734 seen in FIG. 13B. A representation of the actual velocity of coordinate system CMVB functions as the input data from which calculator 734 determines damping force $F_{DMP}$. In the depicted version, the commanded velocity output by the cut guide 390 is employed as the representation of this velocity.

There are a number of different means by which damping force calculator 734 could generate forces in opposition to the advancement of the instrument 160. Calculator 734 may use an algorithm to generate these forces wherein the input variable is the velocity vector. This algorithm is typically in the form of:

$$F_{DMP} = f(V_{CMND}) \tag{21}$$

In some cases:

$$f(V_{CMND}) = D_{DMP} V_{CMND} \tag{21A}$$

Velocity $V_{CMND}$ is the vector comprising the linear and rotational components of commanded velocity, expressed in coordinate system CMVB. Coefficient $D_{DMP}$ is a matrix including the damping coefficients. In many constructions, this matrix is a diagonal matrix in which the linear and rotational coefficients are not equal. Often the linear coefficients are identical and the rotational coefficients are identical. The coefficients of this algorithm may change as a function of the specific range of velocities of the velocity supplied to the calculator. These coefficients are typically stored in a look-up table associated with calculator 734.

Alternatively, damping calculator 734, based on the velocity vector, refers to a look-up table in which a number of different values for damping force $F_{DMP}$ are stored. Based on the specific velocity supplied to the calculator 734, the calculator retrieves data that collectively describe an appropriate force $F_{DMP}$.

Often manipulator 50 is provided with plural sets of damping coefficients $D_{DMP}$ or multiple sets of look up tables in which values for force $F_{DMP}$ are stored. Depending on the mode of operation of the manipulator 50, a particular set of coefficients or look up table is used as the reference data upon which force $F_{DMP}$ is generated. This is because it is often desirable to set the damping force as a function of the mode of operation of the manipulator. For example, in comparison to when being operated in the manual mode, when the manipulator is operated in the semi-autonomous mode it is often desirable to provide a higher magnitude damping force. This increase in damping force has been found to minimize the reaction of the instrument to the forces (the resistance) to which the instrument and energy applicator 184 are exposed. This can improve the precision with which the manipulator 50 advances the energy applicator 184 along the path segment.

Another means by which damping force calculator 734 could generate forces in opposition to the advancement of the instrument 160 is by using an algorithm to generate forces due to "sliding friction." The magnitude of sliding friction is a constant value and is independent of surface area, displacement or position, and velocity. This type of damping is of the first order and is referred to as Coulomb damping. Coulomb damping and the above-described viscous damping may be adjusted independently to maintain the stability of the instrument and to control how the instrument feels to the practitioner.

Also, it is often desirable to output a decreased magnitude damping force $F_{DMP}$ when the practitioner depresses switch 176 to manually set the position of the instrument 176. As soon as switch 176 is released, it is typically desirable to employ coefficients $D_{DMP}$ or reference look up tables that result in the outputting of a damping force $F_{DMP}$ of increased magnitude. This higher magnitude force $F_{DMP}$ is output to rapidly stop the movement of the instrument.

Damping force calculator 734 outputs damping force $F_{DMP}$ as a force to be applied to the center of mass of the virtual rigid body, expressed in coordinate system CMVB. Damping force $F_{DMP}$ is applied to force summer 379.

Force summer 379, the environmental force summer, receives the following inputs: the joint limit force $F_{JL}$; the interference limit force $F_{INF}$; the workspace boundary force $F_{WSB}$; the external force $F_{EXT}$; and the damping force $F_{DMP}$. These forces are summed together. The output of force summer 379 is the environmental force, force $F_{ENV}$.

Environmental force summer 379 may output force $F_{ENV}$ as a weighted sum. Coefficients are applied to the individual inputs to perform this weighting. The weighting may be performed to appropriately balance the relative contribution of each input force. This balancing is performed to increase the extent to which, when the manipulator 50 advances the instrument in the manual mode, the impression the practitioner perceives is the same as that which would be perceived if he/she was directly applying force to advance the instrument. The coefficients may change as a function of the transition of the manipulator between operating modes. During these transitions, the coefficients are typically ramped up or down over a time interval following the transition. Typically, this interval is between 10 and 100 milliseconds.

Environmental force $F_{ENV}$ is applied to the energy applicator force calculator 358 of the tool path force calculator 278. Energy applicator force calculator 358 uses force $F_{ENV}$ as the above described input into its solving of Equation (5). Environmental force $F_{ENV}$ is also applied to total force summer 380.

Total force summer 380 receives as inputs the environmental force $F_{ENV}$, the semi-autonomous instrument advancement force $F_{INST}$ and the force required to maintain the orientation of the instrument, $F_{ORNT}$. Based on these three inputs, total force summer 380 produces the above-discussed outputs: forces $F_{TTL}$; and torques $T_{TTL}$. Forces $F_{TTL}$ and torques $T_{TTL}$ may be weighted sums of the inputs for the same reasons environmental force $F_{ENV}$ may be a weighted sum.

Another module internal to manipulator controller 124 is an instrument manager 702, seen in FIG. 27. Instrument manager 702 controls the on/off state of instrument 160. Inputs into manager 702 include signals indicating the depressed/released states of pendant trigger 194, instrument buttons 164 and 174 and instrument control switch 176. Force overrider 375 provides a signal if it is necessary to deactivate the instrument power generating unit 163. Tool path generator 234 selectively asserts a signal to the instrument manager 702 at the start of semi-autonomous advancement of the instrument. This signal is asserted if the instrument is within the below discussed target region. The cut guide 390 provides a signal to the instrument manager 702 indicating that the boundaries have been defined. The localization engine 270 provides data indicating that the engine is able to generate data describing the relative pose of the instrument and the bone. Inferentially these latter data are data indicating that the signals transmitted by the tracker 212 and 214 are being received by the localizer 216. Based on the above data, the instrument manager 702 selectively asserts signals to activate and deactivate the instrument power generating unit 163. These signals are forwarded to the tool controller 132.

Instrument manager 702 asserts the signals that result in the turning on of the tool power generating unit 163 in response to a number of conditions being meet. One of these conditions is that the cut guide 390 has indicated that the boundaries have been defined. Another condition that should be met is that localization engine 270 is able to track the relative pose of the instrument to the bone.

Instrument manager 702 actuates the instrument 160 when the practitioner takes positive action to intentionally actuate the instrument. When the manipulator is operated in the manual mode, this action is the continued depression of switch 176 in combination with the toggling of one of buttons 164 or 174. When the manipulator is operated in the semi-autonomous mode, instrument manager 702 only sends the signals to the tool controller 132 indicating that the power generating unit 163 should be energized if the manager receives an indication that pendant trigger 194 is depressed.

IV. Operation

A. Manual Mode

Manipulator 50 is prepared for use by attaching the energy applicator 184 to the instrument 160. Instrument 160 is, by way of coupling assembly 111, mounted to end effector 110. Using calibration techniques, the pose of coordinate system EAPP, the pose of coordinate system CMVB, the pose of coordinate system EFCT and the pose of coordinate system TLTR relative to each other are determined. Data describing these relative poses are supplied to the manipulator controller 124, specifically coordinate system transformer 272.

Upon initial actuation of the manipulator 50, the boundaries upon which the cut guide limits the advancement of the instrument have not yet been defined. Instrument manager 702 therefore does not assert signals to the tool controller 132 that can result in the actuation of the instrument power generating unit 163.

Once the bone tracker 212 is fixed to the bone, the bone is registered relative to coordinate system BTRK. Surgical personnel, using navigation interface 220 adjust and confirm the positioning of the boundaries relative to the bone. Once this step is performed, boundary generator 232 employs these data to calculate the pose of the coordinate system associated with the boundaries relative to coordinate system BTRK. This relationship is fixed. These relationship data are applied to the coordinate system transformer 272. Data defining the positions of the boundary-defining tiles are loaded into the cut guide 390.

Once the tile-defining data are loaded into cut guide 390, the cut guide 390 asserts a signal to the instrument manager 702 indicating the boundaries have been defined. Receipt of this signal is recognized by the instrument manager 702 that the practitioner can now actuate the instrument 160.

Also as part of the initial configuration of the instrument, the tool controller 132 is set to output the energization signals needed to cause the instrument to, when actuated, output the energy designated by the practitioner. For example, if the instrument 160 includes a motor, the tool controller 132 is set to cause the instrument motor to operate at the practitioner desired motor speed. If the instrument 160 is an electrosurgical tool, tool controller 132 is set to cause the instrument to source the appropriate current and/or cause an appropriate voltage to develop across two electrodes. If the instrument emits photonic energy, instrument controller 132 is set to cause the instrument 160 to output photonic energy of the appropriate wattage. These setting are performed by entry of commands through user interface 130.

Manipulator 50 is enabled for operation by depressing a button presented on user interface 130 (button not illustrated). In response to the depression of this button, manipulator controller reads the signals from the encoders 112, 114, 116, 117 and 118 as the measured joint angles. Based on these data, the forward kinematics module 562 determines an initial set of calculated joint angles. Forward kinematic module 562 also outputs an initial pose of coordinate system CMVB relative to the origin of manipulator coordinate system MNPL.

Based on the measured joint angles, the calculated joint angles and the initial pose of coordinate system CMVB initial comparisons are performed by comparators 582, 622 and 652. These comparisons are performed to determine if in the initial state, the manipulator is violating any one of the joint limits, the interference limits or workspace limits, (steps not shown). If any of these limits are violated, an error message is displayed on user interface 130. Further operation of the manipulator is blocked until the violation is resolved.

The forward kinematics-derived initial pose of coordinate system CMVB is also employed as the initial commanded pose of this coordinate system. The commanded velocity is initially set to zero.

Integrator 386 therefore has as the first frame initial conditions data representative of the actual pose of coordinate system CMVB and an initial commanded velocity of zero. This commanded pose is initially forwarded to the inverse kinematics module 542.

As with any commanded pose data, the inverse kinematics module uses this commanded pose to determine the commanded joint angles that are applied to the joint motor controllers 126. In this initial frame, the measured joint angles are essentially already at the commanded joint angles.

When the joint motor controllers 126 are initially activated, the brakes are holding the active joints static. After the joint motor controllers 126 are activated, the brakes are released. In response to the release of the brakes, gravity starts to act on the links. As the active joints start to depart from the commanded joint angles, controllers 126 cause the motors 101 to output torques that counteract the force of gravity. Joint motor controllers 126 therefore cause torques to be output that essentially holds the arms static. Once brakes 103 have been released, the manipulator 50 is able to position the instrument 160.

During periods in which switch 176 is not depressed, sensor signal attenuator 697 completely attenuates, blocks, the passing of the signals from the force torque sensor 108 to the external force summer 698. Blocking these signals prevents unintended movement of the manipulator that could result from the drift of and random variations of the signals from sensor 108. If these drifting and varying sensor signals are forwarded beyond attenuator 697, they would be interpreted as an indication that the practitioner has applied forces and/or torques to the instrument. This would result in the other modules internal to the manipulator controller 124 generating commands that would cause the unintended movement of the manipulator.

Even if the practitioner does not attempt to move the instrument, manipulator controller 124 will reposition the instrument 160 if the backdrive force $F_{BDR}$ indicates that one of the arms 68 or 70 or attached components is subjected to an external force. This prevents damage to structural components of the manipulator and instrument 160 if either of these devices is somehow inadvertently bumped. It should be appreciated that these unintended forces must be greater than the minimum forces passed by deadband filter 695.

Manipulator 50 is, by default, initialized in the manual mode. When the manipulator is in the manual mode, instrument 160 is not semi-autonomously advanced. Tool path force calculator 278 does not output signals of forces and torques to total force summer 380 that would facilitate semi-autonomous advancement of the instrument.

For the practitioner to position the instrument, the practitioner depresses switch 176. Simultaneously, the practitioner places forces and torques on the instrument. These forces and torques are similar in magnitude to those that would be placed on an instrument held in the hand to control instrument pose. In response to sensing the state transition of switch 176, sensor signal attenuator 697 ramps up the signals from sensor 108 to their unattenuated levels. This signal ramping ensures that the joint motors 101, when initially applying torques to the arms, do not suddenly apply large amounts of torque to the manipulator 50.

In response to the practitioner placing the forces and torques on the instrument, sensor 108 outputs signals representative of these forces and torques. These signals are passed through the sensor signal attenuator 697 to the external forces summer 698. The external forces summer blends these signals as appropriate with the signals representative of external forces as represented by backdrive force $F_{BDR}$. External forces summer 698, in turn, outputs these signals through environmental force summer 379 to total force summer 380. These practitioner applied forces are consequently components of the forces $F_{TTL}$ and torque $T_{TTL}$ output by total force summer 380.

Consequently, when integrator 386 generates pose and velocity data, it does so based, in part, on the representation of practitioner applied forces and torques. Cut guide 390, based on the integrator-generated pose and velocity, outputs the commanded pose and commanded velocity for coordinate system CMVB. Based on the commanded pose, inverse kinematics module 542 and command dynamics module 544 generate signals indicating, respectively, commanded joint angles and feed forward torques for the active joints. Joint motor controllers 126, based on the commanded joint angles and feed forward torques, apply the necessary currents to joint motors 101. These are the currents that result in the motors 101 outputting torques that result in advancement of the active joints towards their commanded joint angles. This results in motion of the instrument that emulates the motion of the instrument 160 if the forces and torques that the practitioner applied were applied to the center of mass of an instrument held in the hand.

To actuate the instrument 160, either one of buttons 164 or 174 is toggled while switch 176 is depressed. When this condition exists, instrument manager 702 asserts a command signal to the tool controller 132. This is the command signal instructing the controller 132 that it is to now actuate the instrument. Based upon receipt of this command signal, tool controller 132 applies the appropriate energization signals to the instrument 160 to actuate the instrument. In the situation where the instrument 160 includes a motor and the energy applicator 184 is a bur or other cutting accessory, the application of the energization signals result in the rotation of the energy applicator 184.

As the instrument 160 and energy applicator 184 are advanced, the localization engine 270 continually generates data indicating the poses of both the bone tracker 212 and tool tracker 214 relative to the localizer 216. These data are forwarded to the coordinate system transformer 272. Coordinate system transformer 272 receives data from the forward kinematics module 562 that indicates the pose of the end effector 110 relative to the manipulator coordinate system MNPL. Coordinate system transformer 272 generates data indicating the pose of the boundary coordinate system relative to coordinate system MNPL based on the following data: the fixed pose of the boundary coordinate system relative to bone tracker coordinate system BTRK; the moving pose of the bone tracker coordinate system BTRK relative to the localizer coordinate system LCLZ; the moving pose of the localizer coordinate system LCLZ relative to tool tracker coordinate system TLTR; the fixed pose of tool tracker coordinate system TLTR relative to end effector coordinate system EFCT; and, based on the forward kinematics module; the pose of the end effector coordinate system EFCT relative to manipulator coordinate system MNPL.

Based on the fixed pose of energy applicator 184, coordinate system EAPP relative to coordinate system EFCT and the moving pose of the end effector coordinate system EFCT relative to coordinate system MNPL, coordinate system transformer 272 generates data indicating the pose of the coordinate system EAPP relative to coordinate system MNPL.

The coordinate system transformer 272 thus provides the cut guide 390 with data that indicate poses of both coordinate system EAPP and the boundary coordinate system relative to manipulator coordinate system MNPL.

In addition to the above data, cut guide 390 contains the previously stored data defining the poses of the boundary-forming tiles relative to the origin of the boundary coordinate system. Based on these data, the cut guide 390 performs the process steps described above with respect to FIGS. 21A-21C to determine if the practitioner's intended advancement of the instrument 160 would result in the energy applicator 184 crossing a boundary defining tile. If this evaluation tests negative, cut guide 390 outputs the integrator-generated pose and velocity as the commanded pose and velocity.

Alternatively, if it appears that the integrator generated position is beyond a boundary-defining tile, the cut guide 390 generates data determining the impulse or impulses that need to be applied to the virtual rigid body to avoid this motion. The commanded pose output by the cut guide 390 is based on this impulse (or impulses). Manipulator 50 therefore does not advance the arms in a manner that would result in the energy applicator 184 crossing the tile. Instead, the manipulator advances the arms in a manner that maintains the energy applicator 184 within the volume defined by boundary. If the energy applicator 184 is being used to remove tissue, this method of advancement of the energy applicator 184 results in the manipulator only allowing the energy application to remove the tissue the practitioner requires removed. This results in the remaining tissue having the defined shape, surface 242, desired by the practitioner.

As mentioned above, the gear assemblies that transmit torque from the joint motors to the shoulders and links are essentially zero backlash gear assemblies. This feature means that, during the actual rotation of the gears, there is essentially no slippage, looseness, in the movement of the shoulder or link/links being actuated. The minimization of this slippage results in very stable movement of the components. Moreover, this minimization results in the precise positioning of the attached arm and shoulders. Collectively, these features make it possible for the joint motors to rapidly reposition the shoulders and links and to perform such repositioning with a high degree of accuracy. This includes the repositioning that occurs as a result of the reversal of rotational directions of the joint motors and gear assemblies.

During manual mode advancement of the energy applicator 184, the joint limit comparator 582, the interference limit comparator 622 and the workspace limit comparator 652 perform their above described analyses. If a respective one of the boundaries is crossed, an appropriate constraining force is supplied to environmental forces summer 379. The constraining force, which is applied to the virtual rigid body, essentially prevents the manipulator from advancing the arms in such a manner that would cause a joint to exceed a joint limit, a pair of arms to move beyond their interference limit or the energy applicator 184 to exceed the workspace limit.

While not depicted in the flow charts, the joint limit comparator 582 evaluates if any joint has exceeded one of its joint limits; the interference limit comparator 622 evaluates if any pair of arms are at distance less than their interference limit; and the workspace boundary comparator 652 evaluates if the energy applicator 184 has moved beyond its workspace boundary limit. Typically, one of these conditions only occurs if the manipulator is damaged, malfunctioning or being subjected to extremely high external forces. If any of these conditions test true, manipulator controller 124 stops the advancement of the arms and engages the brakes, and the instrument power generating unit 163 is deactivated, connections not shown. An error message is displayed to the user. The manipulator is considered to have entered a disabled state. The manipulator remains in this state until the error is resolved.

As described above, during the advancement of the instrument, the removed material logger 275 generates and stores data. These data identify the volumes of tissue to which the energy applicator 184 was applied.

At any time during the manual mode advancement of the instrument the practitioner can deactivate the instrument by a second toggling of one of buttons 164 or 174. In response to this second toggling of a button 164 or 174, instrument manager 702 asserts a signal to the tool controller 132 that results in the controller deactivating the instrument power generating unit 163. An additional toggling of the button 164 or 174 results in the instrument manager 702 and tool controller 132 reactivating the instrument power generating unit 163.

Once the practitioner completes a particular application of the energy applicator 184 to the tissue, the practitioner releases pressure on switch 176. In response to the release of switch 176, instrument manager 702 asserts the signal to the tool controller 132 that results in the controller deactivating the instrument power generating unit 163. This prevents activation of the instrument when the practitioner has removed his/her hand from the instrument.

Sensor signal attenuator 697 also responds to the release of switch 176. When this event occurs, attenuator 697 ramps down the application of the signals from force/torque sensor 108 to the external forces summer 698. This results in ramping down of the external forces component applied to environmental forces summer 379. The ramping down of this component results in a like ramping down of the extent to which the forces and torques output by total force summer 380 include components based on the practitioner desired instrument positioning.

Integrator 386 also receives data indicating that the switch 176 has been released. In response to receipt of this data, integrator 386 rapidly ramps down the magnitude of the velocity signals output by the integrator. These velocities are ramped down to zero over a time period that is typically 250 milliseconds or less. This velocity ramp down can alternatively be accomplished by momentarily increasing the damping force applied to environmental force summer 379.

Assuming no other forces are applied to environmental force summer 379, the velocity ramp down results in the stopping of the advancement of the instrument 160. Joint motor controllers 126 continue to apply currents to the joint motors 101. These currents cause the joint motors 101 to output torques that hold the shoulder and arms in their last positions based on the last commanded pose output by cut guide 390. The manipulator at least momentarily holds the instrument in the last pose prior to release of switch 176.

At the time switch 176 is released, cut guide 390 may be in the process of applying a force to the virtual rigid body to prevent the energy applicator 184 from crossing a tile. If this condition exists, then the release of switch 176 does not result in the rapid cessation of the instrument advancement. The cut guide 390 continues to output forces that need to be applied to the virtual rigid body. The outputting of these forces therefore results in manipulator continuing to position the instrument in a manner such that the energy applicator 184 remains within the boundaries.

As described above, the release of switch 176 typically results in the cessation of the advancement of the instrument 160 by the manipulator 50. Conditions may exist that foster further movement of the instrument. As was mentioned above, one such condition is the determination by the cut guide 390 that it appears that the energy applicator 184 will cross a tile. In some circumstances, cut guide 390 makes this determination after the release of switch 176. This determination can occur because, even after switch 176 is released, the software modules remain active. The cut guide 390 continues to selectively generate forces that are applied to the virtual rigid body to prevent the energy applicator 184 from crossing a boundary. This event can occur if, when the instrument 160 is stationary, movement of the patient relative to the instrument results in the energy applicator 184 apparently crossing a boundary. If the cut guide 390 determines that this crossing is occurring, the cut guide applies forces to the virtual rigid body that effectively move the energy applicator 184 such that the applicator does not cross the boundary. Stated another way, as a consequence of the movement of the bone, the manipulator 50 may continue to reposition the instrument.

Other conditions may exist that result in some movement of the instrument 160 by the manipulator 184 when switch 176 is in the released state. Specifically, if the joint motors 101 are subject to backdriving forces or one of the behavior control modules outputs a constraining force, non-zero addends are still applied to the environmental forces summer 379. Total force summer 380 in turn, outputs a non-zero total force and total torque to the acceleration calculator 384. If these outputs from total force summer 380 are non zero, integrator 386, after initially ramping down the velocity, ramps up the velocity to the velocity based on the total force and total torque. Thus, if the backdriving or constraining forces are present, the manipulator 50, after initially stopping the advancement of the instrument, continues to reposition the instrument. This advancement occurs until the integrations of these accelerations over time due to these forces fall to zero.

Once the integrations of these accelerations over time fall to zero and the cut guide 390 no longer applies forces to the virtual rigid body, the manipulator 50 holds instrument 160 in a static pose. Manipulator 50 remains in this state until repositioned by the practitioner.

Upon completion of a procedure, the manipulator may be deactivated by depressing a button presented on the user interface 130, button not shown. Upon depression of this button, the brakes 103 are reengaged. Once a sufficient time has elapsed to ensure that the brakes 103 are engaged, manipulator controller 124 sends commands to the joint motor controllers 126. In response to these commands, the joint motor controllers terminate the applied currents to the joint motors 101.

B. Semi-Autonomous Mode

The initialization steps performed to operate the manipulator in the manual mode are performed to prepare the manipulator for semi-autonomous operation. The instrument 160 and energy applicator 184 are connected together and to the end effector 110. The appropriate calibrations, navigation registrations and boundary positioning are performed. The boundaries are loaded into the cut guide 390.

In some versions, manipulator 50, once enabled for manual mode operation, is ready to semi-autonomously advance the instrument 160. By reference to FIG. 28A, it is observed that an initial step in the semi-autonomous operation of the instrument is the generation of the tool path along which the energy applicator 184 should advance, step 760. In step 760, tool path generator 234 generates data defining tool path 248 (FIG. 15C). This tool path, again a set of path segments 256, 262 and 266, defines the locations along the tissue to which the energy applicator 184 should be applied. As part of step 760, tool path generator 234 references the data retrieved from the removed material logger 275. When step 760 is executed at the start of the procedure, these data indicate that there has been no application of the energy applicator 184 to the tissue. If this condition exists, the starting point, point 258, of the tool path against the tissue, is the originally calculated path starting point.

Alternatively, the data from removed material logger 275 may indicate the energy applicator 184 was previously applied to one or more volumes of the tissue. Often this is due to previous removal of tissue by the manual mode advancement of the instrument. If this condition exists, tool path generator 234 generates a revised tool path 248. This revised tool path 248 is a collection of path segments along the remaining tissue, the tissue to which the energy applicator 184 was not applied, over which the energy applicator 184 should now traverse. The generation of the revised tool path 248 avoids having the energy applicator 184 move in free space to attempt to remove tissue that was previously removed. As a consequence of the generation of this revised tool path, the tool path generator may generate a new location for point 258, the starting point for the tool path along the tissue against which the energy applicator 184 is to be applied.

It should be appreciated that even though the tool path generator 234 defines a set of path segments that extend over the tissue to be removed, not all path segments may extend over tissue. Some path segments may extend in free space between path segments that do extend over tissue.

Prior to the start of semi-autonomous advancement of the instrument, the practitioner, by engaging in manual mode operation of the manipulator 50, positions the instrument so that origin of coordinate system EAPP is in what is referred to as a target region, step 762. This target region is a space in close proximity to the starting point of the on-tissue tool path, point 258. In some versions, this target region is the volume above the bone within 2 cm of path start point 258. In other versions, this target region is the volume within 1 cm above the path start point 258. Based in part on the tracking of the instrument and bone by the localization engine, the coordinate system transformer 272 generates data indicating the proximity of the origin of energy applicator 184 coordinate system EAPP to the start point 258. The coordinate system transformer 272 provides data to the navigation processor 218. Based on these data, navigation processor 218 presents images on interface 220 indicating the position of the energy applicator 184 relative to the tool path start point 258. The practitioner references this display in order to so position the instrument.

Once the practitioner completes coarse positioning of the instrument, manipulator controller 124 continues to hold the instrument in the last commanded pose. This assumes that neither the arms nor instrument are subjected to constraining or backdriving forces.

Once it is believed that the instrument is in the target region, and the practitioner wants to initiate semi-autonomous operation, the practitioner depresses the pendant trigger switch 194, step not illustrated. User interface 130 continually monitors pendant 190 to determine whether or not the trigger switch is depressed, step 764. The depressing of trigger 194 places the manipulator in the semi-autonomous mode. Throughout the time period the practitioner wants to advance the instrument semi-autonomously, pendant trigger 194 must remain depressed. As discussed in more detail below, the release of pendant trigger 194 returns manipulator 50 to the manual mode.

One immediate effect of the placement of the instrument in the semi-autonomous mode is that the tool path generator 234 generates a path segment that extends through free space, step 766. The free space path segment is the portion of the tool path along which the energy applicator 184 should advance to reach point 258.

Prior to the depression of trigger 194, user interface 130 sets the user adjustment input to feed rate calculator 284 to zero, step not shown. Consequently, when trigger 194 is initially depressed, the feed rate calculator 284 outputs a default instrument feed rate of zero. These output signals therefore cause the tool path force calculator 278 to initially generate a set of forces and torques to the total force summer 380 that essentially hold the energy applicator 184 in the position in which it is located at the time trigger 194 is depressed. Often the forces and torques output by the tool path force calculator 278 at this stage in the semi-autonomous advancement of the instrument are close to zero.

Upon initial depression of pendant trigger 194, manipulator controller 124 also verifies that the origin of the energy applicator 184 coordinate system EAPP is within the target region. If the energy applicator 184 is outside of the target region, the likelihood increases that the free space path segment may cross one of the boundary defining tiles or a section of tissue that is not to be cut. Accordingly, manipulator 50 only allows semi-autonomous instrument advancement to begin when energy applicator 184 is in the target region.

Figure 28A:
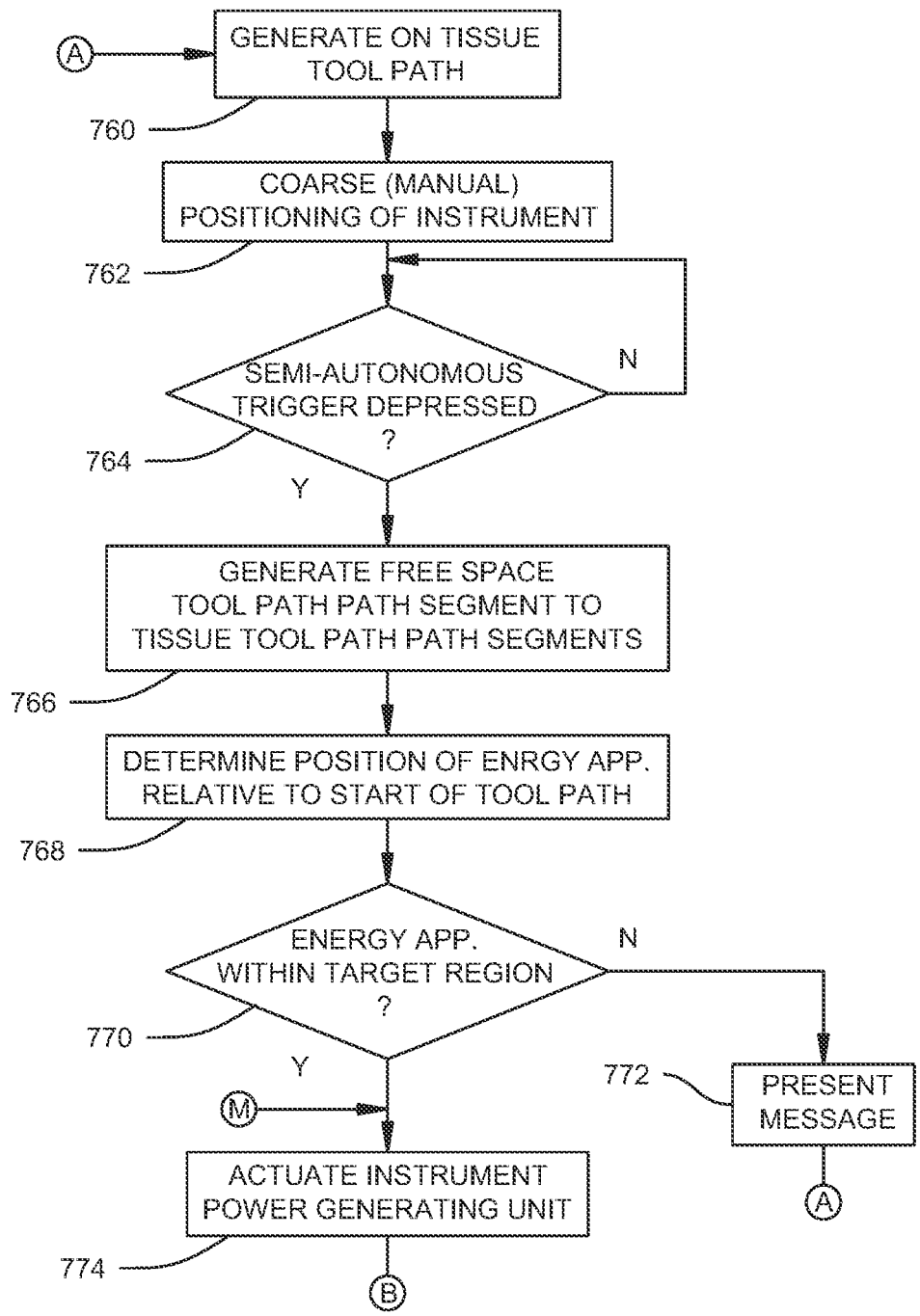
FIG. 28A-28G collectively form a flow chart of process steps executed by the manipulator when engaged in semi-autonomous advancement of the instrument.

In FIG. 28A, steps 768 and 770 represent the process by which the manipulator 50 evaluates the proximity of the origin of the energy applicator 184 coordinate system EAPP to tool path point 258. Step 768 is the determination by the tool path generator 234 of the distance from the energy applicator 184 to point 258. Step 770 is the evaluation of whether or not this distance indicates that the energy applicator 184 is within the target region. If the instrument is not within the target region, a message is presented on interface 220, step 772. The practitioner must then reposition the instrument. To so reposition the instrument, the practitioner must first release trigger 194, step not shown. In the described version, as a consequence of the release of trigger 194, manipulator automatically cycles back to step 760.

When it is determined that the origin of coordinate system EAPP is in the target region, the tool path generator 234 sends data regarding this fact to the instrument manager 702, step not shown. The instrument manager 702, in turn, sends a command to the tool controller 132. This command instructs the tool controller to apply energization signals to the instrument that result in the actuation of the instrument power generating unit 163. Collectively the above steps are represented in FIG. 28A as step 774. To adjust the operational settings used for driving the instrument 160, commands are entered through buttons presented on manipulator display (buttons not illustrated). Based on the depression of these buttons, the user interface 130 sends commands to the tool controller 132 that adjust the operation of the tool power generating unit 163, step not shown.

Should the evaluation of step 770 test positive, the tool orientation regulator 368 defines the reference surface 369, aperture 370 and centering point 371, step 776. These geometric landmarks are defined based on a representation of actual pose of the instrument 160 relative to the bone. The commanded pose, transformed into coordinate system BONE, is employed as the representation of the actual pose.

Once the practitioner is ready to begin semi-autonomous advancement of the instrument 160, the practitioner depresses button 195, step not illustrated. In some versions, user interface 130, based on the depression of buttons 193 and 195, outputs a coefficient representative of the user adjustment of the feed rate. In some versions, the coefficient is 0.0, 0.25, 0.40, 0.70 or 1.0. This is the coefficient that is applied to feed rate calculator 284 as the USER ADJUST input. Each depression of pendant button 193 results in the user interface readjusting the feed rate coefficient down a level. Each depression of pendant button 195 results in the user interface readjusting the feed rate coefficient up to the next higher level. User interface 130 continually monitors the pendant 190 to determine whether or not either of buttons 193 or 195 is depressed, step 778. For the purposes of understanding the invention it should be understood that a necessary command to start instrument advancement is a command to reset the USER ADJUST coefficient to above 0.

The initial depression or depressions of button 195 causes user interface 130 to upwardly adjust the level of the USER ADJUST coefficient applied to the feed rate calculator 284. The level to which this coefficient is set is a function of the number of times button 195 is pulsed. The feed rate calculator 284, in response to receipt of this non-zero coefficient, outputs a non-zero instrument feed rate, step not shown. This assumes that none of the other coefficients applied to feed rate calculator 284 are zero. Based on this indication that the instrument is to advance at a non-zero speed, the downline modules of the tool path force generator 234 cooperate to output the sequence of forces and torques needed to be applied to the virtual rigid body to cause the advancement of the energy applicator 184 along the tool path. These forces and torques are applied to the total force summer 380. In turn, the modules down line from the total force summer 380 cooperate to result in the desired advancement of instrument 160 and energy applicator 184, step 782. While the advancement of the instrument is depicted as a distinct step, it is appreciated that the below described steps occur while the instrument is advancing semi-autonomously.

Initially in this advancement of the energy applicator 184, the energy applicator 184 moves along the free space path segment; the path segment that leads to point 258. From point 258 the energy applicator 184 advances along an on-tissue path segment. In the described version, wherein the energy applicator 184 is a bur, this means that, as a result of this advancement of the energy applicator 184 beyond point 258, the rotating bur head is pressed against tissue. Owing to the geometry of the bur head, the rotation of the bur head by the instrument power generating unit (motor 163), and the force applied to the bur head by the manipulator 50, the bur head removes the tissue against which it is applied, step not identified.

In the FIGS. 28A-28G the steps are depicted as occurring sequentially. It should be appreciated that many of the steps occur both continually and essentially simultaneously throughout the time in which the instrument is semi-autonomously advanced. In some cases the functions represented by the process steps are implemented as independent continuous functions. FIGS. 28A-28G do not represent the order in which process steps are executed by the modules or the decisions made by the modules. The Figures represent the aggregate effect perceived by the practitioner of the above-described processes performed by the modules.

As the energy applicator 184 advances against the tissue, the removed material logger 275 generates and stores data indicating the portions of the tissue to which the energy applicator 184 was applied, step 784. These data are used to update the previously acquired data identifying the portions of the tissue to which the energy applicator 184 was applied. In subsequent executions of step 760, tool path generator 234 employs these updated data to generate the revised tool paths.

During operation of manipulator 50 in the semi-autonomous mode, the force overrider 375 performs its previously described monitoring of the manipulator and the instrument. The determination of the power output by the energy applicator 184 is represented by step 786. A determination that the power output is in excess of the pre-defined lower limit value for the designated time period, is interpreted by the manipulator 50 that the system of this invention may be operating in an undesired state. Accordingly, as part of step 786 the indicia of the power output by the energy applicator 184 is compared to the lower limit value for this indicia. If this evaluation tests true, the force overrider 375 sends a command to the instrument manager 702. In response to this command, instrument manager 702 instructs controller 132 to deactivate the instrument power generating unit 163. Tool controller 132 consequently deactivates the instrument. The above steps collectively form an execution of step 794. Force overrider 375 instructs the feed rate calculator 284 to ramp the instrument feed rate to zero. This results in the manipulator stopping the advancement of the energy applicator 184. This is represented if FIG. 28B as an execution of step 796.

Force overrider 375 also causes the user interface 130 to present a message identifying the reason semi-autonomous advancement of the instrument was terminated, step 798. This gives the surgeon the opportunity to investigate why the instrument is outputting more torque than expected so as to determine if an undesirable condition exists at the site to which the energy applicator 184 is applied.

The stopping of the advancement of the instrument by manipulator 50 in step 796 does not stop the manipulator from continuing to regulate the extent to which the joint motors 101 output torques. The forces and torques output by tool path force calculator 278 are the forces and torques that need to be applied to the virtual rigid body to maintain the energy applicator 184 in its last target position. Total force summer 380 and the downline modules cause the joint motors 101 to output torques that result in the arms 68 and 70 holding the energy applicator 184 in the last target position, step not shown.

While manipulator 50 is still in the semi-autonomous mode, the manipulator, after step 798, is not advancing the energy applicator 184. This provides the practitioner the opportunity to attend to the condition that resulted in the halting of applicator advancement. Manipulator controller 124 allows the practitioner to restart the semi-autonomous advancement of the energy applicator 184 after the warning has been acknowledged. Step 799 represents the force overrider 375 waiting for this acknowledgement. The practitioner makes this acknowledgment by depressing a button. When the manipulator 50 is in this state, instrument button 172 may function as the button that is depressed for the practitioner to acknowledge the warning of step 798.

Once the warning is acknowledged, the force overrider 375 places the manipulator in a state in which it can continue the current semi-autonomous tool advancement. This is represented by the transition from step 799 back to step 774. The instrument manager 702 again asserts commands that result in the actuation of the instrument power generating unit 163. The instrument orientation landmarks are reset in the reexecution of step 776. Then, based on practitioner resetting the USER ADJUST coefficient above 0.0, the reexecution of step 778, the energy applicator 184 is again advanced, step 782 is executed.

Still another component of step 786 is the comparison of the indicia of power output by the energy applicator 184 to the higher limit level of this indicia for the designated time period. The testing true of this evaluation is interpreted by the force overrider 375 that there is a greater likelihood that the manipulator is in an undesirable state. Accordingly, should this evaluation test true, the manipulator controller takes the steps necessary to transition to the manual mode and deactivate the operation of the energy applicator 184. This is represented as the branching from step 786 to the below described steps 864 and 866.

Step 788 represents the monitoring by the force overrider of force $F_{INST}$ output by force calculator 358. In step 788, force overrider 375 compares force $F_{INST}$ to its associated lower limit and upper limit values as described above. If the evaluation indicates that force $F_{INST}$ has exceeded its lower limit value for the designated time period is interpreted as indicating that there is an obstruction 828 in the vicinity of the surgical site that is inhibiting the advancement of the energy applicator 184. Accordingly, should this evaluation of step 788 test true, the force overrider 375 causes the previously described steps 794, 796, 798 and 799 to be executed.

This provides the surgeon the opportunity to determine why the advancement of the energy applicator 184 is being inhibited. The surgeon can, if appropriate, take steps to attend to the condition causing the energy applicator force calculator 358 to indicate that large magnitude forces/torques need to be applied to the virtual rigid body.

In step 788, force overrider 375 may determine that force $F_{INST}$ has exceeded its higher limit value for the designated time period. The testing true of this evaluation is interpreted as an indication that there is a greater likelihood that the manipulator is in an undesirable state. Accordingly, manipulator controller branches to steps 864 and 866 to return to manual mode and deactivate the energy applicator 184.

Force overrider 375 also monitors the signals representative of the forces and torques sensed by sensor 108, step 804. This monitoring is performed to determine if excessive external forces are being applied to the instrument 160 or energy applicator 184. As a result of the normal resistance of the tissue to which the energy applicator 184 is applied, there is some resistance to the advancement of the instrument 160. During semi-autonomous advancement of the instrument, the force/torque sensor 108, in response to the application of the tissue resistance, outputs signals indicating that the sensor is being exposed to a minimal level of forces and torques.

The evaluation may indicate that the forces and torques sensed by sensor 108 exceeded the lower limit values for more than the designated time period. This event could occur if an obstruction 828 imposes some sort of resistive force that inhibits advancement of the energy applicator 184. If this condition tests true, the force overrider 375 branches to steps 794, 796, 798 and 799 to temporarily stop the semi-autonomous advancement of the energy applicator 184.

Further, during semi-autonomous advancement of the instrument, a condition may occur that causes the surgeon to suddenly attempt to reposition the instrument. When taking this action, the practitioner may inadvertently not release the pendant trigger 194. Should this event occur, in response to the practitioner's efforts to displace the instrument away from the tool path, the force/torque sensor 108 is exposed to relatively high forces and torques. These forces and torques are above the high limit force/torque limits maintained by the force overrider 375. Accordingly, in step 804, force overrider also evaluates the output of sensor 108 to determine if these forces/torques have exceeded their higher limit values for a time greater than the designated time period.

If the above evaluation tests true, force overrider 375 asserts commands that result in the deactivation of the instrument power generating unit, step 808. The force overrider 375 also asserts commands that result in the stopping of the semi-autonomous advancement of the instrument, step 810. The same software and hardware components that execute steps 794 and 796 perform, respectively, steps 808 and 810.

The force overrider 375 also ramps the force $F_{INST}$ output by the energy applicator force calculator to zero. This takes the manipulator out of the semi-autonomous mode and returns the manipulator to manual mode operation, represented by step 811. Owing to the magnitude of the forces and torques that are applied by the practitioner, the backdrive forces are greater than the threshold values stored in the deadband filter 695. External forces summer 698, based on the practitioner applied forces, outputs a force to the environmental force summer 379. Consequently, even though switch 176 may not be depressed, the manipulator 50, as represented by step 812, repositions the instrument in response to the forces and torques the practitioner applies to force the energy applicator off the tool path.

Once the instrument is so repositioned, the manipulator returns to step 760. Semi-autonomous advancement of the instrument is reactivated by the depression of the pendant trigger, step 764.

Figure 28B:
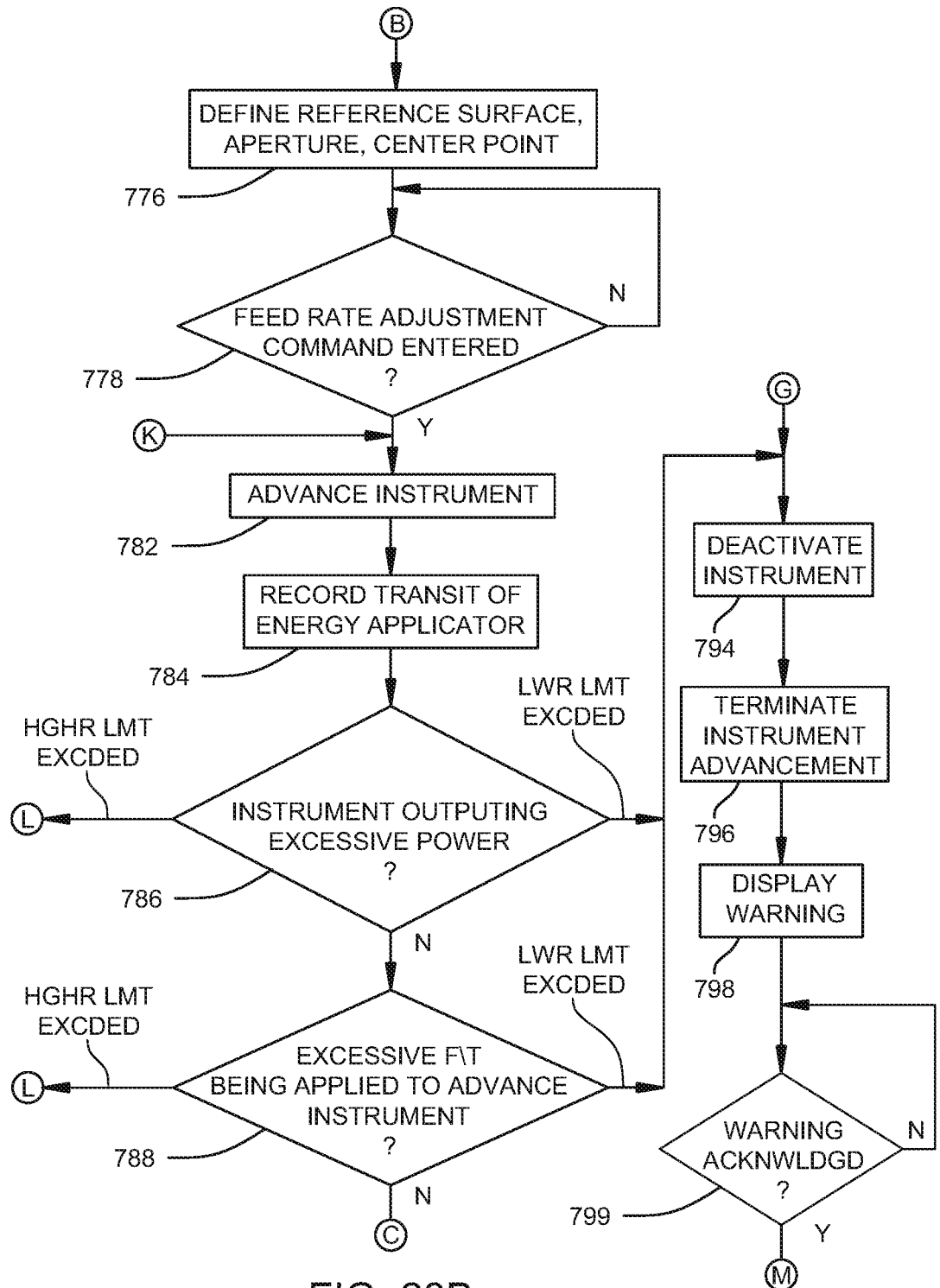
Figure 28C:
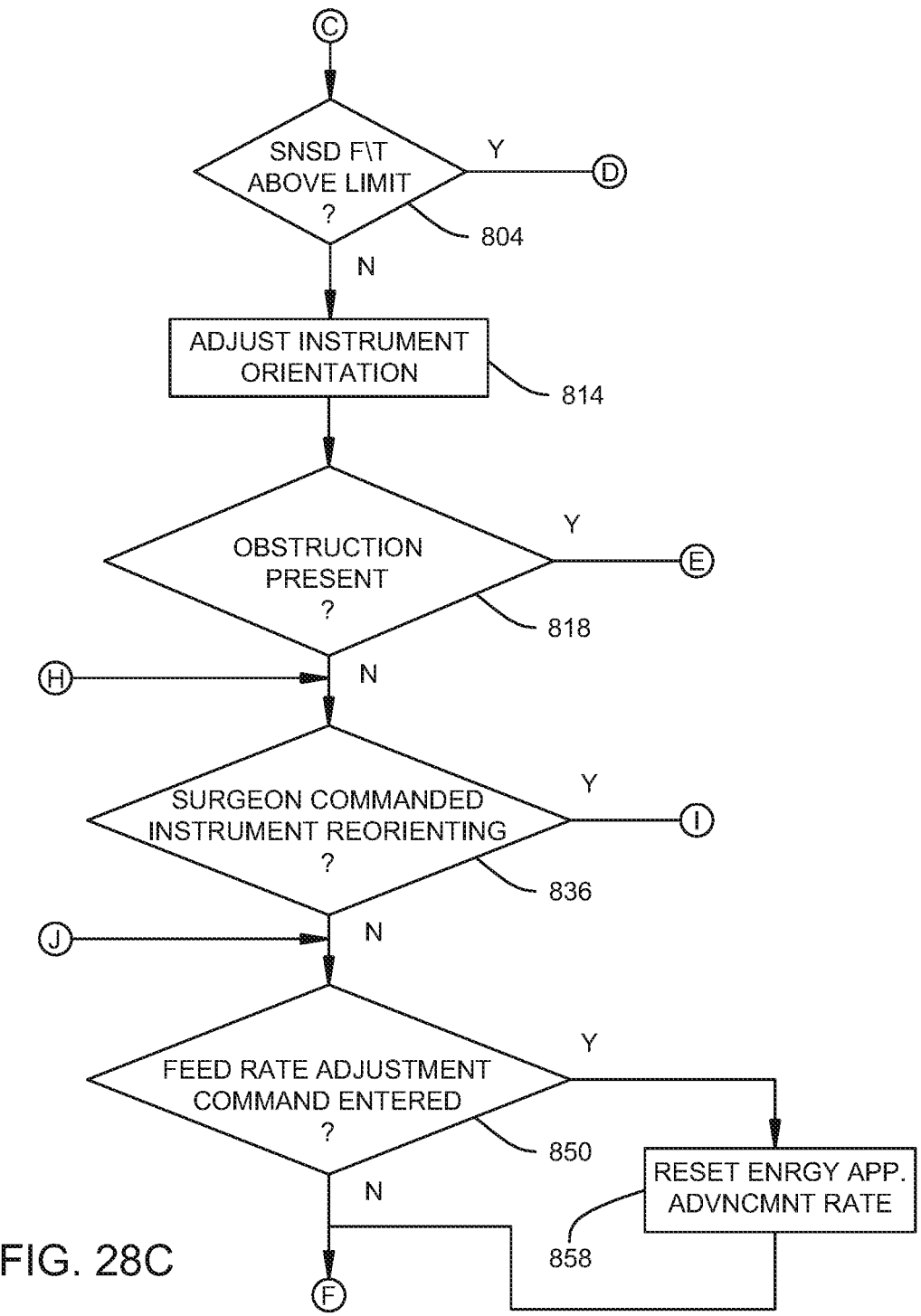

During the advancement of the energy applicator 184, the tool orientation regulator 368 monitors the orientation of the instrument 160. In FIG. 28C this is shown as a separate step 814. It should be understood that this monitoring occurs simultaneously with the advancement of the energy applicator 184. It should be understood that during this process, the location of reference surface 369, aperture 370 and centering point 371 are defined relative to coordinate system BONE.

Figure 29A:
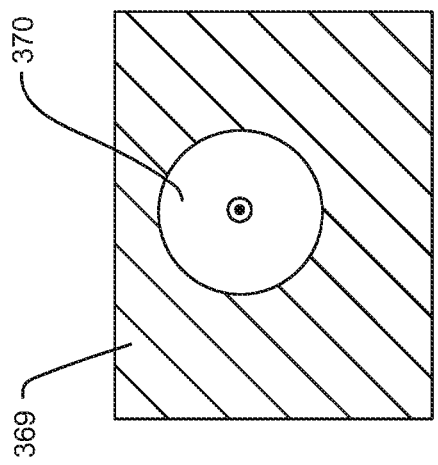
FIGS. 29A and 29B are, respectively, top view and side view diagrammatic depictions of the initial orientation of the instrument when in the semi-autonomous mode.
Figure 29B:
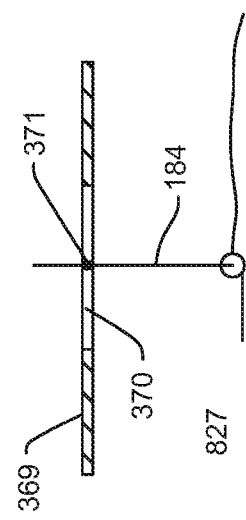

The changes in orientation of the instrument during semi-autonomous advancement are explained by initial reference to FIGS. 29A and 29B. These Figures depict the initial orientation of the instrument and energy applicator 184. Here, the instrument longitudinal axis extends through the centering point 371 in aperture 370. The instrument longitudinal axis is perpendicular to reference surface 369.

During semi-autonomous advancement of the instrument, the objective is to advance the energy applicator 184 along the tool path. From above, it should be appreciated that this is the movement that results from the application of forces and torques that are applied to the virtual rigid body based on the calculations performed by the energy applicator force calculator 358.

As discussed above, the tool orientation regulator 368 generates another set of forces and torques that are applied to the virtual rigid body. This is to ensure that, at a minimum, the manipulator orients the instrument so that the instrument axis remains in the reference surface aperture 370. Ideally, the manipulator is able to orient the instrument so the instrument axis intersects the aperture centering point 371.

Figure 30A:
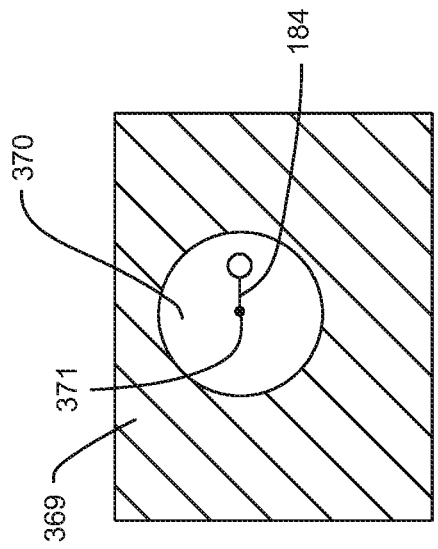
FIGS. 30A and 30B are, respectively, top and side view diagrammatic depictions of how, based on the force and torque commands output by the tool orientation force regulator the manipulator orients the instrument and energy applicator so the common axis extends through the centering point.
Figure 30B:
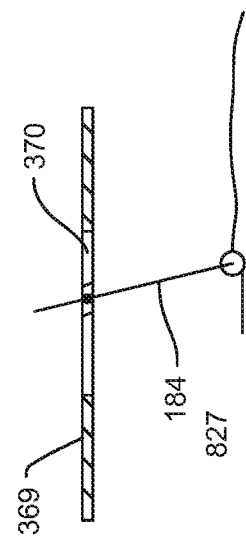

FIGS. 30A and 30B, depict when the origin of the energy applicator coordinate system EAPP is spaced a relatively short distance away from a line extending normal to reference plane 369 through centering point 371. As the energy applicator 184 advances from the position of FIG. 29B to the position of FIG. 30B, forces $F_{ORNT}$ are output by the tool orientation regulator 368 for application to the virtual rigid body. These are force $F_{ORNT}$ that results in the manipulator pivoting the instrument so the common axis continues to extend through centering point 371.

Figure 31:
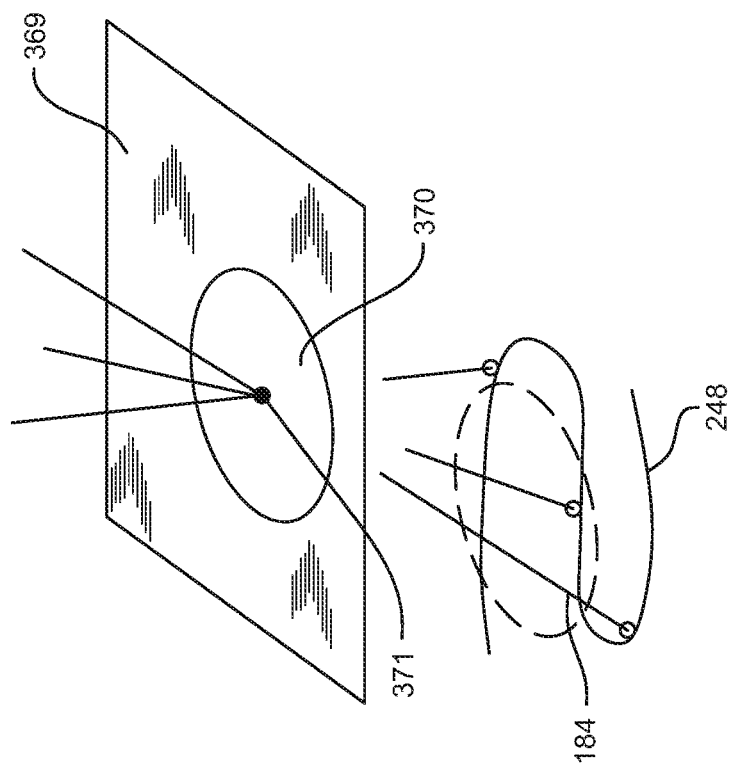
FIG. 31 is a diagrammatic depiction of how, as the energy applicator advances along the tool path, based on the force and torque commands output by the tool orientation force regulator, the orientation of the common axis is held relatively close to the centering point.

As depicted in FIG. 31, during semi-autonomous advancement of the instrument, the manipulator may position the energy applicator 184 so the applicator is advanced along a portion of the tool path 248 located outside of the area subtended by aperture 370. This area is depicted by dashed enclosure. Even when the energy applicator 184 is so positioned, tool orientation regulator 368 applies a force $F_{ORNT}$ that results in the manipulator orienting the instrument so the common axis essentially intersects centering point 371. In some constructions, when the tool orientation regulator 368 defines an aperture 370 having a radius of 3 cm in a reference surface 369 located approximately 15 cm above the surface of the tissue, the manipulator 50 is able to position the energy applicator 184 so it can be located 20 cm or more from the normal line through the centering point 371. Even when the energy applicator 184 is located at the perimeter of this area, the force $F_{ORNT}$ applied to the virtual rigid body will result in the manipulator orienting the instrument so the common axis essentially intersects the centering point 371.

Manipulator 50 is further configured so that minor obstructions 828 that may present themselves above the tool path 248 do not block the advancement of the energy applicator 184 along the tool path. These obstructions 828 include tissue that projects outward above tool path. Instruments, such as suction applicators and retractors may also project above the tool path. In FIG. 28C, whether or not an obstruction is present is depicted as the condition test of step 818. Assuming an obstruction is not present, the condition of step 818 is negative, this semi-autonomous advancement of the instrument continues as represented by the progression to step 836.

If an obstruction is present, the condition of step 818 is positive, the obstruction resists the ability of tool orientation regulator 368 to output a sufficient force $F_{ORNT}$ that results in the manipulator maintaining the common axis through the centering point 371, step not illustrated. In response to this event occurring, manipulator 50 advances the instrument such that the common axis moves toward the perimeter of aperture 370, step not illustrated. The displacement of the common axis away from the centering point 371 can be said to result from the resistive forces of the obstruction being out of equilibrium with, greater than, the force $F_{ORNT}$ applied to the virtual rigid body. In response to this displacement, tool orientation regulator adjusts force $F_{ORNT}$ to ensure that the manipulator 50 orients the instrument so that the common axis remains within the aperture, step 824. Typically, this force $F_{ORNT}$ is greater in magnitude than the previously output force $F_{ORNT}$.

In response to the newly applied force $F_{ORNT}$ the manipulator may position the instrument so that the common axis intersects the aperture through a point in aperture 370 spaced from centering point 371. FIGS. 32A, 32B and 32C depict the instrument in this position. This new location of the common axis is the location where force $F_{ORNT}$ applied to the virtual rigid body and the resistive force of the obstruction 828 is in equilibrium.

The obstruction 828 may yield to the instrument, step 826. This may occur if the obstruction 828 is yieldable material, such as soft tissue. Alternatively, this event may occur if the obstruction 828, though rigid, is fixed to yieldable tissue.

Figure 28D:
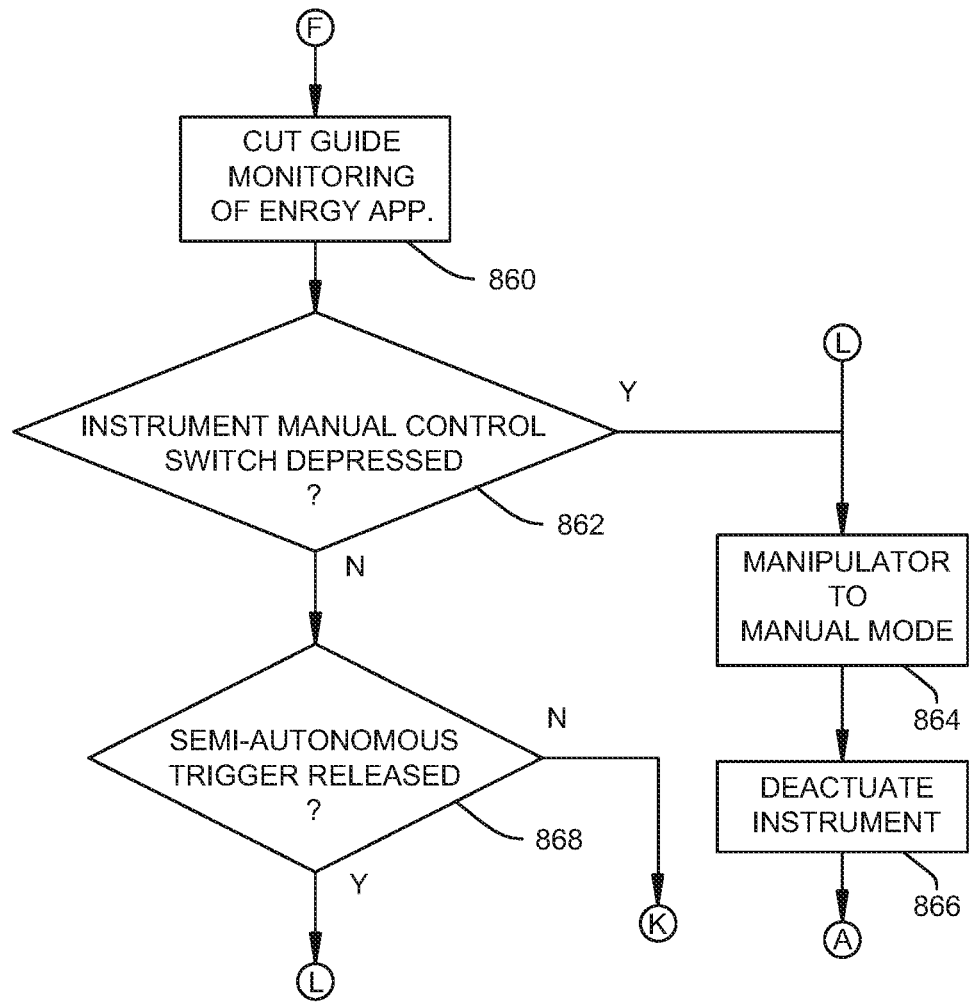
Figure 28E:
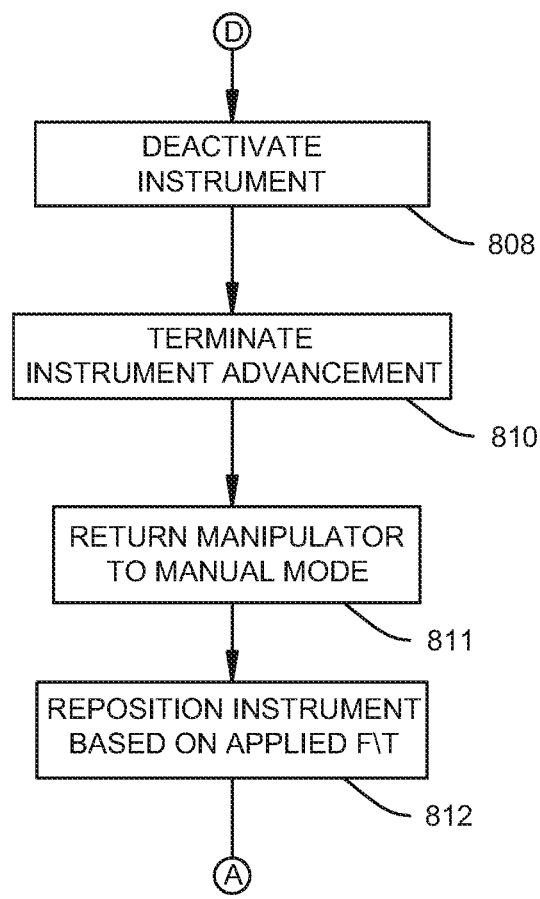
Figure 28F:
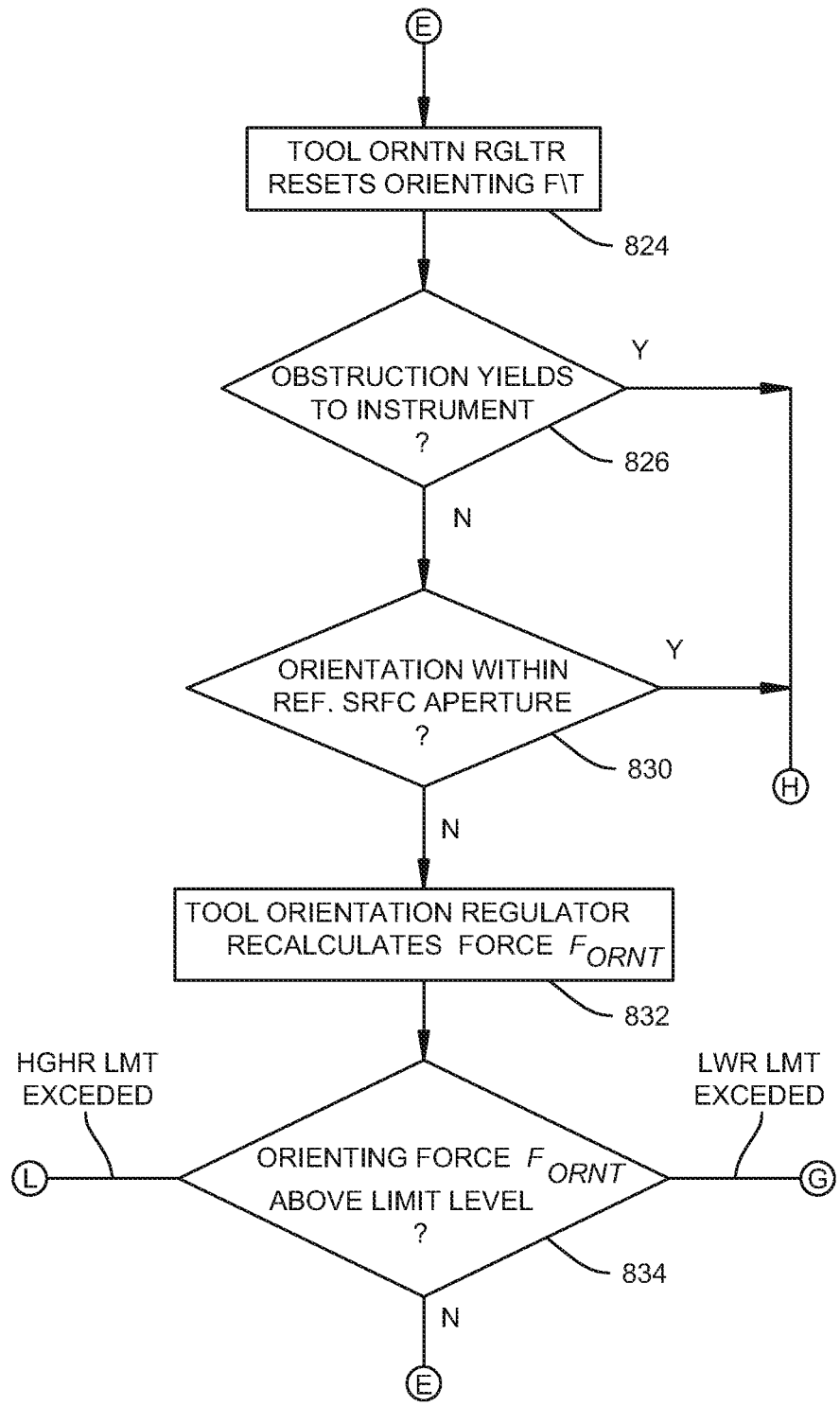

If the obstruction 828 yields, the manipulator continues to advance the instrument. As the obstruction 828 yields, force $F_{ORNT}$ applied to the virtual rigid body becomes greater than the resistive force of the obstruction 828. This results in the manipulator restoring the instrument to an orientation in which the common axis essentially intersects centering point 371, step not shown. In FIG. 28F, the yielding of the obstruction is identified as a branching to step 836.

Even if the obstruction does not yield, the condition of step 826 is negative, the common axis may remain within the reference surface aperture 370, the condition evaluation of step 830. If this condition exists, the manipulator 50 continues the semi-autonomous advancement of the instrument, branching to step 836.

Alternatively, the result of the condition test of step 830 may be negative. In this event, tool orientation force regulator 368 outputs a high magnitude force $F_{ORNT}$. This force $F_{ORNT}$ is based on the table values between inflection point 377 and peak point 378 of FIG. 19. The outputting of this force $F_{ORNT}$ is represented by step 832.

In a step 834 the magnitude of force $F_{ORNT}$ is compared to the low and high limit values associated with this force. This evaluation is performed by the force overrider 375. If both evaluations test negative, the manipulator, in response to the application of the new force $F_{ORNT}$ to the virtual rigid body, reorients the manipulator. This is depicted as the branching back to step 824.

Alternatively, as a result of the evaluation of step 834, force overrider 375 may determine that the force $F_{ORNT}$ is above the lower limit value for this force for the designated time period. If the force overrider 375 makes this determination, the force overrider interprets the manipulator in being in a state in which semi-autonomous advancement should at least be temporarily stopped. This is depicted as the branching to previously described steps 794, 796, 798 and 799.

In some situations, the force $F_{ORNT}$ output by the tool orientation regulator 368 may exceed the high limit value associated with this force for more than the designated time period. This event could occur if an obstruction collides with the instrument 160 or energy applicator 184. Accordingly, force overrider 375 interprets this second evaluation of step 834 testing true as an indication that manipulator is in an undesirable state. Manipulator controller 124 therefore branches to steps 864 and 866 to transition the manipulator back to the manual mode and deactivate the instrument.

During the semi-autonomous advancement of the instrument 160 the practitioner may decide to reset the orientation of the instrument while the energy applicator 184 is advanced along the tool path 252. It may be desirable to so reorient the instrument to avoid having the instrument contact tissue or another instrument that may be in the vicinity of the tool path.

Step 836 represents the decision associated with the practitioner deciding to reorient the instrument. If the practitioner wants to so reorient the instrument, he/she depresses instrument button 172, step not shown. User interface 130 monitors the state of this button. As long as the evaluation of step 836 tests negative, tool orientation regulator 368 continues to output force $F_{ORNT}$ that results in the manipulator orienting the instrument so the common axis, as closely as possible, intersects the previously defined centering point 371. In FIG. 28C, this is represented as a progression to step 850.

If the evaluation of step 836 tests positive, tool orientation regulator 368 redefines the reference surface 369, the tool aperture 370 and centering point 371, step 840. These redefinitions of these geometric reference features are based on the current actual pose of the instrument, represented by the commanded pose.

Consequently, in the subsequent reexecutions of step 814, the input variables into the orientation regulator 368 indicate that the instrument is essentially centered on the centering point 371. Given that the instrument is in this state, the tool orientation regulator determines that there is no need to apply an appreciable orienting force, $F_{ORNT}=0$, to the virtual rigid body, step 842.

During instrument reorientation, the practitioner applies forces and torques to the instrument to reorient the instrument. These forces and torques are typically the largest component of the external force $F_{EXT}$ applied to the environmental forces summer 379. Since $F_{ORNT}$ is zero, tool orientation regulator 368 does not apply forces to the virtual rigid body that oppose the practitioner applied external force $F_{EXT}$. Thus, in response to this external force $F_{EXT}$, manipulator 50 orients the instrument so the instrument orientation is based on the practitioner desired orientation, step 844.

While in this process, $F_{ORNT}$ is zero, energy applicator force calculator 358 and force transformer 362 continue to output a non-zero force $F_{INST}$. This is the force $F_{INST}$ applied to the virtual rigid body that causes the manipulator to advance the energy applicator 184 along the tool path 248. Accordingly, manipulator 50, simultaneously with emulating the reorienting of the instrument desired by the practitioner, continues to position the instrument so the energy applicator 184 advances along the tool path 248, step 782 continues to be executed.

Figure 28G:
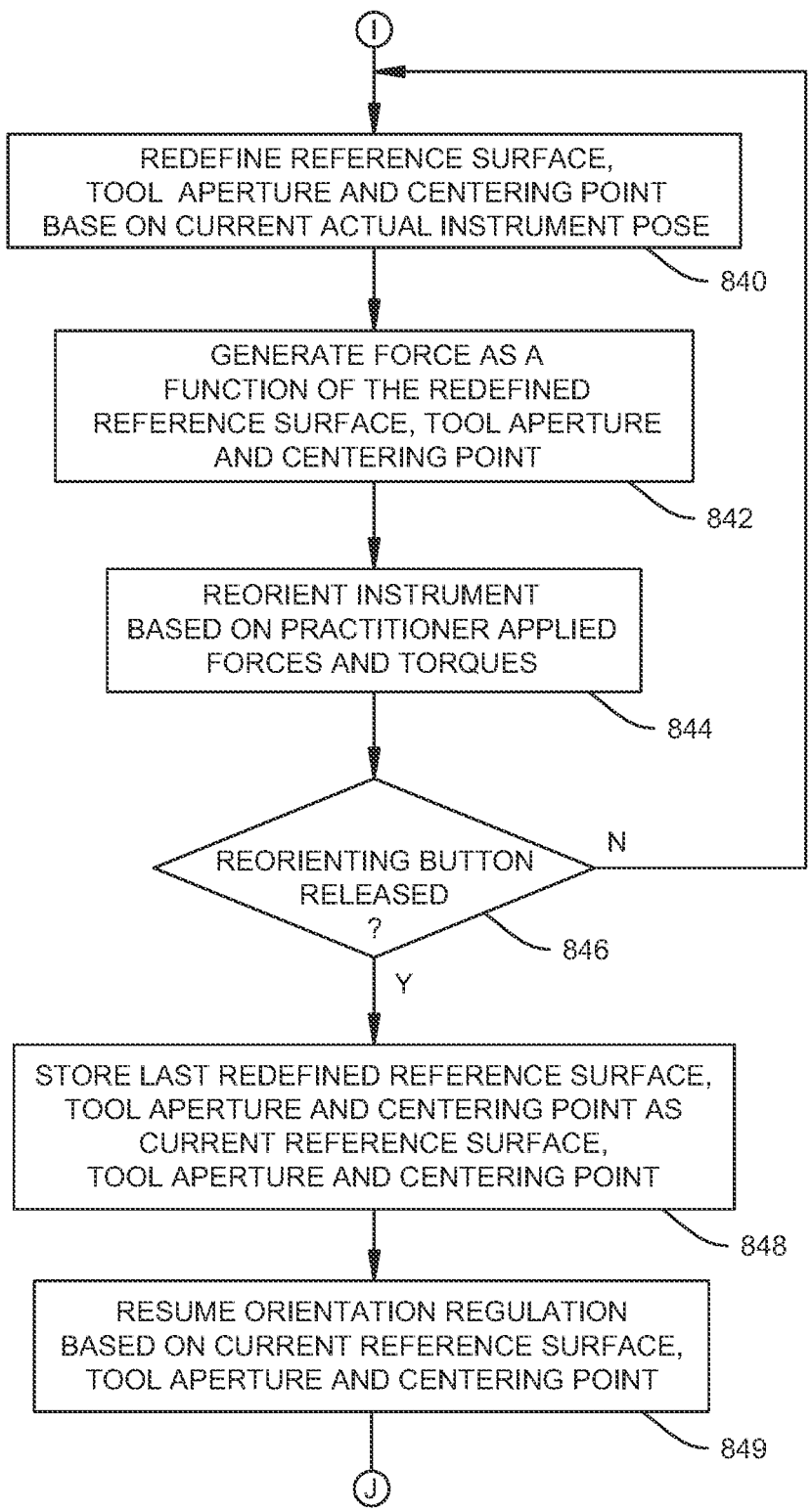

Manipulator continues to reorient the instrument according to the above process steps as long as button 172, remains depressed. This is represented in FIG. 28G as the loop back from decision step 846 to step 840.

Once the instrument is in the orientation desired by the practitioner, the practitioner releases button 172, step not shown. In response to this event occurring, tool orientation regulator 368 no longer continually updates the orientation landmarks based on the commanded pose of the instrument. The landmarks stored when button 172 is released are the landmarks upon which the subsequent calculations to determine force $F_{ORNT}$ are based, step 848. Manipulator continuous with the semi-autonomous regulation of instrument orientation based on these landmarks, step 849. Manipulator 50 can then be considered to advance to step 850.

In some constructions of manipulator 50, the release of button 172 is recognized as indication that the practitioner has performed the step 799 process of clearing the warning presented in step 798. This is because a number of the conditions that may have caused manipulator 50 to temporarily stop semi-autonomous advancement of the instrument 160 are remedied by the reorienting of the instrument.

When manipulator 50 operates in the semi-autonomous mode, user interface 130 continually monitors pendant 190 to determine if either buttons 193 or 195 are depressed. This is represented in FIG. 28C as the manipulator monitoring whether or not surgeon has elected to adjust the feed rate of the advancement of the energy applicator 184 along the tool path, step 850. In response to either of buttons 193 or 195 being depressed, the processes described with respect to step 778 are employed to result in a new USER ADJUST coefficient being applied the feed rate calculator 284, step not shown. This results in controller 124 adjusting the rate at which the manipulator advances the energy applicator 184 along tool path 248, step 858.

If in step 858 the instrument feed rate is set to the zero speed, the tool path force calculator 278 still outputs a force $F_{INST}$. This is the force $F_{INST}$ applied to the virtual rigid body that results in manipulator 50 holding the energy applicator 184 at the last determined target position on the tool path, step not illustrated.

In some versions, when the instrument feed rate is set to zero speed, the instrument manager 702 also asserts commands that result in deactivation of the tool power generating unit 163, step not illustrated. In these versions, when button 195 is again depressed to again cause the semi-autonomous advancement of the instrument, instrument manager 702 causes the instrument power generating unit to be reactivated. User interface 130 applies the non-zero USER ADJUST coefficient to feed rate calculator 284, step not illustrated.

Also, in some versions, upon the resetting of the instrument feed rate to a speed greater than zero, the energy applicator force calculator 358 initially outputs a force $F_{INST}$ that is essentially opposite in direction of the force $F_{INST}$ that results in the forward advancement of the energy applicator 184 along the tool path. As a consequence of this initial force $F_{INST}$ being momentarily applied the virtual rigid body, the manipulator initially moves the energy applicator 184 in a reverse direction along the tool path 248. This movement is typically 2 mm or less. Once the energy applicator 184 engages in this back movement, the instrument power generating unit 163 is reactivated. Once the instrument power generating is reactivated, the energy applicator force calculator 358 outputs a force $F_{INST}$ that results in the manipulator forward advancing the energy applicator 184 along the tool path 248.

The above process steps avoid the condition of reactuating the energy applicator 184 while the applicator is pressed against tissue. This reduces the likelihood that the applicator 184, upon reactuation, binds against the tissue.

During the semi-autonomous advancement of the instrument 160, the cut guide 390 monitors the position of the energy applicator 184 relative to the boundary tiles as if the manipulator is operating in the manual mode, step 860. The method of operation of the cut guide 390 when the manipulator is in the semi-autonomous mode is the same as when the manipulator is operated in the manual mode. Since the manipulator 50 positions the energy applicator 184 along the tool path 248, very rarely does the cut guide 390 determine that the positions cross one of the boundary defining tiles.

However, there is a possibility that the occurrence of an extraneous event will cause the rapid transition of the manipulator from the semi-autonomous mode back into the manual mode. One example of such an event is the above-discussed act of the practitioner applying a force on the instrument to redirect the instrument while the manipulator is performing the semi-autonomous advancement, see step 788. A second example of such event is the below-discussed event of the practitioner depressing instrument switch 176 to position the instrument when the energy applicator 184 is in close proximity to one of the boundary defining tiles.

Thus, even when the manipulator 50 engages in semi-autonomous energy applicator advancement, cut guide 390 still verifies that the commanded position of the energy applicator 184 is within the defined boundary. If the cut guide 390 determines that the energy applicator 184 will cross the boundary, the cut guide applies an impulse or impulses to the virtual rigid body. The application of this force can be considered part of step 860. The application of the impulse (or impulses) causes the manipulator 50 to avoid this motion. Thus, the cut guide 390, even when the manipulator advances the energy applicator 184 semi-autonomously, substantially eliminates the possibility that the energy applicator 184 will move beyond the boundary.

During semi-autonomous advancement of the instrument, the user interface also monitors the state of instrument switch 176, step 862. If switch 176 is depressed, the user interface transitions the manipulator back to manual mode operation, step 864. This process involves the zeroing out of the forces $F_{INST}$ and $F_{ORNT}$ that the tool path force calculator 278 outputs to total force summer 380. Sensor signal attenuator 697 ramps up the extent to which the forces and torques measured by sensor 108 function as components of force $F_{EXT}$. Collectively, these actions transition the manipulator from the state in which it performs semi-autonomous advancement to one in which it performs instrument positioning that emulates the positioning that would have occurred based on the practitioner applied forces and torques.

During this transition between operating modes, instrument manager 702 generates a command to the tool controller to deactuate the instrument, step not shown. Upon receipt of the command, tool controller 132 negates the application of energization signals to the instrument power generating unit, step 866.

Manipulator controller then generates a new on tissue tool path; step 760 is reexecuted.

User interface 130 continually monitors the pendant 190 to determine the state of trigger 194, step 868. If trigger 194 remains depressed, manipulator 50 continues to advance the instrument in the semi-autonomous mode. In FIGS. 28B and 28D, this is depicted as the loop back from step 868 to step 782.

Once trigger 194 is released, the manipulator returns to the manual mode operation and deactuates the energy applicator 184. This is represented by branching from step 868 to steps 864 and 866. It should be understood that in this version of the execution of step 864, the practitioner may not be applying forces and torques to the instrument. Consequently, in addition to forces $F_{INST}$ and $F_{ORNT}$ being zeroed out, force $F_{EXT}$ is also essentially zero. Accordingly, the forces $F_{TTL}$ and torques $T_{TTL}$ output by total force summer 380 are the forces and torques that, applied to the virtual rigid body, result in the manipulator 50 holding the instrument in a static pose. This is the pose in which the energy applicator 184 is in the last target position along the tool path 248.

As described above, once step 866 is executed, a new on tissue tool path is generated, step 760 is reexecuted.

Once semi-autonomous advancement of the instrument has been terminated, the surgeon can position the instrument and actuate the instrument through manual mode operation.

Semi-autonomous advancement of the instrument 160 can be restarted by the surgeon again depressing pendant trigger 194. This will again result in the evaluation of step 764 testing positive.

V. Alternative Embodiments

It should be appreciated that the manipulator of this invention is not limited to the described configuration wherein there is a manipulator controller and a navigation processor. In some versions, a single processor or a multi-core processor, multiple multi-core processors or GPUs, plural DSPs or a set of parallel processors may perform the data processing performed by these processors. Likewise, some versions may have more processors than what has been described. For example, a first processor may perform some of the navigation data processes, a second processor may perform the behavior control functions and a third processor may perform the motion control processes. Likewise, in some versions many of the navigation and behavior control functions may be performed by a processor dedicated to these tasks.

Likewise, the various software modules that have been described should be understood to be illustrative and not limiting. Other software modules may perform the processing steps that result in the joint motors 101 outputting torques necessary to: emulate the advancement of the instrument if the practitioner's forces and torques were applied to the instrument; semi-autonomously advance the instrument; and allow the practitioner to adjust instrument orientation during semi-autonomous advancement.

Also, in some versions, by pressing buttons presented on one of the interfaces 130 or 220, it is possible to change the characteristics of the mass and inertia properties of the virtual rigid body. For example, it is possible to decrease or increase the magnitude of the virtual mass. Decreasing the virtual mass causes the manipulator to respond as if the instrument and energy applicator 184 were, in comparison to their actual mass, lower in mass. Consequently, when the practitioner applies forces and torques to the instrument, the emulated movement of the instrument by the manipulator would cause the instrument to feel both lower in mass in the hand of the practitioner and more responsive to the applied forces and torques. The inertia properties that can be reset include the inertia tensor or matrix.

Another inertia property that can be changed is the location of the center of mass of the virtual rigid body. The movement of the center of mass of the virtual rigid body is performed by redefining the location of this point relative to the origin of end effector coordinate system EFCT. This movement of the center of mass of the virtual rigid body results in the manipulator positioning the instrument in a manner that provides the practitioner the impression that the center of mass of the instrument is shifted. It should be understood that it may even be possible to position the center of mass so it is not located within the instrument 160. It is further possible to redefine the orientation of the coordinate system CMVB relative to coordinate system EFCT or other static coordinate system associated with the instrument 160 or energy applicator 184.

Similarly, there is no requirement that the Z-axis of energy applicator coordinate system EAPP be oriented so to extend in a direction opposite the corresponding axis of coordinate system CMVB. In some implementations, these axes may be oriented in the same direction. Further in some versions, these Z axes may be angled relative to each other. Further, these axes may even be parallel to each other.

Moreover, while the various Z-axes of the different coordinate systems are generally shown being vertical, this should not be interpreted as limiting. In alternative constructions, for one or more coordinate system the X axis or Y axis may be the axis that is most closely perpendicular to the horizontal base plane of the cart 52.

Likewise, the specific processing steps may be different from what has been described and variations in the algorithms and models are possible. For instance, there is no requirement that the forces $F_{EAPP}$ and $F_{BNDR}$ calculated by, respectively, the energy applicator force calculator 358 and the cut guide 390, be calculated for application to the origin of coordinate system EAPP. In alternative versions of this invention, these forces are calculated for application to other points that are typically spaced away from the origin of coordinate system CMVB. The exact location to which these forces are applied is often a function of the geometry of the energy applicator 184. Likewise, there is no requirement that both the energy applicator 358 and cut guide 390 apply the forces they respectively generate to the same point. With regard to the cut guide, the point to which force $F_{BNDR}$ is applied may be recalculated each frame. The point of application of force $F_{BNDR}$ may be a function of a boundary crossing analysis step in which the cut guide 390 determines which point on or section of the energy applicator 184 first would cross a boundary-defining tile. The same alternatives are possible with regard to the calculation of force $F_{EAPP\_SPR}$. As described below, in some version, energy applicator calculator 358 may calculate this force $F_{EAPP\_SPR}$.

For example, there is no requirement that the interference limit calculator comparator 622 always include models of the links that are cylindrical or capsule-shaped. The links could be modeled as rectilinear, conical or triangular structures. In some versions, each link may be modeled as a collection of one or more structures wherein the individual structures are of different sizes and/or shapes.

Similarly, there is no requirement that in all versions that running average filters be employed to generate the target positions along the tool path 248. Alternative smoothing techniques including: using splines; finite impulse response filtering; infinite impulse response filtering; Chebychev filtering; Butterworth filtering; and blending linear segments with parabolic blends.

Likewise, there is no requirement that the signal ramping, such as the signal ramping performed by attenuator 697, always be performed using finite impulse filters. Other processes such as infinite impulse response filtering, Chebychev filtering, Butterworth filtering or adaptive filtering may alternatively be employed to perform this signal ramping.

There is no requirement that in all versions the feed rate calculator 284 always calculate the instrument feed rate based on the instantaneous values of the variables. In some versions, these input variables may be filtered. Likewise, there may be reasons to vary the coefficients that are used as the multipliers to establish the extent any variable effects feed rate. The application of a particular variable may be delayed. The varying of the coefficient may be filtered or ramped to blend in/out the effect of the change in the magnitude of the coefficient. This filtering or blending results in a smoothing out of the advancement of the instrument 160. This smoothing out of the advancing of the instrument may reduce the likelihood that, owing to rapid changes in the positioning of the instrument, the manipulator may become unstable or overshoot the target position. The effect of any variable may be selectively disregarded. For example, it may be desirable to only generate the instrument feed rate based on either the smallest or largest coefficient. The other coefficients are disregarded.

In some versions, two or more variables into feed rate calculator 284 may be combined. This combining may be by summing, multiplying, averaging or dividing. The calculated coefficients may likewise be summed, multiplied, averaged or divided to provide a final coefficient used to, based on the defined feed rate, establish the instrument feed rate. Likewise, there is no requirement that the coefficients may be determined solely on the basis of a variable-to-coefficient feed rate table. Other means to determine these coefficients are based on using the variables as input variables into an equation the result of which is the coefficient used to establish the instrument feed rate. The equations may be polynomial equations or non-linear equations.

Likewise, data other than instrument current draw may be used as the data by the feed rate calculator 284 that serves as the indicia of instrument power. These data include, the voltage or duty cycle required to be applied to the instrument to maintain a constant output. This output may be speed or temperature. In the case of a closed loop energy output device, the measurement of the output can serve as the indicia of instrument power. More specifically, a drop of the output can serve as the indicia of a change in instrument power. For example, if the sensed parameter is motor speed, a drop in speed indicates there was an increase in the power demand of the instrument. Based on this inferential indication that power demand has changed, the INST POWER coefficient applied to the feed rate calculator 284 is adjusted.

Alternative representations of the torques output by the joint motors 101 may be employed to facilitate the determination of the backdrive torques that are output by these motors. For example, it may not always be necessary to employ signals representative of the actual current applied to joint motors 101 as indicia of the torque output by these motors. In alternative configurations of this invention, signals representative of the commanded currents or feed forward torques input into the current control loops of the joint motor controllers 126 are employed as the signals representative of the torques output by the motors.

Data representative of the actual joint torques may also be supplied by sensors attached to the joint motors 101 or other components integral with the active joints. Also, in some versions, there is no backdrive force summer 691. In these versions, a single one of the representations of actual torque is applied to the back drive torque calculator 693.

Alternative methods to determine the backdrive forces and torques may also be employed. For example, in one alternative method of this invention, a first difference between the expected torques and the torques produced by the joint motors 101 is calculated. This set of torque difference values is then converted into coordinate system CMVB as the first set of backdrive forces and torques. A second difference is calculated between the expected torques and the torques sensed by sensors 89. This set of torque difference values is then converted into coordinate system CMVB as the second set of backdrive forces and torques. These two sets of instrument backdrive forces and torques are summed together to produce data representing the backdrive forces and torques. The inputs into this sum may be weighted.

It should be understood that the physical construction of the links forming the manipulator may vary from what has been described. For example, in some manipulators with parallel four bar linkages the linkages may be designed so that the wrists connecting the coupler to the links may rotate around axes that are laterally offset from the axes of the driven links. Likewise, the wrists may not even rotate around axes that are exactly parallel or perpendicular to the drive links. Similarly, there is no requirement that in all versions, the manipulator have plural four bar linkage assemblies. The invention may be constructed out of plural links that collectively form a single-arm serial linkage. In versions that include parallel links that are coupled together, the coupler between the links may not be rigid.

Motors other than permanent magnet synchronous motors may be employed as actuators. For example, brushless DC motors, brush-type DC motors, stepper motors and induction motors. Likewise, there is no requirement that the actuators be electrically driven motors. In some versions the actuators may be hydraulic or pneumatic actuators.

The structure of the joint motor controllers should be understood to be a function of the nature of the motors internal to the actuators. Variations in motor control processes are also possible. For example, it may be possible to omit the speed control loop when regulating motor operation.

In some versions, it may be desirable to provide at least one of the active joints plural encoders. A first encoder monitors the angular position of the shaft integral with the joint motor 101. Data from this encoder is used by the joint motor controller to regulate the actuation of the joint actuator. If the joint actuator is an electric motor, these data are often used to regulate commutation of the motor windings. A second encoder monitors the joint angle. Data from this second encoder is employed by modules such as the forward kinematics module 562 as the representation of actual joint angle. This more direct measurement of the joint angle is not affected by the inherent tolerances of the gear train. Accordingly, employing this more direct measurement of joint angle as the actual representation of joint angle may improve the accuracy with which the manipulator sets the pose of the instrument 160.

In constructions that include plural encoders for at least one of the active joints, the position data from the plural encoders can be used by the joint motor controller to regulate actuation of the joint actuator. For example, in some constructions, the data from one encoder, often the encoder associated with the joint actuator, is used as the primary feedback variable into the position control loop. The data from the second encoder, often the encoder that generates data representative of actual joint angle, is employed as an input to determine the damping component of the output signal. In still other constructions of the manipulator of this invention, the primary feedback variable into the position control loop is a representation of joint angle based on a weighted average of data representative of joint angle from the plural encoders. Further, the damping component may be based on a difference between the representations of the joint angles from the plural encoders. Employing these plural representations of joint angle as input variables into the joint angle position control loop can improve the stability of this control process.

Similarly other methods may be used to map the tissue to which the instrument is to be applied. In one of these methods the practitioner uses a pointer, the positions of which are tracked by the surgical navigation system 210. At the start of the procedure, the practitioner uses the pointer to identify specific landmarks on the body of the patient. Based on the locations of these landmarks, data are generated that define the boundary of the space to which the energy applicator 184 should be applied.

In alternative versions, the cut guide uses other methods to determine the point on the boundary the energy applicator 184 will cross. In regard to this analysis, there is no requirement that it is always assumed that the velocity of coordinate system CMVB is constant when determining where the energy applicator 184 will cross the boundary. The velocity of coordinate system BONE may also vary during a frame. There is no requirement that the plural energy applicator 184 against boundary contacts during a single frame be handled sequentially. These contacts may be aggregated to produce a single effective contact. This single effective contact is mitigated by a single boundary constraining force.

Likewise, cut guide 390 may not rely on impulses to prevent the energy applicator 184 from crossing a boundary. For example, in an alternative construction of manipulator 50, each boundary tile may be modeled as a compliant surface, such as a spring/damper system. When it is determined that the energy applicator 184 will move to a position beyond a tile, the spring defining the tile is considered to be compressed. The force the spring would apply to oppose this compression is calculated.

Similarly, the manipulator of this invention is not designed solely for use with tool path generators that generate tool paths that include parallel path segments. The manipulator of this invention can be used with tool path generators that generate tool paths that include segments that, when connected together form either a two-dimensional or three-dimensional spiral.

In the described version, the tool path is described as being a set of points along the tissue against which the energy applicator 184 is applied. This is only exemplary, not limiting. Depending on the type of instrument, the tool path may be one that is generated to position the instrument so that the energy applicator 184 is both a select distance from the target tissue and in a defined orientation relative to the target tissue. This type of tool path may be generated if, for example, the instrument emits photonic energy. This type of instrument may be designed so that, to perform the desired procedure, the distal end tip of the energy applicator 184 needs to be spaced a given distance, for example 0.1 to 2.0 cm from the tissue to which the energy is to be applied.

Similarly, in some versions, it is further possible to adjust the spacing of the aperture 370 relative to the surface of the tissue to which the energy applicator 184 is to be applied. Generally, as the distance between aperture 370 and the underlying tissue surface increases, the volume of the space in which the instrument can pivot decreases. Controls to perform this adjustment may be presented as buttons on one of the interfaces 128 or 220. This allows the practitioner to perform this adjustment.

Figure 33C:
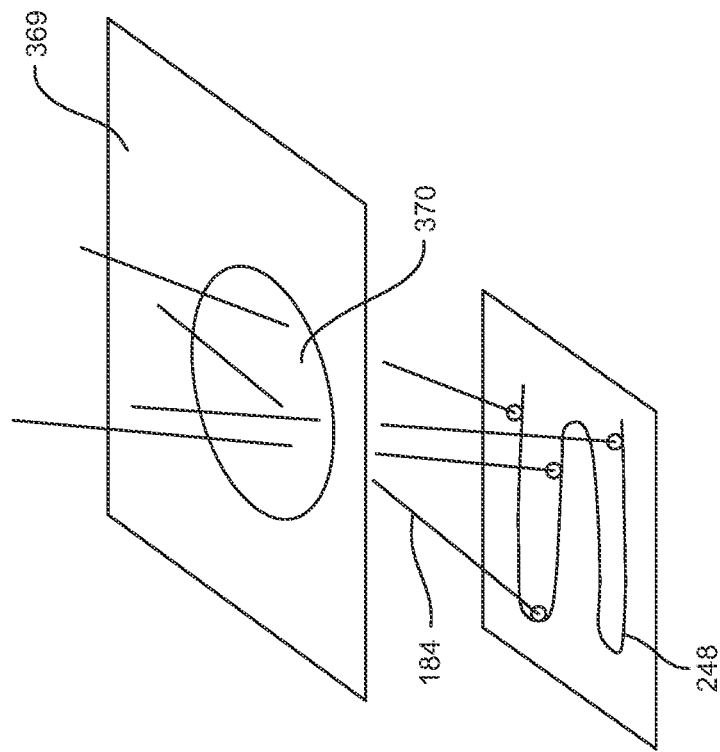
FIG. 33C is a diagrammatic depiction of how, as the energy applicator advances along the tool path, based on the force and torque output by the tool orientation regulator, the orientation of the common axis shifts to maintain the axis in the reference surface aperture.
Figure 33A:
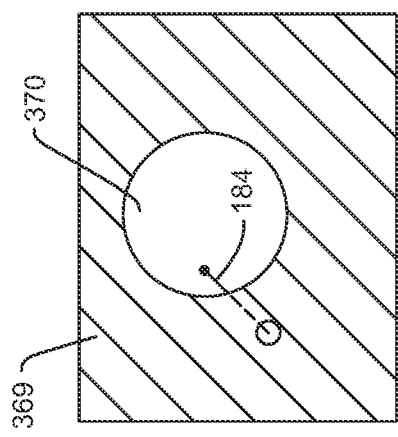
FIGS. 33A and 33B are, respectively, top and side views of how the manipulator adjusts the orientation of the instrument to hold the energy applicator on the tool path while maintaining the common axis within the reference surface aperture.
Figure 33B:
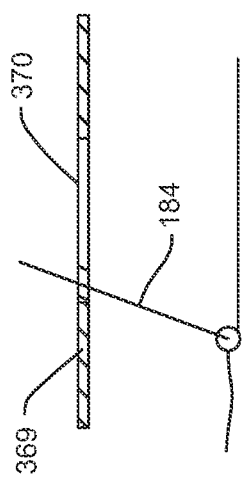

In some versions, the tool orientation regulator 368 may not be configured to, in the general condition, always generate a force $F_{ORNT}$ that results in the manipulator 50 positioning the instrument so that the common axis intersects a fixed centering point. In these versions, even when an obstruction 828 is not present, the tool orientation regulator 368 output forces $F_{ORNT}$ applied to the virtual rigid body that do not always result in the manipulator positioning the instrument so the common axis intersects the fixed centering point. Instead, these forces $F_{ORNT}$ only result in the manipulator positioning the instrument so the common axis intersects the reference surface aperture. FIGS. 33A and 33B illustrate how the instrument is so positioned.

A benefit of this version is that it increases the area of surface of the tissue below the reference plane to which the energy applicator 184 can be applied. An additional benefit of this feature is that it makes it possible to, once a single reference surface and aperture have been defined, position the instrument over a wide area and use the instrument to form shapes that are in appreciably different planes.

Still another benefit of this version is that it makes it possible to, when advancing the energy applicator 184 along the tool path, maintain the instrument in orientations in which the minor angle between the common axis and the reference surface 390 does not appreciably vary from the normal. This benefit of this version is depicted diagrammatically in FIG. 33C. Here, the distal end tip of the energy applicator 184 is seen in various positions as the applicator advances along the tool path 248. When the applicator 184 is in each of these positions, the force $F_{ORNT}$ output by the regulator 368 for application to the virtual rigid body only results in manipulator holding the instrument so the common axis extends through aperture 370. Since the manipulator is not constrained to pivot the instrument so the common axis extends through the center of the aperture 370, the instrument is able to be maintained in orientations that often vary less than 45° from the normal.

This method of operating the instrument can be achieved by having the tool orientation regulator 368 dynamically change the position of the location of the centering point as the energy applicator 184 is advanced semi-autonomously. Each new position of the centering point is based on variables such as the representation of the actual angle of the common axis relative to the reference surface 369, applicator target positions and the commanded pose and commanded velocity of the instrument. Each new position of the centering point it is understood is within the reference surface aperture 370. Distance $DIST_{INST-CP}$ is calculated based on the distance between the dynamically defined centering point and the intersection of the common axis with the reference surface aperture 370.

Likewise, there is no obligation that orientation regulator 368 always calculate forces and torques applied to the virtual rigid body to maintain instrument orientation based on spring/damper modeling. Tool orientation regulator 368 could calculate these forces and torques based on other models that generate the forces and torques applied to the virtual rigid body to maintain the common axis at least in close proximity to the centering point.

Impulse force modeling, the modeling employed to determine forces and torques applied to the virtual rigid body to perform semi-autonomous advancement of the instrument, can be used to define these forces and torques. An equation similar to Equation (5) is employed to determine force $F_{ORNT}$. In this use of Equation (5) the variables upon which direction $D_{xyz}$ is based are the location of the centering point and the intersection of the longitudinal axis of the instrument with the reference plane. Distance $\Delta d$ is the negative of the magnitude of the distance between the centering point and the intersection of the longitudinal axis of the instrument with the reference plane. Velocity $V_0$ is the velocity of coordinate system CMVB expressed in coordinate system CMVB. Velocity $V_1$ is the velocity of the centering point expressed in coordinate system CMVB. The Jacobian used is the Jacobian matrix from the origin of coordinate system CMVB to the centering point along the direction $D_{xyz}$. The remaining terms are the same as are employed for the impulse modeling of semi-autonomous advancement of the energy applicator 184.

The computed forces and torques applied to the virtual rigid body to prevent the joints from exceeding their limits, the links from colliding or the manipulator from extending beyond the workspace boundary may also be calculated using modeling other than spring/damper modeling. Each one of these sets of forces and torques could, for example, be computed using impulse modeling.

When impulse modeling is employed to determine the forces and torques that prevent the joints from moving beyond their minimum and maximum joint limit angles, an equation similar to Equation (5) is employed to determine force $F_{J\_L}$. This equation is employed for each joint when the corresponding boundary exceeded angle for the joint is non-zero. In this use of Equation (5), the angular components of direction $D_{xyz}$ are the components of the unit vector defining the axis of rotation for the joint. The linear components of direction $D_{xyz}$ are set to zero. In many cases as a convention, the z-axis is chosen to define the axis of rotation. In this case direction $D_{xyz}$ is set to [0, 0, 0, 0, 0, 1]. Distance $\Delta d$ is the negative of the boundary exceeded angle. Velocity $V_0$ is the velocity of coordinate system CMVB expressed in coordinate system CMVB. Velocity $V_1$ represents the desired velocity of the joint defined as a vector having components consistent with the definition of direction $D_{xyz}$. For this case it is desired to inhibit advancement of the joint beyond the boundary. This is accomplished by setting the component of velocity $V_1$ corresponding to rotation about the axis to zero. If the above convention is employed, velocity $V_1$ is the null vector. The Jacobian used is the Jacobian matrix from the origin of coordinate system CMVB expressed in coordinate system CMVB to the joint space defined by direction $D_{xyz}$. Using this version of Equation (5), force $F_{ENV}$ is the previously defined force $F_{ENV}$ with the previously defined force $F_{J\_L}$ component removed. The remaining terms are the same as are employed for the impulse modeling of semi-autonomous advancement of the energy applicator 184.

When impulse modeling is employed to determine the forces and torques that prevent the links from colliding, an equation similar to Equation (5) is employed to determine force $F_{INF}$. This equation is employed for each pair of potentially colliding links when the corresponding interference boundary exceeded distance for the pair of links is non-zero. In this use of Equation (5), the linear components of direction $D_y$ are the components of the unit vector defining the line of minimum distance between the links. In many cases this is the common normal between the links. The angular components of direction $D_{xyz}$ are set to zero. In many cases as a convention, the z-axis is chosen to be along the line of minimum distance. In this case direction $D_{xyz}$ is set to [0, 0, 1, 0, 0, 0]. Distance $\Delta d$ is the negative of the boundary exceeded distance. Velocity $V_0$ is the velocity of coordinate system CMVB expressed in coordinate system CMVB. Velocity $V_1$ represents the desired velocity between the links along the line of minimum distance, defined as a vector having components consistent with the definition of direction $D_{xyz}$. For this case it is desired to inhibit advancement of the links towards each other along this line. This is accomplished by setting the component of velocity $V_1$ corresponding to direction of minimum distance to zero. If the above convention is employed, velocity $V_1$ is the null vector. The Jacobian used is the Jacobian matrix from the origin of coordinate system CMVB expressed in coordinate system CMVB to the interference space defined by direction $D_{xyz}$. Using this version of Equation (5), force $F_{ENV}$ is the previously defined force $F_{ENV}$ with the previously defined force $F_{INF}$ component removed. The remaining terms are the same as are employed for the impulse modeling of semi-autonomous advancement of the energy applicator 184.

When impulse modeling is employed to determine the forces and torques that prevent the manipulator from exceeding the workspace boundary, an equation similar to Equation (5) is employed to determine force $F_{WSB}$. This equation is employed when workspace boundary exceeded distance $DIST_{W\_B\_E}$ is non zero. In this use of Equation (5), the linear portion of direction $D_{xyz}$ is the previously defined unit direction vector $D_{W\_B\_E}$. The angular components of direction $D_{xyz}$ are set to zero. Distance $\Delta d$ is the negative of the distance $DIST_{W\_B\_E}$. Velocity $V_0$ is the velocity of coordinate system CMVB expressed in coordinate system CMVB. Velocity $V_1$ represents the desired velocity of coordinate system EAPP away from the workspace boundary defined as a vector having components consistent with the definition of direction $D_{xyz}$. For this case it is desired to inhibit advancement of coordinate system EAPP beyond the workspace boundary. This is accomplished by setting the component of velocity $V_1$ corresponding to the velocity of the movement beyond the boundary to zero. This results in the product of distance $DIST_{W\_B\_E}$ and velocity $V_1$ being the null vector. The Jacobian used is the Jacobian matrix from the origin of coordinate system CMVB expressed in coordinate system CMVB to the point where the line of minimum distance back to the boundary intersects the boundary along direction $D_{xyz}$. This intersection point is expressed in coordinate system MNPL. Using this version of Equation (5), force $F_{ENV}$ is the previously defined force $F_{ENV}$ with the previously defined force $F_{WSB}$ component removed. The remaining terms are the same as are employed for the impulse modeling of semi-autonomous advancement of the energy applicator 184.

If impulse modeling is used to determine plural forces applied to the virtual rigid body, the plural versions of Equation (5) are solved together as a system of equations. The unknowns determined as a result of the solving of these equations are individual corresponding forces. Each of these forces are scalar forces along their respective $D_{xyz}$ directions. Each force is converted to equivalent forces and torques acting at the origin of coordinate system CMVB. These conversions are performed using versions of Equation (6). In each case the respective Jacobian is employed.

If the set of forces that are being solved include any one of forces $F_{J\_L}$, $F_{INF}$ or $F_{WSB}$, the equations are solved as a linear complementarity problem. This is because each one of the forces $F_{J\_L}$, $F_{INF}$ or $F_{WSB}$ has the characteristic that it may not be present if the corresponding boundary is not exceeded. This problem is of the form in which, for each force and velocity pair, the force must be equal to or greater than zero and the velocity also be equal to or greater than zero.

If any one of forces $F_{J\_L}$, $F_{INF}$ or $F_{WSB}$ are solved for as part of the impulse modeling of forces and torques applied to the virtual rigid body, each of the solved forces is applied directly to the total force summer 380. These impulse modeled forces are not applied to the environmental force summer 379.

In a process used to generate the workspace boundary force $F_{WSB}$ there is no need to generate this force based only on the pose of coordinate system EAPP. For example, it may be desirable to perform this modeling based on one of the coordinate systems the pose of which is fixed relative to coordinate system EAPP. These coordinate system include coordinate system EFCT and coordinate system CMVB. This modeling control could also be based on the evaluating the position/positions of one or more moveable points on the arms 68 and 70. It may be desirable to model force $F_{WSB}$ based on the pose of plural coordinate systems. This type of modeling might be performed if it is desirable to avoid having any one of or more than one of plural points on different components attached to the manipulator move beyond the workspace boundary.

In some versions, the evaluation of step 770 to determine whether or not the energy applicator 184 is within the target region at the start of the semi-autonomous operation is performed by evaluating the length of the free space tool path path segment generated in step 766. If the length of this path segment is below a maximum length, manipulator controller 124 considers the origin of energy applicator coordinate system EAPP to be close enough to the start of the on-tissue path segments, point 258, the semi-autonomous advancement of the instrument can proceed.

When manipulator 50 is operated in the semi-autonomous mode processes other than impulse based calculations may be used to determine the force needed to advance the energy applicator 184 to the target position. For example, the forces may be modeled as spring/damping forces. Generally, these spring/damping forces are modeled according to the following formula:

$$F_{EAPP\_SPR} = K_{EAPP} * \text{DIST}_{TRGT-CMND} - D_{EAPP\_REL} * V_{TRGT-CMND} - D_{EAPP\_MNPL} * V_{TRGT} \quad (22)$$

Here, $F_{EAPP\_SPR}$, is the spring/damping force that would need to be applied to the virtual rigid body at the origin of coordinate system EAPP to pull the energy applicator 184 along the path segment towards the target position. Constant $K_{EAPP}$, is a spring constant; $D_{EAPP\_REL}$ is a damping coefficient for the relative velocity; and $D_{EAPP\_MNPL}$ is a damping coefficient for the velocity in manipulator coordinate system MNPL. Distance $\text{DIST}_{TRGT-CMND}$ is a position vector defining the location of the target position relative to the command position. Velocity $V_{TRGT-CMND}$ is a vector that provides the relative velocity of the target position to the commanded position. Velocity $V_{TRGT}$ is a vector that provides the velocity of the target position in manipulator coordinate system MNPL. It may not be necessary to employ the velocity $V_{TRGT}$ as an input variable for determining the force that needs to be applied to the virtual rigid body.

Once $F_{EAPP\_SPR}$ is determined, this force is converted to an equivalent set of forces and torques that would need to be applied to the virtual rigid body at the origin of coordinate system CMVB. This conversion may be performed according to the following formula:

$$F_{INST\_SPR} = J^T F_{EAPP\_SPR} \quad (23)$$

Force $F_{INST\_SPR}$ are the forces and torques applied to the virtual rigid body. This particular Jacobian $J$ is defined from coordinate system CMVB to the coordinate system EAPP. Force/torque vector $F_{INST\_SPR}$ is substituted as an input variable for where force/torque variable $F_{INST}$ is otherwise employed.

If none of forces applied to the virtual rigid body to produce forces $F_{TTL}$ and torques $T_{TTL}$ are determined based on impulse modeling, the forces can all be applied directly to the total force summer 380. This eliminates the need to provide the environmental forces summer 379.

There is no requirement that a specific integration technique be used by either the integrator or cut guide to determine either velocity or pose of a coordinate system. For example, the semi-implicit Euler method, Verlet, rectangular, trapezoidal, Taylor series expansion or Riemann numerical integration techniques may be employed. Likewise, in some versions, the period of the frame or period of the integration may be variable.

In both manual mode and semi-autonomous positioning of the instrument, there is no requirement that the commanded pose/position be the variable representative of actual instrument pose/position employed in the force and torque calculations. In some versions, the measured pose/position of the instrument/energy applicator is employed as the representation of actual position. This "measured" pose/position includes but is not limited to the position determined as a result of: the forward kinematics calculation; and the determination made by monitoring the position and orientation of the tool tracker. Measurements of the joints by direct means, such as with joint angle sensors, or indirect means, such as separate external monitoring unit can also be used to produce data used to determined measured pose/position. A goniometer is one such external monitoring unit.

This measured pose/position data, in addition to being used in the force/torque calculations, may be used as an alternative to the commanded pose/position data in other calculations. These calculations include: the joint limit calculations; the interference limit calculations; and the workspace limit calculations. It should likewise be understood that this substitution need not be absolute. There may be some processes where it is desirable to employ the commanded pose/position as this variable and still others wherein the measured pose/position is employed. Here it is understood that this substitution applies not just to the substitution of measured pose/position data for commanded pose/position data, but also to the substitution of measured joint angles for commanded joint angles.

Similarly, in cases where a representation of actual velocity is needed, either commanded or measured velocity may be employed. This includes representation of actual angular velocity of the joints as well as representations of actual velocity, linear and angular, of the instrument 160 and the coordinate systems that move with the instrument.

Likewise, there may be instances wherein the most appropriate variable that is descriptive of actual instrument pose/position, and or manipulator joint angle is a variable that is derived from a combination of the commanded pose/position/joint angle and the measured pose/position/joint angle. This derived value may be: an unweighted average; a weighted average; a minimum value; and/or a maximum value.

Further, in some versions, one or more of the forces and torques that are supplied to either of the force summers 379 or 380 may be multiplied by a coefficient. The product of this multiplication is then used by the force summer as one of the addend variables upon which the forces $F_{ENV}$ and $F_{TTL}$ and torques $T_{TTL}$ are based. In some versions, depending on the state of the manipulator, one or more of the coefficients may change over time. As with the external forces summer, this blending is performed to smooth the movement of the instrument.

For example, when the practitioner depresses either button 172 to reset the orientation of the instrument 160 or switch 176 when the manipulator is in the manually operated mode, the forces and torques output by the external forces summer 698 may be subjected to a blending process. In this process the forces and torques output by summer 698 are multiplied by coefficients. The products of these multiplications are then employed as the addends representative of the surgeon desired movement of the instrument. Initially, these coefficients may be appreciably below unity, 0.2 or less. Then over a period of time that is typically less than a second and more often less than 0.5 seconds, these coefficients rise to 1.0. Thus if the surgeon, when depressing button 172 or switch 176 is already placing significant forces and torques on the instrument, these forces are and torques are not immediately applied to the force summer 380 as addends. This reduces the extent to which the combining of these forces and torques into the forces $F_{TTL}$ and torques $T_{TTL}$ results in manipulator rapidly resetting the position of the instrument.

Likewise, it should further be appreciated that the tool orientation regulator 368 may not always keep the position of the reference surface and aperture defined within the reference surface constant. Either as a result of preprogrammed instructions or commands entered through the user interface the position and geometries of both these geometric landmarks may be reset.

FIGS. 34A, 34B, and 34C illustrate one situation in which the position and reorientation of the reference surface and aperture are reset. In FIG. 34A a reference surface 910 is shown in relatively close proximity to the surface of the tissue, bone 902, to which the energy applicator 184 is to be applied. The aperture 912 defined in the reference surface is, at least in the depicted plane, shown to have a narrow length. Aperture 912 is thus well suited to define the area through which the axis of the energy applicator 184 should intersect when the energy applicator 184 is applied to a section of tissue that is relatively small in area. This is the section of the tissue which is removed so as to form the initial bore 904 in the bone as depicted in FIG. 34B.

Once bore 904 is formed, the tool orientation regulator defines a new reference surface, surface 918, with aperture 920, as depicted in FIG. 34C. Reference surface 918 is spaced further from the surface of bone 902 than reference surface 910. Aperture 920 is greater in width than aperture 912. The change in position of the reference surface and increase in size in the aperture increases the area in which the origin of the energy applicator coordinate system EAPP can be applied relative to the initial state. This means the energy applicator 184 could then be used, as depicted in FIG. 34C, to form an undercut 906 in the bone 902. This undercut 906, it is observed, has, at least in the depicted plane, a width greater than the diameter across bore 904.

FIGS. 35A, 35B, and 35C depict another situation in which the position and orientation of the reference surface and aperture are reset. FIG. 35A depicts when the reference surface 938 is initially defined so as to be in a plane generally parallel to the surface of the bone 902 that appears generally horizontal in the Figure. Aperture 940 is defined in surface 938. Aperture 940 is an aperture from which the tool orientation regulator 368 regulates the orientation of the energy applicator 184 when the energy applicator 184 is used to define surfaces 930 and 932 in bone, seen in FIG. 35B.

After surfaces 930 and 932 are defined, the procedure may call for the forming of a surface that is tapered away from surface 932. This is why in FIG. 35B, a new reference surface 944 is shown. Tool orientation regulator defines reference surface 944 so that it is angled, not parallel to, the top horizontal surface of bone 902. An aperture 946 is defined in reference surface 944. Given the specifics of the area to which the energy applicator 184 is to be applied, aperture 946 has a width, in the plane of the Figures, less than that of aperture 940.

Once reference surface 944 and aperture 946 are defined, the manipulator may apply the energy applicator 184. Specifically, the energy applicator 184 may be used to remove bone so as to define surface 936 in FIG. 35C. During this process, the tool orientation regulator 368 maintains the orientation of the energy applicator 184 based on the position of aperture 946.

While not illustrated it should further be understood that either the computer generated or manually defined reference surface and, by extension aperture, need not always be planar. The reference surface and aperture may lie in one or more intersecting planes that are angled to each other. All or a portion of the reference surface and associated aperture may even be a curved surface. Likewise, there is no requirement that the aperture used to establish the limits of the orientation of the energy applicator 184 be circular in shape.

It should further be appreciated that, for some procedures, the tool orientation regulator may not even define an aperture. Tool orientation regulator 368 may only define a centering point. In these versions, tool orientation regulator 368 outputs a force $F_{ORNT}$ of such magnitude that the manipulator 50 always orients the instrument so that the common axis, with only minimal variance, intersects the centering point. When operating the manipulator 50 in this mode, the presence of many obstructions 828 may cause the force $F_{ORNT}$ to exceed either the associated lower limit level or higher limit level associated with this force. Force overrider 375 responds as appropriate for the limit level that is exceeded.

Tool orientation regulator 368 may be designed such that the manipulator 50 holds the instrument 160 in a predetermined orientation relative to the surface of the tissue against which the energy applicator 184 is applied. A predetermined orientation may be advantageous when the energy applicator 184 is a milling cutter, which does not cut well on its axis of rotation. For example, when the energy applicator 184 is a ball cutter, the tooth speed approaches zero along this axis and material removal rates and surface finish suffer if cuts are made with the portion of the ball rotating along the axis of rotation presented into the material to be removed. Cutting in this orientation will also increase the required force to push the cutter into the material to be removed and will often generate heat at the surface interface. Thus, a pose is selected that presents the cutting teeth in an orientation that provides the most effective material removal and optimizes the surface finish.

Tool orientation regulator 368 may further be designed to output a force $F_{ORNT}$ that results in the manipulator 50 holding the instrument in a fixed orientation relative to the surface of the tissue against which the energy applicator 184 is applied. One means of performing this orientation regulation is to have the orientation regulator output a force $F_{ORNT}$ that results in the manipulator holding the instrument so the common axis intersects the reference surface at a fixed angle. Often but not always, this angle is a right angle. This type of orientation regulation is employed if the instrument attached to the manipulator is a drill used to form a bore at a precise angle. The fixed angle or the location of the centering point through which common axis intersects can be updated by the tool path generator as the energy applicator 184 is advanced.

In versions in which the surgeon manually sets the extent to which regulator 368 regulates instrument orientation, by entering commands through the user interface 130 the surgeon is able to change the position and orientation of the reference surface as well as the shape and size of the aperture. This allows the surgeon to, in real time, change the extent to which the manipulator 50 regulates the orientation of the instrument 160.

Likewise, there is no requirement that the centering point defined by the orientation regulator be in the center of the aperture defined by the regulator. Using the user interface, the surgeon may be able to define the centering point so that it is spaced from the center of this aperture. Likewise, the surgeon may be able to define this centering point by the selective depression of an instrument switch such as button 172. In this implementation, the aperture itself would still be fixed in shape and location relative to the origin of the coordinate system in which the aperture is defined.

Figure 36A:
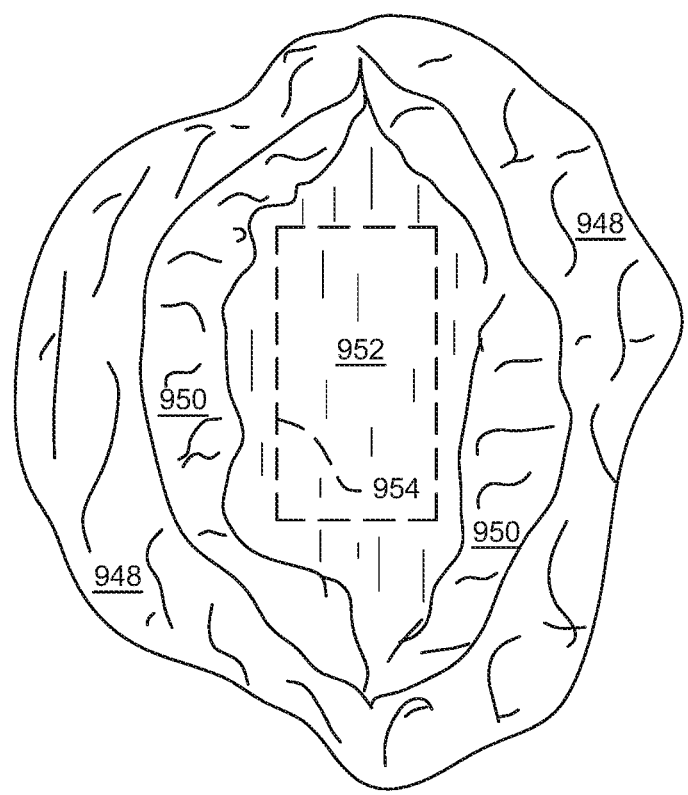
FIGS. 36A, 36B and 36C are a sequence of drawings depicting how the boundary defining where the energy applicator is to be applied is modified during the course of a surgical procedure.

Some manipulators 50 of this invention are further configured to allow the adjustment in essentially real time of the boundaries of the areas to which the instrument energy applicator 184 can be applied. An understanding of the establishment of these boundary settings is understood by reference to FIGS. 36A, 36B, and 36C. FIG. 36A is a top view depicting the bone 952 for which manipulator 50 is used to assist in the performance of the procedure. Dashed rectangle 954 represents the boundary of the surface of the bone to which the energy applicator 184 is to be applied. Also seen is the retracted soft tissue 950 that was initially pulled away to expose the surface of bone 952. The surface of the skin of the patient is called out with identification number 948.

Figure 36B:
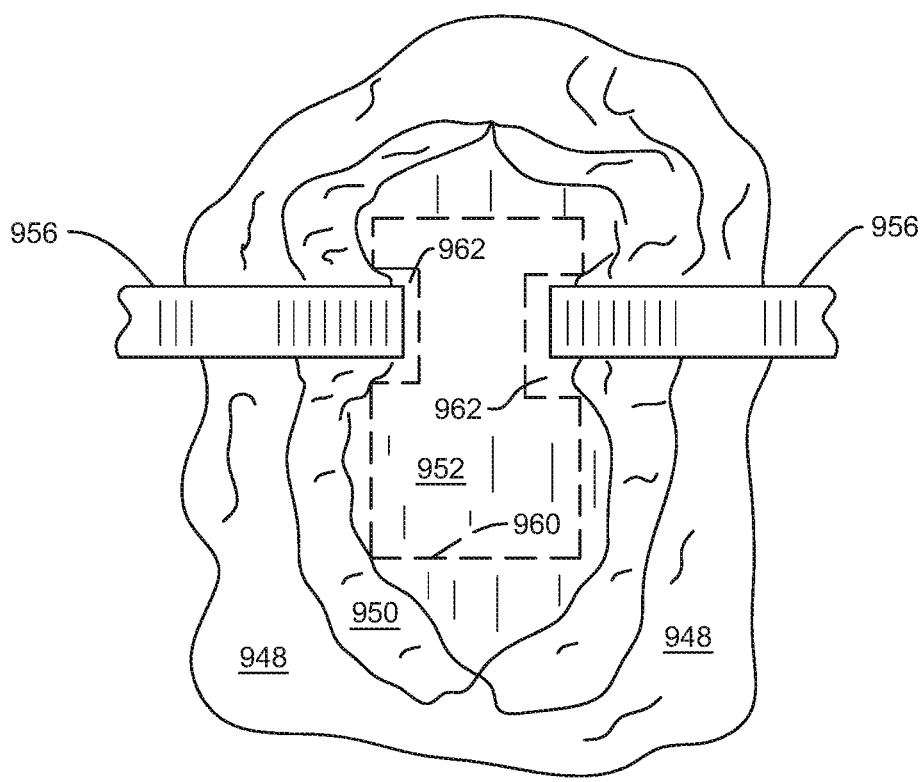

Retractors 956, seen in FIG. 36B, retain the pulled back tissue away from the exposed bone. The retractors 956 extend into the space above area to which the energy applicator 184 is to be applied. Once the retractors 956 are set, a navigation pointer (not illustrated) is pressed against the retractors. The navigation system, by monitoring the position of the pointer, then generates data indicating the positions of the retractors 956 relative to the bone. Based on these data, boundary generator 232, generates a revised boundary represented by dashed line 960. Boundary 960 while similar to boundary 954 has two notches 962. Notches 962 define the sections of the boundary around and spaced from retractors 956. Consequently, during operation of the instrument in either manual or semi-autonomous mode, the behavior control modules now cooperate to prevent the energy applicator 184 from attempting to move against the tissue covered by the retractors 956. This substantially reduces the likelihood that the instrument or energy applicator 184 will collide with the retractors.

Figure 36C:
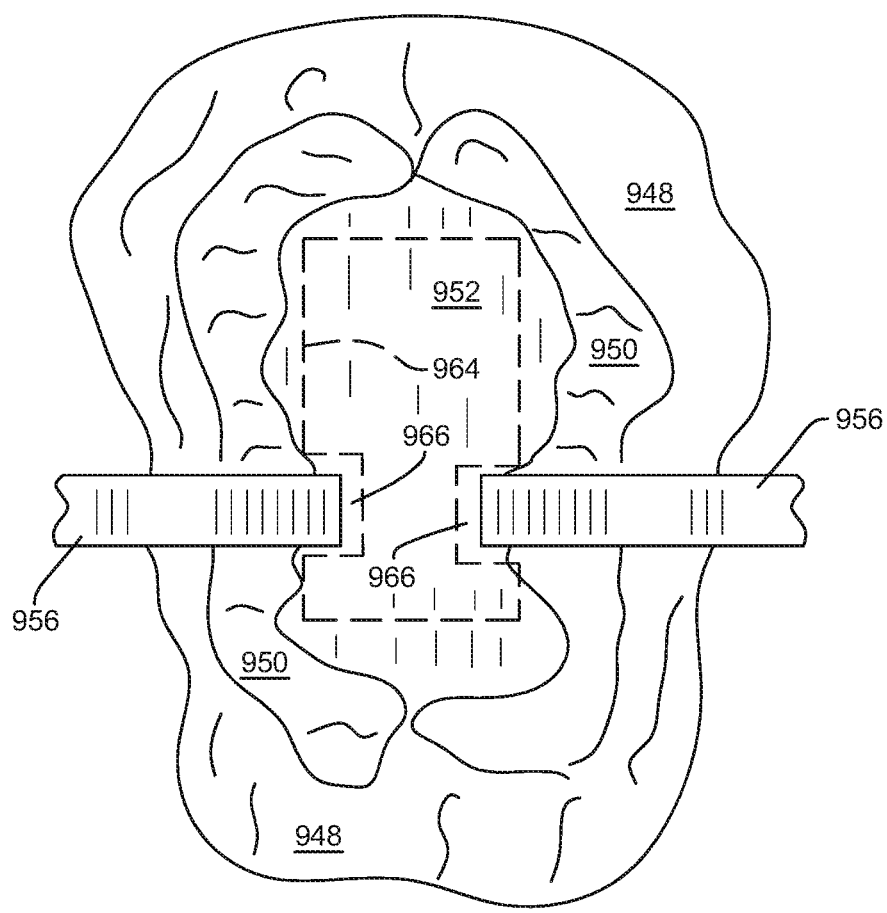

Once the energy applicator 184 has been applied to one section of the bone 952, it may be necessary to, as seen in FIG. 36C, reset the positions of the retractors 956 to hold another section of soft tissue 950 away from the bone. Once the retractors are reset, their positions are again, through the navigation system, forwarded to the boundary generator 232. This results in the generator of a new boundary, represented by dashed line 964, defining the area to which the instrument should be applied. This new boundary defines notches 966. Notches 966 define the out-of-boundary spaces in which the retractors 956 are positioned. This ensures that, even though the retractors 956 have been repositioned, the manipulator will not reposition the instrument in such manner that the energy applicator 184 collides with the retractors 956.

The boundaries of the aperture upon which the orientation regulator 368 determines whether or not the resultant orientation of the instrument is within an acceptable range may likewise be defined using a pointer. In still other versions, the location of markers attached to the patient may be used to define the perimeters of the aperture defined by the orientation regulator 368. The positions of these markers may be monitored by the navigation system 210 or by a separate tracking system. When either pointers or markers are employed to establish the boundary of the aperture defined by the regulator 368, it should be understood that the regulator dynamically changes the shape of this aperture.

Likewise, the physical constructions of some of the control members may change. Manipulator 50 may be provided with a set of foot switches. One of these foot switches may perform one or more of the functions of switch 176. In these versions, in order to have the manipulator emulate manual movement of the instrument and/or actuate the instrument, the practitioner must depress the footswitch.

Similarly, in other versions, the switch that should be depressed in order to cause the semi-autonomous advancement of the instrument may be on the instrument 160. For example, in some versions, the instrument is provided with an additional button or lever. The surgeon depresses this button on order to cause the semi-autonomous advancement of the instrument. When the manipulator is operated in this state, buttons 164 and 174 no longer function as the buttons that regulate the on/off state of the instrument power generating unit 163. Instead, buttons 164 and 170 perform the functions of pendant buttons 193 and 195, respectively. Button 164 is depressed to decrease the semi-autonomous defined feed rate. Button 174 is depressed to increase the semi-autonomous feed rate. Thus, when the manipulator is operated in this configuration, the surgeon, using the hand used to hold the instrument 160, is able to: cause the manual positioning of the instrument; take the instrument in/out of the semi-autonomous mode; and control the semi-autonomous feed rate.

Further, there is no requirement that in all versions, the practitioner must continually depress pendant trigger 194 to cause tool path force calculator 278 to output non-zero forces $F_{INST}$ and $F_{ORNT}$. In some versions, the forces applied to the virtual rigid body that result in the energy applicator 184 advancing along the tool path 248, are output in response to a single pulse to pendant trigger 194. Manipulator 50 advances the instrument until the practitioner applies a second pulse, a stop pulse, to trigger 194.

The navigation system used with this manipulator is not limited to the disclosed system. For example, the manipulator may be used with an electromagnetic navigation system. Also, there may be wired connections between the localizer and the navigation trackers.

Removed tissue logger 275 can provide data that indicates the percent of the volume of tissue marked for removal that was removed. This provides the practitioner with an indication of the extent to which the procedure has been completed. Logger 275 performs this function when the manipulator is operated in either the manual mode or the semi-autonomous mode.

Therefore, it is an object of the appended claims to cover all such modifications and variations that come within the true spirit and scope of this invention.

What is claimed is:

1. A surgical system comprising:
   a robotic manipulator configured to support and move a surgical instrument that includes an energy applicator;
   at least one controller configured to operate the robotic manipulator in a semi-autonomous mode and being configured to calculate an instrument feed rate, wherein the instrument feed rate is a velocity at which the energy applicator advances along a tool path in the semi-autonomous mode; and
   a hand-held pendant coupled to the at least one controller, wherein the hand-held pendant comprises a first control member configured to be placed in a depressed state to initiate operation of the robotic manipulator in the semi-autonomous mode and a second control member to modify the instrument feed rate in the semi-autonomous mode; and
   wherein the at least one controller is configured to: enable continued operation of the robotic manipulator in the semi-autonomous mode in response to the first control member being held in the depressed state; and cease the operation of the robotic manipulator in the semi-autonomous mode in response to the first control member being released from the depressed state.

2. The surgical system of claim 1, wherein the at least one controller is configured to:
   initially output a zero velocity for the instrument feed rate in response to the first control member being placed in the depressed state to initiate operation of the robotic manipulator in the semi-autonomous mode; and
   thereafter, output a non-zero velocity for the instrument feed rate in response to an input from the second control member to modify the instrument feed rate in the semi-autonomous mode.

3. The surgical system of claim 1, wherein the at least one controller is configured to:
   operate the robotic manipulator in a manual mode; and
   switch operation of the robotic manipulator from the manual mode to the semi-autonomous mode in response to the first control member being placed in the depressed state.

4. The surgical system of claim 1, wherein the at least one controller is configured to enable the second control member to modify the instrument feed rate in the semi-autonomous mode only if the first control member is held in the depressed state.

5. The surgical system of claim 1, wherein the at least one controller is configured to:
   operate the robotic manipulator in a manual mode; and
   switch operation of the robotic manipulator from the semi-autonomous mode to the manual mode in response the first control member being released from the depressed state.

6. The surgical system of claim 1, wherein the second control member is configured to increase and/or decrease the instrument feed rate in the semi-autonomous mode.

7. The surgical system of claim 1, wherein the hand-held pendant includes a housing configured to be held in one hand of a user.

8. The surgical system of claim 7, wherein:
   the first control member is located on an underside of the housing; and
   the second control member is located on an upper surface of the housing.

9. The surgical system of claim 8, wherein:
   the first control member comprises a trigger configured to be depressed by a finger of the one hand of the user; and
   the second control member comprises one or more buttons configured to be depressed by a thumb of the one hand of the user.

10. The surgical system of claim 1, wherein the hand-held pendant is spaced apart from the robotic manipulator and configured to remotely control the robotic manipulator.

11. The surgical system of claim 1, further comprising a cart configured to support the robotic manipulator, and wherein a cable is connected between the hand-held pendant and the cart, wherein the cable is configured to enable input signals from the first control member and second control member to be transmitted to the at least one controller.

12. The surgical system of claim 1, further comprising a navigation system, and wherein the hand-held pendant further comprises a third control member configured to enable: commands to be entered to the navigation system and/or data to be transmitted to the navigation system.

13. A user control device for a surgical system that includes a robotic manipulator being configured to support and move a surgical instrument that includes an energy applicator, and at least one controller configured to operate the robotic manipulator in a semi-autonomous mode and being configured to calculate an instrument feed rate, wherein the instrument feed rate is a velocity at which the energy applicator advances along a tool path in the semi-autonomous mode, the user control device comprising:
   a housing configured as a pendant configured to be held in one hand of a user;
   a first control member mounted to the housing and being configured to be: placed in a depressed state to initiate operation of the robotic manipulator in the semi-autonomous mode; held in the depressed state to enable continued operation of the robotic manipulator in the semi-autonomous mode; and released from the depressed state to cease the operation of the robotic manipulator in the semi-autonomous mode; and
   a second control member mounted to the housing and being configured to be depressed to modify the instrument feed rate in the semi-autonomous mode.

14. The user control device of claim 13, wherein:
   the first control member is located on an underside of the housing and the first control member comprises a trigger configured to be depressed by a finger of the one hand of the user; and
   the second control member is located on an upper surface of the housing and the second control member comprises one or more buttons configured to be depressed by a thumb of the one hand of the user, and wherein the second control member is configured to increase and/or decrease the instrument feed rate in the semi-autonomous mode.

15. The user control device of claim 13, further comprising a cable coupled to the housing and being configured to enable transmission of input signals from the first control member and second control member.

16. The user control device of claim 13, further comprising a third control member mounted to the housing and being configured to be depressed to enable commands to be entered to a navigation system and/or data to be transmitted to a navigation system.

17. A method of operating a surgical system, the surgical system comprising a robotic manipulator configured to support and move a surgical instrument that includes an energy applicator, a hand-held pendant comprising a first control member and a second control member, and at least one controller coupled to the robotic manipulator and the hand-held pendant, the method comprising the at least one controller performing the following steps:

initiating operation of the robotic manipulator in a semi-autonomous mode in response to the first control member of the hand-held pendant being placed in a depressed state;

enabling continued operation of the robotic manipulator in the semi-autonomous mode in response to the first control member of the hand-held pendant being held in the depressed state;

advancing the energy applicator along a tool path in the semi-autonomous mode according to an instrument feed rate;

modifying the instrument feed rate during operation of the robotic manipulator in the semi-autonomous mode in response to receiving user input from the second control member of the hand-held pendant; and ceasing the operation of the robotic manipulator in the semi-autonomous mode in response to the first control member of the hand-held pendant being released from the depressed state.

18. A surgical system comprising:

a robotic manipulator configured to support and move a surgical instrument that includes an energy applicator;

at least one controller configured to operate the robotic manipulator in a semi-autonomous mode and being configured to calculate an instrument feed rate, wherein the instrument feed rate is a velocity at which the energy applicator advances along a tool path in the semi-autonomous mode; and a hand-held pendant coupled to the at least one controller, wherein the hand-held pendant comprises a first control member configured to be placed in a depressed state to control operation of the robotic manipulator in the semi-autonomous mode and a second control member to modify the instrument feed rate in the semi-autonomous mode; and wherein the at least one controller is configured to: initiate the operation of the robotic manipulator in the semi-autonomous mode in response to the first control member being temporarily placed in the depressed state at a first moment; and cease the operation of the robotic manipulator in the semi-autonomous mode in response to the first control member being temporarily placed in the depressed state at a second moment occurring after the first moment.

19. The surgical system of claim 18, wherein:

the hand-held pendant includes a housing configured to be held in one hand of a user;

the first control member is located on an underside of the housing; and the second control member is located on an upper surface of the housing.

20. The surgical system of claim 19, wherein:

the first control member comprises a trigger configured to be depressed by a finger of the one hand of the user; and the second control member comprises one or more buttons configured to be depressed by a thumb of the one hand of the user.

* * * * *